(12) United States Patent
Boudko et al.

(10) Patent No.: US 10,934,554 B2
(45) Date of Patent: Mar. 2, 2021

(54) CANNABIS PLANTS HAVING MODIFIED EXPRESSION OF THCA SYNTHASE

(71) Applicant: Tweed, Inc., Smiths Falls (CA)

(72) Inventors: Ekaterina Alexandra Boudko, Smiths Falls (CA); Thomas IV Shipley, Smiths Falls (CA); Douglas Johnson, Ottawa (CA)

(73) Assignee: Tweed, Inc., Smiths Falls (CA)

( * ) Notice: Subject to any disclaimer, the term of this patent is extended or adjusted under 35 U.S.C. 154(b) by 178 days.

(21) Appl. No.: 15/577,708

(22) PCT Filed: May 27, 2016

(86) PCT No.: PCT/IB2016/000814
§ 371 (c)(1),
(2) Date: Nov. 28, 2017

(87) PCT Pub. No.: WO2016/189384
PCT Pub. Date: Dec. 1, 2016

(65) Prior Publication Data
US 2018/0258439 A1 Sep. 13, 2018

Related U.S. Application Data

(60) Provisional application No. 62/167,462, filed on May 28, 2015.

(51) Int. Cl.
*C12N 15/82* (2006.01)
*C12N 15/10* (2006.01)
*A61K 36/185* (2006.01)
*C12N 9/02* (2006.01)
*A61K 31/352* (2006.01)

(52) U.S. Cl.
CPC ........ *C12N 15/8218* (2013.01); *A61K 31/352* (2013.01); *A61K 36/185* (2013.01); *C12N 9/0004* (2013.01); *C12N 15/102* (2013.01); *C12N 15/8243* (2013.01); *C12N 2310/14* (2013.01); *C12N 2310/20* (2017.05); *C12Y 121/03007* (2015.07)

(58) Field of Classification Search
CPC .................................................. C12N 15/8218
See application file for complete search history.

(56) References Cited

U.S. PATENT DOCUMENTS

| | | | |
|---|---|---|---|
| 6,630,507 B1 | 10/2003 | Hampson et al. | |
| 7,105,685 B2 | 9/2006 | Travis | |
| 7,109,245 B2 | 9/2006 | Kunos et al. | |
| 9,035,130 B2* | 5/2015 | De Meijer | A01H 1/00 424/765 |
| 9,095,554 B2* | 8/2015 | Lewis | A01H 6/28 |
| 2010/0286098 A1 | 11/2010 | Robson et al. | |
| 2011/0257256 A1 | 10/2011 | Fuchs et al. | |
| 2012/0311744 A1 | 12/2012 | Sirkowski | |
| 2013/0067619 A1 | 3/2013 | Page et al. | |
| 2015/0098954 A1 | 4/2015 | Hyde et al. | |
| 2016/0139055 A1 | 5/2016 | Pierce, III et al. | |

FOREIGN PATENT DOCUMENTS

| | | |
|---|---|---|
| CA | 2796465 | 10/2012 |
| CA | 2851316 | 4/2014 |
| WO | 93/03161 | 2/1993 |
| WO | WO 2007/148094 | 12/2007 |
| WO | WO 2009/147439 | 12/2009 |
| WO | 2011017798 | 2/2011 |
| WO | 2011127589 | 10/2011 |
| WO | 2013006953 | 1/2013 |

OTHER PUBLICATIONS

Belhaj, K. et al., Plant Methods, published Oct. 11, 2013; vol. 9, No. 39, pp. 1-10. (Year: 2013).*
Fischedick, J. et al. Phytochemistry 2010, vol. 71; pp. 2058-2073. (Year: 2010).*
Baysal, C. et al. Molecular Breeding, (2016) vol. 36, No. 108, pp. 1-11. (Year: 2016).*
International Search Report and Written Opinion regarding International Application No. PCT/IB2016/000814, dated Sep. 14, 2016.
Fischedick et al., "Metabolic fingerprinting of *Cannabis sativa* L., cannabinoids and terpenoids for chemotaxonomic and drug standardization purposes," Phytochemistry 71:2058-2073, 2010.
Sirikantaramas et al., "Recent Advances in Cannabis sativa Research: Biosynthetic Studies and Its Potential in Biotechnology," Current Pharmaceutical Biotechnology 8(4):237-243, 2007.
MacKinnon et al., "Progress toward transformation of Fibre Hemp," Scottish Crop Research Institute Annual Report. vol. 2000/2001, pp. 84-86, 2001.
Feeney et al., "Tissue culture and Agrobacterium-mediated transformation of hemp (*Cannabis sativa* L.)," In Vitro Cell. De. Biol. 39(6):578-585, 2003.
Lata et al., "High frequency plant regeneration from leaf derived callus of high delta9-tetrahydrocannabinol yielding *Cannabis sativa* L.," Planta Med. 76:1629-1633, 2010.
Taura et al., "Production of Delta(1)-tetrahydrocannabinolic acid by the biosynthetic enzyme secreted from transgenic Pichia pastoris," Biochemical and Biophysical Research Communications, 361(3):675-80, 2007.
European Extended Search Report regarding Application No. 16799427, dated Oct. 2, 2018.
Allen et al., "Complex Variability within the THCA and CBDA Synthase Genes in *Cannabis* Species," J. Forensic Investigation 4(1):7, 2016.

* cited by examiner

*Primary Examiner* — Russell Kallis
(74) *Attorney, Agent, or Firm* — Dentons US LLP

(57) ABSTRACT

The invention relates to novel genetically modified plants and methods or materials, such as polynucleotides, expression cassettes, or vectors for producing the same. Moreover, the invention relates to altering the content of cannabinoids in plants and to medical compositions derived from such plants. In particular embodiments, the present invention relates to *cannabis* plants having modified expression of tetrahydrocannabinolic acid (THCA) synthase and methods of modifying the amount of delta-9-tetrahydrocannabinol (THC) and cannabidiol (CBD) in *cannabis* by modifying expression of THCA synthase.

13 Claims, 39 Drawing Sheets

Specification includes a Sequence Listing.

FIG. 1

| | | |
|---|---|---|
| gi\|433359248\|dbj\|AB731220.1\|:16-1630 | ATGAAGTACTCAACATTCTCTTTTGGTTTCTTCTTGCAAAATATTAGTTCACTTCTCTCA | 60 |
| gi\|149999824\|dbj\|AB292682.1\|:1-1632 | ATGAAGTGCTCAACATTCTCCTTTGGTTTCTTGGTTGTTGCAAGATAATATTTTCTCTCA | 60 |
| gi\|149999826\|dbj\|AB292683.1\|:1-1635 | ATGAAGTGCTCAACATTCTGTTTTGGTATGTTGCAAGATAATATTTTCTTCTCTCA | 60 |
| gi\|149999828\|dbj\|AB292684.1\|:1-1635 | ATGAAGTGCTCAACATTCTGTTTTGGTATGTTGCAAGATAATATTTTCTTCTCTCA | 60 |
| gi\|81157981\|dbj\|AB212829.1\|:1-1635 | ATGAATTGCTCAGCATTCCTTTCCTTGGTTTGTTGCAAAATAATATTTTCTTCTCTCA | 60 |
| gi\|81157999\|dbj\|AB212838.1\|:1-1635 | ATGAATTGCTCAGCATTCCTTTCCTTGGTTTGTTGCAAAATAATATTTTCTTCTCTCA | 60 |
| gi\|81157997\|dbj\|AB212837.1\|:1-1635 | ATGAATTGCTCAGCATTCCTTTCCTTGGTTTGTTGCAAAATAATATTTTCTTCTCTCA | 60 |
| gi\|81157993\|dbj\|AB212835.1\|:1-1635 | ATGAATTGCTCAGCATTCCTTTCCTTGGTTTGTTGCAAAATAATATTTTCTTCTCTCA | 60 |
| gi\|81157991\|dbj\|AB212834.1\|:1-1635 | ATGAATTGCTCAGCATTCCTTTCCTTGGTTTGTTGCAAAATAATATTTTCTTCTCTCA | 60 |
| gi\|81157987\|dbj\|AB212832.1\|:1-1635 | ATGAATTGCTCAGCATTCCTTTCCTTGGTTTGTTGCAAAATAATATTTTCTTCTCTCA | 60 |
| gi\|26005813\|dbj\|AB057805.1\|:27-1661 | ATGAATTGCTCAGCATTCCTTTCCTTGGTTTGTTGCAAAATAATATTTTCTTCTCTCA | 60 |
| gi\|81157989\|dbj\|AB212833.1\|:1-1635 | ATGAATTGCTCAGCATTCCTTTCCTTGGTTTGTTGCAAAATAATATTTTCTTCTCTCA | 60 |
| gi\|81157995\|dbj\|AB212836.1\|:1-1635 | ATGAATTGCTCAGCATTCCTTTCCTTGGTTTGTTGCAAAATAATATTTTCTTCTCTCA | 60 |
| gi\|81158005\|dbj\|AB212841.1\|:1-1635 | ATGAATTGCTCAGCATTCCTTTCCTTGGTTTGTTGCAAAATAATATTTTCTTCTCTCA | 60 |
| gi\|81157985\|dbj\|AB212831.1\|:1-1635 | ATGAATTGCTCAGCATTCCTTTCCTTGGTTTGTTGCAAAATAATATTTTCTTCTCTCA | 60 |
| gi\|81158001\|dbj\|AB212839.1\|:1-1635 | ATGAATTGCTCAGCATTCCTTTCCTTGGTTTGTTGCAAAATAATATTTTCTTCTCTCA | 60 |
| gi\|81157983\|dbj\|AB212830.1\|:1-1635 | ATGAATTGCTCAGCATTCCTTTCCTTGGTTTGTTGCAAAATAATATTTTCTTCTCTCA | 60 |
| gi\|81158003\|dbj\|AB212840.1\|:1-1635 | ATGAATTGCTCAGCATTCCTTTCCTTGGTTTGTTGCAAAATAATATTTTCTTCTCTCA | 60 |
| gi\|384598986\|gb\|JQ437490.1\|:1-1635 | ATGAATTGCTCAGCATTCCTTTCCTTGGTTTGTTGCAAAATAATATTTTCTTCTCTCA | 60 |
| gi\|384598976\|gb\|JQ437485.1\|:1-1635 | ATGAATTGCTCAGCATTCCTTTCCTTGGTTTGTTGCAAAATAATATTTTCTTCTCTCA | 60 |
| gi\|384598980\|gb\|JQ437487.1\|:1-1635 | ATGAATTGCTCAGCATTCCTTTCCTTGGTTTGTTGCAAAATAATATTTTCTTCTCTCA | 60 |
| gi\|384598978\|gb\|JQ437486.1\|:1-1635 | ATGAATTGCTCAGCATTCCTTTCCTTGGTTTGTTGCAAAATAATATTTTCTTCTCTCA | 60 |
| gi\|384598968\|gb\|JQ437481.1\|:1-1635 | ATGAATTGCTCAGCATTCCTTTCCTTGGTTTGTTGCAAAATAATATTTTCTTCTCTCA | 60 |
| gi\|384598970\|gb\|JQ437482.1\|:1-1635 | ATGAATTGCTCAGCATTCCTTTCCTTGGTTTGTTGCAAAATAATATTTTCTTCTCTCA | 60 |
| gi\|384598972\|gb\|JQ437483.1\|:1-1635 | ATGAATTGCTCAGCATTCCTTTCCTTGGTTTGTTGCAAAATAATATTTTCTTCTCTCA | 60 |
| gi\|384598974\|gb\|JQ437484.1\|:1-1635 | ATGAATTGCTCAGCATTCCTTTCCTTGGTTTGTTGCAAAATAATATTTTCTTCTCTCA | 60 |
| gi\|384598982\|gb\|JQ437488.1\|:1-1635 | ATGAATTGCTCAGCATTCCTTTCCTTGGTTTGTTGCAAAATAATATTTTCTTCTCTCA | 60 |
| gi\|384598990\|gb\|JQ437492.1\|:1-1635 | ATGAATTGCTCAGCATTCCTTTCCTTGGTTTGTTGCAAAATAATATTTTCTTCTCTCA | 60 |
| gi\|384598984\|gb\|JQ437489.1\|:1-1635 | ATGAATTGCTCAGCATTCCTTTCCTTGGTTTGTTGCAAAATAATATTTTCTTCTCTCA | 60 |
| gi\|384598988\|gb\|JQ437491.1\|:1-1635 | ATGAATTGCTCAGCATTCCTTTCCTTGGTTTGTTGCAAAATAATATTTTCTTCTCTCA | 60 |
| | ***** * **** ***** * ******* * ******* *** *** ** ***** |

FIG. 1 continued

| Accession | Range | Sequence | |
|---|---|---|---|
| gi\|433359248\|dbj\|AB731220.1\| | :16-1630 | TTCTCTATCCAAACTTCTCAAGCTAATCCACATGACAACTTTCTTCAATGCTTCTCCAAA | 120 |
| gi\|149999824\|dbj\|AB292682.1\| | :1-1632 | TTCAATATCCAAACTTCCATTGCTAATAGCTAATCCTCGAGAAAAACTTCCTTAAATGCTTCTCGCAA | 120 |
| gi\|149999826\|dbj\|AB292683.1\| | :1-1635 | TTCAATATCCAAATTTCAATAGCTAATAGCTAATCCTCGAGAAAAACTTCCTTAAATGCTTCTCACAA | 120 |
| gi\|149999828\|dbj\|AB292684.1\| | :1-1635 | TTCAATATCCAAATTTCAATAGCTAATAGCTAATCCTCGAGAAAAACTTCCTTAAATGCCTCTCACAA | 120 |
| gi\|811157981\|dbj\|AB212829.1\| | :1-1635 | TTCCATATCCAAATTTCAATAGCTAATAGCTAATCCTCGAGAAAAACTTCCTTAAATGCTTCTCAAAA | 120 |
| gi\|811157999\|dbj\|AB212838.1\| | :1-1635 | TTCCATATCCAAATTTCAATAGCTAATAGCTAATCCTCGAGAAAAACTTCCTTAAATGCTTCTCAAAA | 120 |
| gi\|811157997\|dbj\|AB212837.1\| | :1-1635 | TTCCATATCCAAATTTCAATAGCTAATAGCTAATCCTCGAGAAAAACTTCCTTAAATGCTTCTCAAAA | 120 |
| gi\|811157993\|dbj\|AB212835.1\| | :1-1635 | TTCCATATCCAAATTTCAATAGCTAATAGCTAATCCTCGAGAAAAACTTCCTTAAATGCTTCTCAAAA | 120 |
| gi\|811157991\|dbj\|AB212834.1\| | :1-1635 | TTCCATATCCAAATTTCAATAGCTAATAGCTAATCCTCGAGAAAAACTTCCTTAAATGCTTCTCAAAA | 120 |
| gi\|811157987\|dbj\|AB212832.1\| | :1-1635 | TTCCATATCCAAATTTCAATAGCTAATAGCTAATCCTCGAGAAAAACTTCCTTAAATGCTTCTCAAAA | 120 |
| gi\|26005813\|dbj\|AB057805.1\| | :27-1661 | TTCCATATCCAAATTTCAATAGCTAATAGCTAATCCTCGAGAAAAACTTCCTTAAATGCTTCTCAAAA | 120 |
| gi\|811157989\|dbj\|AB212833.1\| | :1-1635 | TTCAATATCCAAATTTCAATAGCTAATAGCTAATCCTCAAGAAAAACTTCCTTAAATGCTTCTCGGAA | 120 |
| gi\|811157995\|dbj\|AB212836.1\| | :1-1635 | TTCAATATCCAAATTTCAATAGCTCATTAGCTAATCCTCAAGAAAAACTTCCTTAAATGCTTCTCGGAA | 120 |
| gi\|811158005\|dbj\|AB212841.1\| | :1-1635 | TTCAATATCCAAATTTCAATAGCTCATTAGCTAATCCTCAAGAAAAACTTCCTTAAATGCTTCTCGGAA | 120 |
| gi\|811157985\|dbj\|AB212831.1\| | :1-1635 | TTCAATATCCAAATTTCAATAGCTAATAGCTAATCCTCAAGAAAAACTTCCTTAAATGCTTCTCGGAA | 120 |
| gi\|811158001\|dbj\|AB212839.1\| | :1-1635 | TTCAATATCCAAATTTCAATAGCTAATAGCTAATCCTCAAGAAAAACTTCCTTAAATGCTTCTCGGAA | 120 |
| gi\|811157983\|dbj\|AB212830.1\| | :1-1635 | TTCAATATCCAAATTTCAATAGCTAATAGCTAATCCTCAAGAAAAACTTCCTTAAATGCTTCTCGGAA | 120 |
| gi\|811158003\|dbj\|AB212840.1\| | :1-1635 | TTCAATATCCAAATTTCAATAGCTAATAGCTAATCCTCAAGAAAAACTTCCTTAAATGCTTCTCGGAA | 120 |
| gi\|384598986\|gb\|JQ437490.1\| | :1-1635 | TTCAATATCCAAATTTCAATAGCTAATAGCTAATCCTCAAGAAAAACTTCCTTAAATGCTTCTCGGAA | 120 |
| gi\|384598976\|gb\|JQ437485.1\| | :1-1635 | TTCAATATCCAAATTTCAATAGCTAATAGCTAATCCTCAAGAAAAACTTCCTTAAATGCTTCTCGGAA | 120 |
| gi\|384598980\|gb\|JQ437487.1\| | :1-1635 | TTCAATATCCAAATTTCAATAGCTAATAGCTAATCCTCAAGAAAAACTTCCTTAAATGCTTCTCGGAA | 120 |
| gi\|384598978\|gb\|JQ437486.1\| | :1-1635 | TTCAATATCCAAATTTCAATAGCTAATAGCTAATCCTCAAGAAAAACTTCCTTAAATGCTTCTCGGAA | 120 |
| gi\|384598968\|gb\|JQ437481.1\| | :1-1635 | TTCAATATCCAAATTTCAATAGCTAATAGCTAATCCTCAAGAAAAACTTCCTTAAATGCTTCTCGGAA | 120 |
| gi\|384598970\|gb\|JQ437482.1\| | :1-1635 | TTCAATATCCAAATTTCAATAGCTAATAGCTAATCCTCAAGAAAAACTTCCTTAAATGCTTCTCGGAA | 120 |
| gi\|384598972\|gb\|JQ437483.1\| | :1-1635 | TTCAATATCCAAATTTCAATAGCTAATAGCTAATCCTCAAGAAAAACTTCCTTAAATGCTTCTCGGAA | 120 |
| gi\|384598974\|gb\|JQ437484.1\| | :1-1635 | TTCAATATCCAAATTTCAATAGCTAATAGCTAATCCTCAAGAAAAACTTCCTTAAATGCTTCTCGGAA | 120 |
| gi\|384598982\|gb\|JQ437488.1\| | :1-1635 | TTCAATATCCAAATTTCAATAGCTAATAGCTAATCCTCAAGAAAAACTTCCTTAAATGCTTCTCGGAA | 120 |
| gi\|384598990\|gb\|JQ437492.1\| | :1-1635 | TTCAATATCCAAATTTCAATAGCTAATAGCTAATCCTCAAGAAAAACTTCCTTAAATGCTTCTCGGAA | 120 |
| gi\|384598984\|gb\|JQ437489.1\| | :1-1635 | TTCAATATCCAAATTTCAATAGCTAATAGCTAATCCTCAAGAAAAACTTCCTTAAATGCTTCTCGGAA | 120 |
| gi\|384598988\|gb\|JQ437491.1\| | :1-1635 | TTCAATATCCAAATTTCAATAGCTAATAGCTAATCCTCAAGAAAAACTTCCTTAAATGCTTCTCGGAA | 120 |
| | | *** ******** * ** ******** * ** ***** *** ***** **** ** | |

FIG. 1 continued

| | | |
|---|---|---|
| gi\|433359248\|dbj\|AB731220.1\| | :16-1630 | CATATCAACAACAATAACAATAAATCAATTGTAAAACTCATACACACTCCAAATGATCCA 180 |
| gi\|149999824\|dbj\|AB292682.1\| | :1-1632 | TATATTCCCAATAAT------GCAACAAATCTAAAACTCTATACACTCAAAACAACCCA 174 |
| gi\|149999826\|dbj\|AB292683.1\| | :1-1635 | TATATTCCCACCAAT------GTAACAAATGCAAAACTCGTATACACTCAACACGACCAA 174 |
| gi\|149999828\|dbj\|AB292684.1\| | :1-1635 | TATATTCCCACCAAT------GTAACAAATGCAAAACTCGTATACACTCAACACGACCAA 174 |
| gi\|81157981\|dbj\|AB212829.1\| | :1-1635 | CATATTCCCAACAAT------GTAGCAAATCCAAAACTCGTATACACTCAACACGACCAA 174 |
| gi\|81157999\|dbj\|AB212838.1\| | :1-1635 | CATATTCCCAACAAT------GTAGCAAATCCAAAACTCGTATACACTCAACACGACCAA 174 |
| gi\|81157997\|dbj\|AB212837.1\| | :1-1635 | CATATTCCCAACAAT------GTAGCAAATCCAAAACTGTATACACTCAACACGACCAA 174 |
| gi\|81157993\|dbj\|AB212835.1\| | :1-1635 | CATATTCCCAACAAT------GTAGCAAATCCAAAACTCGTATACACTCAACACGACCAA 174 |
| gi\|81157991\|dbj\|AB212834.1\| | :1-1635 | CATATTCCCAACAAT------GTAGCAAATCCAAAACTCGTATACACTCAACACGACCAA 174 |
| gi\|81157987\|dbj\|AB212832.1\| | :1-1635 | CATATTCCCAACAAT------GTAGCAAATCCAAAACTCGTATACACTCAACACGACCAA 174 |
| gi\|26005813\|dbj\|AB057805.1\| | :27-1661 | CATATTCCTAACAAT------GTAGCAAATCCAAAACTCGTATACACTCAACACGACCAA 174 |
| gi\|81157989\|dbj\|AB212833.1\| | :1-1635 | TATATTCCTAACAAT------CCAGCAAATCCAAAATTCATATACACTCAACACGACCAA 174 |
| gi\|81157995\|dbj\|AB212836.1\| | :1-1635 | TATATTCCTAACAAT------CCAGCAAATCCAAAATTCATATACACTCAACACGACCAA 174 |
| gi\|81158005\|dbj\|AB212841.1\| | :1-1635 | TATATTCCTAACAAT------CCAGCAAATCCAAAATTCATATACACTCAACACGACCAA 174 |
| gi\|81157985\|dbj\|AB212831.1\| | :1-1635 | TATATTCCTAACAAT------CCAGCAAATCCAAAATTCATATACACTCAACACGACCAA 174 |
| gi\|81158001\|dbj\|AB212839.1\| | :1-1635 | TATATTCCTAACAAT------CCAGCAAATCCAAAATTCATATACACTCAACACGACCAA 174 |
| gi\|81157983\|dbj\|AB212830.1\| | :1-1635 | TATATTCCTAACAAT------CCAGCAAATCCAAAATTCATATACACTCAACACGACCAA 174 |
| gi\|81158003\|dbj\|AB212840.1\| | :1-1635 | TATATTCCTAACAAT------CCAGCAAATCCAAAATTCATATACACTCAACACGACCAA 174 |
| gi\|384598986\|gb\|JQ437490.1\| | :1-1635 | TATATTCCTAACAAT------CCAGCAAATCCAAAATTCATATACACTCAACACGACCAA 174 |
| gi\|384598976\|gb\|JQ437485.1\| | :1-1635 | TATATTCCTAACAAT------CCAGCAAATCCAAAATTCATATACACTCAACACGACCAA 174 |
| gi\|384598980\|gb\|JQ437487.1\| | :1-1635 | TATATTCCTAACAAT------CCAGCAAATCCAAAATTCATATACACTCAACACGACCAA 174 |
| gi\|384598978\|gb\|JQ437486.1\| | :1-1635 | TATATTCCTAACAAT------CCAGCAAATCCAAAATTCATATACACTCAACACGACCAA 174 |
| gi\|384598968\|gb\|JQ437481.1\| | :1-1635 | TATATTCCTAACAAT------CCAGCAAATCCAAAATTCATATACACTCAACACGACCAA 174 |
| gi\|384598970\|gb\|JQ437482.1\| | :1-1635 | TATATTCCTAACAAT------CCAGCAAATCCAAAATTCATATACACTCAACACGACCAA 174 |
| gi\|384598972\|gb\|JQ437483.1\| | :1-1635 | TATATTCCTAACAAT------CCAGCAAATCCAAAATTCATATACACTCAACACGACCAA 174 |
| gi\|384598974\|gb\|JQ437484.1\| | :1-1635 | TATATTCCTAACAAT------CCAGCAAATCCAAAATTCATATACACTCAACACGACCAA 174 |
| gi\|384598982\|gb\|JQ437488.1\| | :1-1635 | TATATTCCTAACAAT------CCAGCAAATCCAAAATTCATATACACTCAACACGACCAA 174 |
| gi\|384598990\|gb\|JQ437492.1\| | :1-1635 | TATATTCCTAACAAT------CCAGCAAATCCAAAATTCATATACACTCAACACGACCAA 174 |
| gi\|384598984\|gb\|JQ437489.1\| | :1-1635 | TATATTCCTAACAAT------CCAGCAAATCCAAAATTCATATACACTCAACACGACCAA 174 |
| gi\|384598988\|gb\|JQ437491.1\| | :1-1635 | TATATTCCTAACAAT------CCAGCAAATCCAAAATTCATATACACTCAACACGACCAA 174 |
| | | **** * *** * **** ** ****** ** ****** * * |

FIG. 1 continued

```
gi|433359248|dbj|AB731220.1|:16-1630    TCATATATCTCTGTCCTAAATTCAACTATACAAAACCTTAGATTCGCTTCTCCTTCAACA 240
gi|149999824|dbj|AB292682.1|:1-1632     TTGTATGTCTGTCCTAAATTCGACAATACACAATCTTAGATTCACCTCTGACACAACC 234
gi|149999826|dbj|AB292683.1|:1-1635     TTTATGTCTATCCTGAATTCGACCATACAAAATCTTAGATTACCTCTGACACAACC 234
gi|149999828|dbj|AB292684.1|:1-1635     TTTATGTCTATCTTAAATTCGACCGTACAAAATCTTAGATTACCTCTGACACAACC 234
gi|81157981|dbj|AB212829.1|:1-1635      TTGTATGTCTCTCCTGAATTCGACAATACAAAATCTTAGATTCATCTCTGATACAACC 234
gi|81157999|dbj|AB212838.1|:1-1635      TTGTATGTCTATCCTGAATTCGACAATACAAAATCTTAGATTCATCTCTGATACAACC 234
gi|81157997|dbj|AB212837.1|:1-1635      TTGTATGTCTATCCTGAATTCGACAATACAAAATCTTAGATTCATCTCTGATACAACC 234
gi|81157993|dbj|AB212835.1|:1-1635      TTGTATGTCTATCCTGAATTCGACAATACAAAATCTTAGATTCATCTCTGATACAACC 234
gi|81157991|dbj|AB212834.1|:1-1635      TTGTATGTCTATCCTGAATTCGACAATACAAAATCTTAGATTCATCTCTGATACAACC 234
gi|81157987|dbj|AB212832.1|:1-1635      TTGTATGTCTATCCTGAATTCGACAATACAAAATCTTAGATTCATCTCTGATACAACC 234
gi|26005813|dbj|AB057805.1|:27-1661     TTGTATGTCTATCCTGAATTCGACAATACAAAATCTTAGATTCATCTCTGATACAACC 234
gi|81157989|dbj|AB212833.1|:1-1635      TTGTATATGTCTGTCCTGAATTCGACAATACAAAATCTTAGATTCACCTCTGATACAACC 234
gi|81157995|dbj|AB212836.1|:1-1635      TTGTATATGTCTGTCCTGAATTCGACAATACAAAATCTTAGATTCACCTCTGATACAACC 234
gi|81158005|dbj|AB212841.1|:1-1635      TTGTATATGTCTGTCCTGAATTCAACAATACAAAATCTTAGATTCACCTCTGATACAACC 234
gi|81157985|dbj|AB212831.1|:1-1635      TTGTATATGTCTGTCCTGAATTCGACAATACAAAATCTTAGATTCACCTCTGATACAACC 234
gi|81158001|dbj|AB212839.1|:1-1635      TTGTATATGTCTGTCCTGAATTCGACAATACAAAATCTTAGATTCACCTCTGATACAACC 234
gi|81157983|dbj|AB212830.1|:1-1635      TTGTATATGTCTGTCCTGAATTCGACAATACAAAATCTTAGATTCACCTCTGATACAACC 234
gi|81158003|dbj|AB212840.1|:1-1635      TTGTATATGTCTGTCCTGAATTCGACAATACAAAATCTTAGATTCACCTCTGATGCAACC 234
gi|384598986|gb|JQ437490.1|:1-1635      TTGTATATGTCTGTCCTGAATTCGACAATACAAAATCTTAGATTCACCTCTGATACAACC 234
gi|384598976|gb|JQ437485.1|:1-1635      TTGTATATGTCTGTCCTGAATTCGACAATACAAAATCTTAGATTCACCTCTGATACAACC 234
gi|384598980|gb|JQ437487.1|:1-1635      TTGTATATGTCTGTCCTGAATTCGACAATACAAAATCTTAGATTCACCTCTGATACAACC 234
gi|384598978|gb|JQ437486.1|:1-1635      TTGTATATGTCTGTCCTGAATTCGACAATACAAAATCTTAGATTCACCTCTGATACAACC 234
gi|384598968|gb|JQ437481.1|:1-1635      TTGTATATGTCTGTCCTGAATTCGACAATACAAAATCTTAGATTCACCTCTGATACAACC 234
gi|384598970|gb|JQ437482.1|:1-1635      TTGTATATGTCTGTCCTGAATTCGACAATACAAAATCTTAGATTCACCTCTGATACAACC 234
gi|384598972|gb|JQ437483.1|:1-1635      TTGTATATGTCTGTCCTGAATTCGACAATACAAAATCTTAGATTCACCTCTGATACAACC 234
gi|384598974|gb|JQ437484.1|:1-1635      TTGTATATGTCTGTCCTGAATTCGACAATACAAAATCTTAGATTCACCTCTGATACAACC 234
gi|384598982|gb|JQ437488.1|:1-1635      TTGTATATGTCTGTCCTGAATTCGACAATACAAAATCTTAGATTCACCTCTGATACAACC 234
gi|384598990|gb|JQ437492.1|:1-1635      TTGTATATGTCTGTCCTGAATTCGACAATACAAAATCTTAGATTCACCTCTGATACAACC 234
gi|384598984|gb|JQ437489.1|:1-1635      TTGTATATGTCTGTCCTGAATTCGACAATACAAAATCTTAGATTCACCTCTGATACAACC 234
gi|384598988|gb|JQ437491.1|:1-1635      TTGTATATGTCTGTCCTGAATTCGACAATACAAAATCTTAGATTCACCTCTGATACAACC 234
                                        *  ***** *** ** ** ****** ** ******** ** ******** ****
```

FIG. 1 continued

| | | | |
|---|---|---|---|
| gi\|433359248\|dbj\|AB731220.1\|:16-1630 | CCAAAACCACTAGTTATCATCACACCTTCAAATACATCCATGTCCAAGCCTGTGTTTTA | 300 |
| gi\|149999824\|dbj\|AB292682.1\|:1-1632 | CCAAAACCACTTGTTATCATCACACCTCCTTCACATGTCTCCATATCCAAGGCACTATTCTA | 294 |
| gi\|149999826\|dbj\|AB292683.1\|:1-1635 | CCAAAACCACTTGTTATCATCACACCTCCTTAAATGTCTCCATATCCAAGGCACTATTCTA | 294 |
| gi\|149999828\|dbj\|AB292684.1\|:1-1635 | CCAAAACCACTTGTTATCACCACTCCTTAAATGTCTCCATATCCAAGGCACTATTCTA | 294 |
| gi\|811157981\|dbj\|AB212829.1\|:1-1635 | CCAAAACCACTCGTTATTGTCACTCCTTCAAATAACTCCATATCCAAGCAACTATTTTA | 294 |
| gi\|811157999\|dbj\|AB212838.1\|:1-1635 | CCAAAACCACTCGTTATTGTCACTCCTTCAAATAACTCCATATCCAAGCAACTATTTTA | 294 |
| gi\|811157997\|dbj\|AB212837.1\|:1-1635 | CCAAAACCACTCGTTATTGTCACTCCTTCAAATAACTCCATATCCAAGCAACTATTTTA | 294 |
| gi\|811157993\|dbj\|AB212835.1\|:1-1635 | CCAAAACCACTCGTTATTGTCACTCCTTCAAATAACTCCATATCCAAGCAACTATTTTA | 294 |
| gi\|811157991\|dbj\|AB212834.1\|:1-1635 | CCAAAACCACTCGTTATTGTCACTCCTTCAAATAACTCCATATCCAAGCAACTATTTTA | 294 |
| gi\|811157987\|dbj\|AB212832.1\|:1-1635 | CCAAAACCACTCGTTATTGTCACTCCTTCAAATAACTCCATATCCAAGCAACTATTTTA | 294 |
| gi\|26005813\|dbj\|AB057805.1\|:27-1661 | CCAAAACCACTCGTTATTGTCACTCCTTCAAATGTCTCCATATCCAGGCCAGTATTCTC | 294 |
| gi\|811157989\|dbj\|AB212833.1\|:1-1635 | CCAAAACCACTCGTTATTGTCACTCCTTCAAATGTCTCCATATCCAGGCCAGTATTCTC | 294 |
| gi\|811157995\|dbj\|AB212836.1\|:1-1635 | CCAAAACCACTCGTTATTGTCACTCCTTCAAATGTCTCCATATCCAGGCCAGTATTCTC | 294 |
| gi\|811158005\|dbj\|AB212841.1\|:1-1635 | CCAAAACCACTCGTTATTGTCACTCCTTCAAATGTCTCCATATCCAGGCCAGTATTCTC | 294 |
| gi\|811157985\|dbj\|AB212831.1\|:1-1635 | CCAAAACCACTCGTTATTGTCACTCCTTCAAATGTCTCCATATCCAGGCCAGTATTCTC | 294 |
| gi\|811158001\|dbj\|AB212839.1\|:1-1635 | CCAAAACCACTCGTTATTGTCACTCCTTCAAATGTCTCCATATCCAGGCCAGTATTCTC | 294 |
| gi\|811157983\|dbj\|AB212830.1\|:1-1635 | CCAAAACCACTCGTTATTGTCACTCCTTCAAATGTCTCCATATCCAGGCCAGTATTCTC | 294 |
| gi\|811158003\|dbj\|AB212840.1\|:1-1635 | CCAAAACCACTCGTTATTGTCACTCCTTCAAATGTCTCCATATCCAGGCCAGTATTCTC | 294 |
| gi\|384598986\|gb\|JQ437490.1\|:1-1635 | CCAAAACCACTCGTTATTGTCACTCCTTCAAATGTCTCCATATCCAGGCCAGTATTCTC | 294 |
| gi\|384598976\|gb\|JQ437485.1\|:1-1635 | CCAAAACCACTCGTTATTGTCACTCCTTCAAATGTCTCCATATCCAGGCCAGTATTCTC | 294 |
| gi\|384598980\|gb\|JQ437487.1\|:1-1635 | CCAAAACCACTCGTTATTGTCACTCCTTCAAATGTCTCCATATCCAGGCCAGTATTCTC | 294 |
| gi\|384598978\|gb\|JQ437486.1\|:1-1635 | CCAAAACCACTCGTTATTGTCACTCCTTCAAATGTCTCCATATCCAGGCCAGTATTCTC | 294 |
| gi\|384598968\|gb\|JQ437481.1\|:1-1635 | CCAAAACCACTCGTTATTGTCACTCCTTCAAATGTCTCCATATCCAGGCCAGTATTCTC | 294 |
| gi\|384598970\|gb\|JQ437482.1\|:1-1635 | CCAAAACCACTCGTTATTGTCACTCCTTCAAATGTCTCCATATCCAGGCCAGTATTCTC | 294 |
| gi\|384598972\|gb\|JQ437483.1\|:1-1635 | CCAAAACCACTCGTTATTGTCACTCCTTCAAATGTCTCCATATCCAGGCCAGTATTCTC | 294 |
| gi\|384598974\|gb\|JQ437484.1\|:1-1635 | CCAAAACCACTCGTTATTGTCACTCCTTCAAATGTCTCCATATCCAGGCCAGTATTCTC | 294 |
| gi\|384598982\|gb\|JQ437488.1\|:1-1635 | CCAAAACCACTCGTTATTGTCACTCCTTCAAATGTCTCCATATCCAGGCCAGTATTCTC | 294 |
| gi\|384598990\|gb\|JQ437492.1\|:1-1635 | CCAAAACCACTCGTTATTGTCACTCCTTCAAATGTCTCCATATCCAGGCCAGTATTCTC | 294 |
| gi\|384598984\|gb\|JQ437489.1\|:1-1635 | CCAAAACCACTCGTTATTGTCACTCCTTCAAATGTCTCCATATCCAGGCCAGTATTCTC | 294 |
| gi\|384598988\|gb\|JQ437491.1\|:1-1635 | CCAAAACCACTCGTTATTGTCACTCCTTCAAATGTCTCCATATCCAGGCCAGTATTCTC | 294 |
| | *********** *****  *** ** ** ** *** **** * *** * | |

| | | |
|---|---|---|
| gi\|433359248\|dbj\|AB731220.1\|:16-1630 | GCCTCCTATGTGTCTAAAGTCCCATTTGTGATATTAGATATGAGAAATCTACGTTCAATC | 420 |
| gi\|149999824\|dbj\|AB292682.1\|:1-1632 | ATGCCTACATATCTCAAGTCCCATTTGTTATAGACTTATAGTAGACTGAGAAACATGCTTCAATC | 414 |
| gi\|149999826\|dbj\|AB292683.1\|:1-1635 | ATGCCTACATATCTCAAGTCCCATTTGTTATAGTAGACTGAGAAACATGCATTCGGTC | 414 |
| gi\|149999828\|dbj\|AB292684.1\|:1-1635 | ATGCCTACATATCTCAAGTCCCATTTGTTATAGTAGACTGAGAAACATGCATTCGATC | 414 |
| gi\|811579981\|dbj\|AB212829.1\|:1-1635 | ATGCCTACATTTCTCAAGTCCCATTTGTCTAGTAGACTGAGGAACATGCATTCGATC | 414 |
| gi\|811577999\|dbj\|AB212838.1\|:1-1635 | ATGCCTACATATCTCAAGTCCCATTTGTCTAGTAGACTGAGAAACATGCATTCGATC | 414 |
| gi\|811577997\|dbj\|AB212837.1\|:1-1635 | ATGCCTACATATCTCAAGTCCCATTTGTCTAGTAGACTGAGAAACATGCATTCGATC | 414 |
| gi\|811577993\|dbj\|AB212835.1\|:1-1635 | ATGCCTACATATCTCAAGTCCCATTTGTCTAGTAGACTGAGAAACATGCATTCGATC | 414 |
| gi\|811577991\|dbj\|AB212834.1\|:1-1635 | ATGCCTACATATCTCAAGTCCCATTTGTCTAGTAGACTGAGAAACATGCATTCGATC | 414 |
| gi\|811577987\|dbj\|AB212832.1\|:1-1635 | ATGCCTACATATCTCAAGTCCCATTTGTCTAGTAGACTGAGAAACATGCATTCGATC | 414 |
| gi\|26005813\|dbj\|AB057805.1\|:27-1661 | ATGCCTACATATCTCAAGTCCCATTTGCTATAGTAGACTGAGAAACATGCATACGGTC | 414 |
| gi\|811579989\|dbj\|AB212833.1\|:1-1635 | TTGCCTACATATCTCAAGTCCCATTTGCTATAGTAGACTGAGAAACATGCATACGGTC | 414 |
| gi\|811158005\|dbj\|AB212841.1\|:1-1635 | TTGCCTACATATCTCAAGTCCCATTTGCTATAGTAGACTGAGAAACATGCATACGGTC | 414 |
| gi\|811157985\|dbj\|AB212831.1\|:1-1635 | TTGCCTACATATCTCAAGTCCCATTTGCTATAGTAGACTGAGAAACATGCATACGGTC | 414 |
| gi\|811158001\|dbj\|AB212839.1\|:1-1635 | TGTCCTACATATCTCAAGTCCCATTTGCTATAGTAGACTGAGAAACATGCATACGGTC | 414 |
| gi\|811157983\|dbj\|AB212830.1\|:1-1635 | TTGCCTACATATCTCAAGTCCCATTTGCTATAGTAGACTGAGAAACATGCATACGGTC | 414 |
| gi\|811158003\|dbj\|AB212840.1\|:1-1635 | TTGCCTACATATCTCAAGTCCCATTTGCTATAGTAGACTGAGAAACATGCATACGGTC | 414 |
| gi\|384598986\|gb\|JQ437490.1\|:1-1635 | ATGCCTACATATCTCAAGTCCCATTTGTTGTAGTAGACTGAGAAACATGCATTCGATC | 414 |
| gi\|384598976\|gb\|JQ437485.1\|:1-1635 | ATGCCTACATATCTCAAGTCCCATTTGTTGTAGTAGACTGAGAAACATGCATTCGATC | 414 |
| gi\|384598980\|gb\|JQ437487.1\|:1-1635 | ATGCCTACATATCTCAAGTCCCATTTGTTGTAGTAGACTGAGAAACATGCATTCGATC | 414 |
| gi\|384598978\|gb\|JQ437486.1\|:1-1635 | ATGCCTACATATCTCAAGTCCCATTTGTTGTAGTAGACTGAGAAACATGCATTCGATC | 414 |
| gi\|384598968\|gb\|JQ437481.1\|:1-1635 | ATGCCTACATATCTCAAGTCCCATTTGTTGTAGTAGACTGAGAAACATGCATTCGATC | 414 |
| gi\|384598970\|gb\|JQ437482.1\|:1-1635 | ATGCCTACATATCTCAAGTCCCATTTGTTGTAGTAGACTGAGAAACATGCATTCGATC | 414 |
| gi\|384598972\|gb\|JQ437483.1\|:1-1635 | ATGCCTACATATCTCAAGTCCCATTTGTTGTAGTAGACTGAGAAACATGCATTCGATC | 414 |
| gi\|384598974\|gb\|JQ437484.1\|:1-1635 | ATGCCTACATATCTCAAGTCCCATTTGTTGTAGTAGACTGAGAAACATGCATTCGATC | 414 |
| gi\|384598988\|gb\|JQ437488.1\|:1-1635 | ATGCCTACATATCTCAAGTCCCATTTGTTGTAGTAGACTGAGAAACATGCATTCGATC | 414 |
| gi\|384598992\|gb\|JQ437492.1\|:1-1635 | ATGCCTACATTTCTCAAGTCCCATTTGTCTAGTAGACTGAGGAACATGCATTCGATC | 414 |
| gi\|384598984\|gb\|JQ437489.1\|:1-1635 | ATGCCTACATTTCTCAAGTCCCATTTGTCTAGTAGACTGAGGAACATGCATTCGATC | 414 |
| gi\|384598988\|gb\|JQ437491.1\|:1-1635 | ATGCCTACATTTCTCAAGTCCCATTTGTCTAGTAGACTGAGGAACATGCATTCGATC | 414 |
| | ***** * *** ************ ** **** ** **** * * * ** | |

FIG. 1 continued

| | | | |
|---|---|---|---|
| gi\|433359248\|dbj\|AB731220.1\| | :16-1630 | ACTGTAGACCTAGATACCAAAACTGCATGGGTTGAAGCTGGAGCTACCATTGGTGAACTT | 480 |
| gi\|149999824\|dbj\|AB292682.1\| | :1-1632 | AAAATAGATGTTCATAGCCAAACTGCATGGGTTGAAGCCGGAGCTACCCTTGGAGAAGTT | 474 |
| gi\|149999826\|dbj\|AB292683.1\| | :1-1635 | AAAATAGATGTTCATAGCCAAACTGCATGGGTTGAAGCCGGAGCTACCCTTGGAGAAGTT | 474 |
| gi\|149999828\|dbj\|AB292684.1\| | :1-1635 | AAAATAGATGTTCATAGCCAAACTGCATGGGTTGAATCCGGAGCCGGAGCTACCCTTGGAGAAGTT | 474 |
| gi\|81157981\|dbj\|AB212829.1\| | :1-1635 | AAAATAGATGTTCATAGCCAAACTGCGTGGGTTGAAGCCGGAGCCGGAGCTACCCTTGGAGAAGTT | 474 |
| gi\|81157999\|dbj\|AB212838.1\| | :1-1635 | AAAATAGATGTTCATAGCCAAACTGCCTGGGTTGAAGCCGGAGCCGGAGCTACCCTTGGAGAAGTT | 474 |
| gi\|81157997\|dbj\|AB212837.1\| | :1-1635 | AAAATAGATGTTCATAGCCAAACTGCGTGGGTTGAAGCCGGAGCCGGAGCTACCCTTGGAGAAGTT | 474 |
| gi\|81157993\|dbj\|AB212835.1\| | :1-1635 | AAAATAGATGTTCATAGCCAAACTGCGTGGGTTGAAGCCGGAGCCGGAGCTACCCTTGGAGAAGTT | 474 |
| gi\|81157991\|dbj\|AB212834.1\| | :1-1635 | AAAATAGATGTTCATAGCCAAACTGCGTGGGTTGAAGCCGGAGCCGGAGCTACCCTTGGAGAAGTT | 474 |
| gi\|81157987\|dbj\|AB212832.1\| | :1-1635 | AAAATAGATGTTCATAGCCAAACTGCGTGGGTTGAAGCCGGAGCCGGAGCTACCCTTGGAGAAGTT | 474 |
| gi\|26005813\|dbj\|AB057805.1\| | :27-1661 | AAAATAGATGTTCATAGCCAAACTGCGTGGGTTGAAGCCGGAGCCGGAGCTACCCTTGGAGAAGTT | 474 |
| gi\|81157989\|dbj\|AB212833.1\| | :1-1635 | AAGTAGATATTCATAGCCAAACTGCGTGGGTTGAAGCCGGAGCCGGAGCTACCCTTGGAGAAGTT | 474 |
| gi\|81157995\|dbj\|AB212836.1\| | :1-1635 | AAAGTAGATATTCATAGCCAAACTGCGTGGGTTGAAGCCGGAGCCGGAGCTACCCTTGGAGAAGTT | 474 |
| gi\|81158005\|dbj\|AB212841.1\| | :1-1635 | AAAGTAGATATTCATAGCCAAACTGCGTGGGTTGAAGCCGGAGCCGGAGCTACCCTTGGAGAAGTT | 474 |
| gi\|81157985\|dbj\|AB212831.1\| | :1-1635 | AAAATAGATATTCATAGCCAAACTGCGTGGGTTGAAGCCGGAGCCGGAGCTACCCTTGGAGAAGTT | 474 |
| gi\|81158001\|dbj\|AB212839.1\| | :1-1635 | AAAGTAGATATTCATAGCCAAACTGCGTGGGTTGAAGCCGGAGCCGGAGCTACCCTTGGAGAAGTT | 474 |
| gi\|81157983\|dbj\|AB212830.1\| | :1-1635 | AAAGTAGATATTCATAGCCAAACTGCGTGGGTTGAAGCCGGAGCCGGAGCTACCCTTGGAGAAGTT | 474 |
| gi\|81158003\|dbj\|AB212840.1\| | :1-1635 | AAAATAGATATTCATAGCCAAACTGCGTGGGTTGAAGCCGGAGCCGGAGCTACCCTTGGAGAAGTT | 474 |
| gi\|384598986\|gb\|JQ437490.1\| | :1-1635 | AAAATAGATGTTCATAGCCAAACTGCGTGGGTTGAAGCCGGAGCCGGAGCTACCCTTGGAGAAGTT | 474 |
| gi\|384598976\|gb\|JQ437485.1\| | :1-1635 | AAAATAGATGTTCATAGCCAAACTGCGTGGGTTGAAGCCGGAGCCGGAGCTACCCTTGGAGAAGTT | 474 |
| gi\|384598980\|gb\|JQ437487.1\| | :1-1635 | AAAATAGATGTTCATAGCCAAACTGCGTGGGTTGAAGCCGGAGCCGGAGCTACCCTTGGAGAAGTT | 474 |
| gi\|384598978\|gb\|JQ437486.1\| | :1-1635 | AAAATAGATGTTCATAGCCAAACTGCGTGGGTTGAAGCCGGAGCCGGAGCTACCCTTGGAGAAGTT | 474 |
| gi\|384598968\|gb\|JQ437481.1\| | :1-1635 | AAAATAGATGTTCATAGCCAAACTGCGTGGGTTGAAGCCGGAGCCGGAGCTACCCTTGGAGAAGTT | 474 |
| gi\|384598970\|gb\|JQ437482.1\| | :1-1635 | AAAATAGATGTTCATAGCCAAACTGCGTGGGTTGAAGCCGGAGCCGGAGCTACCCTTGGAGAAGTT | 474 |
| gi\|384598972\|gb\|JQ437483.1\| | :1-1635 | AAAATAGATGTTCATAGCCAAACTGCGTGGGTTGAAGCCGGAGCCGGAGCTACCCTTGGAGAAGTT | 474 |
| gi\|384598974\|gb\|JQ437484.1\| | :1-1635 | AAAATAGATGTTCATAGCCAAACTGCGTGGGTTGAAGCCGGAGCCGGAGCTACCCTTGGAGAAGTT | 474 |
| gi\|384598982\|gb\|JQ437488.1\| | :1-1635 | AAAATAGATGTTCATAGCCAAACTGCGTGGGTTGAAGCCGGAGCCGGAGCTACCCTTGGAGAAGTT | 474 |
| gi\|384598990\|gb\|JQ437492.1\| | :1-1635 | AAAATAGATGTTCATAGCCAAACTGCGTGGGTTGAAGCCGGAGCCGGAGCTACCCTTGGAGAAGTT | 474 |
| gi\|384598984\|gb\|JQ437489.1\| | :1-1635 | AAAATAGATGTTCATAGCCAAACTGCGTGGGTTGAAGCCGGAGCCGGAGCTACCCTTGGAGAAGTT | 474 |
| gi\|384598988\|gb\|JQ437491.1\| | :1-1635 | AAAATAGATGTTCATAGCCAAACTGCGTGGGTTGAAGCCGGAGCCGGAGCTACCCTTGGAGAAGTT | 474 |
| | | * **** * *** * ******** ********* * ********** **** *** * ** | |

| Accession | Range | Sequence | End |
|---|---|---|---|
| gi\|433359248\|dbj\|AB731220.1\| | :16-1630 | TCTGTTAGTAAAAACTTGGAGATGAATGACACTGTGAAGATATATAACAAATGGCAAAAT | 840 |
| gi\|149999824\|dbj\|AB292682.1\| | :1-1632 | AGTGTTAAAAAGATCATGGAGAATGGAGATACATGAGCTTGTCAAGTTAGTAACAAATGGCAAAAT | 831 |
| gi\|149999826\|dbj\|AB292683.1\| | :1-1635 | AGTGTTAAAAAGAACATGGAGAATGGAGATACATGAGCTTGTCAAGTTAGTAACAAATGGCAAAAT | 834 |
| gi\|149999828\|dbj\|AB292684.1\| | :1-1635 | AGTGTTAAAAAGAACATGGAGAATGGAGATACATGAGCTTGTCAAGTTAGTAACAAATGGCAAAAT | 834 |
| gi\|81157981\|dbj\|AB212829.1\| | :1-1635 | AGTGTTAAAAAGAACATGGAGAATGGAGATACATGGCCTTGTCAAGTTATTTAACAAATGGCAAAAT | 834 |
| gi\|81157999\|dbj\|AB212838.1\| | :1-1635 | AGTGTTAAAAAGAACATGGAGAATGGAGATACATGGCCTTGTCAAGTTATTTAACAAATGGCAAAAT | 834 |
| gi\|81157997\|dbj\|AB212837.1\| | :1-1635 | AGTGTTAAAAAGAACATGGAGAATGGAGATACATGGCCTTGTCAAGTTATTTAACAAATGGCAAAAT | 834 |
| gi\|81157993\|dbj\|AB212835.1\| | :1-1635 | AGTGTTAAAAAGAACATGGAGAATGGAGATACATGGCCTTGTCAAGTTATTTAACAAATGGCAAAAT | 834 |
| gi\|81157991\|dbj\|AB212834.1\| | :1-1635 | AGTGTTAAAAAGAACATGGAGAATGGAGATACATGGCCTTGTCAAGTTATTTAACAAATGGCAAAAT | 834 |
| gi\|81157987\|dbj\|AB212832.1\| | :1-1635 | AGTGTTAAAAAGAACATGGAGAATGGAGATACATGGCCTTGTCAAGTTATTTAACAAATGGCAAAAT | 834 |
| gi\|26005813\|dbj\|AB057805.1\| | :27-1661 | AGTGTTAAAAAGAACATGGAGAATGGAGATACATGGCCTTGTCAAGTTATTTAACAAATGGCAAAAT | 834 |
| gi\|81157989\|dbj\|AB212833.1\| | :1-1635 | AGTGTTAAAAAGAACATGGAGAATGGAGATACCTGGCCTTGTCAAGTTATTTAACAAATGGCAAAAT | 834 |
| gi\|81157995\|dbj\|AB212836.1\| | :1-1635 | AGTGTTAAAAAGAACATGGAGAATGGAGATACATGGCCTTGTCAAGTTATTTAACAAATGGCAAAAT | 834 |
| gi\|81158005\|dbj\|AB212841.1\| | :1-1635 | AGTGTTAAAAAGAACATGGAGAATGGAGATACATGGCCTTGTCAAGTTATTTAACAAATGGCAAAAT | 834 |
| gi\|81157985\|dbj\|AB212831.1\| | :1-1635 | AGTGTTAAAAAGAACATGGAGAATGGAGATACATGGCCTTGTCAAGTTATTTAACAAATGGCAAAAT | 834 |
| gi\|81158001\|dbj\|AB212839.1\| | :1-1635 | AGTGTTAAAAAGAACATGGAGAATGGAGATACATGGCCTTGTCAAGTTATTTAACAAATGGCAAAAT | 834 |
| gi\|81157983\|dbj\|AB212830.1\| | :1-1635 | AGTGTTAAAAAGAACATGGAGAATGGAGATACATGGCCTTGTCAAGTTATTTAACAAATGGCAAAAT | 834 |
| gi\|81158003\|dbj\|AB212840.1\| | :1-1635 | AGTGTTAAAAAGAACATGGAGAATGGAGATACATGGCCTTGTCAAGTTATTTAACAAATGGCAAAAT | 834 |
| gi\|384598986\|gb\|JQ437490.1\| | :1-1635 | AGTGTTAAAAAGAACATGGAGAATGGAGATACATGGCCTTGTCAAGTTATTTAACAAATGGCAAAAT | 834 |
| gi\|384598976\|gb\|JQ437485.1\| | :1-1635 | AGTGTTAAAAAGAACATGGAGAATGGAGATACATGGCCTTGTCAAGTTATTTAACAAATGGCAAAAT | 834 |
| gi\|384598980\|gb\|JQ437487.1\| | :1-1635 | AGTGTTAAAAAGAACATGGAGAATGGAGATACATGGCCTTGTCAAGTTATTTAACAAATGGCAAAAT | 834 |
| gi\|384598978\|gb\|JQ437486.1\| | :1-1635 | AGTGTTAAAAAGAACATGGAGAATGGAGATACATGGCCTTGTCAAGTTATTTAACAAATGGCAAAAT | 834 |
| gi\|384598968\|gb\|JQ437481.1\| | :1-1635 | AGTGTTAAAAAGAACATGGAGAATGGAGATACATGGCCTTGTCAAGTTATTTAACAAATGGCAAAAT | 834 |
| gi\|384598970\|gb\|JQ437482.1\| | :1-1635 | AGTGTTAAAAAGAACATGGAGAATGGAGATACATGGCCTTGTCAAGTTATTTAACAAATGGCAAAAT | 834 |
| gi\|384598972\|gb\|JQ437483.1\| | :1-1635 | AGTGTTAAAAAGAACATGGAGAATGGAGATACATGGCCTTGTCAAGTTATTTAACAAATGGCAAAAT | 834 |
| gi\|384598974\|gb\|JQ437484.1\| | :1-1635 | AGTGTTAAAAAGAACATGGAGAATGGAGATACATGGCCTTGTCAAGTTATTTAACAAATGGCAAAAT | 834 |
| gi\|384598982\|gb\|JQ437488.1\| | :1-1635 | AGTGTTAAAAAGAACATGGAGAATGGAGATACATGGCCTTGTCAAGTTATTTAACAAATGGCAAAAT | 834 |
| gi\|384598990\|gb\|JQ437492.1\| | :1-1635 | AGTGTTAAAAAGAACATGGAGAATGGAGATACATGGCCTTGTCAAGTTATTTAACAAATGGCAAAAT | 834 |
| gi\|384598984\|gb\|JQ437489.1\| | :1-1635 | AGTGTTAAAAAGAACATGGAGAATGGAGATACATGGCCTTGTCAAGTTATTTAACAAATGGCAAAAT | 834 |
| gi\|384598988\|gb\|JQ437491.1\| | :1-1635 | AGTGTTAAAAAGAACATGGAGAATGGAGATACATGGCCTTGTCAAGTTATTTAACAAATGGCAAAAT | 834 |
| | | ***** ** * * ******** ** *** *** * ****************** | |

FIG. 1 continued

| | | | |
|---|---|---|---|
| gi\|433359248\|dbj\|AB731220.1\| | :16-1630 | ACTGCTTACAAGTTTGACAAAGATTTGTTACTCTTTGTTAGCTCATGACTATTAATTCT | 900 |
| gi\|149999824\|dbj\|AB292682.1\| | :1-1632 | ATTGCTTACAAGTATGACAAAGATTTATTACTCATGACTCATGACTCATAACTAGGAACATT | 891 |
| gi\|149999826\|dbj\|AB292683.1\| | :1-1635 | ATTGCTTACATGTATGAAAAAGAATTATTACTCTTTACTCACTTTATAACCAGGAATATT | 894 |
| gi\|149999828\|dbj\|AB292684.1\| | :1-1635 | ATTGCTTACATGTATGAAAAAGAATTATTACTCTTTACTCACTTTATAACCAGGAATATT | 894 |
| gi\|811157981\|dbj\|AB212829.1\| | :1-1635 | ATTGCTTACAAGTATGACAAAGATTTAGTACTCATGACTCACTCATAACAAAGAATATT | 894 |
| gi\|811157999\|dbj\|AB212838.1\| | :1-1635 | ATTGCTTACAAGTATGACAAAGATTTAGTACTCATGACTCACTCATAACAAAGAATATT | 894 |
| gi\|811157997\|dbj\|AB212837.1\| | :1-1635 | ATTGCTTACAAGTATGACAAAGATTTAGTACTCATGACTCATGACTCATAACAAAGAATATT | 894 |
| gi\|811157993\|dbj\|AB212835.1\| | :1-1635 | ATTGCTTACAAGTATGACAAAGATTTAGTACTCATGACTCACTCATAACAAAGAATATT | 894 |
| gi\|811157991\|dbj\|AB212834.1\| | :1-1635 | ATTGCTTACAAGTATGACAAAGATTTAGTACTCATGACTCACTCATAACAAAGAATATT | 894 |
| gi\|811157987\|dbj\|AB212832.1\| | :1-1635 | ATTGCTTACAAGTATGACAAAGATTTAGTACTCATGACTCACTCATAACAAAGAATATT | 894 |
| gi\|26005813\|dbj\|AB057805.1\| | :27-1661 | ATTGCTTACAAGTATGACAAAGATTTAATGCTCACGACTCACTCAGAACTCATAACAAAGAATATT | 894 |
| gi\|811157989\|dbj\|AB212833.1\| | :1-1635 | ATTGCTTACAAGTATGACAAAGATTTAATGCTCACGACTCACTCAGAACTCATAACAAAGAATATT | 894 |
| gi\|811157995\|dbj\|AB212836.1\| | :1-1635 | ATTGCTTACAAGTATGACAAAGATTTAATGCTCACGACTCACTCAGAACTCATAACAAAGAATATT | 894 |
| gi\|811158005\|dbj\|AB212841.1\| | :1-1635 | ATTGCTTACAAGTATGACAAAGATTTAATGCTCACGACTCACTCAGAACTCATAACAAAGAATATT | 894 |
| gi\|811157985\|dbj\|AB212831.1\| | :1-1635 | ATTGCTTACAAGTATGACAAAGATTTAATGCTCACGACTCACTCAGAACTCATAACAAAGAATATT | 894 |
| gi\|811158001\|dbj\|AB212839.1\| | :1-1635 | ATTGCTTACAAGTATGACAAAGATTTAATGCTCACGACTCACTCAGAACTCATAACAAAGAATATT | 894 |
| gi\|811157983\|dbj\|AB212830.1\| | :1-1635 | ATTGCTTACAAGTATGACAAAGATTTAATGCTCACGACTCACTCAGAACTCATAACAAAGAATATT | 894 |
| gi\|811158003\|dbj\|AB212840.1\| | :1-1635 | ATTGCTTACAAGTATGACAAAGATTTAATGCTCACGACTCACTCAGAACTCATAACAAAGAATATT | 894 |
| gi\|384598986\|gb\|JQ437490.1\| | :1-1635 | ATTGCTTACAAGTATGACAAAGATTTAGTACTCATGACTCACTCATAACAAAGAATATT | 894 |
| gi\|384598976\|gb\|JQ437485.1\| | :1-1635 | ATTGCTTACAAGTATGACAAAGATTTAGTACTCATGACTCACTCATAACAAAGAATATT | 894 |
| gi\|384598980\|gb\|JQ437487.1\| | :1-1635 | ATTGCTTACAAGTATGACAAAGATTTAGTACTCATGACTCACTCATAACAAAGAATATT | 894 |
| gi\|384598978\|gb\|JQ437486.1\| | :1-1635 | ATTGCTTACAAGTATGACAAAGATTTAGTACTCATGACTCACTCATAACAAAGAATATT | 894 |
| gi\|384598968\|gb\|JQ437481.1\| | :1-1635 | ATTGCTTACAAGTATGACAAAGATTTAGTACTCATGACTCACTCATAACAAAGAATATT | 894 |
| gi\|384598970\|gb\|JQ437482.1\| | :1-1635 | ATTGCTTACAAGTATGACAAAGATTTAGTACTCATGACTCACTCATAACAAAGAATATT | 894 |
| gi\|384598972\|gb\|JQ437483.1\| | :1-1635 | ATTGCTTACAAGTATGACAAAGATTTAGTACTCATGACTCACTCATAACAAAGAATATT | 894 |
| gi\|384598974\|gb\|JQ437484.1\| | :1-1635 | ATTGCTTACAAGTATGACAAAGATTTAGTACTCATGACTCACTCATAACAAAGAATATT | 894 |
| gi\|384598982\|gb\|JQ437488.1\| | :1-1635 | ATTGCTTACAAGTATGACAAAGATTTAGTACTCATGACTCACTCATAACAAAGAATATT | 894 |
| gi\|384598990\|gb\|JQ437492.1\| | :1-1635 | ATTGCTTACAAGTATGACAAAGATTTAGTACTCATGACTCACTCATAACAAAGAATATT | 894 |
| gi\|384598984\|gb\|JQ437489.1\| | :1-1635 | ATTGCTTACAAGTATGACAAAGATTTAGTACTCATGACTCACTCATAACAAAGAATATT | 894 |
| gi\|384598988\|gb\|JQ437491.1\| | :1-1635 | ATTGCTTACAAGTATGACAAAGATTTAGTACTCATGACTCACTCATAACAAAGAATATT | 894 |
| | | * ********* ** *** ***** ** * *** * * ** ** *** | * |

FIG. 1 continued

| | | | |
|---|---|---|---|
| gi\|433359248\|dbj\|AB731220.1\|:16-1630 | ACGGATTCACAAGGGAAATACAAGACAACTATACAAGCTTCATTCTTCTTCTATATTCTT | 960 |
| gi\|149999824\|dbj\|AB292682.1\|:1-1632 | ACAGATAATCAAGGAAGGAAGAATAAGACAACAGCAATACACACTTACTTCTTCTTCAGTTTTCCTT | 951 |
| gi\|149999826\|dbj\|AB292683.1\|:1-1635 | ACAGATAATCAAGGAAGGAAGAATAAGACAACAATACACAGTTACTTCTCCTCCATTTTCCAT | 954 |
| gi\|149999828\|dbj\|AB292684.1\|:1-1635 | ACAGATAATCAAGGAAGGAAGAATAAGACAACAATACACAGTTACTTCTCCTCCATTTTCCAT | 954 |
| gi\|811157981\|dbj\|AB212829.1\|:1-1635 | ACAGATAATCATGGGAAGAATAAGACTACAGTTACTTCTCCTCTTCAATTTTTCAT | 954 |
| gi\|811157999\|dbj\|AB212838.1\|:1-1635 | ACAGATAATCATGGGAAGAATAAGACTACAGTTACTTCTCCTCTTCAATTTTTCAT | 954 |
| gi\|811157997\|dbj\|AB212837.1\|:1-1635 | ACAGATAATCATGGGAAGAATAAGACTACAGTTACTTCTCCTCTTCAATTTTTCAT | 954 |
| gi\|811157993\|dbj\|AB212835.1\|:1-1635 | ACAGATAATCATGGGAAGAATAAGACTACAGTTACTTCTCCTCTTCAATTTTTCAT | 954 |
| gi\|811157991\|dbj\|AB212834.1\|:1-1635 | ACAGATAATCATGGGAAGAATAAGACTACAGTTACTTCTCCTCTTCAATTTTTCAT | 954 |
| gi\|811157987\|dbj\|AB212832.1\|:1-1635 | ACAGATAATCATGGGAAGAATAAGACTACAGTTACTTCTCCTCTTCAATTTTTCAT | 954 |
| gi\|26005813\|dbj\|AB057805.1\|:27-1661 | ACAGATAATCATGGGAAGAATAAGACTACAGTTACTTCTCCTCTTCAATTTTTCTT | 954 |
| gi\|811157989\|dbj\|AB212833.1\|:1-1635 | ACAGATAATCATGGGAAGAATAAGACTACAGTTACTTCTCCTCTTCAATTTTTCTT | 954 |
| gi\|811157995\|dbj\|AB212836.1\|:1-1635 | ACAGATAATCATGGGAAGAATAAGACTACAGTTACTTCTCCTCTTCAATTTTTCAT | 954 |
| gi\|811158005\|dbj\|AB212841.1\|:1-1635 | ACAGATAATCATGGGAAGAATAAGACTACAGTTACTTCTCCTCTTCAATTTTTCAT | 954 |
| gi\|811157985\|dbj\|AB212831.1\|:1-1635 | ACAGATAATCATGGGAAGAATAAGACTACAGTTACTTCTCCTCTTCAATTTTTCTT | 954 |
| gi\|811158001\|dbj\|AB212839.1\|:1-1635 | ACAGATAATCATGGGAAGAATAAGACTACAGTTACTTCTCCTCTTCAATTTTTCTT | 954 |
| gi\|811157983\|dbj\|AB212830.1\|:1-1635 | ACAGATAATCATGGGAAGAATAAGACTACAGTTACTTCTCCTCTTCAATTTTTCTT | 954 |
| gi\|811158003\|dbj\|AB212840.1\|:1-1635 | ACAGATAATCATGGGAAGAATAAGACTACAGTTACTTCTCCTCTTCAATTTTTCTT | 954 |
| gi\|384598986\|gb\|JQ437490.1\|:1-1635 | ACAGATAATCATGGGAAGAATAAGACTACAGTTACTTCTCCTCTTCAATTTTTCAT | 954 |
| gi\|384598976\|gb\|JQ437485.1\|:1-1635 | ACAGATAATCATGGGAAGAATAAGACTACAGTTACTTCTCCTCTTCAATTTTTCAT | 954 |
| gi\|384598980\|gb\|JQ437487.1\|:1-1635 | ACAGATAATCATGGGAAGAATAAGACTACAGTTACTTCTCCTCTTCAATTTTTCAT | 954 |
| gi\|384598978\|gb\|JQ437486.1\|:1-1635 | ACAGATAATCATGGGAAGAATAAGACTACAGTTACTTCTCCTCTTCAATTTTTCAT | 954 |
| gi\|384598968\|gb\|JQ437481.1\|:1-1635 | ACAGATAATCATGGGAAGAATAAGACTACAGTTACTTCTCCTCTTCAATTTTTCAT | 954 |
| gi\|384598970\|gb\|JQ437482.1\|:1-1635 | ACAGATAATCATGGGAAGAATAAGACTACAGTTACTTCTCCTCTTCAATTTTTCAT | 954 |
| gi\|384598972\|gb\|JQ437483.1\|:1-1635 | ACAGATAATCATGGGAAGAATAAGACTACAGTTACTTCTCCTCTTCAATTTTTCAT | 954 |
| gi\|384598974\|gb\|JQ437484.1\|:1-1635 | ACAGATAATCATGGGAAGAATAAGACTACAGTTACTTCTCCTCTTCAATTTTTCAT | 954 |
| gi\|384598982\|gb\|JQ437488.1\|:1-1635 | ACAGATAATCATGGGAAGAATAAGACTACAGTTACTTCTCCTCTTCAATTTTTCAT | 954 |
| gi\|384598990\|gb\|JQ437492.1\|:1-1635 | ACAGATAATCATGGGAAGAATAAGACTACAGTTACTTCTCCTCTTCAATTTTTCAT | 954 |
| gi\|384598984\|gb\|JQ437489.1\|:1-1635 | ACAGATAATCATGGGAAGAATAAGACTACAGTTACTTCTCCTCTTCAATTTTTCAT | 954 |
| gi\|384598988\|gb\|JQ437491.1\|:1-1635 | ACAGATAATCATGGGAAGAATAAGACTACAGTTACTTCTCCTCTTCAATTTTTCAT | 954 |
| | ** *** ***** * **** ** * ***** ** ***** * * | |

FIG. 1 continued

| | | |
|---|---|---|
| gi\|433359248\|dbj\|AB731220.1\|:16-1630 | GGTAGGCTTGAGAGTCTCCTCATATTGATGCAAAAGAAATTCCTGAGTTGGGAATTGAA | 1020 |
| gi\|149999824\|dbj\|AB292682.1\|:1-1632 | GGTGGAGTGGATAGTCTAGTCGACTTGATGATGAACAAGAGAGTTCCTGAGTTGGGTATTAAA | 1011 |
| gi\|149999826\|dbj\|AB292683.1\|:1-1635 | GGTGGAGTGGATAGTCTAGTCGACTTGATGATGAACAAGAGAGCTTCCTGAATTGGGTATTAAA | 1014 |
| gi\|149999828\|dbj\|AB292684.1\|:1-1635 | GGTGGAGTGGATAGTCTAGTCGACTTGATGATGAACAAGAGAGCTTCCTGAATTGGGTATTAAA | 1014 |
| gi\|81157981\|dbj\|AB212829.1\|:1-1635 | GGTGGAGTGGATAGTCTAGTCGACTTGATGATGAACAAGAGAGCTTCCTGAGTTGGGTATTAAA | 1014 |
| gi\|81157999\|dbj\|AB212838.1\|:1-1635 | GGTGGAGTGGATAGTCTAGTCGACTTGATGATGAACAAGAGAGCTTCCTGAGTTGGGTATTAAA | 1014 |
| gi\|81157997\|dbj\|AB212837.1\|:1-1635 | GGTGGAGTGGATAGTCTAGTCGACTTGATGATGAACAAGAGAGCTTCCTGAGTTGGGTATTAAA | 1014 |
| gi\|81157993\|dbj\|AB212835.1\|:1-1635 | GGTGGAGTGGATAGTCTAGTCGACTTGATGATGAACAAGAGAGCTTCCTGAGTTGGGTATTAAA | 1014 |
| gi\|81157991\|dbj\|AB212834.1\|:1-1635 | GGTGGAGTGGATAGTCTAGTCGACTTGATGATGAACAAGAGAGCTTCCTGAGTTGGGTATTAAA | 1014 |
| gi\|81157987\|dbj\|AB212832.1\|:1-1635 | GGTGGAGTGGATAGTCTAGTCGACTTGATGATGAACAAGAGAGCTTCCTGAGTTGGGTATTAAA | 1014 |
| gi\|26005813\|dbj\|AB057805.1\|:27-1661 | GGTGGAGTGGATAGTCTAGTCGACTTGATGATGAACAAGAGAGCTTCCTGAGTTGGGTATTAAA | 1014 |
| gi\|81157989\|dbj\|AB212833.1\|:1-1635 | GGTGGAGTGGATAGTCTAGTTGACTTGATGATGAACAAGAGAGCTTCCTGAGTTGGGTATTAAA | 1014 |
| gi\|81157995\|dbj\|AB212836.1\|:1-1635 | GGTGGAGTGGATAGTCTAGTCGACTTGATGATGAACAAGAGAGCTTCCTGAGTTGGGTATTAAA | 1014 |
| gi\|81158005\|dbj\|AB212841.1\|:1-1635 | GGTGGAGTGGATAGTCTAGTCGACTTGATGATGAACAAGAGAGCTTCCTGAGTTGGGTATTAAA | 1014 |
| gi\|81157985\|dbj\|AB212831.1\|:1-1635 | GGTGGAGTGGATAGTCTAGTCGACTTGATGATGAACAAGAGAGCTTCCTGAGTTGGGTATTAAA | 1014 |
| gi\|81158001\|dbj\|AB212839.1\|:1-1635 | GGTGGAGTGGATAGTCTAGTCGACTTGATGATGAACAAGAGAGCTTCCTGAGTTGGGTATTAAA | 1014 |
| gi\|81157983\|dbj\|AB212830.1\|:1-1635 | GGTGGAGTGGATAGTCTAGTCGACTTGATGATGAACAAGAGAGCTTCCTGAGTTGGGTATTAAA | 1014 |
| gi\|81158003\|dbj\|AB212840.1\|:1-1635 | GGTGGAGTGGATAGTCTAGTCGACTTGATGATGAACAAGAGAGCTTCCTGAGTTGGGTATTAAA | 1014 |
| gi\|384598986\|gb\|JQ437490.1\|:1-1635 | GGTGGAGTGGATAGTCTAGTCGACTTGATGATGAACAAGAGAGCTTCCTGAGTTGGGTATTAAA | 1014 |
| gi\|384598976\|gb\|JQ437485.1\|:1-1635 | GGTGGAGTGGATAGTCTAGTCGACTTGATGATGAACAAGAGAGCTTCCTGAGTTGGGTATTAAA | 1014 |
| gi\|384598980\|gb\|JQ437487.1\|:1-1635 | GGTGGAGTGGATAGTCTAGTCGACTTGATGATGAACAAGAGAGCTTCCTGAGTTGGGTATTAAA | 1014 |
| gi\|384598978\|gb\|JQ437486.1\|:1-1635 | GGTGGAGTGGATAGTCTAGTCGACTTGATGATGAACAAGAGAGCTTCCTGAGTTGGGTATTAAA | 1014 |
| gi\|384598968\|gb\|JQ437481.1\|:1-1635 | GGTGGAGTGGATAGTCTAGTCGACTTGATGATGAACAAGAGAGCTTCCTGAGTTGGGTATTAAA | 1014 |
| gi\|384598970\|gb\|JQ437482.1\|:1-1635 | GGTGGAGTGGATAGTCTAGTCGACTTGATGATGAACAAGAGAGCTTCCTGAGTTGGGTATTAAA | 1014 |
| gi\|384598972\|gb\|JQ437483.1\|:1-1635 | GGTGGAGTGGATAGTCTAGTCGACTTGATGATGAACAAGAGAGCTTCCTGAGTTGGGTATTAAA | 1014 |
| gi\|384598974\|gb\|JQ437484.1\|:1-1635 | GGTGGAGTGGATAGTCTAGTCGACTTGATGATGAACAAGAGAGCTTCCTGAGTTGGGTATTAAA | 1014 |
| gi\|384598982\|gb\|JQ437488.1\|:1-1635 | GGTGGAGTGGATAGTCTAGTCGACTTGATGATGAACAAGAGAGCTTCCTGAGTTGGGTATTAAA | 1014 |
| gi\|384598990\|gb\|JQ437492.1\|:1-1635 | GGTGGAGTGGATAGTCTAGTCGACTTGATGATGAACAAGAGAGCTTCCTGAGTTGGGTATTAAA | 1014 |
| gi\|384598984\|gb\|JQ437489.1\|:1-1635 | GGTGGAGTGGATAGTCTAGTCGACTTGATGATGAACAAGAGAGCTTCCTGAGTTGGGTATTAAA | 1014 |
| gi\|384598988\|gb\|JQ437491.1\|:1-1635 | GGTGGAGTGGATAGTCTAGTCGACTTGATGATGAACAAGAGAGCTTCCTGAGTTGGGTATTAAA | 1014 |
| | *** * ** ***** * ****** * **** ******** ***** *** * ** | |

| Accession | Range | Sequence | End |
|---|---|---|---|
| gi\|433359248\|dbj\|AB731220.1\| | :16–1630 | GTATTTTCAAGGTGAAATTAGACTATGTGAAGAAGCCAGTTCCAGAAGTTGTGATGGTA | 1188 |
| gi\|149999824\|dbj\|AB292682.1\| | :1–1632 | GGTGCTTCAAGATTAAGTTAGACTACGTTAAGAAGACATCTGTATTTGTC | 1191 |
| gi\|149999826\|dbj\|AB292683.1\| | :1–1635 | GCGGCTTTCTGATTAAGTTAGACTATGTTAAGAAACCGATTCCAGAAACCCAATGGTC | 1194 |
| gi\|149999828\|dbj\|AB292684.1\| | :1–1635 | GCGGCTTTCTGATTAAGTTAGACTATGTTAAGAAACCGATTCCAGAAACCCAATGGTC | 1194 |
| gi\|811579981\|dbj\|AB212829.1\| | :1–1635 | ACGGCTTTCTCAATTAAGTTAGACTATGTTAAGAAACCAATTCCAGAAACTGAAACTGCAATGGTC | 1194 |
| gi\|811579999\|dbj\|AB212838.1\| | :1–1635 | ACGGCTTTCTCAATTAAGTTAGACTATGTTAAGAAACCAATTCCAGAAACTGAAACTGCAATGGTC | 1194 |
| gi\|811579997\|dbj\|AB212837.1\| | :1–1635 | ACGGCTTTCTCAATTAAGTTAGACTATGTTAAGAAACCAATTCCAGAAACTGAAACTGCAATGGTC | 1194 |
| gi\|811579993\|dbj\|AB212835.1\| | :1–1635 | ACGGCTTTCTCAATTAAGTTAGACTATGTTAAGAAACCAATTCCAGAAACTGAAACTGCAATGGTC | 1194 |
| gi\|811579991\|dbj\|AB212834.1\| | :1–1635 | ACGGCTTTCTCAATTAAGTTAGACTATGTTAAGAAACCAATTCCAGAAACTGAAACTGCAATGGTC | 1194 |
| gi\|811579987\|dbj\|AB212832.1\| | :1–1635 | ACGGCTTTCTCAATTAAGTTAGACTATGTTAAGAAACCAATTCCAGAAACTGAAACTGCAATGGTC | 1194 |
| gi\|26005813\|dbj\|AB057805.1\| | :27–1661 | ACGGCTTTCTCAATTAAGTTAGACTATGTTAAGAAACCAATTCCAGAAACTGAAACTGCAATGGTC | 1194 |
| gi\|811579989\|dbj\|AB212833.1\| | :1–1635 | ACGGCTTTCTCAATTAAGTTAGACTATGTTAAGAAACTAATACCTGAAACTGCAATGGTC | 1194 |
| gi\|811579995\|dbj\|AB212836.1\| | :1–1635 | ACGGCTTTCTCAATTAAGTTAGACTATGTTAAGAAACTAATACCTGAAACTGCAATGGTC | 1194 |
| gi\|811580005\|dbj\|AB212841.1\| | :1–1635 | ACGGCTTTCTCAATTAAGTTAGACTATGTTAAGAAACTAATACCTGAAACTGCAATGGTC | 1194 |
| gi\|811579985\|dbj\|AB212831.1\| | :1–1635 | ACGGCTTTCTCAATTAAGTTAGACTATGTTAAGAAACTAATACCTGAAACTGCAATGGTC | 1194 |
| gi\|811580001\|dbj\|AB212839.1\| | :1–1635 | ACGGCTTTCTCAATTAAGTTAGACTATGTTAAGAAACTAATACCTGAAACTGCAATGGTC | 1194 |
| gi\|811579983\|dbj\|AB212830.1\| | :1–1635 | ACGGCTTTCTCAATTAAGTTAGACTATGTTAAGAAACTAATACCTGAAACTGCAATGGTC | 1194 |
| gi\|811580003\|dbj\|AB212840.1\| | :1–1635 | ACGGCTTTCTCAATTAAGTTAGACTATGTTAAGAAACCAATTCCAGAAACTGAAACTGCAATGGTC | 1194 |
| gi\|384598986\|gb\|JQ437490.1\| | :1–1635 | ACGGCTTTCTCAATTAAGTTAGACTATGTTAAGAAACCAATTCCAGAAACTGAAACTGCAATGGTC | 1194 |
| gi\|384598976\|gb\|JQ437485.1\| | :1–1635 | ACGGCTTTCTCAATTAAGTTAGACTATGTTAAGAAACCAATTCCAGAAACTGAAACTGCAATGGTC | 1194 |
| gi\|384598980\|gb\|JQ437487.1\| | :1–1635 | ACGGCTTTCTCAATTAAGTTAGACTATGTTAAGAAACCAATTCCAGAAACTGAAACTGCAATGGTC | 1194 |
| gi\|384598978\|gb\|JQ437486.1\| | :1–1635 | ACGGCTTTCTCAATTAAGTTAGACTATGTTAAGAAACCAATTCCAGAAACTGAAACTGCAATGGTC | 1194 |
| gi\|384598968\|gb\|JQ437481.1\| | :1–1635 | ACGGCTTTCTCAATTAAGTTAGACTATGTTAAGAAACCAATTCCAGAAACTGAAACTGCAATGGTC | 1194 |
| gi\|384598970\|gb\|JQ437482.1\| | :1–1635 | ACGGCTTTCTCAATTAAGTTAGACTATGTTAAGAAACCAATTCCAGAAACTGAAACTGCAATGGTC | 1194 |
| gi\|384598972\|gb\|JQ437483.1\| | :1–1635 | ACGGCTTTCTCAATTAAGTTAGACTATGTTAAGAAACCAATTCCAGAAACTGAAACTGCAATGGTC | 1194 |
| gi\|384598974\|gb\|JQ437484.1\| | :1–1635 | ACGGCTTTCTCAATTAAGTTAGACTATGTTAAGAAACCAATTCCAGAAACTGAAACTGCAATGGTC | 1194 |
| gi\|384598982\|gb\|JQ437488.1\| | :1–1635 | ACGGCTTTCTCAATTAAGTTAGACTATGTTAAGAAACCAATTCCAGAAACTGAAACTGCAATGGTC | 1194 |
| gi\|384598990\|gb\|JQ437492.1\| | :1–1635 | ACGGCTTTCTCAATTAAGTTAGACTATGTTAAGAAACCAATTCCAGAAACTGAAACTGCAATGGTC | 1194 |
| gi\|384598984\|gb\|JQ437489.1\| | :1–1635 | ACGGCTTTCTCAATTAAGTTAGACTATGTTAAGAAACCAATTCCAGAAACTGAAACTGCAATGGTC | 1194 |
| gi\|384598988\|gb\|JQ437491.1\| | :1–1635 | ACGGCTTTCTCAATTAAGTTAGACTATGTTAAGAAACCAATTCCAGAAACTGAAACTGCAATGGTC | 1194 |

```
gi|433359248|dbj|AB731220.1|:16-1630   TATGGTGGTAAAATGGATGAGAGATTTCAGAATCAGCAATTCCATTCCCTCATCGAGCTGGA 1308
gi|149999824|dbj|AB292682.1|:1-1632    TACGGTGGTATAATGGATGAGAGATTTCAGAATCAGCAATTCCATTCCCTCATCGAGCTGGA 1311
gi|149999826|dbj|AB292683.1|:1-1635    TATGGTGGTATAATGGATGAGAGATTTCAGAATCAGCAATTCCATTCCCTCATCGAGCTGGA 1314
gi|149999828|dbj|AB292684.1|:1-1635    TATGGTGGTATAATGGATGAGAGATTTCAGAATCAGCAATTCCATTCCCTCATCGAGCTGGA 1314
gi|811157981|dbj|AB212829.1|:1-1635    TACGGTGGTATAATGGAGGAGAGATTTCAGAATCAGCAATTCCATTCCCTCATCGAGCTGGA 1314
gi|811157999|dbj|AB212838.1|:1-1635    TACGGTGGTATAATGGAGGAGAGATTTCAGAATCAGCAATTCCATTCCCTCATCGAGCTGGA 1314
gi|811157997|dbj|AB212837.1|:1-1635    TACGGTGGTATAATGGAGGAGAGATTTCAGAATCAGCAATTCCATTCCCTCATCGAGCTGGA 1314
gi|811157995|dbj|AB212835.1|:1-1635    TACGGTGGTATAATGGAGGAGAGATTTCAGAATCAGCAATTCCATTCCCTCATCGAGCTGGA 1314
gi|811157991|dbj|AB212834.1|:1-1635    TACGGTGGTATAATGGAGGAGAGATTTCAGAATCAGCAATTCCATTCCCTCATCGAGCTGGA 1314
gi|811157987|dbj|AB212832.1|:1-1635    TACGGTGGTATAATGGAGGAGAGATTTCAGAATCAGCAATTCCATTCCCTCATCGAGCTGGA 1314
gi|26005813|dbj|AB057805.1|:27-1661    TACGGTGGTATAATGGAGGAGAGATTTCAGAATCAGCAATTCCATTCCCTCATCGAGCTGGA 1314
gi|811157989|dbj|AB212833.1|:1-1635    TACGGTGGTATAATGGAGGAGAGATTTCAGAATCAGCAATTCCATTCCCTCATCGAGCTGGA 1314
gi|811157995|dbj|AB212836.1|:1-1635    TACGGTGGTATAATGGAGGAGAGATTTCAGAATCAGCAATTCCATTCCCTCATCGAGCTGGA 1314
gi|811158005|dbj|AB212841.1|:1-1635    TACGGTGGTATAATGGAGGAGAGATTTCAGAATCAGCAATTCCATTCCCTCATCGAGCTGGA 1314
gi|811157985|dbj|AB212831.1|:1-1635    TACGGTGGTATAATGGAGGAGAGATTTCAGAATCAGCAATTCCATTCCCTCATCGAGCTGGA 1314
gi|811158001|dbj|AB212839.1|:1-1635    TACGGTGGTATAATGGATGAGAGATTTCAGAATCAGCAATTCCATTCCCTCATCGAGCTGGA 1314
gi|811157983|dbj|AB212830.1|:1-1635    TACGGTGGTATAATGGATGAGAGATTTCAGAATCAGCAATTCCATTCCCTCATCGAGCTGGA 1314
gi|811158003|dbj|AB212840.1|:1-1635    TACGGTGGTATAATGGATGAGAGATTTCAGAATCAGCAATTCCATTCCCTCATCGAGCTGGA 1314
gi|384598986|gb|JQ437490.1|:1-1635     TACGGTGGTATAATGGAGGAGAGATTTCAGAATCAGCAATTCCATTCCCTCATCGAGCTGGA 1314
gi|384598976|gb|JQ437485.1|:1-1635     TACGGTGGTATAATGGAGGAGAGATTTCAGAATCAGCAATTCCATTCCCTCATCGAGCTGGA 1314
gi|384598980|gb|JQ437487.1|:1-1635     TACGGTGGTATAATGGAGGAGAGATTTCAGAATCAGCAATTCCATTCCCTCATCGAGCTGGA 1314
gi|384598978|gb|JQ437486.1|:1-1635     TACGGTGGTATAATGGAGGAGAGATTTCAGAATCAGCAATTCCATTCCCTCATCGAGCTGGA 1314
gi|384598968|gb|JQ437481.1|:1-1635     TACGGTGGTATAATGGAGGAGAGATTTCAGAATCAGCAATTCCATTCCCTCATCGAGCTGGA 1314
gi|384598970|gb|JQ437482.1|:1-1635     TACGGTGGTATAATGGAGGAGAGATTTCAGAATCAGCAATTCCATTCCCTCATCGAGCTGGA 1314
gi|384598972|gb|JQ437483.1|:1-1635     TACGGTGGTATAATGGAGGAGAGATTTCAGAATCAGCAATTCCATTCCCTCATCGAGCTGGA 1314
gi|384598974|gb|JQ437484.1|:1-1635     TACGGTGGTATAATGGAGGAGAGATTTCAGAATCAGCAATTCCATTCCCTCATCGAGCTGGA 1314
gi|384598982|gb|JQ437488.1|:1-1635     TACGGTGGTATAATGGAGGAGAGATTTCAGAATCAGCAATTCCATTCCCTCATCGAGCTGGA 1314
gi|384598990|gb|JQ437492.1|:1-1635     TACGGTGGTATAATGGAGGAGAGATTTCAGAATCAGCAATTCCATTCCCTCATCGAGCTGGA 1314
gi|384598984|gb|JQ437489.1|:1-1635     TACGGTGGTATAATGGAGGAGAGATTTCAGAATCAGCAATTCCATTCCCTCATCGAGCTGGA 1314
gi|384598988|gb|JQ437491.1|:1-1635     TACGGTGGTATAATGGAGGAGAGATTTCAGAATCAGCAATTCCATTCCCTCATCGAGCTGGA 1314
                                       ** ******* ******* ****************************************
```

| | | |
|---|---|---|
| gi\|433359248\|dbj\|AB731220.1\|:16-1630 | GCTACATATCTCAATTATATAGGGACCCTGATTTGGGAACAAATAACGAGAAGGGTCCTATT | 1488 |
| gi\|149999824\|dbj\|AB292682.1\|:1-1632 | TTGGCATATCTCAATTATAGAGAGGGACCCTGATTTGATATAGGAATAAATGATCCCAAGAATCCAAAT | 1491 |
| gi\|149999826\|dbj\|AB292683.1\|:1-1635 | ATGCGTATCTCAATTATATAGGGACCCTGATTTGATTTAGGAAAAACTAATTTCGAGAGTCCTAAT | 1494 |
| gi\|149999828\|dbj\|AB292684.1\|:1-1635 | ATGCGTATCTCAATTATATAGGGACCCTGATTTGATTTAGGAAAAACTAATTTCGAGAGTCCTAAT | 1494 |
| gi\|811579981\|dbj\|AB212829.1\|:1-1635 | TTGGCGTATCTCAATTATATAGGGACCCTGATTTGATTTAGGAAAAACTAATCATGCGAGTCCTAAT | 1494 |
| gi\|811579999\|dbj\|AB212838.1\|:1-1635 | TTGGCGTATCTCAATTATATAGGGACCCTGATTTGATTTAGGAAAAACTAATCATGCGAGTCCTAAT | 1494 |
| gi\|811579997\|dbj\|AB212837.1\|:1-1635 | TTGGCGTATCTCAATTATATAGGGACCCTGATTTGATTTAGGAAAAACTAATCATGCGAGTCCTAAT | 1494 |
| gi\|811579993\|dbj\|AB212835.1\|:1-1635 | TTGGCGTATCTCAATTATATAGGGACCCTGATTTGATTTAGGAAAAACTAATCATGCGAGTCCTAAT | 1494 |
| gi\|811579991\|dbj\|AB212834.1\|:1-1635 | TTGGCGTATCTCAATTATATAGGGACCCTGATTTGATTTAGGAAAAACTAATCATGCGAGTCCTAAT | 1494 |
| gi\|811579987\|dbj\|AB212832.1\|:1-1635 | TTGGCGTATCTCAATTATATAGGGACCCTGATTTGATTTAGGAAAAACTAATCATGCGAGTCCTAAT | 1494 |
| gi\|26005813\|dbj\|AB057805.1\|:27-1661 | TTGGCGTATCTCAATTATATAGGGACCCTGATTTGATTTAGGAAAAACTAATCATGCGAGTCCTAAT | 1494 |
| gi\|811579989\|dbj\|AB212833.1\|:1-1635 | TTGGCGTATCTCAATTATATAGGGACCCTGATTTGATTTAGGAAAAACTAATCCTGAGAGTCCTAAT | 1494 |
| gi\|811579995\|dbj\|AB212836.1\|:1-1635 | TTGGCGTATCTCAATTATATAGGGACCCTGATTTGATTTAGGAAAAACTAATCCTGAGAGTCCTAAT | 1494 |
| gi\|811580005\|dbj\|AB212841.1\|:1-1635 | TTGGCGTATCTCAATTATATAGGGACCCTGATTTGATTTAGGAAAAACTAATCCTGAGAGTCCTAAT | 1494 |
| gi\|811579985\|dbj\|AB212831.1\|:1-1635 | TTGGCGTATCTCAATTATATAGGGACCCTGATTTGATTTAGGAAAAACTAATCCTGAGAGTCCTAAT | 1494 |
| gi\|811580001\|dbj\|AB212839.1\|:1-1635 | TTGGCGTATCTCAATTATATAGGGACCCTGATTTGATTTAGGAAAAACTAATCCTGAGAGTCCTAAT | 1494 |
| gi\|811579983\|dbj\|AB212830.1\|:1-1635 | TTGGCGTATCTCAATTATATAGGGACCCTGATTTGATTTAGGAAAAACTAATCCTGAGAGTCCTAAT | 1494 |
| gi\|811580003\|dbj\|AB212840.1\|:1-1635 | TTGGCGTATCTCAATTATATAGGGACCCTGATTTGATTTAGGAAAAACTAATCCTGAGAGTCCTAAT | 1494 |
| gi\|384598986\|gb\|JQ437490.1\|:1-1635 | TTGGCGTATCTCAATTATATAGGGACCCTGATTTGATTTAGGAAAAACTAATCCTGAGAGTCCTAAT | 1494 |
| gi\|384598976\|gb\|JQ437485.1\|:1-1635 | TTGGCGTATCTCAATTATATAGGGACCCTGATTTGATTTAGGAAAAACTAATCCTGAGAGTCCTAAT | 1494 |
| gi\|384598980\|gb\|JQ437487.1\|:1-1635 | TTGGCGTATCTCAATTATATAGGGACCCTGATTTGATTTAGGAAAAACTAATCCTGAGAGTCCTAAT | 1494 |
| gi\|384598978\|gb\|JQ437486.1\|:1-1635 | TTGGCGTATCTCAATTATATAGGGACCCTGATTTGATTTAGGAAAAACTAATCCTGAGAGTCCTAAT | 1494 |
| gi\|384598968\|gb\|JQ437481.1\|:1-1635 | TTGGCGTATCTCAATTATATAGGGACCCTGATTTGATTTAGGAAAAACTAATCCTGAGAGTCCTAAT | 1494 |
| gi\|384598970\|gb\|JQ437482.1\|:1-1635 | TTGGCGTATCTCAATTATATAGGGACCCTGATTTGATTTAGGAAAAACTAATCCTGAGAGTCCTAAT | 1494 |
| gi\|384598972\|gb\|JQ437483.1\|:1-1635 | TTGGCGTATCTCAATTATATAGGGACCCTGATTTGATTTAGGAAAAACTAATCCTGAGAGTCCTAAT | 1494 |
| gi\|384598974\|gb\|JQ437484.1\|:1-1635 | TTGGCGTATCTCAATTATATAGGGACCCTGATTTGATTTAGGAAAAACTAATCCTGAGAGTCCTAAT | 1494 |
| gi\|384598982\|gb\|JQ437488.1\|:1-1635 | TTGGCGTATCTCAATTATATAGGGACCCTGATTTGATTTAGGAAAAACTAATCCTGAGAGTCCTAAT | 1494 |
| gi\|384598990\|gb\|JQ437492.1\|:1-1635 | TTGGCGTATCTCAATTATATAGGGACCCTGATTTGATTTAGGAAAAACTAATCCTGAGAGTCCTAAT | 1494 |
| gi\|384598984\|gb\|JQ437489.1\|:1-1635 | TTGGCGTATCTCAATTATATAGGGACCCTGATTTGATTTAGGAAAAACTAATCCTGAGAGTCCTAAT | 1494 |
| gi\|384598988\|gb\|JQ437491.1\|:1-1635 | TTGGCGTATCTCAATTATATAGGGACCCTGATTTGATTTAGGAAAAACTAATCCTGAGAGTCCTAAT | 1494 |
| | * ************* * ********* ************** * **** ** * *** * * | |

FIG. 1 continued

| Accession | Range | Sequence | End |
|---|---|---|---|
| gi\|433359248\|dbj\|AB731220.1\| | :16-1630 | AGTTACTCACAAGCAAGTGTTTGGGGTAAAAAGTATATTTGGTATGAACTTTAAGAGGTTA | 1548 |
| gi\|149999824\|dbj\|AB292682.1\| | :1-1632 | AATTACACACAAGCAAGCACGTATTTGGGGTGAGAAGTATATTTGGTAAAAATTTTGACAGGCTA | 1551 |
| gi\|149999826\|dbj\|AB292683.1\| | :1-1635 | AATTACACACAAGCAAGCACGTATTTGGGGTGAAAAGTATATTTGGTAAAAATTTTAATAGGTTA | 1554 |
| gi\|149999828\|dbj\|AB292684.1\| | :1-1635 | AATTACACACAAGCAAGCACGTATTTGGGGTGAAAAGTATATTTGGTAAAAATTTTAATAGGTTA | 1554 |
| gi\|811157981\|dbj\|AB212829.1\| | :1-1635 | AATTACACACAAGCAAGCACGTATTTGGGGTGAAAAGTATATTTGGTAAAAATTTTAACAGGTTA | 1554 |
| gi\|811157999\|dbj\|AB212838.1\| | :1-1635 | AATTACACACAAGCAAGCACGTATTTGGGGTGAAAAGTATATTTGGTAAAAATTTTAACAGGTTA | 1554 |
| gi\|811157997\|dbj\|AB212837.1\| | :1-1635 | AATTACACACAAGCAAGCACGTATTTGGGGTGAAAAGTATATTTGGTAAAAATTTTAACAGGTTA | 1554 |
| gi\|811157993\|dbj\|AB212835.1\| | :1-1635 | AATTACACACAAGCAAGCACGTATTTGGGGTGAAAAGTATATTTGGTAAAAATTTTAACAGGTTA | 1554 |
| gi\|811157991\|dbj\|AB212834.1\| | :1-1635 | AATTACACACAAGCAAGCACGTATTTGGGGTGAAAAGTATATTTGGTAAAAATTTTAACAGGTTA | 1554 |
| gi\|811157987\|dbj\|AB212832.1\| | :1-1635 | AATTACACACAAGCAAGCACGTATTTGGGGTGAAAAGTATATTTGGTAAAAATTTTAACAGGTTA | 1554 |
| gi\|26005813\|dbj\|AB057805.1\| | :27-1661 | AATTACACACAAGCAAGCACGTATTTGGGGTGAAAAGTATATTTGGTAAAAATTTTAACAGGTTA | 1554 |
| gi\|811157989\|dbj\|AB212833.1\| | :1-1635 | AATTACACACAAGCAAGCACGTATTTGGGGTGAAAAGTATATTTGGTAAAAATTTTAACAGGTTA | 1554 |
| gi\|811157995\|dbj\|AB212836.1\| | :1-1635 | AATTACACACAAGCAAGCACGTATTTGGGGTGAAAAGTATATTTGGTAAAAATTTTAACAGGTTA | 1554 |
| gi\|811158005\|dbj\|AB212841.1\| | :1-1635 | AATTACACACAAGCAAGCACGTATTTGGGGTGAAAAGTATATTTGGTAAAAATTTTAACAGGTTA | 1554 |
| gi\|811157985\|dbj\|AB212831.1\| | :1-1635 | AATTACACACAAGCAAGCACGTATTTGGGGTGAAAAGTATATTTGGTAAAAATTTTAACAGGTTA | 1554 |
| gi\|811158001\|dbj\|AB212839.1\| | :1-1635 | AATTACACACAAGCAAGCACGTATTTGGGGTGAAAAGTATATTTGGTAAAAATTTTAACAGGTTA | 1554 |
| gi\|811157983\|dbj\|AB212830.1\| | :1-1635 | AATTACACACAAGCAAGCACGTATTTGGGGTGAAAAGTATATTTGGTAAAAATTTTAACAGGTTA | 1554 |
| gi\|811158003\|dbj\|AB212840.1\| | :1-1635 | AATTACACACAAGCAAGCACGTATTTGGGGTGAAAAGTATATTTGGTAAAAATTTTAACAGGTTA | 1554 |
| gi\|384598986\|gb\|JQ437490.1\| | :1-1635 | AATTACACACAAGCAAGCACGTATTTGGGGTGAAAAGTATATTTGGTAAAAATTTTAACAGGTTA | 1554 |
| gi\|384598976\|gb\|JQ437485.1\| | :1-1635 | AATTACACACAAGCAAGCACGTATTTGGGGTGAAAAGTATATTTGGTAAAAATTTTAACAGGTTA | 1554 |
| gi\|384598980\|gb\|JQ437487.1\| | :1-1635 | AATTACACACAAGCAAGCACGTATTTGGGGTGAAAAGTATATTTGGTAAAAATTTTAACAGGTTA | 1554 |
| gi\|384598978\|gb\|JQ437486.1\| | :1-1635 | AATTACACACAAGCAAGCACGTATTTGGGGTGAAAAGTATATTTGGTAAAAATTTTAACAGGTTA | 1554 |
| gi\|384598968\|gb\|JQ437481.1\| | :1-1635 | AATTACACACAAGCAAGCACGTATTTGGGGTGAAAAGTATATTTGGTAAAAATTTTAACAGGTTA | 1554 |
| gi\|384598970\|gb\|JQ437482.1\| | :1-1635 | AATTACACACAAGCAAGCACGTATTTGGGGTGAAAAGTATATTTGGTAAAAATTTTAACAGGTTA | 1554 |
| gi\|384598972\|gb\|JQ437483.1\| | :1-1635 | AATTACACACAAGCAAGCACGTATTTGGGGTGAAAAGTATATTTGGTAAAAATTTTAACAGGTTA | 1554 |
| gi\|384598974\|gb\|JQ437484.1\| | :1-1635 | AATTACACACAAGCAAGCACGTATTTGGGGTGAAAAGTATATTTGGTAAAAATTTTAACAGGTTA | 1554 |
| gi\|384598982\|gb\|JQ437488.1\| | :1-1635 | AATTACACACAAGCAAGCACGTATTTGGGGTGAAAAGTATATTTGGTAAAAATTTTAACAGGTTA | 1554 |
| gi\|384598990\|gb\|JQ437492.1\| | :1-1635 | AATTACACACAAGCAAGCACGTATTTGGGGTGAAAAGTATATTTGGTAAAAATTTTAACAGGTTA | 1554 |
| gi\|384598984\|gb\|JQ437489.1\| | :1-1635 | AATTACACACAAGCAAGCACGTATTTGGGGTGAAAAGTATATTTGGTAAAAATTTTAACAGGTTA | 1554 |
| gi\|384598988\|gb\|JQ437491.1\| | :1-1635 | AATTACACACAAGCAAGCACGTATTTGGGGTGAAAAGTATATTTGGTAAAAATTTTAACAGGTTA | 1554 |
| | | * **** ********* ** ********* * ************* ** *** * *** ** | |

FIG. 1 continued

```
gi|433359248|dbj|AB731220.1|:16-1630    GTTAATGTGAAAACCAAGGTCGATCCAAGTAATTCTTTAGAAACGAACAAAGCATCCCA 1608
gi|149999824|dbj|AB292682.1|:1-1632     GTAAAGTGAAAACCCTGGTTGATCCCAATAACTTTTTCTTTAGAAACGAACAAAGCATCCCA 1611
gi|149999826|dbj|AB292683.1|:1-1635     GTAAAGTAAAAACCAAGGTTGATCCCGATAATTCTTTTAGAAACGAACAAAGTATCCCA 1614
gi|149999828|dbj|AB292684.1|:1-1635     GTAAAGTAAAAACCAAGGTTGATCCCAATAATTTTTTTTAGAAACGAACAAAGTATCCCA 1614
gi|81157981|dbj|AB212829.1|:1-1635      GTTAAGGTGAAAACTAAAGTTGATCCCAATAATTTTTTTTAGAAACGAACAAAGTATCCCA 1614
gi|81157999|dbj|AB212838.1|:1-1635      GTTAAGGTGAAAACTAAAGTTGATCCCAATAATTTTTTTTAGAAACGAACAAAGTATCCCA 1614
gi|81157997|dbj|AB212837.1|:1-1635      GTTAAGGTGAAAACTAAAGTTGATCCCAATAATTTTTTTTAGAAACGAACAAAGTATCCCA 1614
gi|81157993|dbj|AB212835.1|:1-1635      GTTAAGGTGAAAACTAAAGTGATCCCAATAATTTTTTTTAGAAACGAACAAAGTATCCCA 1614
gi|81157991|dbj|AB212834.1|:1-1635      GTTAAGGTGAAAACTAAAGTTGATCCCAATAATTTTTTTTAGAAACGAACAAAGTATCCCA 1614
gi|81157987|dbj|AB212832.1|:1-1635      GTTAAGGTGAAAACTAAAGTTGATCCCAATAATTTTTTTTAGAAACGAACAAAGTATCCCA 1614
gi|26005813|dbj|AB057805.1|:27-1661     GTTAAGGTGAAAACTAAAGTTGATCCCAATAATTTTTTTTAGAAACGAACAAAGTATCCCA 1614
gi|81157989|dbj|AB212833.1|:1-1635      GTTAAGGTGAAAACCAAAGCTGATCCCAATAATTTTTTTTAGAAACGAACAAAGTATCCCA 1614
gi|81157995|dbj|AB212836.1|:1-1635      GTTAAGGTGAAAACCAAAGCTGATCCCAATAATTTTTTTTAGAAACGAACAAAGTATCCCA 1614
gi|81158005|dbj|AB212841.1|:1-1635      GTTAAGGTGAAAACCAAAGCTGATCCCAATAATTTTTTTTAGAAACGAACAAAGTATCCCA 1614
gi|81157985|dbj|AB212831.1|:1-1635      GTTAAGGTGAAAACCAAAGCTGATCCCAATAATTTTTTTTAGAAACGAACAAAGTATCCCA 1614
gi|81158001|dbj|AB212839.1|:1-1635      GTTAAGGTGAAAACCAAAGCTGATCCCAATAATTTTTTTTAGAAACGAACAAAGTATCCCA 1614
gi|81157983|dbj|AB212830.1|:1-1635      GTTAAGGTGAAAACCAAAGCTGATCCCAATAATTTTTTTTAGAAACGAACAAAGTATCCCA 1614
gi|81158003|dbj|AB212840.1|:1-1635      GTTAAGGTGAAAACCAAAGCTGATCCCAATAATTTTTTTTAGAAACGAACAAAGTATCCCA 1614
gi|384598986|gb|JQ437490.1|:1-1635      GTTAAGGTGAAAACCAAAGCTGATCCCAATAATTTTTTTTAGAAACGAACAAAGTATCCCA 1614
gi|384598976|gb|JQ437485.1|:1-1635      GTTAAGGTGAAAACCAAAGCTGATCCCAATAATTTTTTTTAGAAACGAACAAAGTATCCCA 1614
gi|384598980|gb|JQ437487.1|:1-1635      GTTAAGGTGAAAACCAAAGCTGATCCCAATAATTTTTTTTAGAAACGAACAAAGTATCCCA 1614
gi|384598978|gb|JQ437486.1|:1-1635      GTTAAGGTGAAAACCAAAGCTGATCCCAATAATTTTTTTTAGAAACGAACAAAGTATCCCA 1614
gi|384598968|gb|JQ437481.1|:1-1635      GTTAAGGTGAAAACCAAAGCTGATCCCAATAATTTTTTTTAGAAACGAACAAAGTATCCCA 1614
gi|384598970|gb|JQ437482.1|:1-1635      GTTAAGGTGAAAACCAAAGCTGATCCCAATAATTTTTTTTAGAAACGAACAAAGTATCCCA 1614
gi|384598972|gb|JQ437483.1|:1-1635      GTTAAGGTGAAAACCAAAGCTGATCCCAATAATTTTTTTTAGAAACGAACAAAGTATCCCA 1614
gi|384598974|gb|JQ437484.1|:1-1635      GTTAAGGTGAAAACCAAAGCTGATCCCAATAATTTTTTTTAGAAACGAACAAAGTATCCCA 1614
gi|384598982|gb|JQ437488.1|:1-1635      GTTAAGGTGAAAACCAAAGCTGATCCCAATAATTTTTTTTAGAAACGAACAAAGTATCCCA 1614
gi|384598990|gb|JQ437492.1|:1-1635      GTTAAGGTGAAAACCAAAGCTGATCCCAATAATTTTTTTTAGAAACGAACAAAGTATCCCA 1614
gi|384598984|gb|JQ437489.1|:1-1635      GTTAAGGTGAAAACCAAAGCTGATCCCAATAATTTTTTTTAGAAACGAACAAAGTATCCCA 1614
gi|384598988|gb|JQ437491.1|:1-1635      GTTAAGGTGAAAACCAAAGCTGATCCCAATAATTTTTTTTAGAAACGAACAAAGTATCCCA 1614
                                        ** ** ** *****   *     *  *****          *  ******************
```

FIG. 1 continued

| | | | |
|---|---|---|---|
| gi\|433359248\|dbj\|AB731220.1\| | :16-1630 | CCACTTC------- | 1615 |
| gi\|149999824\|dbj\|AB292682.1\| | :1-1632 | CCTCTTCCACGGCATCGTCAT | 1632 |
| gi\|149999826\|dbj\|AB292683.1\| | :1-1635 | CCTCTTCCCCTGCGTCATCAT | 1635 |
| gi\|149999828\|dbj\|AB292684.1\| | :1-1635 | CCTCTTCCCCTGCGTCATCAT | 1635 |
| gi\|811157981\|dbj\|AB212829.1\| | :1-1635 | CCTCTTCCACGGCATCATCAT | 1635 |
| gi\|811157999\|dbj\|AB212838.1\| | :1-1635 | CCTCTTCCACGGCATCATCAT | 1635 |
| gi\|811157997\|dbj\|AB212837.1\| | :1-1635 | CCTCTTCCACGGCATCATCAT | 1635 |
| gi\|811157993\|dbj\|AB212835.1\| | :1-1635 | CCTCTTCCACGGCATCATCAT | 1635 |
| gi\|811157991\|dbj\|AB212834.1\| | :1-1635 | CCTCTTCCACGGCATCATCAT | 1635 |
| gi\|811157987\|dbj\|AB212832.1\| | :1-1635 | CCTCTTCCACGGCATCATCAT | 1635 |
| gi\|26005813\|dbj\|AB057805.1\| | :27-1661 | CCTCTTCCACGGCATCATCAT | 1635 |
| gi\|811157989\|dbj\|AB212833.1\| | :1-1635 | CCTCTTCCACGGCATCATCAT | 1635 |
| gi\|811157995\|dbj\|AB212836.1\| | :1-1635 | CCTCTTCCACGGCATCATCAT | 1635 |
| gi\|811158005\|dbj\|AB212841.1\| | :1-1635 | CCTCTTCCACGGCATCATCAT | 1635 |
| gi\|811157985\|dbj\|AB212831.1\| | :1-1635 | CCTCTTCCACGGCATCATCAT | 1635 |
| gi\|811158001\|dbj\|AB212839.1\| | :1-1635 | CCTCTTCCACGGCATCATCAT | 1635 |
| gi\|811157983\|dbj\|AB212830.1\| | :1-1635 | CCTCTTCCACGGCATCATCAT | 1635 |
| gi\|811158003\|dbj\|AB212840.1\| | :1-1635 | CCTCTTCCACGGCATCATCAT | 1635 |
| gi\|384598986\|gb\|JQ437490.1\| | :1-1635 | CCTCTTCCACGGCATCATCAT | 1635 |
| gi\|384598976\|gb\|JQ437485.1\| | :1-1635 | CCTCTTCCACGGCATCATCAT | 1635 |
| gi\|384598980\|gb\|JQ437487.1\| | :1-1635 | CCTCTTCCACGGCATCATCAT | 1635 |
| gi\|384598978\|gb\|JQ437486.1\| | :1-1635 | CCTCTTCCACGGCATCATCAT | 1635 |
| gi\|384598968\|gb\|JQ437481.1\| | :1-1635 | CCTCTTCCACGGCATCATCAT | 1635 |
| gi\|384598970\|gb\|JQ437482.1\| | :1-1635 | CCTCTTCCACGGCATCATCAT | 1635 |
| gi\|384598972\|gb\|JQ437483.1\| | :1-1635 | CCTCTTCCACGGCATCATCAT | 1635 |
| gi\|384598974\|gb\|JQ437484.1\| | :1-1635 | CCTCTTCCACGGCATCATCAT | 1635 |
| gi\|384598982\|gb\|JQ437488.1\| | :1-1635 | CCTCTTCCACGGCATCATCAT | 1635 |
| gi\|384598990\|gb\|JQ437492.1\| | :1-1635 | CCTCTTCCACGGCATCATCAT | 1635 |
| gi\|384598984\|gb\|JQ437489.1\| | :1-1635 | CCTCTTCCACGGCATCATCAT | 1635 |
| gi\|384598988\|gb\|JQ437491.1\| | :1-1635 | CCTCTTCCACGGCATCATCAT | 1635 |

```
AB057805-1   ATGAATGCTCACCATTTCCTTTTGGTTTGTTTGCAAAATAATATTTTT   50
AB212829-1   ATGAATGCTCACCATTTCCTTTTGGTTTGTTTGCAAAATAATATTTTT   50
AB212833-1   ATGAATGCTCACCATTTCCTTTTGGTTTGTTTGCAAAATAATATTTTT   50
AB292683-1   ATGAAGTGCTCAACATTCTGTTTTTGGTATGTTTGCAAGATAATATTTTT  50
JQ437487-1   ATGAATGCTCACCATTTCGTTTTTGGTTTGTTTGCAAAATAATATTTTT  50
JQ437491-1   ATGAATGCTCACCATTTCCTTTTGGTTTGTTTGCAAAATAATATTTTT   50
DK-1_full    ATGAATGCTCACCATTTCCTTTTGGTTTGTTTGCAAAATAATATTTTT   50
SH-4_full    ATGAATGCTCACCATTTCCTTTTGGTTTGTTTGCAAAATAATATTTTT   50
Consensus     atgaa tgctca catt t  ttttggt tgtttgcaa ataatattttt AB057805-1   CTTTCTCTCATTCCATATCCAAATTTCAATAGCTAATCCTCGAGAAAACT  100
AB212829-1   CTTTCTCTCATTCCATATCCAAATTTCAATAGCTAATCCTCGAGAAAACT  100
AB212833-1   CTTTCTCTCATTCAATATCCAAATTTCAATAGCTAATCCTCAAGAAAACT  100
AB292683-1   CTTTCTCTCATTCAATATCCAAATTTCAATAGCTAATCCTCAAGAAAACT  100
JQ437487-1   CTTTCTCTCATTCAATATCCAAATTTCAATAGCTAATCCTCAAGAAAACT  100
JQ437491-1   CTTTCTCTCATTCAATATCCAAATTTCAATAGCTAATCCTCAAGAAAACT  100
DK-1_full    CTTTCTCTCATTCCATATCCAAATTTCAATAGCTAATCCTCGAGAAAACT  100
SH-4_full    CTTTCTCTCATTCCATATCCAAATTTCAATAGCTAATCCTCGAGAAAACT  100
Consensus    ctttctctcattc atatccaaatttcaatagctaatcctc agaaaact AB057805-1   TCCTTAAATGCTTCTCAAAACATATTCCCAACAATGTAACAAATCCAAAA  150
AB212829-1   TCCTTAAATGCTTCTCAAAACATATTCCCAACAATGTAACAAATCCAAAA  150
AB212833-1   TCCTTAAATGCTTCTCGGAATATATTCCTAACAATCCACAAATCCAAAA   150
AB292683-1   TCCTTAAATGCTTCTCACAATATATTCCACCAATGTAACAAATGCAAAA   150
JQ437487-1   TCCTTAAATGCTTCTCGGAATATATTCCTAACAATCCACAAATCCAAAA   150
JQ437491-1   TCCTTAAATGCTTCTCGGAATATATTCCTAACAATCCACAAATCCAAAA   150
DK-1_full    TCCTTAAATGCTTCTCAAAACATATTCCCAACAATGTACAAATCCAAAA   150
SH-4_full    TCCTTAAATGCTTCTCAAAACATATTCCCAACAATGTACAAATCCAAAA   150
Consensus    tccttaaatgcttctc  aa atattcc a caat  a caaat caaaa AB057805-1   CTCGTATACACTCAACACGACCAATTCTATATGTCTATCCTGAATTCGAC  200
AB212829-1   CTCGTATACACTCAACACGACCAATTCTATATGTCTCTCCTGAATTCGAC  200
AB212833-1   TTCATATACACTCAACACGACCAATTCTATATGTCTGTCCTGAATTCGAC  200
AB292683-1   CTCGTATACACTCAACACGACCAATTTTATATGTCTATCCTGAATTCGAC  200
JQ437487-1   TTCATATACACTCAACACGACCAATTCTATATGTCTGTCCTGAATTCGAC  200
JQ437491-1   TTCATATACACTCAACACGACCAATTCTATATGTCTGTCCTGAATTCGAC  200
DK-1_full    CTCGTATACACTCAACACGACCAATTCTATATGTCTATCCTGAATTCGAC  200
SH-4_full    CTCGTATACACTCAACACGACCAATTCTATATGTCTATCCTGAATTCGAC  200
Consensus      tc tatacactcaacacgaccaatt tatatgtct tcctgaattcgac AB057805-1   AATACAAAATCTTAGATTCATCTCTGAAACAACCCCAAAACCACTCGTTA  250
AB212829-1   AATACAAAATCTTAGATTCATCTCTGAAACAACCCCAAAACCACTCGTTA  250
AB212833-1   AATACAAAATCTTAGATTCACCTCTGAAACAACCCCAAAACCACTCGTTA  250
AB292683-1   CATACAAAATCTTAGATTTACCTCTGACACAACCCCAAAACCACTTGTTA  250
JQ437487-1   AATACAAAATCTTAGATTCACCTCTGATACAACCCCAAAACCACTCGTTA  250
JQ437491-1   AATACAAAATCTTAGATTCACCTCTGATACAACCCCAAAACCACTCGTTA  250
DK-1_full    AATACAAAATCTTAGATTCATCTCTGAAACAACCCCAAAACCACTCGTTA  250
SH-4_full    AATACAAAATCTTAGATTCATCTCTGAAACAACCCCAAAACCACTCGTTA  250
Consensus     atacaaaatcttagatt a ctctga acaaccccaaaaccact gtta
```

FIG. 2 continued

```
AB057805-1   TTCTCACTCCTTCAAATAACTCCCATATCCAAGCAACTATTTTATGCTCT   300
AB212829-1   TTCTCACTCCTTCAAATAACTCCCATATCCAAGCAACTATTTTATGCTCT   300
AB212833-1   TTCTCACTCCTTCAAATGTCTCCCATATCCAGGCCAGTATTCTCTGCTCC   300
AB292683-1   TCATCACTCCTTTAAATGTCTCCCATATCCAAGGCACTATTCTATGCTCC   300
JQ437487-1   TTCTCACTCCTTCAAATGTCTCCCATATCCAGGCCAGTATTCTCTGCTCC   300
JQ437491-1   TTCTCACTCCTTCAAATGTCTCCCATATCCAGGCCAGTATTCTCTGCTCC   300
DK-1_full    TTCTCACTCCTTCAAATAACTCCCATATCCAAGCAACTATTTTATGCTCT   300
SH-4_full    TTCTCACTCCTTCAAATAACTCCCATATCCAAGCAACTATTTTATGCTCT   300
Consensus    t  tcactcctt aaat  ctcccatatcca g  a tatt t tgctc AB057805-1   AAGAAAGTTGGCTTGCAGATTCGAACTCGAAGCGGTGGCCATGATGCTGA   350
AB212829-1   AAGAAAGTTGGCTTGCAGATTCGAACTCGAAGCGGTGGCCATGATGCTGA   350
AB212833-1   AAGAAAGTTGGTTTGCAGATTCGAACTCGAAGCGGTGGCCATGATGCTGA   350
AB292683-1   AAGAAAGTTGGCTTGCAGATTCGAACTCGAAGCGGTGGTCATGATGCTGA   350
JQ437487-1   AAGAAAGTTGGTTTGCAGATTCGAACTCGAAGCGGTGGCCATGATGCTGA   350
JQ437491-1   AAGAAAGTTGGTTTGCAGATTCGAACTCGAAGCGGTGGCCATGATGCTGA   350
DK-1_full    AAGAAAGTTGGCTTGCAGATTCGAACTCGAAGCGGTGGCCATGATGCTGA   350
SH-4_full    AAGAAAGTTGGCTTGCAGATTCGAACTCGAAGCGGTGGCCATGATGCTGA   350
Consensus    aagaaagttgg ttgcagattcgaactcgaagcggtgg catgatgctga AB057805-1   GGGTATGTCCTACATATCTCAAGTCCCATTTGTTGTAGTAGACTTGAGAA   400
AB212829-1   GGGTATGTCCTACATTTCTCAAGTCCCATTTGTTGTAGTAGACTTGAGGA   400
AB212833-1   GGGTTTGTCCTACATATCTCAAGTCCCATTTGCTATAGTAGACTTGAGAA   400
AB292683-1   GGGCATGTCCTACATATCTCAAGTCCCATTTGTTATAGTAGACTTGAGAA   400
JQ437487-1   GGGTATGTCCTACATATCTCAAGTCCCATTTGTTGTAGTAGACTTGAGAA   400
JQ437491-1   GGGTATGTCCTACATTTCTCAAGTCCCATTTGTTGTAGTAGACTTGAGGA   400
DK-1_full    GGGTATGTCCTACATATCTCAAGTCCCATTTGTTGTAGTAGACTTGAGAA   400
SH-4_full    GGGTATGTCCTACATATCTCAAGTCCCATTTGTTGTAGTAGACTTGAGAA   400
Consensus    ggg  tgtcctacat tctcaagtcccatttg t tagtagacttgag a AB057805-1   ACATGCATTCGATCAAAATAGATGTTCATAGCCAAACTGCCTGGGTTGAA   450
AB212829-1   ACATGCATTCGATCAAAATAGATGTTCATAGCCAAACTGCCTGGGTTGAA   450
AB212833-1   ACATGCATACGGTCAAAGTAGATATTCATAGCCAAACTGCCTGGGTTGAA   450
AB292683-1   ACATGCATTCGGTCAAAATAGATGTTCATAGCCAAACTGCATGGGTTGAA   450
JQ437487-1   ACATGCATTCGATCAAAATAGATGTTCATAGCCAAACTGCCTGGGTTGAA   450
JQ437491-1   ACATGCATTCGATCAAAATAGATGTTCATAGCCAAACTGCCTGGGTTGAA   450
DK-1_full    ACATGCATTCGATCAAAATAGATGTTCATAGCCAAACTGCCTGGGTTGAA   450
SH-4_full    ACATGCATTCGATCAAAATAGATGTTCATAGCCAAACTGCCTGGGTTGAA   450
Consensus    acatgcat cg tcaaa tagat ttcatagccaaactgc tgggttgaa AB057805-1   GCCGGAGCTACCCTTGGAGAAGTTTATTATTGGATCAATGAGAACAATGA   500
AB212829-1   GCCGGAGCTACCCTTGGAGAAGTTTATTATTGGATCAATGAGAACAATGA   500
AB212833-1   GCCGGAGCTACCCTTGGAGAAGTTTATTATTGGATCAATGAGATCAATGA   500
AB292683-1   GCCGGAGCTACCCTTGGAGAAGTTTATTATTGGATCAATGAGAACAATGA   500
JQ437487-1   GCCGGAGCTACCCTTGGAGAAGTTTATTATTGGATCAATGAGAACAATGA   500
JQ437491-1   GCCGGAGCTACCCTTGGAGAAGTTTATTATTGGATCAATGAGAACAATGA   500
DK-1_full    GCCGGAGCTACCCTTGGAGAAGTTTATTATTGGATCAATGAGAACAATGA   500
SH-4_full    GCCGGAGCTACCCTTGGAGAAGTTTATTATTGGATCAATGAGAACAATGA   500
Consensus    gccggagctacccttggagaagtttattattggatcaatgaga  aatga
```

FIG. 2 continued

```
AB057805-1    GAATCTTAGTTTTCCTGCTGGGTAGTGCCCTACTGTTGGCGTAGGTGGAC    550
AB212829-1    GAATCTTAGTTTTCCTGCTGGGTAGTGCCCTACTGTTGGCGTAGGTGGAC    550
AB212833-1    GAATTTTAGTTTTCCTGCTGGGTAGTGCCCTACTGTTGGCGAGGTGGAC     550
AB292683-1    GAATCTTAGTTTTCCTGCTGGGTACTGCCCTACTGTTGGCGCGGGTGGAC    550
JQ437487-1    GAATTTTAGTTTTCCTGCTGGGTAGTGCCCTACTGTTGGCGTAGGTGGAC    550
JQ437491-1    GAATCTTAGTTTTCCTGCTGGGTAGTGCCCTACTGTTGGCGTAGGTGGAC    550
DK-1_full     GAATCTTAGTTTTCCTGCTGGGTAGTGCCCTACTGTTGGCGTAGGTGGAC    550
SH-4_full     GAATCTTAGTTTTCCTGCTGGGTAGTGCCCTACTGTTGGCGTAGGTGGAC    550
Consensus     gaat ttagttttcctg tgggta tgccctactgttggcg   ggtggac AB057805-1    ACTTTAGTGGAGGAGGCTATGGAGCATTGATGCGAAATTATGGCCTTGCG    600
AB212829-1    ACTTTAGTGGAGGAGGCTATGGAGCATTGATGCGAAATTATGGCCTTGCG    600
AB212833-1    ACTTTAGTGGAGGAGGCTATGGAGCATTGATGCGAAATTATGGCCTTGCG    600
AB292683-1    ACTTTAGTGGAGGAGGCTATGGAGCATTGATGCGAAATTATGGCCTCGCG    600
JQ437487-1    ACTTTAGTGGAGGAGGCTATGGAGCATTGATGCGAAATTATGGCCTTGCG    600
JQ437491-1    ACTTTAGTGGAGGAGGCTATGGAGCATTGATGCGAAATTATGGCCTTGCG    600
DK-1_full     ACTTTAGTGGAGGAGGCTATGGAGCATTGATGCGAAATTATGGCCTTGCG    600
SH-4_full     ACTTTAGTGGAGGAGGCTATGGAGCATTGATGCGAAATTATGGCCTTGCG    600
Consensus     actttagtggaggaggctatggagcattgatgcgaaattatggcct gcg AB057805-1    GCTGATAATATTATTGATCCACTTAGTCAATGTTGATGGAAAAGTTT      650
AB212829-1    GCTGATAATATTATTGATCCACTTAGTCAATGTTGATGGAAAAGTTT      650
AB212833-1    GCTGATAATATCATTGATTCCACTTAGTCAATGTTGATGGAAAAGTTT     650
AB292683-1    GCTGATAATATCATTGATCGCACTTAGTCAATGTTGATGGAAAAGTTTT    650
JQ437487-1    GCTGATAATATCATTGATCCACTTAGTCAATGTTGATGGAAAAGTTT      650
JQ437491-1    GCTGATAATATTATTGATCCACTTAGTCAATGTTGATGGAAAAGTTT      650
DK-1_full     GCTGATAATATTATTGATCCACTTAGTCAATGTTGATGGAAAAGTTT      650
SH-4_full     GCTGATAATATTATTGATCCACTTAGTCAATGTTGATGGAAAAGTTT      650
Consensus     gctgataatat attgat c cacttagtcaatgttgatggaaaagtt t AB057805-1    AGATCGAAAATCCATGGGAGAAGATTCTTTTGGGCTATACGTGGTGCG     700
AB212829-1    AGATCGAAAATCCATGGGAGAAGATTCTTTTGGGCTATACGTGGTGCG     700
AB212833-1    AGATCGAAAATCCATGGGAGAAGATTATTTTGGGCTATACGTGGTGGG     700
AB292683-1    AGATCGAAAATCCATGGGGAGAATTTCTTTTGGGCTATACGTGGTGCG    700
JQ437487-1    AGATCGAAAATCCATGGGAGAAGATTATTTTGGGCTATACGTGGTGGAG   700
JQ437491-1    AGATCGAAAATCCATGGGAGAAGATTCTTTTGGGCTATACGTGGTGCG    700
DK-1_full     AGATCGAAAATCCATGGGAGAAGATTCTTTTGGGCTATACGTGGTGCG    700
SH-4_full     AGATCGAAAATCCATGGGAGAAGATTCTTTTGGGCTATACGTGGTGCG    700
Consensus     agatcgaaaatccatggg gaagat t ttttgggctatacgtggtgg g AB057805-1    GAGGAGAAAACTTTGGAATCATTGCAGCATGGAAAATCAAACTCGTTGT   750
AB212829-1    GAGGAGAAAACTTTGGAATCATTGCAGCATGGAAAATCAAACTCGTTGT   750
AB212833-1    GAGGAGAAAACTTTGGAATCATTGCAGCATGGAAAATCAAACTTGTTGTT  750
AB292683-1    GAGGAGAAAACTTTGGAATCATTGCAGCGTGGAAAATTAGACTTGTTCT   750
JQ437487-1    GAGGAGAAAACTTTGGAATCATTGCAGCATGGAAAATCAAACTCGTTGTT  750
JQ437491-1    GAGGAGAAAACTTTGGAATCATTGCAGCATGGAAAATCAAACTCGTTGT   750
DK-1_full     GAGGAGAAAACTTTGGAATCATTGCAGCATGGAAAATCAAACTCGTTGT   750
SH-4_full     GAGGAGAAAACTTTGGAATCATTGCAGCATGGAAAATCAAACTCGTTGT   750
Consensus     gaggagaaaactttggaatcattgcagc tggaaaat a act gttg t
```

FIG. 2 continued

```
AB057805-1   GTCCCATCAAAGTCTACTATATTCAGTGTTAAAAAGAACATGGAGATACA   800
AB212829-1   GTCCCATCAAAGTCTACTATATTCAGTGTTAAAAAGAACATGGAGATACA   800
AB212833-1   GTCCCATCAAGGCTACTATATTCAGTGTTAAAAAGAACATGGAGATACA    800
AB292683-1   GTCCCATCAATGTCTACTATATTCAGTGTTAAAAAGAACATGGAGATACA   800
JQ437487-1   GTCCCATCAAAGTCTACTATATTCAGTGTTAAAAAGAACATGGAGATACA   800
JQ437491-1   GTCCCATCAAAGTCTACTATATTCAGTGTTAAAAAGAACATGGAGATACA   800
DK-1_full    GTCCCATCAAAGTCTACTATATTCAGTGTTAAAAAGAACATGGAGATACA   800
SH-4_full    GTCCCATCAAAGTCTACTATATTCAGTGTTAAAAAGAACATGGAGATACA   800
Consensus    gtcccatcaa g ctactatattcagtgttaaaaagaacatggagataca AB057805-1   TGGGCTTGTCAAGTTATTAACAAATGGCAAAATATTGCTTACAAGTATG    850
AB212829-1   TGGGCTTGTCAAGTTATTAACAAATGGCAAAATATTGCTTACAGGTATG    850
AB212833-1   TGGGCTTGTCAAGTTATTAACAAATGGCAAAATATTGCTTACAGGTATG    850
AB292683-1   TGAGCTTGTCAAGTTAGTTAACAAATGGCAAAATATTGCTTACATGTATG   850
JQ437487-1   TGGGCTTGTCAAGTTATTAACAAATGGCAAAATATTGCTTACAAGTATG    850
JQ437491-1   TGGGCTTGTCAAGTTATTAACAAATGGCAAAATATTGCTTACAAGTATG    850
DK-1_full    TGGGCTTGTCAAGTTATTAACAAATGGCAAAATATTGCTTACAAGTATG    850
SH-4_full    TGGGCTTGTCAAGTTATTAACAAATGGCAAAATATTGCTTACAAGTATG    850
Consensus    tg gcttgtcaagtta ttaacaaatggcaaaatattgcttaca gtatg AB057805-1   AAAAGATTACTACTCATGACTCACTTCAAACAAAGAATATTACAGAT     900
AB212829-1   AAAAGATTACTACTCATGACTCACTTCAAACAAAGAATATTACAGAT     900
AB212833-1   AAAAGATTAATGCTCACGACTCACTTCAGAACTAGGAATATTACAGAT    900
AB292683-1   AAAAGAATTATTACTCTTTACTCACTTTAAACCAGGAATATTACAGAT    900
JQ437487-1   AAAAGATTACTACTCATGACTCACTTCAAACAAAGAATATTACAGAT     900
JQ437491-1   AAAAGATTACTACTCATGACTCACTTCAAACAAAGAATATTACAGAT     900
DK-1_full    AAAAGATTACTACTCATGACTCACTTCAAACAAAGAATATTACAGAT     900
SH-4_full    AAAAGATTACTACTCATGACTCACTTCAAACAAAGAATATTACAGAT     900
Consensus    a aaaga tta t ctc   actcactt a aac a gaatattacagat AB057805-1   AATCAGGGAAGAATAAGACAACATACAGGTTACTTCTCTTCAATTTT     950
AB212829-1   AATCAGGGAAGAATAAGACAACATACAGGTTACTTCTCTTCAATTTT     950
AB212833-1   AATCAGGGAAGAATAAGACAACATACAGGTTACTTCTCTTCCATTTT     950
AB292683-1   AATCAAGGGAAGAATAAGACAACATACACAGTTACTTCTCCTCCATTTT   950
JQ437487-1   AATCAGGGAAGAATAAGACAACATACAGGTTACTTCTCTTCCATTTT     950
JQ437491-1   AATCAGGGAAGAATAAGACAACATACAGGTTACTTCTCTTCAATTTT     950
DK-1_full    AATCAGGGAAGAATAAGACAACATACAGGTTACTTCTCTTCAATTTT     950
SH-4_full    AATCAGGGAAGAATAAGACAACATACAGGTTACTTCTCTTCAATTTT     950
Consensus    aatca gggaagaataagac aca taca  gttacttctc tc atttt AB057805-1   TCATGGTGGAGTGGATAGTCTAGTGGACTTGATGAACAAGAGCTTTCCTG   1000
AB212829-1   TCATGGTGGAGTGGATAGTCTAGTGGACTTGATGAACAAGAGCTTTCCTG   1000
AB212833-1   TCTTGGTGGAGTGGATAGTCTAGTTGACTTGATGAACAAGAGCTTTCCTG   1000
AB292683-1   CCATGGTGGAGTGGATAGTCTAGTGGACTTGATGAACAAGAGCTTTCCTG   1000
JQ437487-1   TCATGGTGGAGTGGATAGTCTAGTGGACTTGATGAACAAGAGCTTTCCTG   1000
JQ437491-1   TCATGGTGGAGTGGATAGTCTAGTGGACTTGATGAACAAGAGCTTTCCTG   1000
DK-1_full    TCATGGTGGAGTGGATAGTCTAGTGGACTTGATGAACAAGAGCTTTCCTG   1000
SH-4_full    TCATGGTGGAGTGGATAGTCTAGTGGACTTGATGAACAAGAGCTTTCCTG   1000
Consensus    c tggtggagtggatagtctagt gacttgatgaacaagagctttcctg
```

FIG. 2 continued

```
AB057805-1   A TTGGGTATTAAAAAAAC GATTGCAAA A TT AGCTGGATTGATAC    1050
AB212829-1   A TTGGGTATTAAAAAAAC GATTGCAAA A TT AGCTGGATTGATAC    1050
AB212833-1   A TTGGGTATTAAAAAAAC GATTGCAAA A TT GAGCTGGATTGATAC   1050
AB292683-1   AATTGGGTATTAAAAAAACAGATTGCAAACAGTTGAGCTGGATTGATACT   1050
JQ437487-1   A TTGGGTATTAAAAAAAC GATTGCAAA A TT AGCTGGATTGATAC    1050
JQ437491-1   A TTGGGTATTAAAAAAAC GATTGCAAA A TT AGCTGGATTGATAC    1050
DK-1_full    A TTGGGTATTAAAAAAAC GATTGCAAA A TT AGCTGGATTGATAC    1050
SH-4_full    A TTGGGTATTAAAAAAAC GATTGCAAA A TT AGCTGGATTGATAC    1050
Consensus    a ttgggtattaaaaaaac gattgcaaa a tt  agctggattgatac AB057805-1   A CATCTTCTACAGTGGTGTTGT AATT  AACAC  CT ATTTTAAAAA    1100
AB212829-1   A CATCTTCTACAGTGGTGTTGT AATT  AACAC  CT ATTTTAAAAA    1100
AB212833-1   A CATCTTCTACAGTGGTGTTGT CAATTACAACAC  CT ATTTTAAAAA   1100
AB292683-1   A TCATCTTCTACAGTGGTGTTGT AATTACAACACAA CT ATTTTAAAAA  1100
JQ437487-1   A CATCTTCTACAGTGGTGTTGT AATT  AACAC  CT ATTTTAAAAA    1100
JQ437491-1   A CATCTTCTACAGTGGTGTTGT AATT  AACAC  CT ATTTTAAAAA    1100
DK-1_full    A CATCTTCTACAGTGGTGTTGT AATT  AACAC  CT ATTTTAAAAA    1100
SH-4_full    A CATCTTCTACAGTGGTGTTGT AATT  AACAC  CT ATTTTAAAAA    1100
Consensus    a catcttctacagtggtgttgt aatt    aacac  ct attttaaaaa AB057805-1    GAAATTTTGCTTGATAGATCAG TGGG  GAAG CGGCTTTCTC ATTA    1150
AB212829-1    GAAATTTTGCTTGATAGATCAG TGGG  GAAG CGGCTTTCTC ATTA    1150
AB212833-1    GAAATTTTGCTTGATAGATCAG TGGG  GAAG CGGCTTTCTC ATTA    1150
AB292683-1   AGAAATTTTGCTTGATAGATCAGGTGGGCGGAAGGCGGCTTTCTCGATTA   1150
JQ437487-1    GAAATTTTGCTTGATAGATCAG TGGG  GAAG CGGCTTTCTC ATTA    1150
JQ437491-1    GAAATTTTGCTTGATAGATCAG TGGG  GAAG CGGCTTTCTC ATTA    1150
DK-1_full     GAAATTTTGCTTGATAGATCAG TGGG  GAAG CGGCTTTCTC ATTA    1150
SH-4_full     GAAATTTTGCTTGATAGATCAG TGGG  GAAG CGGCTTTCTC ATTA    1150
Consensus     gaaatttgcttgatagatcag tggg   gaag cggctttctc atta AB057805-1   AGTTAGACTATGTTAAGAAAC AT  CC GAAAC GCAATGGTCA AATT    1200
AB212829-1   AGTTAGACTATGTTAAGAAAC AT  CCT GAAAC GCAATGGTCA AATT   1200
AB212833-1   AGTTAGACTATGTTAAGAAACTAATACCT GAAAC GCAATGGTCA AATT   1200
AB292683-1   AGTTAGACTATGTTAAGAAACGAT CCAGAAAC GCAATGGTCACAATT    1200
JQ437487-1   AGTTAGACTATGTTAAGAAAC AT  CCT GAAAC GCAATGGTCA AATT   1200
JQ437491-1   AGTTAGACTATGTTAAGAAAC AT  CCT GAAAC GCAATGGTCA AATT   1200
DK-1_full    AGTTAGACTATGTTAAGAAAC AT  CCA GAAAC GCAATGGTCA AATT   1200
SH-4_full    AGTTAGACTATGTTAAGAAAC AT  CCA GAAAC GCAATGGTCA AATT   1200
Consensus    agttagactatgttaagaaac  at  cc  gaaac gcaatggtca aatt AB057805-1   TTGGAAAAATTATATGAAGAAGA GTAGGAG TGGGATGT TGTGTT  TA   1250
AB212829-1   TTGGAAAAATTATATGAAGAAGA GTAGGAG TGGGATGT TGTGTT  TA   1250
AB212833-1   TTGGAAAAATTATATGAAGAAGAGGTAGGAGTTGGGATGT TGTGTT  TA   1250
AB292683-1   TTGGAAAAATTATATGAAGAAGA GTAGGAGTTGGGATGTTTGTGTTTTA   1250
JQ437487-1   TTGGAAAAATTATATGAAGAAGA GTAGGAGTTGGGATGT TGTGTT  TA   1250
JQ437491-1   TTGGAAAAATTATATGAAGAAGAGGTAGGAGTTGGGATGT TGTGTT  TA   1250
DK-1_full    TTGGAAAAATTATATGAAGAAGA GTAGGAG TGGGATGT TGTGTT  TA   1250
SH-4_full    TTGGAAAAATTATATGAAGAAGA GTAGGAG TGGGATGT TGTGTT  TA   1250
Consensus    ttggaaaaattatatgaagaaga gtaggag tgggatgt tgtgtt  ta
```

FIG. 2 continued

```
AB057805-1  CCCTTA GGTGGTATAATGGA GAGATTTCAGAATCAGCAATTCCATTCC  1300
AB212829-1  CCCTTA GGTGGTATAATGGA GAGATTTCAGAATCAGCAATTCCATTCC  1300
AB212833-1  CCCTTA GGTGGTATAATGGAT GAGATTTCAGAATCAGCAATTCCATTCC  1300
AB292683-1  CCCTTAT GGTGGTATAATGGAT GAGATTTCAGAATCAGCAATTCCATTCC  1300
JQ437487-1  CCCTTA GGTGGTATAATGGA GAGATTTCAGAATCAGCAATTCCATTCC  1300
JQ437491-1  CCCTTA GGTGGTATAATGGA GAGATTTCAGAATCAGCAATTCCATTCC  1300
DK-1_full   CCCTTA GGTGGTATAATGGA GAGATTTCAGAATCAGCAATTCCATTCC  1300
SH-4_full   CCCTTA GGTGGTATAATGGA GAGATTTCAGAATCAGCAATTCCATTCC  1300
Consensus   ccctta ggtggtataatgga gagatttcagaatcagcaattccattcc AB057805-1  CTCATCGAGCTGGAAT ATGTATGAA TTTGGTACA GCT C  TGGGAG  1350
AB212829-1  CTCATCGAGCTGGAAT ATGTATGAA TTTGGTACA GCT C  TGGGAG  1350
AB212833-1  CTCATCGAGCTGGAAT ATGTATGAA TTTGGTACA GCTA C  TGGGAG  1350
AB292683-1  CTCATCGAGCTGGAATC ATGTATGAA TTTGGTACATA GCT CA TGGGAG  1350
JQ437487-1  CTCATCGAGCTGGAAT ATGTATGAA TTTGGTACA GCT C  TGGGAG  1350
JQ437491-1  CTCATCGAGCTGGAAT ATGTATGAA TTTGGTACA GCT C  TGGGAG  1350
DK-1_full   CTCATCGAGCTGGAAT ATGTATGAA TTTGGTACA GCT C  TGGGAG  1350
SH-4_full   CTCATCGAGCTGGAAT ATGTATGAA TTTGGTACA GCT C  TGGGAG  1350
Consensus   ctcatcgagctggaat atgtatgaa tttggtaca     gct c  tgggag AB057805-1  AAGCAAGAAGATAA GAAAAGCATATAAACTGG TTCG A TGTTTATAA  1400
AB212829-1  AAGCAAGAAGATAA GAAAAGCATATAAACTGG TTCG A TGTTTATAA  1400
AB212833-1  AAGCAAGAAGATAAC GAAAAGCATATAAACTGG TTCG A TGTTTATAA  1400
AB292683-1  AAGCAAGAAGATAA GAAAAGCATATAAACTGGA TTCG A TGTTTATAA  1400
JQ437487-1  AAGCAAGAAGATAA GAAAAGCATATAAACTGG TTCG A TGTTTATAA  1400
JQ437491-1  AAGCAAGAAGATAA GAAAAGCATATAAACTGG TTCG A TGTTTATAA  1400
DK-1_full   AAGCAAGAAGATAA GAAAAGCATATAAACTGG TTCG A TGTTTATAA  1400
SH-4_full   AAGCAAGAAGATAA GAAAAGCATATAAACTGG TTCG A TGTTTATAA  1400
Consensus   aagcaagaagataa gaaaagcatataaactgg ttcg a tgtttataa AB057805-1  TTTTAC ACTCCTTATGTGTCCCAAAATCCAAGA TGGCGTATCTCAATT  1450
AB212829-1  TTTTAC ACTCCTTATGTGTCCCAAAATCCAAGA TGGCGTATCTCAATT  1450
AB212833-1  TTTCACA ACTCCTTATGTGTCCCAAAATCCAAGA TGGCGTATCTCAATT  1450
AB292683-1  TTTCAC ACTCCTTATGTGTCCCAAAATCCAAGAA TGGCGTATCTCAATT  1450
JQ437487-1  TTTTAC ACTCCTTATGTGTCCCAAAATCCAAGA TGGCGTATCTCAATT  1450
JQ437491-1  TTTCACA ACTCCTTATGTGTCCCAAAATCCAAGA TGGCGTATCTCAATT  1450
DK-1_full   TTTTAC ACTCCTTATGTGTCCCAAAATCCAAGA TGGCGTATCTCAATT  1450
SH-4_full   TTTTAC ACTCCTTATGTGTCCCAAAATCCAAGA TGGCGTATCTCAATT  1450
Consensus   ttt ac actccttatgtgtcccaaaatccaaga tggcgtatctcaatt AB057805-1  ATAGGGACCTTGATTTAGGAAAAACTAAT A GC GAGTCCTAATAATTAC  1500
AB212829-1  ATAGGGACCTTGATTTAGGAAAAACTAAT A GC GAGTCCTAATAATTAC  1500
AB212833-1  ATAGGGACCTTGATTTAGGAAAAACTAAT C GA GAGTCCTAATAATTAC  1500
AB292683-1  ATAGGGACCTTGATTTAGGAAAAACTAAT TTC GA GAGTCCTAATAATTAC  1500
JQ437487-1  ATAGGGACCTTGATTTAGGAAAAACTAAT C T GA GAGTCCTAATAATTAC  1500
JQ437491-1  ATAGGGACCTTGATTTAGGAAAAACTAAT C T GA GAGTCCTAATAATTAC  1500
DK-1_full   ATAGGGACCTTGATTTAGGAAAAACTAAT A GC GAGTCCTAATAATTAC  1500
SH-4_full   ATAGGGACCTTGATTTAGGAAAAACTAAT A GC GAGTCCTAATAATTAC  1500
Consensus   atagggaccttgatttaggaaaaactaat      g gagtcctaataattac
```

FIG. 2 continued

```
AB057805-1  ACACAAGCACGTATTTGGGGTGAAAAGTATTTTGGTAAAAATTTTAACAG  1550
AB212829-1  ACACAAGCACGTATTTGGGGTGAAAAGTATTTTGGTAAAAATTTTAACAG  1550
AB212833-1  ACACAAGCACGTATTTGGGGTGAAAAGTATTTTGGTAAAAATTTTAACAG  1550
AB292683-1  ACACAAGCACGTATTTGGGGTGAAAAGTATTTTGGTAAAAATTTTAATAG  1550
JQ437487-1  ACACAAGCACGTATTTGGGGTGAAAAGTATTTTGGTAAAAATTTTAACAG  1550
JQ437491-1  ACACAAGCACGTATTTGGGGTGAAAAGTATTTTGGTAAAAATTTTAACAG  1550
DK-1_full   ACACAAGCACGTATTTGGGGTGAAAAGTATTTTGGTAAAAATTTTAACAG  1550
SH-4_full   ACACAAGCACGTATTTGGGGTGAAAAGTATTTTGGTAAAAATTTTAACAG  1550
Consensus   acacaagcacgtatttggggtgaaaagtattttggtaaaaattttaa ag AB057805-1  GTTAGTAAAGTCAAAACTAAAGTTGATCCCAATAATTTTTTTAGAAACG   1600
AB212829-1  GTTAGTAAAGTCAAAACTAAAGTTGATCCCAATAATTTTTTTAGAAACG   1600
AB212833-1  GTTAGTAAAGTCAAAACCAAAGCTGATCCCAATAATTTTTTTAGAAACG   1600
AB292683-1  GTTAGTAAAAGTAAAAACCAAGGTTGATCCCGATAATTTCTTTAGAAACG  1600
JQ437487-1  GTTAGTAAAGTCAAAACCAAAGCTGATCCCAATAATTTTTTTAGAAACG   1600
JQ437491-1  GTTAGTAAAGTCAAAACCAAAGCTGATCCCAATAATTTTTTTAGAAACG   1600
DK-1_full   GTTAGTAAAGTCAAAACTAAAGTTGATCCCAATAATTTTTTTAGAAACG   1600
SH-4_full   GTTAGTAAAGTCAAAACTAAAGTTGATCCCAATAATTTTTTTAGAAACG   1600
Consensus   gttagt aa gt aaaac aa g tgatccc ataattt tttagaaacg AB057805-1  AACAAAGCATCCCACCTCTTCCACCGCATCATCATTAA              1638
AB212829-1  AACAAAGCATCCCACCTCTTCCACCGCATCATCAT...              1635
AB212833-1  AACAAAGCATCCCACCTCTTCCACCGCATCATCAT...              1635
AB292683-1  AACAAAGCATCCCACCTCTTCCCTGCGTCATCATTAA              1638
JQ437487-1  AACAAAGCATCCCACCTCTTCCACCGCATCATCAT...              1635
JQ437491-1  AACAAAGCATCCCACCTCTTCCACCGCATCATCAT...              1635
DK-1_full   AACAAAGCATCCCACCTCTTCCACCGCATCATCATATC              1638
SH-4_full   AACAAAGCATCCCACCTCTTCCACCGCATCATCATATC              1638
Consensus   aacaaag atcccacctcttcc c gc tcatcat
```

CANNABIS PLANTS HAVING MODIFIED EXPRESSION OF THCA SYNTHASE

REFERENCE TO RELATED APPLICATIONS

This application is a 371 National Stage application of International Application No. PCT/IB2016/000814, filed May 27, 2016, which application claims the benefit of priority to United States Provisional Application No. 62/167,462, filed May 28, 2015, which is herein incorporated by reference in its entirety.

INCORPORATION OF SEQUENCE LISTING

A computer readable form of the Sequence Listing is filed herewith by electronic submission. The Sequence Listing is incorporated by reference in its entirety, is contained in the file created on May 23, 2016, having the file name "TWED002WO_ST25.txt" and which is 112 kb in size (as measured in MS-Windows operating system).

FIELD OF THE INVENTION

The present invention pertains to genetically modified *cannabis* plants and *cannabis* plant derived products as well as expression cassettes, vectors, compositions, and materials and methods for producing the same. In particular, the present invention relates to *cannabis* plants having modified expression of tetrahydrocannabinolic acid (THCA) synthase and methods of modifying the amount of delta-9-tetrahydrocannabinol (THC) and cannabidiol (CBD) in *cannabis* by modifying expression of THCA synthase.

BACKGROUND OF THE INVENTION

*Cannabis* (also referred to as marihuana or marijuana) has been used for medicinal purposes throughout history. *Cannabis* has been shown to provide therapeutic benefits as an appetite stimulant, as an antiemetic, as an analgesic and in the management of various conditions including glaucoma, Parkinson's Disease, Alzheimer's Disease, Multiple Sclerosis and chronic inflammation.

*Cannabis* contains numerous chemically distinct components many of which have therapeutic properties. The main therapeutic components of medical *cannabis* are delta-9-tetrahydrocannabinol (THC) and cannabidiol (CBD). THC is the primary psychoactive component of *cannabis* and has been shown to provide therapeutic benefits as an antiemetic, analgesic and in the management of glaucoma. Conversely, strains of medical *cannabis* with high proportions of THC may cause feelings of anxiety and/or disorientation. CBD is the main non-psychoactive component in *cannabis*. CBD is an agonist to serotonin receptors and has been shown to have therapeutic benefit in therapies for neuropathic pain and neural inflammation. Side effects of high doses of CBD include variable drowsiness and sedation.

The amount of particular components in the *cannabis* may impact the efficacy of the therapy and potential side effects. Accordingly, *cannabis* plants having a modified therapeutic component(s) profile may be useful in the production of medical *cannabis* and/or may also be useful in the production of specific components.

SUMMARY OF THE INVENTION

Described are methods for altering a content of one or more cannabinoids in a *cannabis* plant, the method comprising down-regulating activity of tetrahydrocannabinolic acid (THCA) synthase in the *cannabis* plant. In particular embodiments, the methods comprise decreasing delta-9-tetrahydrocannabinol (THC) content, increasing cannabidiol (CBD) content, or decreasing THC and increasing CBD content in a *cannabis* plant, the method comprising down-regulating activity of a tetrahydrocannabinolic acid (THCA) synthase in the *cannabis* plant. In certain embodiments, the down-regulating the activity of THCA synthase comprises introducing into the plant an expression cassette comprising a selected DNA encoding an antisense RNA or a siRNA effective to suppress expression of the THCA synthase, the selected DNA operably linked to a heterologous promoter. In particular embodiments, the method may further comprise selecting a *cannabis* plant with a decreased level of THCA synthase mRNA relative to a *cannabis* plant of a similar genotype that does not comprise the expression cassette, or selecting a *cannabis* plant with reduced THC content, increased CBD content, or reduced THC content and increased CBD content relative to a *cannabis* plant of a similar genotype that does not comprise the expression cassette. In particular embodiments, introducing the expression cassette comprises genetic transformation. The heterologous promoter may be selected from the group consisting of a leaf-specific promoter, a flower-specific promoter, a THCA synthase promoter, a CaMV35S promoter, a FMV35S promoter, and a tCUP promoter in some embodiments. In certain aspects, the siRNA is encoded by a polynucleotide sequence having at least 85 percent sequence identity to a sequence selected from the group consisting of SEQ ID NO:61, 63, 64, 69, 71, 72, 68, and a complement thereof; or a polynucleotide sequence comprising at least 21 contiguous nucleotides of a sequence selected from the group consisting of SEQ ID NO:61, 63, 64, 69, 71, 72, 68, and a complement thereof, or a polynucleotide sequence comprising at least 21 contiguous nucleotides of a THCA synthase, or a complement thereof, the THCA having at least 85 percent sequence identity to a sequence selected from the group consisting of SEQ ID NO:1-47. In other aspects, the antisense RNA is encoded by a polynucleotide sequence comprising SEQ ID NO:81 or a fragment thereof capable of reducing the expression of the THCA synthase, or a polynucleotide sequence that is at least 85 percent identical to at least 200 contiguous nucleotides of SEQ ID NO:81, and wherein transcription of the selected DNA suppresses expression of the THCA synthase.

In other embodiment, down-regulating the activity of a THCA synthase comprises introducing into a *cannabis* plant or a cell thereof (i) at least one RNA-guided endonuclease comprising at least one nuclear localization signal or nucleic acid encoding at least one RNA-guided endonuclease comprising at least one nuclear localization signal, (ii) at least one guide RNA or DNA encoding at least one guide RNA, and, optionally, (iii) at least one donor polynucleotide; and culturing the *cannabis* plant or cell thereof such that each guide RNA directs an RNA-guided endonuclease to a targeted site in the chromosomal sequence where the RNA-guided endonuclease introduces a double-stranded break in the targeted site, and the double-stranded break is repaired by a DNA repair process such that the chromosomal sequence is modified, wherein the targeted site is located in the THCA synthase gene and the chromosomal modification interrupts or interferes with transcription and/or translation of the THCA synthase gene.

In further embodiments, down-regulating the activity of a THCA synthase comprises identifying at least one THCA synthase gene locus within a DNA sequence in a *cannabis* plant or a cell thereof identifying at least one custom endonuclease recognition sequence within the at least one THCA synthase gene locus, introducing into the at least one *cannabis* plant or a cell thereof at least a first custom endonuclease, wherein the *cannabis* plant or a cell thereof comprises the recognition sequence for the custom endonuclease in or proximal to the THCA synthase gene locus, and the custom endonuclease is expressed transiently or stably, assaying the *cannabis* plant or a cell thereof for a custom endonuclease-mediated modification in the DNA making up or flanking the THCA synthase gene locus, and identifying the *cannabis* plant, a cell thereof, or a progeny cell thereof as comprising a modification in the THCA synthase gene locus.

Included are in various embodiments, also transgenic *cannabis* plant produced by the method, and a seed of the transgenic plant, wherein the seed comprises the expression cassette.

Additional embodiments include *cannabis* plant with reduced delta-9-tetrahydrocannabinol (THC) content, increased cannabidiol (CBD) content, or decreased THC and increased CBD content comprising decreased expression of tetrahydrocannabinolic acid (THCA) synthase. In certain aspects, the *cannabis* plant comprises a selected DNA encoding an antisense RNA or a siRNA effective to suppress expression of THCA synthase, the selected DNA operably linked to a heterologous promoter, wherein the *cannabis* plant comprises reduced THC content, increased CBD content, or decreased THC and increased CBD content relative to a *cannabis* plant of a similar genotype that does not comprise the selected DNA. In particular aspects, included are a seed, cell, or part of the *cannabis* plant, and a *cannabis* plant derived product from the plant.

In particular embodiments, the *cannabis* plant derived product comprises a combined cannabidiolic acid and cannabidiol concentration of about 18% to about 60% by weight and/or a combined delta-9-tetrahydrocannabinol and tetrahydrocannabinolic acid concentration of between about 0% to about 3% by weight. In various embodiments, the *cannabis* plant derived product comprises *cannabis* oil, *cannabis* tincture, dried *cannabis* flowers, and/or dried *cannabis* leaves and/or may also be adapted for inhalation, oral consumption, sublingual consumption, or topical consumption.

In a particular embodiment, included are methods for producing a medical *cannabis* composition, the method comprising obtaining the *cannabis* plant, growing the *cannabis* plant under plant growth conditions to produce plant tissue from the *cannabis* plant, and preparing the medical *cannabis* composition from the plant tissue.

Described are also recombinant expression cassettes comprising a selected DNA operably linked to a heterologous promoter, the selected DNA encoding an antisense RNA, a RNAi, or a siRNA effective to suppress expression of a tetrahydrocannabinolic acid (THCA) synthase gene. In particular embodiments, the THCA synthase gene comprises a polynucleotide sequence having at least 83, 84, 85, 86, 87, 88, 89, 90, 91, 92, 93, 94, 95, 96, 97, 98, or 99 percent sequence identity to a sequence selected from the group consisting of SEQ ID NO:1-47. In certain embodiments, the heterologous promoter is a leaf-specific promoter or a flower-specific promoter; a promoter that is functional in plants; and/or a promoter that is selected from the group consisting of CaMV35S promoter, FMV35S promoter, and tCUP promoter. In various embodiments, the selected DNA encodes a siRNA that comprises a sequence that is complementary to at least 21 contiguous nucleotides of the THCA synthase gene; encodes an antisense RNA that comprises SEQ ID NO:81 or a fragment thereof capable of reducing the expression of the THCA synthase gene; comprises a polynucleotide sequence having at least 85, 86, 87, 88, 89, 90, 91, 92, 93, 94, 95, 96, 97, 98, or 99 percent sequence identity to a sequence selected from the group consisting of SEQ ID NO:61, 63, 64, 69, 71, 72, 68, and a complement thereof; and/or encodes a siRNA that comprises at least 21 contiguous nucleotides of a sequence selected from the group consisting of SEQ ID NO:61, 63, 64, 69, 71, 72, 68, and a complement thereof; and wherein the siRNA is capable of reducing the expression of the THCA synthase gene.

In further embodiments, the selected DNA is operably linked to the promoter in antisense orientation. In particular embodiments, the selected DNA induces gene silencing, mRNA cleavage, or repressed translation of mRNA of the THCA synthase gene; and/or the selected DNA is at least 90, 91, 92, 93, 94, 95, 96, 97, 98, or 99 percent identical to at least 200 contiguous nucleotides of SEQ ID NO:81 or a complement thereof; or comprises at least 18, 19, 20, 21, or 22 contiguous nucleotides of SEQ ID NO:61, 63, 64, 69, 71, 72, 68, or a complement thereof, wherein transcription of the selected DNA suppresses expression of the THCA synthase gene. Described are also a vector comprising the expression cassette; a transgenic plant comprising the expression cassette of claim 1. In specific embodiments the transgenic plant is defined as a *cannabis* plant, wherein the *cannabis* plant comprises reduced delta-9-tetrahydrocannabinol (THC) and increased cannabidiol (CBD) relative to a *cannabis* plant of the same genotype that does not comprise the expression cassette. In particular embodiments, the transgenic plant is further defined as an R0 transgenic plant; and/or as a progeny plant of any generation of an R0 transgenic plant, wherein the transgenic plant has inherited the selected DNA from the R0 transgenic plant. Described are also, in certain embodiments, seed of the transgenic plant, wherein the seed comprises the expression cassette; a transgenic cell of the transgenic plant, wherein the cell comprises the expression cassette.

In another aspect, provided are processed product of the plant or of a progeny thereof, wherein the processed product comprises reduced delta-9-tetrahydrocannabinol (THC) and increased cannabidiol (CBD) relative to a processed product of a *cannabis* plant of the same genotype that does not comprise the expression cassette. In various embodiments, the processed product comprises a *cannabis* oil, a tincture, dried *cannabis* flowers, and/or dried *cannabis* leaves; is adapted for inhalation, oral consumption, sublingual consumption, or topical consumption.

In another aspect are described composition for topical application to a plant or part thereof, comprising an amount of a tetrahydrocannabinolic acid (THCA) synthase inhibitory compound effective to suppress expression of a THCA synthase gene, wherein the THCA synthase inhibitory compound comprises an antisense oligonucleotide, a dsRNA, or a nucleic acid encoding an antisense oligonucleotide effective to suppress expression of the THCA synthase gene. In certain embodiments, the THCA synthase inhibitory compound comprises a polynucleotide molecule that is at least 18 to about 24, about 25 to about 50, about 51 to about 100, about 101 to about 300, about 301 to about 500, or at least about 500 or more nucleotides in length, wherein the plant is *cannabis* and the THCA synthase gene comprises a polynucleotide sequence having at least about 83, 84, 85, 86, 87, 88, 89, 90, 91, 92, 93, 94, 95, 96, 97, 98, or 99 percent sequence identity or 100% sequence identity to a sequence selected from the group consisting of SEQ ID NO:1-47.

Other embodiments provide for methods of down-regulating activity of a THCA synthase gene in a *cannabis* plant, the method comprising introducing into the plant the expression cassette of claim 1; and selecting a plant with decreased abundance of THCA synthase mRNA compared to a plant in which the expression cassette has not been introduced; or selecting a plant with reduced delta-9-tetrahydrocannabinol (THC) and/or increased cannabidiol (CBD) content relative to a *cannabis* plant of a similar genotype that does not comprise the expression cassette. In certain aspects, the THCA synthase gene comprises a polynucleotide sequence having at least 85, 86, 87, 88, 89, 90, 91, 92, 93, 94, 95, 96, 97, 98, or 99 percent sequence identity to a sequence selected from the group consisting of SEQ ID NO:1-47. In particular aspects, introducing the expression cassette comprises genetic transformation.

In other aspects are described methods of producing a medical *cannabis* composition, the method comprising obtaining the plant, growing the plant under plant growth conditions to produce plant tissue from the plant; and preparing the medical *cannabis* composition for human or animal consumption from the plant tissue.

Additional embodiments describe methods for identifying plants having reduced expression or lacking expression of a THCA synthase gene, comprising obtaining a plurality of *cannabis* plants, screening the plurality of the *cannabis* plants for expression of the THCA synthase gene, and selecting one or more screened *cannabis* plants comprising decreased expression of the THCA synthase gene relative to expression of the THCA synthase gene in an isogenic *cannabis* plant that does not comprise the expression cassette. In particular embodiments, the methods further comprise testing the selected one or more *cannabis* plants for reduced delta-9-tetrahydrocannabinol (THC) and/or increased cannabidiol (CBD) content relative to an isogenic *cannabis* plant that does not comprise the expression cassette; the plurality of *cannabis* plants are obtained by random mutagenesis or site-specific mutagenesis; the plurality of plants are transgenic plants; and/or the plurality of plants comprise 10, 100, or 1000 or more plants. In particular embodiments, the method further comprises crossing the one or more *cannabis* plants with decreased expression of the THCA synthase gene to a different plant.

In other aspect are described methods for identifying a polymorphism genetically linked to a THCA synthase gene or, comprising obtaining DNA of a population of plants wherein members of the population vary for expression of THCA synthase; and identifying at least a first polymorphism in said population that is associated with a reduced expression of THCA synthase relative to members of the population that do not comprise said polymorphism.

In a different aspect are described methods for producing a *cannabis* plant cell having a modified chromosomal sequence in a THCA synthase gene, the method comprising introducing into the *cannabis* plant cell (i) at least one RNA-guided endonuclease comprising at least one nuclear localization signal or nucleic acid encoding at least one RNA-guided endonuclease comprising at least one nuclear localization signal, (ii) at least one guide RNA or DNA encoding at least one guide RNA, and, optionally, (iii) at least one donor polynucleotide; and culturing the *cannabis* plant cell such that each guide RNA directs an RNA-guided endonuclease to a targeted site in the chromosomal sequence where the RNA-guided endonuclease introduces a double-stranded break in the targeted site, and the double-stranded break is repaired by a DNA repair process such that the chromosomal sequence is modified, wherein the targeted site is located in the THCA synthase gene and the chromosomal modification interrupts or interferes with transcription and/or translation of the THCA synthase gene. In particular embodiment, the RNA-guided endonuclease is derived from a Cas9 protein; the nucleic acid encoding the RNA-guided endonuclease is mRNA or DNA; and/or the modification is an insertion or deletion. In particular embodiments, the DNA is part of a vector that further comprises a sequence encoding the guide RNA, a *cannabis* plant cell is obtained by the method. In particular aspects, a *cannabis* plant comprises the cell, wherein the plant comprises a reduced delta-9-tetrahydrocannabinol (THC) and/or increased cannabidiol (CBD) content relative to an isogenic *cannabis* plant in which the chromosomal sequence of the THCA synthase gene is not modified.

Other aspects include methods for modifying THCA synthase gene locus in a plant cell comprising identifying at least one THCA synthase gene locus within a DNA sequence in the plant cell, identifying at least one custom endonuclease recognition sequence within the at least one THCA synthase gene locus, introducing into at least one plant cell at least a first custom endonuclease, wherein the cell comprises the recognition sequence for the custom endonuclease in or proximal to the THCA synthase gene locus, and the custom endonuclease is expressed transiently or stably, assaying the cell for a custom endonuclease-mediated modification in the DNA making up or flanking the THCA synthase gene locus, and identifying the cell or a progeny cell thereof as comprising a modification in the THCA synthase gene locus. In particular embodiments, the custom endonuclease comprises a "LAGLIDADG," "GIY-YIG," "His-Cys Box," "ZFN," or "HNH" sequence motif; and/or the endonuclease recognition sequence is present only once in the genome of said plant cell. In certain embodiments, the method further comprises identifying at least a second custom endonuclease recognition sequence within a locus of interest; or further comprises introducing into the plant cell at least a second custom endonuclease, wherein the cell comprises a second recognition sequence for the second custom endonuclease. In particular embodiments, the endonuclease-mediated modification is detected using a genotyping reaction, a PCR reaction, high throughput sequencing, other molecular genetic assay, biochemical assay, visual assay, immunological assay, or other phenotypic marker assay. And in certain aspects are described plants produced by the method.

BRIEF DESCRIPTION OF THE DRAWINGS

FIG. 1 depicts an alignment of the coding regions of *Cannabis sativa* tetrahydrocannabinolic acid (THCA) synthase sequences. Alignment was performed with CLUSTAL 0 (1.2.1) multiple sequence alignment available at world wide web.ebi.ac.uk/Tools/msa/clustalw2. Aligned are the following sequences: JQ437488.1 (SEQ ID NO:1); JQ437487.1 (SEQ ID NO:2); JQ437486.1 (SEQ ID NO:3); JQ437485.1 (SEQ ID NO:4); JQ437484.1 (SEQ ID NO:5); JQ437483.1 (SEQ ID NO:6); JQ437482.1 (SEQ ID NO:7); JQ437481.1 (SEQ ID NO:8); JQ437492.1 (SEQ ID NO:12); JQ437491.1 (SEQ ID NO:13); JQ437490.1 (SEQ ID NO:14); JQ437489.1 (SEQ ID NO:15); AB212841.1 (SEQ ID NO:16); AB212840.1 (SEQ ID NO:17); AB212839.1 (SEQ ID NO:18); AB212838.1 (SEQ ID NO:19); AB212837.1 (SEQ ID NO:20); AB212836.1 (SEQ ID NO:21); AB212835.1 (SEQ ID NO:22); AB212834.1 (SEQ ID NO:23); AB212833.1 (SEQ ID NO:24); AB212832.1 (SEQ ID NO:25); AB212831.1 (SEQ ID NO:26);

AB212830.1 (SEQ ID NO:27); AB212829.1 (SEQ ID NO:28); AB731220.1 (SEQ ID NO:39); AB057805.1 (SEQ ID NO:40); AB292683.1 (SEQ ID NO:41); AB292682.1 (SEQ ID NO:42); and AB292684.1 (SEQ ID NO:43).

FIG. 2 depicts an alignment of *Cannabis sativa* tetrahydrocannabinolic acid (THCA) synthase coding sequences from DK-1 and SH-4 strains with NCBI THCA synthase sequences. Aligned are the following sequences: AB057805.1 (SEQ ID NO:40); AB212829.1 (SEQ ID NO:28); AB212833.1 (SEQ ID NO:24); AB292683.1 (SEQ ID NO:41); JQ437487.1 (SEQ ID NO:2); JQ437491.1 (SEQ ID NO:13); DK-1_full (SEQ ID NO:46); and SH-4_full (SEQ ID NO:47). Depicted are also the regions with identical sequence (Consensus) (SEQ ID NO:86).

Figure 3:
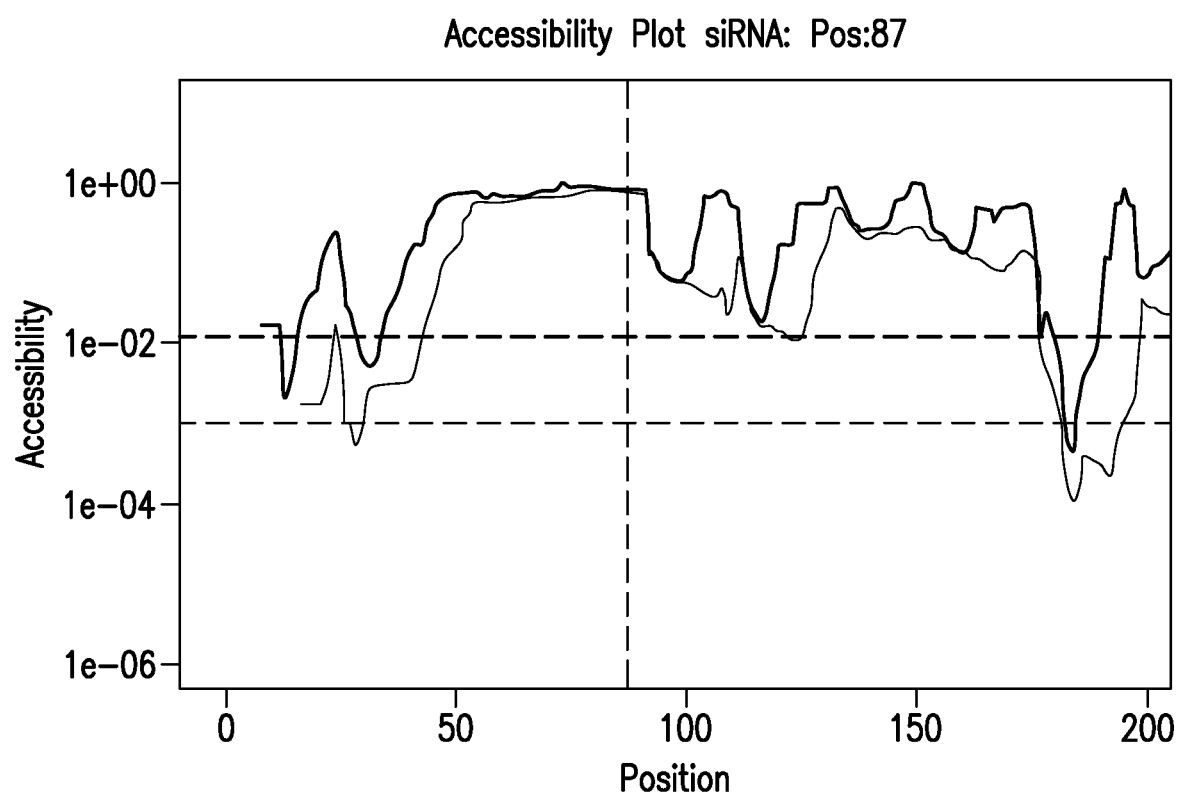

FIG. 3 depicts an RNAi accessibility analysis showing a good candidate region in the THCA gene (good RNA accessibility) for RNAi targeting located in the N-terminal region (corresponding to the 5'-end) of the THCA gene. This region of the gene does not encode any conserved protein domains and is therefore suitable for RNAi targeting with only a minimal risk of off-target effects. This region was used for the design of a small hair pin RNA interference construct. Analysis was performed using RNAxs Webserver, available at rna.tbi.univie.ac.at/cgi-bin/RNAxs.

Figure 4:
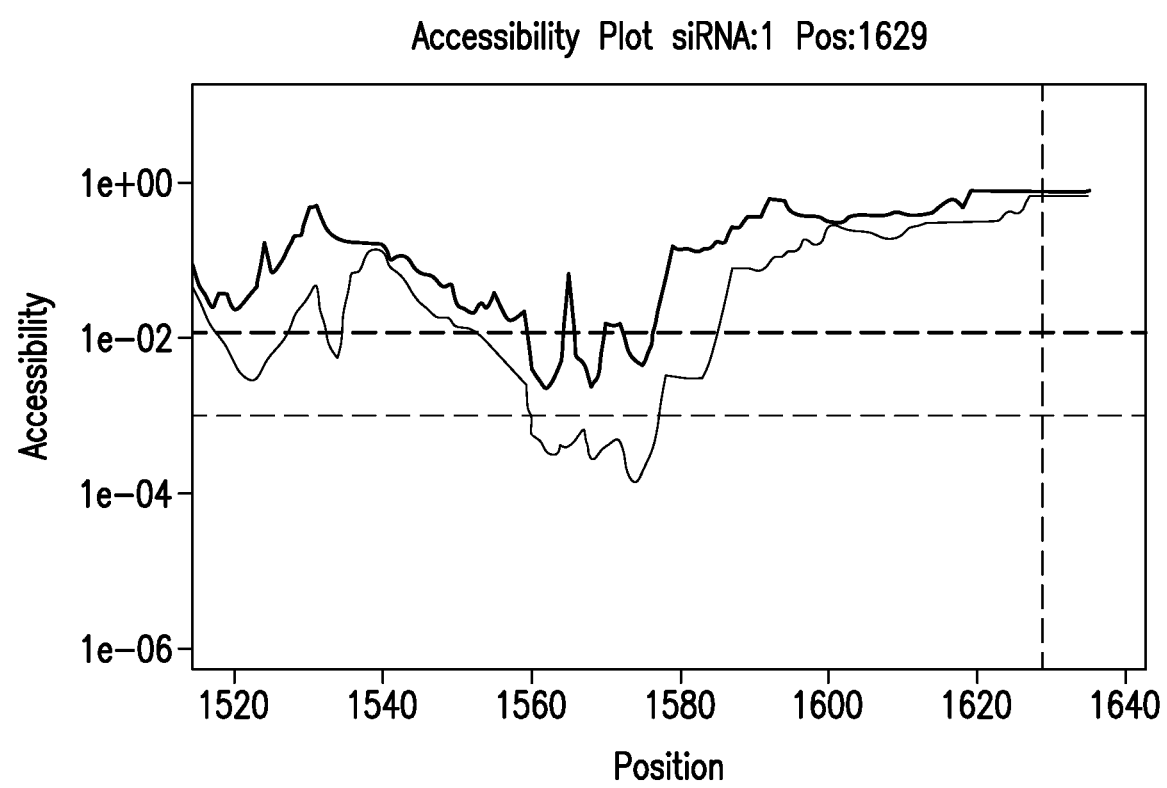

FIG. 4 depicts an RNAi accessibility analysis showing a candidate region in the THCA gene (RNA accessibility) for RNAi targeting. Depicted is the C-terminal BBE conserved domain. As this domain may be present in other secondary metabolism enzymes, this area was avoided due to the risk to induce silencing in other secondary metabolite-enzymes encoding genes. Analysis was performed using RNAxs Webserver, available at rna.tbi.univie.ac.at/cgi-bin/RNAxs.

Figure 5:
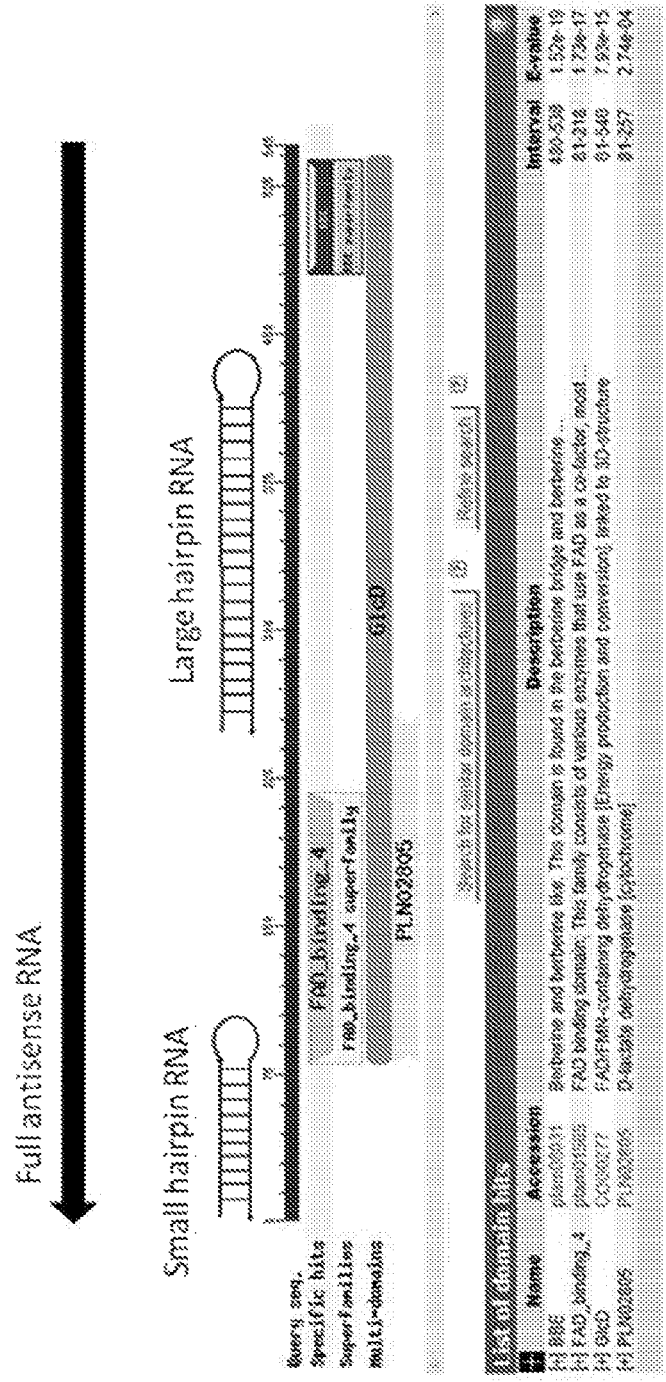

FIG. 5 depicts conserved protein domains in THCA synthase as analyzed using the National Center for Biotechnology Information (NCBI) database. The following conserved protein domains were found: berberine and berberine like (amino acid interval 480-538), FAD binding domain (amino acid interval 81-218), FAD/FMN containing dehydrogenase (amino acid interval 81-540), and D-lactate dehydrogenase (GlcD, amino acid interval 81-540). Depicted are also a full antisense RNA, a small hairpin RNA, and a large hairpin RNA relative to the schematic diagram of the conserved protein domains.

Figure 6:
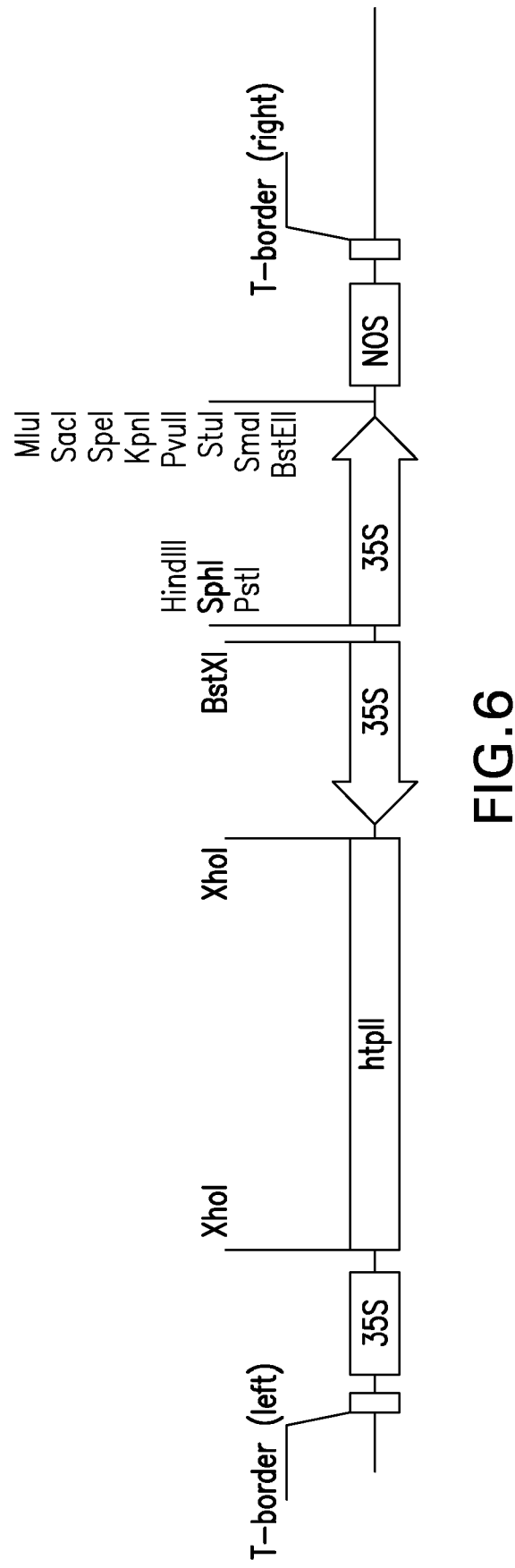

FIG. 6 depicts a diagram of pCAM1391-35S vector T-DNA employed in the cloning of antisense and RNAi constructs. Shown are Cauliflower mosaic virus promoter, (35S, on the right and in the center of FIG. 6, in arrowed boxes), hygromycin resistance gene (hptII); 35S terminator (35S, on the left of FIG. 6); nopaline synthase terminator (NOS). Restriction sites in MCS for cloning of gene of interested between 35S and NOS are also depicted. The vector can be used for *Agrobacterium*-mediated transformation, biolistic particle bombardment, and protoplast transformation of plants.

BRIEF DESCRIPTION OF THE SEQUENCES

SEQ ID NOs:1-38 are *Cannabis sativa* THCA synthase genes, or partial coding sequence (cds) thereof.

SEQ ID NO:39 is a *Cannabis sativa* gene for a hypothetical protein, complete cds.

SEQ ID NO:40 is a *Cannabis sativa* mRNA for THCA synthase precursor, complete cds.

SEQ ID NO:41 is a mRNA for cannabidiolic acid synthase homolog (CBDAS2); complete cds.

SEQ ID NO:42 is a *Cannabis sativa* CBDAS mRNA for cannabidiolic acid synthase, complete cds.

SEQ ID NO:43 is a *Cannabis sativa* mRNA for cannabidiolic acid synthase homolog (CBDAS3), complete cds.

SEQ ID NO:44 is a *Cannabis sativa* THCA synthase gene.

SEQ ID NO:45 is a *Cannabis sativa* THCA synthase gene.

SEQ ID NO:46 is the *Cannabis sativa* THCA synthase gene sequence of DK-1 *Cannabis sativa* strain.

SEQ ID NO:47 is the *Cannabis sativa* THCA synthase gene sequence of SH-4 *Cannabis sativa* strain.

SEQ ID NO:48 is the forward primer of Kojoma et al., (TGAAGAAAAAAAATGAATTGCTCAGCATTTTCC).

SEQ ID NO:49 is the complement of the reverse primer of Kojoma et al., (2006) (CCACCGCATCATCATTAATTATCTTTAAATAGA).

SEQ ID NO:50 is the actual reverse primer of Kojoma et al., (TCTATTTAAAGATAATTAATGATGATGCGGTGG).

SEQ ID NO:51 is the THCA-hpRNA1-SN-F1 (sense forward) RNAi construct primer.

SEQ ID NO:52 is the THCA-hpRNA1-SN-R1 (sense reverse) RNAi construct primer.

SEQ ID NO:53 is the THCA-hpRNA1-AS-F1 RNAi (antisense forward) construct primer.

SEQ ID NO:54 is the THCA-hpRNA1-AS-R1 (antisense reverse) RNAi construct primer.

SEQ ID NO:55 is the THCA-hpRNA2-SN-F2 RNAi construct primer.

SEQ ID NO:56 is the THCA-hpRNA2-SN-R2 RNAi construct primer.

SEQ ID NO:57 is the THCA-hpRNA2-AS-F2 RNAi construct primer.

SEQ ID NO:58 is the THCA-hpRNA2-AS-R2 RNAi construct primer.

SEQ ID NO:59 is the THCA-FullAS-F construct primer.

SEQ ID NO:60 is the THCA-FullAS-R construct primer.

SEQ ID NO:61 is the sense sequence of a small hair pin construct.

SEQ ID NO:62 is the loop sequence of a small hair pin construct.

SEQ ID NO:63 is the antisense sequence of the small hair pin construct.

SEQ ID NO:64 is the complete insert sequence of the small hair pin construct.

SEQ ID NO:65 is the THCA-hpRNA1-SN-F1 (sense forward) primer without restriction sites.

SEQ ID NO:66 is the THCA-hpRNA1-SN-R1 (sense reverse) primer without restriction sites.

SEQ ID NO:67 is the THCA-hpRNA1-AS-F1 RNAi (antisense forward) primer without restriction sites.

SEQ ID NO:68 is the THCA-hpRNA1-AN-R1 (antisense reverse) RNAi primer without restriction sites.

SEQ ID NO:69 is the sense strand of the large hair pin construct.

SEQ ID NO:70 is the loop strand of the large hair pin construct.

SEQ ID NO:71 is the antisense strand of the large hair pin construct.

SEQ ID NO:72 is the complete insert sequence of the large hair pin construct.

SEQ ID NO:73 is the THCA-hpRNA2-SN-F2 (sense forward) primer with SacI-MluI.

SEQ ID NO:74 is the THCA-hpRNA2-SN-F2 (sense forward) primer with out restriction sites.

SEQ ID NO:75 is the THCA-hpRNA2-SN-R2 primer.

SEQ ID NO:76 is the THCA-hpRNA2-SN-R2 primer without restriction sites.

SEQ ID NO:77 is the THCA-hpRNA2-AS-F2 primer.

SEQ ID NO:78 is THCA-hpRNA2-AS-F2 primer without restriction sites.
SEQ ID NO:79 is the THCA-hpRNA2-AS-R2 primer.
SEQ ID NO:80 is the THCA-hpRNA2-AS-R2 primer without restriction sites.
SEQ ID NO:81 is the full antisense THCA synthase.
SEQ ID NO:82 is the THCA-Full AS-F (antisense forward) primer.
SEQ ID NO:83 is the THCA-Full AS-F (antisense forward) primer, without restriction sites.
SEQ ID NO:84 is the THCA-Full AS-R (antisense reverse) primer.
SEQ ID NO:85 is the THCA-Full AS-R (antisense reverse) primer, without restriction sites.
SEQ ID NO:86 is the Consensus THCA-Full AS-R (antisense reverse) primer, without restriction sites.

DETAILED DESCRIPTION OF THE INVENTION

Described are genetically modified *cannabis* plants and *cannabis* plant derived products as well as expression cassettes, vectors, compositions, and materials and methods for producing the same. In particular, the present invention relates to *cannabis* plants that have modified expression of tetrahydrocannabinolic acid (THCA) synthase and methods of modifying the amount of delta-9-tetrahydrocannabinol (THC) and cannabidiol (CBD) in *cannabis* by modifying expression of THCA synthase.

Cannabis (*Cannabis sativa*) is well known and widely used for the production of medical *cannabis*. Along with key *cannabis* compound, tetrahydrocannabinolic acid (THC), *cannabis* also produces a range of other secondary metabolites with proven and potential value as pharmaceuticals. However, only low levels are produced within the plant and, thus, high production and purification costs represent the major barriers to commercial viability of these pharmaceuticals. Metabolic engineering of *cannabis* secondary metabolite biosynthesis pathways can re-direct biochemical reactions, intermediates and energy from biosynthesis of THC to alternative compounds. This approach can lead to the development of new *cannabis* strains with value added production of novel pharmaceuticals.

Plant secondary metabolite production results from tightly regulated biosynthetic pathways leading to the production of one or more bioactive metabolites that accumulate in the plant tissues at different concentrations. Metabolic engineering of these pathways can be used to generate plant lines with increased production of specific metabolite(s) of interest. Plant genetic engineering technologies can be applied to selectively modify *cannabis* secondary metabolism through the down regulation of key enzyme involved in THC biosynthesis. As demonstrated in multiple studies on variety of eukaryotic organisms, the down regulation of key steps in metabolic pathway re-directs intermediates and energy to alternative metabolic pathways and results in increased production and accumulation of other end products. Since THC and other valuable pharmaceutical compounds produced by *cannabis* share specific steps and intermediates in secondary metabolism biosynthetic pathways, the reduction of THC production is expected to increase the production of other compounds of interest.

In certain embodiments, the modification of tetrahydrocannabinolic acid (THCA) synthase enzyme can be achieved by targeted gene silencing induced by antisense RNA (asRNA) and small interfering RNA (siRNA) via RNA interference (RNAi) technologies. Both RNA mediated gene regulation mechanisms have been found in nature in all eukaryotes and today are successfully applied in numerous organisms as gene silencing tools. The advantage of such genetic modification strategies is that the transformation of the construct resulting in gene silencing does not require full gene knock-out by targeting a specific genome locus. In addition, the generated genetically modified plant lines can possess different levels of target gene down-regulation and can be screened for production of the most desirable set of pharmaceutical compounds.

The THCA synthase gene can be cloned from genomic DNA isolated from various *Cannabis sativa* strains. The cloning and sequencing of this gene from specific strains is an essential step as the variability in the sequence of this gene in different *Cannabis sativa* lines was demonstrated to affect production of *cannabis* compounds. Consensus sequence of the THCA synthase gene can be used to design and generate antisense RNA and RNA interference constructs. Synthesized RNA silencing constructs can be introduced into vectors designed for plant transformation. Different promoters can be used to drive expression of RNA silencing constructs such as constitutive promoters of different strength and origin. In addition, a THCA synthase gene regulatory region (promoter) may also be employed to direct expression of the silencing construct within the same tissues and during the same plant developmental phases as the native gene. This approach will help to avoid transgene expression in non-targeted plant tissues and minimize the risk of other possible and undesired effects of genetic modification.

In certain embodiments, vectors may have novel polylinkers such that pairs of restriction enzyme sites (RES) can be used for directional cloning. By choosing relatively rare RES, their presence in the DNA to be cloned is unlikely. Even if they do occur, a different pair of RES can be used and the presence of all four enzymes in a small piece of target DNA is very unlikely.

In certain embodiments, the THCA synthase gene can be cloned based upon sequence similarity.

In certain embodiments, asRNA can be synthesized using a strong promoter in the vector to transcribe asDNA from the vector. Several approaches can be used: In one approach, the entire THCA synthase gene will be cloned in the antisense orientation. Thus potentially any region of the gene can form an antisense complex with the plant's sense mRNA that cannot be translated to make functional THCA synthase.

In a different approach, various asDNAs that correspond to parts of the gene can be expressed with the following orientation: about 30 base pair from the gene or complement thereof—loop domain—same gene as the gene in the complement orientation. This will produce a siRNA that has been successfully used in a variety of organisms.

For both asDNA and vector construction a mixture of PCR+RES or DNA synthesis approaches can be used.

Described are polynucleotides as well as methods for modifying metabolite biosynthesis pathways in *cannabis* plants and/or *cannabis* plant cells, *cannabis* plants and/or plant cells exhibiting modified metabolite biosynthesis pathways. In particular, described are methods for modifying production of THC and/or CBD in *cannabis* plants by modulating the expression and/or activity of THCA synthase and *cannabis* plants having modified expression and/or activity of THCA synthase.

Accordingly, in certain embodiments, the present invention provides methods of downregulating production of THC. In particular embodiments, there is provided methods of downregulating expression and/or activity THCA synthase. Also provided are plants and/or plant cells having modified production of production of THC. In certain embodiments, there are provided *cannabis* plants and/or cells having down-regulated expression of and/or activity of THCA synthase.

Down regulation of key steps in metabolic pathway re-directs intermediates and energy to alternative metabolic pathways and results in increased production and accumulation of other end products. THC and other *cannabis* metabolites share a biosynthetic pathway; that cannabigerolic acid is a precursor of THC, CBD and Cannabichromene. In particular, THCA synthase catalyzes the production of delta-9-tetrahydrocannabinolic acid from cannabigerolic acid; delta-9-tetrahydrocannabinolic undergoes thermal conversion to form THC. CBDA synthase catalyzes the production of cannabidiolic acid from cannabigerolic acid; cannabidiolic acid undergoes thermal conversion to CBD. CBCA synthase catalyzes the production of cannabichromenic acid from cannabigerolic acid; cannabichromenic acid undergoes thermal conversion to cannabichromene.

A reduction in the production of THC, CBD, or Cannabichromene will enhance production of the remaining metabolites in this shared pathway. For example, production of CBD and/or Cannabichromene is enhanced by inhibiting production of THC. THC production may be inhibited by inhibiting expression and/or activity of tetrahydrocannabinolic acid (THCA) synthase enzyme.

Described are certain embodiments of enhancing production of one or more secondary metabolites by downregulation of the production of one or more metabolites having a shared biosynthetic pathway. Certain embodiments provide methods of enhancing production of one or more secondary metabolites that share steps and intermediates in the THC biosynthetic pathway by downregulation of THC production. In specific embodiments, there are provided methods of enhancing production of CBD and/or Cannabichromene by inhibiting production of THC.

Certain embodiments provide methods of enhancing production of one or more secondary metabolites which share steps and intermediates in the THC biosynthetic pathway by downregulation of expression and/or activity of THCA synthase. In specific embodiments, there are provided methods of enhancing production of CBD and/or Cannabichromene by downregulation of expression and/or activity of THCA synthase.

Also provided are plants and plant cells having modified production of one or more metabolites having a shared biosynthetic pathway. In certain embodiments, there are provided *cannabis* plants and cells enhanced production of one or more secondary metabolites and downregulation of one or more other metabolites having a shared biosynthetic pathway. In certain embodiments, there are provided *cannabis* plants and cells having enhanced production of one or more secondary metabolites and downregulation of one or more other metabolites in the THC biosynthetic pathway. In certain embodiments, there are provided *cannabis* plants and cells having enhanced production of one or more secondary metabolites in the THC biosynthetic pathway and downregulated THC production. In specific embodiments, there are provided *cannabis* plants and cells having enhanced production of CBD and/or Cannabichromene and downregulated THC production.

Certain embodiments provide for *cannabis* plants and/or cells having enhanced production of one or more secondary metabolites that share steps and intermediates in the THC biosynthetic pathway and downregulated expression and/or activity of THCA synthase. In specific embodiments, there are provided *cannabis* plants and/or cells having enhanced production of CBD and/or Cannabichromene and down-regulated expression and/or activity of THCA synthase.

Definitions

In the description and tables herein, a number of terms are used. In order to provide a clear and consistent understanding of the specification and claims, the following definitions are provided. Unless otherwise noted, terms are to be understood according to conventional usage by those of ordinary skill in the relevant art.

Where a term is provided in the singular, the inventors also contemplate aspects of the invention described by the plural of that term.

As used herein, the term "tetrahydrocannabinolic acid (THCA) synthase inhibitory compound" refers to a compound that suppresses or reduces an activity of THCA synthase enzyme activity, or expression of THCA synthase enzyme, such as for example synthesis of mRNA encoding a THCA synthase enzyme (transcription) and/or synthesis of a THCA synthase polypeptide from THCA synthase mRNA (translation). In some embodiments the selective THCA synthase inhibitory compound specifically inhibits a THCA synthase that decreases formation of delta-9-tetrahydrocannabinol (THC) and/or increases cannabidiol (CBD).

As used herein, the term "expression cassette" refers to a DNA molecule that comprises a selected DNA to be transcribed. In addition, the expression cassette comprises at least all DNA elements required for expression. After successful transformation, the expression cassette directs the cell's machinery to transcribe the selected DNA to RNA. In certain embodiments, the expression cassette expresses an antisense RNA, iRNA, or siRNA that suppresses expression of a THCA synthase.

Different expression cassettes can be transformed into different organisms including bacteria, yeast, plants, and mammalian cells as long as the correct regulatory sequences are used.

As used herein, the term "expression" refers to the combination of intracellular processes, including transcription and translation undergone by a coding DNA molecule such as a structural gene to produce a polypeptide. Expression of antisense RNA, iRNA, or siRNA refers to the process of transcribing DNA into RNA.

As used herein, the term "abundance of a protein" refers to the amount of the specific protein relative to the amount of total protein or relative to the weight or volume of the cell, tissue, plant, or plant part tested.

As used herein, the term "abundance of a mRNA" refers to the amount of the specific mRNA relative to the amount of total protein or relative to the weight or volume of the cell, tissue, plant, or plant part tested.

As used herein, the term "genetic transformation" refers to process of introducing a DNA sequence or construct (e.g., a vector or expression cassette) into a cell or protoplast in which that exogenous DNA is incorporated into a chromosome or is capable of autonomous replication.

As used herein, the term "heterologous" refers to a sequence which is not normally present in a given host genome in the genetic context in which the sequence is currently found. In this respect, the sequence may be native to the host genome, but be rearranged with respect to other genetic sequences within the host sequence. For example, a regulatory sequence may be heterologous in that it is linked to a different coding sequence relative to the native regulatory sequence.

As used herein, the term "obtaining" when used in conjunction with a transgenic plant cell or transgenic plant, means transforming a non-transgenic plant cell or plant to create the transgenic plant cell or plant, or planting transgenic plant seed to produce the transgenic plant cell or plant. Such a transgenic plant seed may be from an R0 transgenic plant or may be from a progeny of any generation thereof that inherits a given transgenic sequence from a starting transgenic parent plant. In addition, "obtaining" includes obtaining plants through breeding.

As used herein, the term "R0 transgenic plant" refers to a plant that has been genetically transformed or has been regenerated from a plant cell or cells that have been genetically transformed.

As used herein, the term "transformation construct" refers to a chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

As used herein, the term "transgene" refers to a segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

As used herein, the term "transgenic plant" refers to a plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

As used herein, the term "vector" refers to a DNA molecule designed for transformation into a host cell. Some vectors may be capable of replication in a host cell. A plasmid is an exemplary vector, as are expression cassettes isolated therefrom.

As used herein, the terms "DNA," "DNA molecule," and "DNA polynucleotide molecule" refer to a single-stranded DNA or double-stranded DNA molecule of genomic or synthetic origin, such as, a polymer of deoxyribonucleotide bases or a DNA polynucleotide molecule.

As used herein, the terms "DNA sequence," "nucleotide sequence," and "polynucleotide sequence" refer to the nucleotide sequence of a DNA molecule. ssDNA refers to single-stranded DNA; dsDNA refers to double-stranded DNA.

As used herein, the terms "RNA" or "RNA molecule" refer to a single-stranded RNA or double-stranded RNA molecule of genomic or synthetic origin, such as, a polymer of ribonucleotide bases that comprise single or double stranded regions. "ssRNA" specifically refers to single-stranded RNA; "dsRNA" refers to double-stranded RNA.

Unless otherwise stated, nucleotide sequences in the text of this specification are given, when read from left to right, in the 5' to 3' direction. The nomenclature used herein is that required by Title 37 of the United States Code of Federal Regulations § 1.822 and set forth in the tables in WIPO Standard ST.25 (1998), Appendix 2, Tables 1 and 3.

As used herein, a polynucleotides may be in the form of ssDNA, encompass dsDNA equivalents, dsRNA equivalents, ssRNA equivalents, ssRNA complements, ssDNA, and ssDNA complements.

As used herein, a first nucleic-acid sequence, selected DNA, or polynucleotide is "operably" connected or "linked" with a second nucleic acid sequence when the first nucleic acid sequence is placed in a functional relationship with the second nucleic acid sequence. For instance, a promoter is operably linked to an RNA and/or protein-coding sequence, or a sequence encoding an iRNA, an siRNA, or a nucleic acid encoding an antisense oligonucleotide if the promoter provides for transcription or expression of the RNA or coding sequence. Generally, operably linked DNA sequences are contiguous and, where necessary to join two protein-coding regions, are in the same reading frame.

In certain embodiment, the selected DNA encodes an antisense RNA or RNAi construct. In another embodiment, the selected DNA encodes a ribozyme, or zinc-finger protein.

As used herein, the phrase "wherein said plant does not comprise a transgene" refers to a plant that lacks either a DNA molecule comprising a promoter that is operably linked to a polynucleotide or a recombinant viral vector.

As used herein, the term "transcript" corresponds to any RNA that is produced from a gene by the process of transcription. A transcript of a gene can thus comprise a primary transcription product which can contain introns or can comprise a mature RNA that lacks introns.

As used herein, "nucleases" means natural and engineered (i.e. modified) polypeptides with nuclease activity such as endonucleases possessing sequence motifs and catalytic activities of the "LAGLIDADG," "GIY-YIG," "His-Cys box," and HNH families (e.g. Chevalier and Stoddard, 2001), as well as zinc finger nucleases (ZFNs), naturally occurring or engineered for a given target specificity (e.g. Durai et al., 2005; U.S. Pat. No. 7,220,719), among others. Another contemplated endonuclease is the *Saccharomyces cerevisiae* HO nuclease (e.g. Nickoloff et al., 1986), or variant thereof.

As used herein, a "custom endonuclease" means an endonuclease that has been evolved or rationally designed (e.g. WO06097853, WO06097784, WO04067736, or US20070117128) to cut within or adjacent to one or more recognition sequences. Such a custom endonuclease would have properties making it amenable to genetic modification such that its recognition, binding and/or nuclease activity could be manipulated.

As used herein, an "allele" refers to an alternative sequence at a particular locus; the length of an allele can be as small as 1 nucleotide base, but is typically larger. Allelic sequence can be denoted as nucleic acid sequence or as amino acid sequence that is encoded by the nucleic acid sequence. Alternatively, an allele can be one form of a gene, and may exhibit simple dominant or recessive behavior, or more complex genetic relationships such as incomplete dominance, co-dominance, conditional dominance, epistasis, or one or more combinations thereof with respect to one or more other allele(s).

A "locus" is a position on a genomic sequence that is usually found by a point of reference; e.g., a short DNA sequence that is a gene, or part of a gene or intergenic region. The loci of this invention comprise one or more polymorphisms in a population; i.e., alternative alleles present in some individuals.

Nucleic Acids

The present invention provides for nucleic acids comprising nucleotide sequences or sequences complementary to the nucleotide sequence encoding THCA synthase and fragments thereof. Nucleic acids include, but are not limited to, genomic DNA, cDNA, RNA, fragments and modified versions thereof.

As used herein, "polynucleotide" may refer to a DNA or RNA molecule containing multiple nucleotides and generally refers both to "oligonucleotides" (a polynucleotide molecule of 18-25 nucleotides in length) and longer polynucleotides of 26 or more nucleotides. Embodiments of this invention include compositions including oligonucleotides having a length of 18-25 nucleotides (18-mers, 19-mers, 20-mers, 21-mers, 22-mers, 23-mers, 24-mers, or 25-mers), and longer, or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e.g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target THCA synthase gene, including coding or non-coding or both coding and non-coding portions of the THCA synthase gene. Where a polynucleotide is double-stranded, its length can be similarly described in terms of base pairs.

Polynucleotide compositions used in the various embodiments of this invention include compositions including oligonucleotides, polynucleotides, or a mixture of both, including: RNA or DNA or RNA/DNA hybrids or chemically modified oligonucleotides or polynucleotides or a mixture thereof. In certain embodiments, the polynucleotide may be a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In certain embodiments, the polynucleotide includes non-canonical nucleotides such as inosine, thiouridine, or pseudouridine. In certain embodiments, the polynucleotide includes chemically modified nucleotides. Examples of chemically modified oligonucleotides or polynucleotides are well known in the art; see, for example, U.S. Patent Publication 2011/0171287, U.S. Patent Publication 2011/0171176, U.S. Patent Publication 2011/0152353, U.S. Patent Publication 2011/0152346, and U.S. Patent Publication 2011/0160082, which are herein incorporated by reference. Illustrative examples include, but are not limited to, the naturally occurring phosphodiester backbone of an oligonucleotide or polynucleotide which can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (e.g., fluorescein or rhodamine) or other label (e.g., biotin).

Polynucleotides can be single- or double-stranded RNA, single- or double-stranded DNA, double-stranded DNA/RNA hybrids, and modified analogues thereof. In certain embodiments of the invention, the polynucleotides that provide single-stranded RNA in the plant cell may be: (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, (f) a single-stranded DNA molecule including that is transcribed to an RNA molecule, (g) a double-stranded DNA molecule (dsDNA), (h) a double-stranded DNA molecule that is transcribed to an RNA molecule, and (i) a double-stranded, hybridized RNA/DNA molecule, or combinations thereof. In certain embodiments, these polynucleotides can comprise both ribonucleic acid residues and deoxyribonucleic acid residues. In certain embodiments, these polynucleotides include chemically modified nucleotides or non-canonical nucleotides. In certain embodiments of the methods, the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In certain embodiments where the polynucleotide is a dsRNA, the anti-sense strand may comprise at least 18 nucleotides that are essentially complementary to the target THCA synthase gene. In certain embodiments the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for suppression.

The polynucleotide molecules of the present invention are designed to modulate expression by inducing regulation or suppression of an endogenous THCA synthase gene, to reduce the content of THC and/or increase content of CDB in a *cannabis* plant and are designed to have a nucleotide sequence essentially identical or essentially complementary to the nucleotide sequence of an endogenous THCA synthase gene of a plant or to the sequence of RNA transcribed from an endogenous THCA synthase gene of a plant, which can be coding sequence or non-coding sequence. These effective polynucleotide molecules that modulate expression are referred to herein as "a trigger, or triggers."

By "essentially identical" or "essentially complementary" it is meant that the trigger polynucleotides (or at least one strand of a double-stranded polynucleotide) have sufficient identity or complementarity to the endogenous gene or to the RNA transcribed from the endogenous THCA synthase gene (e.g., the transcript) to suppress expression of the endogenous THCA synthase gene (e.g., to effect a reduction in levels or activity of the gene transcript and/or encoded protein). Polynucleotides of the methods and compositions provided herein need not have 100 percent identity to a complementarity to the endogenous THCA synthase gene or to the RNA transcribed from the endogenous THCA synthase gene (i.e., the transcript) to suppress expression of the endogenous THCA synthase gene (i.e., to effect a reduction in levels or activity of the gene transcript or encoded protein). Thus, in certain embodiments, the polynucleotide or a portion thereof is designed to be essentially identical to, or essentially complementary to, a sequence of at least 18 or 19 contiguous nucleotides in either the target gene or messenger RNA transcribed from the target gene (e.g., the transcript). In certain embodiments, an "essentially identical" polynucleotide has 100 percent sequence identity or at least about 85, 86, 87, 88, 89, 90, 91, 92, 93, 94, 95, 96, 97, 98, or 99 percent sequence identity when compared to the sequence of 18 or more contiguous nucleotides in either the endogenous target gene or to an RNA transcribed from the target gene (e.g., the transcript). In certain embodiments, an "essentially complementary" polynucleotide has 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene. Complements of polynucleotides include complete complementary and complete reverse complimentary sequences of the reference sequence.

In certain embodiments, polynucleotides used in the methods and compositions provided herein can be essentially identical or essentially complementary to any of: i) conserved regions of the THCA synthase gene, non-conserved regions of THCA synthase gene. Such polynucleotides that are essentially identical or essentially complementary to such regions can be used to reduce delta-9-tetrahydrocannabinol (THC) and/or increase cannabidiol (CBD).

Polynucleotides containing mismatches to the target gene or transcript can thus be used in certain embodiments of the compositions and methods provided herein. In certain embodiments, a polynucleotide can comprise at least 19 contiguous nucleotides that are essentially identical or essentially complementary to said gene or said transcript or comprises at least 19 contiguous nucleotides that are essentially identical or essentially complementary to the target gene or target gene transcript. In certain embodiments, a polynucleotide of 19 continuous nucleotides that is essentially identical or essentially complementary to the endogenous target gene or to a RNA transcribed from the target gene (e.g., the transcript) can have 1 or 2 mismatches to the target gene or transcript. In certain embodiments, a polynucleotide of 20 or more nucleotides that contains a contiguous 19 nucleotide span of identity or complementarity to the endogenous target gene or to an RNA transcribed from the target gene can have 1 or 2 mismatches to the target gene or transcript. In certain embodiments, a polynucleotide of 21 continuous nucleotides that is essentially identical or essentially complementary to the endogenous target gene or to an RNA transcribed from the target gene (e.g., the transcript) can have 1, 2, or 3 mismatches to the target gene or transcript. In certain embodiments, a polynucleotide of 22 or more nucleotides that contains a contiguous 21 nucleotide span of identity or complementarity to the endogenous target gene or to an RNA transcribed from the target gene can have 1, 2, or 3 mismatches to the target gene or transcript. In designing polynucleotides with mismatches to an endogenous target gene or to an RNA transcribed from the target gene, mismatches of certain types and at certain positions that are more likely to be tolerated can be used. In certain exemplary embodiments, mismatches formed between adenine and cytosine or guanosine and uracil residues are used as described by Du et al. Nucleic Acids Research, 2005, Vol. 33, No. 5 1671-1677. In certain exemplary embodiments, mismatches in 19 base pair overlap regions can be at the low tolerance positions 5, 7, 8 or 11 (from the 5' end of a 19 nucleotide target) with well tolerated nucleotide mismatch residues, at medium tolerance positions 3, 4, and 12-17, and/or at the high tolerance nucleotide positions at either end of the region of complementarity (i.e., positions 1, 2, 18, and 19) as described by Du et al. Nucleic Acids Research, 2005, Vol. 33, No. 5 1671-1677. It is further anticipated that tolerated mismatches can be empirically determined in assays where the polynucleotide is applied to the plants via the methods provided herein and the treated plants assayed for suppression of THCA synthase gene expression or appearance of improved shelf life and reduced postharvest losses.

In certain embodiments, polynucleotide molecules are designed to have 100 percent sequence identity with or complementarity to one allele or one family member of a given THCA synthase gene coding or non-coding sequence. Target THCA synthase genes include the THCA synthase genes of SEQ ID NO:1-47. In other embodiments, the polynucleotide molecules are designed to have 100 percent sequence identity with or complementarity to multiple alleles or family members of a given target gene.

In certain embodiments, polynucleotide compositions and methods provided herein typically effect regulation or modulation (e. g., suppression) of gene expression during a period during the life of the treated plant of at least 1 week or longer and typically in systemic fashion. For instance, within days of treating a plant leaf with a polynucleotide composition of this invention, primary and transitive siRNAs can be detected in other leaves lateral to and above the treated leaf and in apical tissue. In certain embodiments, methods of systemically suppressing expression of a gene in a plant, the methods comprising treating said plant with a composition comprising at least one polynucleotide and a transfer agent, wherein said polynucleotide comprises at least 18 or at least 19 contiguous nucleotides that are essentially identical or essentially complementary to a gene or a transcript encoding a THCA synthase gene of the plant are provided, whereby expression of the gene in said plant or progeny thereof is systemically suppressed in comparison to a control plant that has not been treated with the composition.

Compositions used to suppress a target gene can comprise one or more polynucleotides that are essentially identical or essentially complementary to multiple genes, or to multiple segments of one or more genes. In certain embodiments, compositions used to suppress a target gene can comprise one or more polynucleotides that are essentially identical or essentially complementary to multiple consecutive segments of a target gene, multiple non-consecutive segments of a target gene, multiple alleles of a target gene, or multiple target genes from one or more species.

In certain embodiments, the polynucleotide includes two or more copies of a nucleotide sequence (of 18 or more nucleotides) where the copies are arranged in tandem fashion. In another embodiment, the polynucleotide includes two or more copies of a nucleotide sequence (of 18 or more nucleotides) where the copies are arranged in inverted repeat fashion (forming an at least partially self-complementary strand). The polynucleotide can include both tandem and inverted-repeat copies. Whether arranged in tandem or inverted repeat fashion, each copy can be directly contiguous to the next, or pairs of copies can be separated by an optional spacer of one or more nucleotides. The optional spacer can be unrelated sequence (i.e., not essentially identical to or essentially complementary to the copies, nor essentially identical to, or essentially complementary to, a sequence of 18 or more contiguous nucleotides of the endogenous target gene or RNA transcribed from the endogenous target gene). Alternatively the optional spacer can include sequence that is complementary to a segment of the endogenous target gene adjacent to the segment that is targeted by the copies. In certain embodiments, the polynucleotide includes two copies of a nucleotide sequence of between about 20 to about 30 nucleotides, where the two copies are separated by a spacer no longer than the length of the nucleotide sequence.

In certain embodiments, the nucleic acid molecule comprises the sequence or the compliment of the sequences as set forth in GenBank Accession number JQ437488.1 (SEQ ID NO:1); JQ437487.1 (SEQ ID NO:2); JQ437486.1 (SEQ ID NO:3); JQ437485.1 SEQ ID NO:4); JQ437484.1 (SEQ ID NO:5); JQ437483.1 (SEQ ID NO:6); JQ437482.1 (SEQ ID NO:7); JQ437481.1 (SEQ ID NO:8); JQ437496.1 (SEQ ID NO:9); JQ437495.1 (SEQ ID NO:10), JQ437494.1 (SEQ ID NO:11); JQ437493.1 (SEQ ID NO:38); JQ437492.1 (SEQ ID NO:12); JQ437491.1 (SEQ ID NO:13); JQ437490.1 (SEQ ID NO:14); JQ437489.1 (SEQ ID NO:15); AB212841.1 (SEQ ID NO:16), AB212840.1 (SEQ ID NO:17); AB212839.1 (SEQ ID NO:18); AB212838.1 (SEQ ID NO:19); AB212837.1 (SEQ ID NO:20); AB212836.1 (SEQ ID NO:21); AB212835.1 (SEQ ID NO:22); AB212834.1 (SEQ ID NO:23); AB212833.1 (SEQ ID NO:24); AB212832.1 (SEQ ID NO:25); AB212831.1 (SEQ ID NO:26); AB212830.1 (SEQ ID NO:27); AB212829.1 (SEQ ID NO:28); AB183705.1 (SEQ ID NO:29) AB183704.1 (SEQ ID NO:30); AB183703.1 (SEQ ID NO:31); AB183702.1 (SEQ ID NO:32); AB183701.1 (SEQ ID NO:33); AB183700.1 (SEQ ID NO:34); AB183699.1 (SEQ ID NO:35); AB183698.1 (SEQ ID NO:36), EU839988.1 (SEQ ID NO:37); AB057805.1 (SEQ ID NO:40); E33090.1 (SEQ ID NO:44), E33091.1 (SEQ ID NO:45), AB731220.1 (SEQ ID NO:39); a variant or fragment thereof, or a polynucleotide sequence having at least about 83, 84, 85, 86, 87, 88, 89, 90, 91, 92, 93, 94, 95, 96, 97, 98, or 99 percent sequence identity or 100% sequence identity to a nucleic acid molecules. In certain embodiments the fragment has at least 18, 19, 20, 21, 22, 24, 25, 80, 100, 150, or 200 consecutive nucleotides.

In certain embodiments, the nucleic acid molecule comprises the sequence or the compliment of the sequences as set forth in GenBank Accession number AB731220.1 (SEQ ID NO:39); AB292682.1 (SEQ ID NO:42); AB292683.1 (SEQ ID NO:41); AB292684.1 (SEQ ID NO:43); AB212829.1 (SEQ ID NO:28); AB212838.1 (SEQ ID NO:19); AB212837.1 (SEQ ID NO:20); AB212835.1 (SEQ ID NO:22); AB212834.1 (SEQ ID NO:23); AB212832.1 (SEQ ID NO:25); AB057805.1 (SEQ ID NO:40) AB731220.1 (SEQ ID NO:39); AB212833.1 (SEQ ID NO:24); AB212836.1 (SEQ ID NO:21); AB212841.1 (SEQ ID NO:16); AB212831.1 (SEQ ID NO:26); AB212839.1 (SEQ ID NO:18); AB212830.1 (SEQ ID NO:27); AB212840.1 (SEQ ID NO:17); JQ437490.1 (SEQ ID NO:14); JQ437485.1 SEQ ID NO:4); JQ437487.1 (SEQ ID NO:2); JQ437486.1 (SEQ ID NO:3); JQ437481.1 (SEQ ID NO:8); JQ437482.1 (SEQ ID NO:7); JQ437483.1 (SEQ ID NO:6); JQ437484.1 (SEQ ID NO:5); JQ437488.1 (SEQ ID NO:1); JQ437492.1 (SEQ ID NO:12); JQ437489.1 (SEQ ID NO:15); JQ437491.1 (SEQ ID NO:13); a variant or fragment thereof, or a polynucleotide sequence having at least about 83, 84, 85, 86, 87, 88, 89, 90, 91, 92, 93, 94, 95, 96, 97, 98, or 99 percent sequence identity or 100% sequence identity to a nucleic acid molecules. In certain embodiments the fragment has at least 18, 19, 20, 21, 22, 24, 25, 80, 100, 150, or 200 consecutive nucleotides.

In other embodiments, there is provided a nucleic acid comprising a sequence having at least 50%, 55%, 60%, 65%, 70%, 75%, 80%, 85%, 90%, 95%, 96%, 97%, 98%, 99% or 100% identity to sequences encoding THCA synthase and fragments thereof or the complement thereof.

In some embodiments of the present invention, the nucleotide sequences comprise one or more substitutions, insertions and/or deletions. For certain embodiments, the nucleotide sequence includes one or more T-DNA insertions. In other embodiments, the nucleic acid comprises a selection marker cassette. In other embodiments, the nucleotide sequence includes one or more point mutations. In certain embodiments, the nucleotide sequence includes a deletion. In certain embodiments, the nucleotide sequence includes a rearrangement. In certain embodiments, the nucleotide sequence includes a frame shift.

Also provided are nucleic acids that hybridize to the nucleic acids of the present invention or the complement thereof. In certain embodiments, there is provided a nucleic acid that hybridizes to any one of the sequences under conditions of low, moderate or high stringency. A worker skilled in the art readily appreciates that hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids. Such a worker could readily determine appropriate stringent conditions (see, for example, Sambrook, et al., Molecular Cloning: A Laboratory Manual, 2nd ed., Cold Spring Harbor Laboratory Press, New York (1989) pp. 9.50-51, 11.48-49 and 11.2-11.3).

Typically under high stringency conditions only highly similar sequences will hybridize (typically >95% identity). Under moderate stringency conditions typically those sequence having greater than 80% identity will hybridize and under low stringency conditions those sequences having greater than 50% identity will hybridize.

A non-limiting example of "high stringency conditions" when used in reference to nucleic acid hybridization comprise conditions equivalent to binding or hybridization at 42° C. in a solution consisting of 5×SSPE (43.8 g/l NaCl, 6.9 g/l NaH2PO4H2O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed. A non-limiting example of "medium stringency conditions" when used in reference to nucleic acid hybridization comprise conditions equivalent to binding or hybridization at 42° C. in a solution consisting of 5×SSPE (43.8 g/l NaCl, 6.9 g/l NaH2PO4H2O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed. A non-limiting example "low stringency conditions" when used in reference to nucleic acid hybridization comprise conditions equivalent to binding or hybridization at 42° C. in a solution consisting of 5×SSPE (43.8 g/l NaCl, 6.9 g/l NaH2PO4H2O and 1.85 g/l EDTA, pH adjusted to 7.4 with NaOH), 0.5% SDS, 5×Denhardt's reagent and 100 μg/ml denatured salmon sperm DNA followed by washing in a solution comprising 5×SSPE, 0.1% SDS at 42° C. when a probe of about 500 nucleotides in length is employed. The nucleic acids may include additional sequences. For example, the nucleic acids may include multiple restriction sites, additional coding sequences (e.g., a purification tag, a localization signal, as a fusion-protein, as a pre-protein, or the like) and/or with non-coding sequences (e.g., introns or inteins, regulatory elements such as promoters (including constitutive promoters such as the CaMV 35S promoter, inducible promoters, tissue-specific promoters (such as root-specific, flower-specific promoters, fruit-specific promoters, seed specific promoters or leaf specific promoters), enhancers, terminators, and the like), and/or in a vector or host environment in which the polynucleotide encoding a transcription factor or transcription factor homologue polypeptide is an endogenous or exogenous gene. Appropriate additional coding sequences (e.g., a purification tag, a localization signal, as a fusion-protein, as a pre-protein, or the like), non-coding sequences (e.g., introns, regulatory elements such as promoters (including constitutive promoters, inducible promoters, tissue specific promoters), enhancers, terminators, and the like), and vectors for use in plants/plant cells are known in the art.

Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. The PAL2 promoter may in particular be useful with the invention (U.S. Pat. Appl. Pub. 2004/0049802, the entire disclosure of which is specifically incorporated herein by reference).

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

It is envisioned that polynucleotide sequences or selected DNA sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue. In certain embodiments, promoters can be employed that cause low expression of the selected DNA. Low expression promoters can be obtained by mutation and/or recombination of DNA elements of promoters that cause high expression or by selecting upstream regulatory elements of genes that cause expression of mRNA or protein with low abundance.

Promoters have been described in the art; thus the invention provides, in certain embodiments, novel combinations of promoters and a selected DNA. In one embodiment, a constitutive promoter is cloned 5' to selected DNA in order to constitutively express the selected DNA in transformed cells.

In another embodiment, an inducible promoter can be used to turn on expression of the selected DNA under certain conditions. For example, a cold shock promoter cloned upstream of selected DNA might be used to induce the selected DNA under cold temperatures. Other environmentally inducible promoters have been described and can be used in a novel combination with a selected DNA. Another type of inducible promoter is a chemically-inducible promoter. Such promoters can be precisely activated by the application of a chemical inducer. Examples of chemical inducible promoters include the steroid inducible promoter and a quorum sensing promoter (see, e.g., You et al., 2006; U.S. Patent Application Publication No. 2005/0227285). Recently it has been shown that modified RNA molecules comprising a ligand specific aptamer and riboswitch can be used to chemically regulate the expression of a target gene (Tucker et al, 2005; International Publication No. WO2006073727). Such a riboregulator can be used to control the expression of a TALER-encoding gene by the addition or elimination of a chemical ligand.

The construct may comprise a nucleotide sequence of the invention operably linked to a promoter sequence that functions in the host cell. Such a promoter may be tissue-specific and may, for example, be specific to a tissue type which is the subject of pest attack. In the case of rootworms, for example, it may be desired to use a promoter providing leaf-preferred expression.

Promoters that function in different plant species are also well known in the art. Promoters useful for expression of polypeptides in plants include those that are inducible, viral, synthetic, or constitutive as described in Odell et al. (1985), and/or promoters that are temporally regulated, spatially regulated, and spatio-temporally regulated. Preferred promoters include the enhanced CaMV35S promoters, and the FMV35S promoter. For the purpose of the present invention, e.g., for optimum control of species that feed on roots, it may be preferable to achieve the highest levels of expression of these genes within the roots of plants. A number of root-enhanced promoters have been identified and are known in the art (Lu et al., 2000; U.S. Pat. Nos. 5,837,848 and 6,489,542).

Examples of leaf-specific promoter are described in U.S. Pat. No. 6,229,067, which is hereby incorporated by reference in its entirety, and flower-specific promoter are known in the art and described in Du L., et al., Plant Molecular Biology Reporter, February 2014, Volume 32, Issue 1, pp 234-245.

Terminators

Transformation constructs prepared in accordance with the invention will typically include a 3' end DNA sequence that acts as a signal to terminate transcription and allow for the poly-adenylation of the mRNA produced by coding sequences operably linked to a promoter. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

Marker Genes

By employing a selectable or screenable marker protein, one can provide or enhance the ability to identify transformants "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a beta-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an alpha-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a beta-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228). The gene that encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

Plants/Plant Cells Having Modified Expression and/or Activity of THCA Synthase

Described are *cannabis* plants and/or plant cells having modified production of THC as compared to wild-type plants (for example, original cultivars). In certain embodiments, there is provided *cannabis* plants and/or cells having downregulated expression and/or activity of THCA synthase as compared to wild-type plants (for example, original cultivars). In certain embodiments the *cannabis* plants and/or cells produce reduced amounts or no THC. In certain embodiments of the *cannabis* plants and/or cells with reduced amounts or no THC, there is increased production of other metabolites on the THC biosynthesis pathway.

In certain embodiments, there is provided *cannabis* plants and cells having enhanced production of one or more secondary metabolites in the THC biosynthetic pathway and downregulated THC production. In specific embodiments, there is provided *cannabis* plants and cells having enhanced production of CBD and/or Cannabichromene and down-regulated THC production.

In certain embodiments, there is provided *cannabis* plants and/or cells having enhanced production of one or more secondary metabolites which share steps and intermediates in the THC biosynthetic pathway and down-regulated expression and/or activity of THCA synthase. In specific embodiments, there is provided *cannabis* plants and/or cells having enhanced production of CBD and/or Cannabichromene and down-regulated expression and/or activity of THCA synthase.

*Cannabis* plants can be engineered to have modified expression and/or activity of other proteins in addition to THCA synthase. For example, the *cannabis* plants may also include modified expression and/or activity of other enzymes sharing intermediates with THCA synthase, such as CBDA synthase, CBCA synthase. Likewise, the *cannabis* plants of the invention may be crossed with plants having specific phenotypes.

The *cannabis* plants with modified secondary metabolite production may be non-mutagenized, mutagenized, or transgenic, and the progeny thereof.

In certain embodiments, the *cannabis* plants exhibiting modified secondary metabolite are the result of spontaneous mutations.

In certain embodiments, the *cannabis* plants exhibiting modified secondary metabolite have been mutagenized by chemical or physical means. For example, ethylmethane sulfonate (EMS) may be used as a mutagen or radiation, such as x-ray, gamma-ray, and fast-neutron radiation may be used as a mutagen.

In certain other embodiments, the *cannabis* plants exhibiting modified secondary metabolite are genetically engineered.

Antisense, siRNA and RNAi

Antisense or RNA interference approaches may be used to down-regulate expression of a nucleic acid of the invention, e.g., as a further mechanism for modulating plant phenotype. That is, antisense sequences of the nucleic acids of the invention, or subsequences thereof, may be used to block expression of naturally occurring homologous nucleic acids. A variety of sense and antisense technologies, e.g., as set forth in Lichtenstein and Nellen (Antisense Technology: A Practical Approach IRL Press at Oxford University, Oxford, England, 1997), can be used.

In certain embodiments, sense or antisense sequences are introduced into a cell, where they are transcribed. Such sequences may include both simple oligonucleotide sequences and catalytic sequences such as ribozymes.

In certain embodiments, a reduction or elimination of expression (i.e., a "knock-out" or "knockdown") THCA synthase in a transgenic plant is produced by introduction of a construct which expresses an antisense of THCA synthase coding strand or fragment thereof. For antisense suppression, the THCA synthase cDNA or fragment thereof is arranged in reverse orientation (with respect to the coding sequence) relative to the promoter sequence in the expression vector. In certain embodiments, the introduced sequence need not correspond to the full length cDNA or gene, and need not be identical to the cDNA or gene found in the plant to be transformed.

In certain embodiments, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, in some embodiments, the introduced antisense sequence in the vector is at least 30 nucleotides in length in certain embodiments. In certain embodiments, the length of the antisense sequence is increased, and improved antisense suppression is observed. In some embodiments, the length of the antisense sequence in the vector is greater than 100 nucleotides. Transcription of an antisense construct as described results in the production of RNA molecules that comprise a sequence that is the reverse complement of the mRNA molecules transcribed from the endogenous gene to be repressed. The antisense nucleic acid may also include additional sequences.

In certain embodiments, a reduction or elimination of expression (i.e., a "knock-out" or "knockdown") of THCA synthase in a transgenic plant is accomplished by introduction of a construct that expresses siRNA that targets THCA synthase. In certain embodiments, siRNAs are short (20 to 24-bp) double-stranded RNA (dsRNA) with phosphorylated 5' ends and hydroxylated 3' ends with two overhanging nucleotides.

Antisense and RNAi treatments represent one way of altering THCA synthase activity in accordance with the invention. In particular, constructs comprising a THCA synthase coding sequence, including fragments thereof, in antisense orientation, or combinations of sense and antisense orientation, may be used to decrease or effectively eliminate the expression of THCA synthase in a plant and obtain an improvement in shelf life as is described herein. Accordingly, this may be used to "knock-out" the THCA synthase or homologous sequences thereof.

Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the invention, such oligonucleotide may comprise any unique portion of a nucleic acid sequence provided herein. In certain embodiments of the invention, such a sequence comprises at least 18, 19, 20, 21, 22, 23, 24, 25, 26, 27, 28, 29, or 30 or more contiguous nucleic acids of the nucleic acid sequence of a THCA synthase, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs will include regions complementary to intron/exon splice junctions. Thus, one embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. The term "complement" also includes sequences that are inverse complementary to the reference sequence. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

Tiling

Polynucleotide trigger molecules can be identified by "tiling" gene targets in random length fragments, e.g., 200-300 polynucleotides in length, with partially overlapping regions, e.g., 25 or so nucleotide overlapping regions along the length of the target gene. Multiple gene target sequences can be aligned and polynucleotide sequence regions with homology in common are identified as potential trigger molecules for multiple targets. Multiple target sequences can be aligned and sequence regions with poor homology are identified as potential trigger molecules for selectively distinguishing targets. To selectively suppress a single gene, trigger sequences may be chosen from regions that are unique to the target gene either from the transcribed region or the non-coding regions, e.g., promoter regions, 3' untranslated regions, introns and the like.

In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

Insertion Mutagenesis

In one embodiment, a reduction or elimination of expression (i.e., a "knock-out") of THCA synthase in a transgenic plant can be obtained by insertion mutagenesis using the T-DNA of *Agrobacterium tumefaciens* or a selection marker cassette or any other non-sense DNA fragments. After generating the insertion mutants, the mutants can be screened to identify those containing the insertion in the THCA synthase gene. Plants containing one or more transgene insertion events at the desired gene can be crossed to generate homozygous plants for the mutation, as described in Koncz et al., (Methods in *Arabidopsis* Research; World Scientific, 1992).

Ribozyme

Suppression of gene expression may also be achieved using a ribozyme. Ribozymes are RNA molecules that possess highly specific endoribonuclease activity. The production and use of ribozymes are disclosed in U.S. Pat. Nos. 4,987,071 and 5,543,508, which are incorporated by reference in their entirety. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Dominant Negative Transcription Factors

Vectors expressing a mutated form of a transcription factor mRNA, e.g., sequences comprising one or more stop codon, or nonsense mutation) may also be used to suppress expression of a gene, such as THCA synthase, thereby reducing or eliminating it's activity and modifying one or more traits. Methods for producing such constructs are described in U.S. Pat. No. 5,583,021, which is incorporated herein by reference in its entirety. In certain embodiments, such constructs are made by introducing a premature stop codon into the transcription factor gene. Alternatively, a plant trait can be modified by gene silencing using double-strand RNA as described in Sharp (Genes and Development 13: 139-141, 1999).

Homologous Recombination or Site-Directed Mutagenesis

Plant phenotype may also be altered by eliminating an endogenous gene, e.g., by homologous recombination (Kempin et al. (1997) Nature 389: 802).

Targeted genome modification is a powerful tool for genetic manipulation of plant cells. For example, exogenous sequences can be integrated at targeted genomic locations and/or specific endogenous chromosomal sequences can be deleted, inactivated, or modified. In certain embodiments, engineered nuclease enzymes, such as, for example, zinc finger nucleases (ZFNs) or transcription activator-like effector nucleases (TALENs) are used.

In certain embodiments, custom designed genome-modifying enzymes using molecular biology methods can be used. At least one plant cell can be obtained comprising at least one recognition sequence for a custom endonuclease, wherein the custom endonuclease is a fusion protein and the fusion protein comprises a zinc finger DNA binding domain or a Vir protein domain. Further, the custom endonuclease can comprise a polypeptide, a catalytically active RNA, an RNA-directed endonuclease, or a synthetic aptamer. The custom endonuclease can, for instance, be a meganuclease, wherein the meganuclease is selected from the group consisting of I-CreI, PI-SceI, and I-CeuI. The custom endonuclease can, for instance, comprise a "LAGLIDADG," "GIY-YIG," "His-Cys Box," "ZFN," or "HNH" sequence motif.

In certain embodiments, the custom endonuclease is delivered as a protein or as a nucleic acid molecule. The nucleic acid molecule can be operably linked to a promoter active in the plant cell, wherein the promoter is a constitutive promoter, an inducible promoter, a tissue specific promoter, a cell cycle regulated promoter, or a developmentally regulated promoter. The nucleic acid construct can comprise at least one nucleic acid molecule that encodes at least one custom endonuclease flanked by one or more T-DNA borders. The construct can comprise a selectable or screenable marker gene.

The plant cell can further comprise a second exogenous custom endonuclease, wherein the first and the second exogenous custom endonuclease each comprise different recognition sequences within the genome of the plant cell and are capable of producing a cut proximal to said recognition sequences. The plant cell can further comprise a selected DNA, wherein selected DNA comprises a promoter, intron, coding sequence or 3' UTR.

A locus of interest in a plant cell is modified by introducing into a plant cell at least a first custom endonuclease, wherein the cell comprises a recognition sequence for the custom endonuclease in or proximal to the locus of interest; allowing the custom endonuclease to create a double stranded break in the DNA making up or flanking the locus of interest; and identifying the cell or a progeny cell thereof as comprising a modification in said locus of interest.

In certain cases, only one custom endonuclease recognition sequence is introduced in the genome of a plant cell; alternatively, at least a second custom endonuclease may be introduced to a plant cell, wherein the cell comprises a second recognition sequence for the second custom endonuclease and the at least a second endonuclease is introduced at the same time as the first endonuclease or under serial transformation. Any endonuclease introduced into the plant cell can be expressed transiently or stably.

Following transient or stable transformation of a plant cell with an expression construct encoding at least one custom endonuclease as well as a selectable or screenable marker gene, the plant or plant cell can be selected or screened based on the presence of the selectable or screenable marker gene.

Following transformation the custom endonuclease can produce a double stranded break in the genome of the plant cell proximal to the recognition sequence, wherein the double stranded break is in a sequence that encodes the gene product of interest. Further, the modification in the locus of interest comprises gene conversion, gene replacement, homologous recombination, heterologous recombination, a deletion, or homeologous recombination and wherein the modification is in a sequence that regulates the expression of a gene of interest.

Methods known in the art for assaying the cell or progeny cell thereof for evidence of the modification, including a genotypic assay, a phenotypic assay, or associating a plant genotype and a plant phenotype are used. The genotypic assay comprises PCR or nucleic acid sequencing. The phenotypic assay may comprise: a visual assay, measurement of an agronomic parameter, a biochemical assay, or an immunological assay.

Thus the invention provides a method for altering an allele at a locus of interest in a plant genome comprising: expressing in a plant cell a first and second custom endonucleases, wherein the first and second custom endonucleases introduce double stranded breaks that flank the locus of interest; and allowing genetic recombination to occur at the locus of interest. This method may further comprise introducing into the plant cell a target DNA, wherein the genetic recombination results in the replacement of the allele with the target DNA.

A plant trait may also be modified by using the Cre-lox system (for example, as described in U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

In addition, silencing approach using short hairpin RNA (shRNA) system, complementary mature CRISPR RNA (crRNA) by CRISPR/Cas system, virus inducing gene silencing (VIGS) system may also be used to make down regulated or knockout of THCA synthase mutants. Dominant negative approaches may also be used to make down regulated or knockout of THCA synthase mutants.

Other examples of site-directed mutagenesis include but are not limited to meganucleases and TALENs and also appreciate that post-translational gene silencing can be used to down regulate gene expression.

In certain embodiments, transgenic plants (or plant cells, or plant explants, or plant tissues) are produced by a variety of techniques as described above or known in the art. Following construction of a vector, the vector or a polynucleotide is introduced into a plant, a plant cell, a plant explant or a plant tissue of interest. In certain embodiments, the plant cell, explant or tissue can be regenerated to produce a transgenic plant.

RNA-Guided Endonucleases

In certain embodiments, RNA-guided endonucleases may be used for silencing target sequences as part of a protein-RNA complex comprising a guide RNA. The guide RNA interacts with the RNA-guided endonuclease to direct the endonuclease to a specific target site, wherein the 5' end of the guide RNA base pairs with a specific protospacer sequence.

The RNA-guided endonuclease can be derived from a clustered regularly interspersed short palindromic repeats (CRISPR)/CRISPR-associated (Cas) system. The CRISPR/Cas system can be a type I, a type II, or a type III system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

In general, CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNAse domains, protein-protein interaction domains, dimerization domains, as well as other domains.

The CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzyme activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein.

Transformation

Appropriate transformation techniques can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence into a plant in a manner to cause stable or transient expression of the sequence.

Examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369; and 5,610,042.

Following transformation, plants may be selected using a dominant selectable marker incorporated into the transformation vector. In certain embodiments, such marker confers antibiotic or herbicide resistance on the transformed plants, and selection of transformants can be accomplished by exposing the plants to appropriate concentrations of the antibiotic or herbicide. After transformed plants are selected and grown to maturity, those plants showing a modified trait are identified. The modified trait can be any of those traits described above. Additionally, expression levels or activity of the polypeptide or polynucleotide of the invention can be determined by analyzing mRNA expression using Northern blots, RT-PCR, RNA seq or microarrays, or protein expression using immunoblots or Western blots or gel shift assays.

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

*Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Microprojectile Bombardment

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.
Selection It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty□ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins m 2 s−1 of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with 10-5M abscisic acid and then transferred to growth regulator-free medium for germination.

Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzyme function; plant part assays, such as leaf or root assays; and also, by analyzing the phenotype of the whole regenerated plant.

DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

Gene Expression

While Southern blotting and PCR™ may be used to detect the gene(s) in question, they do not provide information as to whether the corresponding protein is being expressed. Expression may be evaluated by specifically identifying the protein products or the RNA products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzyme activity by following production of radiolabeled acetylated phosphinothricin from phosphinothricin and 14C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected lignin biosynthesis coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants.

As used herein the term "progeny" denotes the offspring of any generation of a parent plant prepared in accordance with the instant invention, wherein the progeny comprises a selected DNA construct. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

Medical Benefits of *Cannabis*, Content of Cannabinoids and Analysis Thereof

Some of the medical benefits attributable to one or more of the cannabinoids isolated from *cannabis* include treatment of pain, nausea, AIDS-related weight loss and wasting, multiple sclerosis, allergies, infection, depression, migraine, bipolar disorders, hypertension, post-stroke neuroprotection, epilepsy, and fibromyalgia, as well as inhibition of tumor growth, angiogenesis and metastasis. Studies have shown that cannabinoids may also be useful for treating conditions such as glaucoma, Parkinson's disease, Huntington's disease, migraines, inflammation, Crohn's disease, dystonia, rheumatoid arthritis, emesis due to chemotherapy, inflammatory bowel disease, atherosclerosis, posttraumatic stress disorder, cardiac reperfusion injury, prostate carcinoma, and Alzheimer's disease. For example, U.S. Pat. No. 6,630,507 discloses cannabinoids for use as antioxidants and neuroprotectants; U.S. Pat. No. 7,105,685 discloses cannabinoids for the treatment of diseases associated with immune dysfunction, particularly HIV disease and neoplastic disorders; U.S. Pat. No. 7,109,245 discloses cannabinoids useful as vasoconstrictors; U.S. Pat. Publication US2011/0257256 discloses THC-CBD composition for use in treating or preventing Cognitive Impairment and Dementia; PCT Publication WO/2009/147439 discloses use of cannabinoids in the manufacture of a medicament for use in the treatment of cancer, in particular the glioma tumor; PCT Publication WO/2007/148094 discloses use of cannabinoids composition for the treatment of neuropathic pain; and U.S. Pat. Publication US2010/0286098 discloses a method of treating tissue injury in a patient with colitis administering the cannabinoids.

While a wide range of medical uses has been identified, the benefits achieved by cannabinoids for a particular disease or condition are believed to be attributable to a subgroup of cannabinoids or to individual cannabinoids. That is to say that different subgroups or single cannabinoids have beneficial effects on certain conditions, while other subgroups or individual cannabinoids have beneficial effects on other conditions. For example, THC is the main psychoactive cannabinoid produced by cannabis and is well-characterized for its biological activity and potential therapeutic application in a broad spectrum of diseases. CBD, another major cannabinoid constituent of cannabis, acts as an inverse agonist of the CB1 and CB2 cannabinoid receptors. Unlike THC, CBD does not produce psychoactive effects in humans. CBD is reported to exert analgesic, antioxidant, anti-inflammatory, and immunomodulatory effects.

Terpenes, including terpenoids, are another class of compounds that are produced by cannabis. Reportedly, as many as 200 or more terpenes can be produced by cannabis plants, although the types and ratios of terpenes produced by a cannabis strain are dependent on genetics and growth conditions (e.g., lighting, fertilization, soil, watering frequency/amount, humidity, carbon dioxide concentration, and the like), as well as age, maturation, and time of day. Terpenes have been shown to have medicinal properties, and may be responsible for at least a portion of the medicinal value of cannabis.

Some of the medical benefits attributable to one or more of the terpenes isolated from cannabis include treatment of sleep disorders, psychosis, anxiety, epilepsy and seizures, pain, microbial infections (fungal, bacterial, etc.), cancer, inflammation, spasms, gastric reflux, depression, and asthma. Some terpenes have been shown to: lower the resistance across the blood-brain barrier, act on cannabinoid receptors and other neuronal receptors, stimulate the immune system, and/or suppress appetite.

To date, however, medicinal cannabis is used as a generic product whereby the patient utilizes the entirety of the different cannabinoids to achieve medicinal results. Efforts have been made to maximize the medicinal benefit of cannabis for a patient having a particular condition, but such efforts are invariably complicated. For example, because THC is psychoactive, some patients and regulatory authorities view cannabis with high CBD (and low THC) as being an alternative to traditional cannabis that is acceptable, legally, medically, and/or culturally. Additionally, cannabis as currently employed by a patient may lack consistent cannabinoid components and concentrations, and thereby fails to provide the maximum benefit to the patient.

Cannabis expresses a large number of cannabinoids which are useful in the treatment of a variety of diseases. However, the usefulness of a cannabis cultivar for a particular disease is dependent upon the concentration of one or more specific cannabinoids, and/or the ratio between amounts of cannabinoids, produced by the cultivar.

Other components of cannabis that have therapeutic effects include Cannabigerol (antimicrobial properties as well as inhibits proliferation of keratinocytes and cancer cells), delta-8-tetrahydrocannabinol (appetite stimulant). Other components of cannabis include Cannabielsoin, Cannabitriol, Cannabichromene, Cannabinol, Cannabicycol, and Terpenoids (including alpha-pinene, linalool, myrcene, beta-caryophyllene, carophyllene oxide, humulene-humulene, limonene and terpinolene).

Cannabinoid biosynthesis occurs primarily in glandular trichomes that cover female flowers at a high density. Cannabigerolic acid is a precursor of THC, CBD, and Cannabichromene. In particular, THCA synthase catalyzes the production of delta-9-tetrahydrocannabinolic acid from cannabigerolic acid; delta-9-tetrahydrocannabinolic acid undergoes thermal conversion to form THC. CBDA synthase catalyzes the production of cannabidiolic acid from cannabigerolic acid; cannabidiolic acid undergoes thermal conversion to CBD. CBCA synthase catalyzes the production of cannabichromenic acid from cannabigerolic acid; cannabichromenic acid undergoes thermal conversion to cannabichromene. U.S. 2013/0067619 describes the pathway leading to the main cannabinoid types in Cannabis sativa and is incorporated herein by reference in its entirety.

"Cannabis," "cannabis species," "cannabis plant," or "marijuana" refers to a flowering plant including the species (or sub-species) Cannabis sativa, Cannabis ruderalis, and Cannabis indica.

"Cannabinoids" refers to a class of chemical compounds that act on the cannabinoid receptors. "Endocannabinoids" are produced naturally in animals, including humans "Phytocannabinoids" are naturally-occurring cannabinoids produced in plants. "Synthetic cannabinoids" are artificially manufactured cannabinoids.

cannabis species express at least 85 different phytocannabinoids, which are concentrated in resin produced in glandular trichomes. The phytocannabinoids are divided into subclasses based on structure, including cannabigerols, cannabichromenes, cannabidiols, tetrahydrocannabinols, cannabinols and cannabinodiols, and other cannabinoids.

Cannabinoids found in cannabis include, without limitation: cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), and tetrahydrocannabivarinic acid (THCVA). Phytocannabinoids and their structures are discussed in more detail in U.S. Patent Application Pub. No. 2013/0059018, which is incorporated herein by reference in its entirety.

Phytocannabinoids can occur as either the pentyl(5 carbon atoms) or propyl(3 carbon atoms) variant. The propyl and pentyl variants may have distinct properties from one another. For example, THC is a CB1 receptor agonist, whereas the propyl variant THCV is a CB1 receptor antagonist meaning that it has almost opposite effects from THC.

"Terpenes" or "terpenoids" refers to a class of chemicals produced by plants, including *cannabis*. The term "terpenoid" generally refers to a chemically modified terpene (e.g., by oxidation). As used herein, the terpenes include terpenoids. Terpenes and terpenoids are often aromatic hydrocarbons and may have strong smells associated with them.

Terpenes known to be produced by *cannabis* include, without limitation, aromadendrene, bergamottin, bergamotol, bisabolene, borneol, 4-3-carene, caryophyllene, cineole/eucalyptol, p-cymene, dihydroj asmone, elemene, farnesene, fenchol, geranylacetate, guaiol, humulene, isopulegol, limonene, linalool, menthone, menthol, menthofuran, myrcene, nerylacetate, neomenthylacetate, ocimene, perillylalcohol, phellandrene, pinene, pulegone, sabinene, terpinene, terpineol, terpineol-4-ol, terpinolene, and derivatives, isomers, enantiomers, etc. of each thereof.

*cannabis* plants and products may also comprise other pharmaceutically relevant compounds, including flavonoids and phytosterols (e.g., apigenin, quercetin, cannflavin A, .beta.-sitosterol and the like).

The terms "product of *cannabis*," "plant-derived product," "*Cannabis* plant derived product," "*cannabis*-derived product," or "processed products" as used herein refer to any products derived from the *cannabis* plant, including but not limited to the flower, resin (hashish), and oil (hash oil), as well as any preparations thereof. Preparations include, by way of non-limiting example, dried flower, kief, hashish, tincture, hash oil, infusions, pipe resins, edibles, and the like.

As used herein, the term "flower," "bud," or "dried flower" refers to dried *cannabis* flowers, as well as the leaves (e.g., bracts) and stems associated therewith. This is the most widely consumed form of *cannabis*.

The term "tincture" refers to *cannabis* extracts made using high-proof alcohol.

The term "*cannabis* oil" refers to oil extracted from *cannabis* flower and leaves.

The term "infusion" refers to infusion of *cannabis* in a variety of products. Non-limiting examples include tea, cocoa butter, dairy butter, cooking oil, glycerine, and other oils (e.g., skin moisturizers). Infusions include edibles like beer, soda, peanut butter, and the like.

An "edible" *cannabis* product refers to any *cannabis* product that can be consumed as food. In some cases, edibles are made by infusion of the *cannabis* into a foodstuff. In some cases, edibles are made by combining a *cannabis* product (e.g., dried flower, kief, hashish, tincture, hash oil, or infusion) with other ingredients to make an edible (e.g., a cookie, chocolate, lollipop, beer, popcorn, etc.).

Plants go through a vegetative stage of growth, followed by a flowering cycle. The period of growth between germination or cutting rooting and flowering is known as the vegetative phase of plant development. Vegetation is the sporophytic state of the *cannabis* plant. Plants do not produce flowers during the vegetative stage and are bulking up to a desired production size for flowering. During the vegetative phase, plants are busy carrying out photosynthesis and accumulating resources that will be needed for flowering and reproduction.

"Flowering cycle" or "flowering stage" (also called "bud cycle") refers to the period during which the plant produces buds and flowers. This is the reproductive phase of plant growth, *cannabis* is dioecious having female and male reproduction parts on separate plants. Flowering is the gametophytic or reproductive state of *cannabis*. For production, only females are selected for cultivation. For some cultivars, the switch from the vegetative stage to the flowering stage is light-dependent. Some cultivars are autoflowering, meaning they switch to the flowering stage automatically (e.g., with age).

"*Cannabis* cultivar" refers to *cannabis* plants that have been selected for one or more desirable characteristics and propagated. Where the term cultivar is used, it is to be understood that the cultivar may be a result of breeding and/or the result of genetic manipulation. A *cannabis* cultivar as described herein is not naturally-occurring. Propagation may occur in any manner, including, without limitation, sexual reproduction (e.g., seed), cloning (e.g., cuttings, vegetative propagation), self-pollination, and the like.

A "plurality" as used herein refers to more than one. For example, a plurality of cannabinoids may be two, three, four, five, or more cannabinoids.

The term "active cannabinoid" as used herein refers to the non-acid form of the cannabinoid plus the amount of non-acid form estimated to be formed upon decarboxylation of the acid form.

Cannabinoids in their acid forms (e.g., CBDA or THCA) can be converted to their non-acid forms (e.g., THC or CBD) by decarboxylation. Decarboxylation occurs when the cannabinoid is heated. In addition, cannabinoid acid forms have been shown to have therapeutic activity. Cannabinoids lose mass when they are converted from the acid to non-acid ("active") form. In order to determine the estimated amount of active cannabinoid that will be present after decarboxylation, the amount of the acid form can be multiplied by 87.7%. This is a rough estimate, and the actual amount of active cannabinoid that will be produced may be dependent upon the cannabinoid, method of decarboxylation, further breakdown of the cannabinoid during the decarboxylation process (e.g., due to heat), etc.

In one embodiment, "therapeutically effective amount" refers to that amount of a compound that results in prevention or amelioration of symptoms in a patient or a desired biological outcome, e.g., improved clinical signs, delayed onset of disease, etc. The effective amount can be determined by one of ordinary skill in the art. The selected dosage level can depend upon factors including, but not limited to, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

The term "modulate" or "modulating" means any treatment of a disease or disorder in a subject, such as a mammal, including: preventing or protecting against the disease or disorder, that is, causing the abnormal biological reaction or symptoms not to develop; inhibiting the disease or disorder, that is, arresting or suppressing the development of abnormal biological reactions and/or clinical symptoms; and/or relieving the disease or disorder that is, causing the regression of abnormal biological reactions and/or clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

As used herein, the term "condition" refers to a disease state for which the compounds, compositions and methods provided herein are being used.

As used herein, the term "patient" or "subject" refers to mammals and includes humans and non-human mammals. In particular embodiments herein, the patient or subject is a human.

In one aspect, described herein is a *cannabis* plant that is a *cannabis* cultivar that produces high levels of CBD (and/or CBDA) and low levels of THC (and/or THCA). In one embodiment, the *cannabis* cultivar produces an assayable combined cannabidiolic acid and cannabidiol concentration of about 18% to about 60% by weight. In one embodiment, the *cannabis* cultivar produces an assayable combined cannabidiolic acid and cannabidiol concentration of about 20% to about 40% by weight. In one embodiment, the *cannabis* cultivar produces an assayable combined cannabidiolic acid and cannabidiol concentration of about 20% to about 30% by weight. In one embodiment, the *cannabis* cultivar produces an assayable combined cannabidiolic acid and cannabidiol concentration of about 25% to about 35% by weight. It should be understood that any subvalue or subrange from within the values described above are contemplated for use with the embodiments described herein.

In one embodiment, the *cannabis* cultivar produces an assayable combined cannabidiolic acid and cannabidiol concentration of at least about 18% by weight. In one embodiment, the *cannabis* cultivar produces an assayable combined cannabidiolic acid and cannabidiol concentration of at least about 19% by weight. In a preferred embodiment, the *cannabis* cultivar produces an assayable combined cannabidiolic acid and cannabidiol concentration of at least about 20% by weight. In one embodiment, the *cannabis* cultivar produces an assayable combined cannabidiolic acid and cannabidiol concentration of at least about 21% by weight. In one embodiment, the *cannabis* cultivar produces an assayable combined cannabidiolic acid and cannabidiol concentration of at least about 22% by weight. In one embodiment, the *cannabis* cultivar produces an assayable combined cannabidiolic acid and cannabidiol concentration of at least about 23% by weight. In one embodiment, the *cannabis* cultivar produces an assayable combined cannabidiolic acid and cannabidiol concentration of at least about 24% by weight. In one embodiment, the *cannabis* cultivar produces an assayable combined cannabidiolic acid and cannabidiol concentration of at least about 25% by weight. In one embodiment, the *cannabis* cultivar produces an assayable combined cannabidiolic acid and cannabidiol concentration of at least about 26% by weight. In one embodiment, the *cannabis* cultivar produces an assayable combined cannabidiolic acid and cannabidiol concentration of at least about 27% by weight. In one embodiment, the *cannabis* cultivar produces an assayable combined cannabidiolic acid and cannabidiol concentration of at least about 28% by weight. In one embodiment, the *cannabis* cultivar produces an assayable combined cannabidiolic acid and cannabidiol concentration of at least about 29% by weight. In one embodiment, the *cannabis* cultivar produces an assayable combined cannabidiolic acid and cannabidiol concentration of at least about 30% by weight.

In one embodiment, the *cannabis* cultivar produces an assayable combined delta-9-tetrahydrocannabinol and tetrahydrocannabinolic acid concentration of between about 0% to about 3% by weight. In one embodiment, the *cannabis* cultivar produces an assayable combined delta-9-tetrahydrocannabinol and tetrahydrocannabinolic acid concentration of between about 0% to about 2% by weight. In one embodiment, the *cannabis* cultivar produces an assayable combined delta-9-tetrahydrocannabinol and tetrahydrocannabinolic acid concentration of between about 0% to about 1% by weight. In one embodiment, the *cannabis* cultivar produces an assayable combined delta-9-tetrahydrocannabinol and tetrahydrocannabinolic acid concentration of between about 0% to about 0.3% by weight. In one embodiment, the *cannabis* cultivar produces an assayable combined delta-9-tetrahydrocannabinol and tetrahydrocannabinolic acid concentration of between about 0% to about 0.1% by weight. In one embodiment, the *cannabis* cultivar produces an assayable combined delta-9-tetrahydrocannabinol and tetrahydrocannabinolic acid concentration of between about 0% to about 0.09% by weight. In one embodiment, the *cannabis* cultivar produces an assayable combined delta-9-tetrahydrocannabinol and tetrahydrocannabinolic acid concentration of between about 0% to about 0.08% by weight. In one embodiment, the *cannabis* cultivar produces an assayable combined delta-9-tetrahydrocannabinol and tetrahydrocannabinolic acid concentration of between about 0% to about 0.07% by weight. In one embodiment, the *cannabis* cultivar produces an assayable combined delta-9-tetrahydrocannabinol and tetrahydrocannabinolic acid concentration of between about 0% to about 0.06% by weight. In one embodiment, the *cannabis* cultivar produces an assayable combined delta-9-tetrahydrocannabinol and tetrahydrocannabinolic acid concentration of between about 0% to about 0.05% by weight. In one embodiment, the *cannabis* cultivar produces an assayable combined delta-9-tetrahydrocannabinol and tetrahydrocannabinolic acid concentration of between about 0% to about 0.04% by weight. In one embodiment, the *cannabis* cultivar produces an assayable combined delta-9-tetrahydrocannabinol and tetrahydrocannabinolic acid concentration of between about 0% to about 0.03% by weight. In one embodiment, the *cannabis* cultivar produces an assayable combined delta-9-tetrahydrocannabinol and tetrahydrocannabinolic acid concentration of between about 0% to about 0.02% by weight. In one embodiment, the *cannabis* cultivar produces an assayable combined delta-9-tetrahydrocannabinol and tetrahydrocannabinolic acid concentration of between about 0% to about 0.01% by weight. In one embodiment, the *cannabis* cultivar produces an assayable combined delta-9-tetrahydrocannabinol and tetrahydrocannabinolic acid concentration of between about 0.02% to about 3% by weight. In a preferred embodiment, the *cannabis* cultivar produces an assayable combined delta-9-tetrahydrocannabinol and tetrahydrocannabinolic acid concentration of between about 0.02% to about 2% by weight. In one embodiment, the *cannabis* cultivar produces an assayable combined delta-9-tetrahydrocannabinol and tetrahydrocannabinolic acid concentration of between about 0.03% to about 2% by weight. In one embodiment, the *cannabis* cultivar produces an assayable combined delta-9-tetrahydrocannabinol and tetrahydrocannabinolic acid concentration of between about 0.05% to about 2% by weight. In one embodiment, the *cannabis* cultivar produces an assayable combined delta-9-tetrahydrocannabinol and tetrahydrocannabinolic acid concentration of between about 0.07% to about 2% by weight. It should be understood that any subvalue or subrange from within the values described above are contemplated for use with the embodiments described herein.

In one embodiment, the *cannabis* cultivar produces an assayable combined delta-9-tetrahydrocannabinol and tetrahydrocannabinolic acid concentration of less than about 3% by weight. In one embodiment, the *cannabis* cultivar produces an assayable combined delta-9-tetrahydrocannabinol and tetrahydrocannabinolic acid concentration of less than about 2% by weight. In one embodiment, the *cannabis* cultivar produces an assayable combined delta-9-tetrahydrocannabinol and tetrahydrocannabinolic acid concentration of less than about 1.9% by weight. In one embodiment, the *cannabis* cultivar produces an assayable combined delta-9-tetrahydrocannabinol and tetrahydrocannabinolic acid concentration of less than about 1.8% by weight. In one embodiment, the *cannabis* cultivar produces an assayable combined delta-9-tetrahydrocannabinol and tetrahydrocannabinolic acid concentration of less than about 1.7% by weight. In one embodiment, the *cannabis* cultivar produces an assayable combined delta-9-tetrahydrocannabinol and tetrahydrocannabinolic acid concentration of less than about 1.6% by weight. In one embodiment, the *cannabis* cultivar produces an assayable combined delta-9-tetrahydrocannabinol and tetrahydrocannabinolic acid concentration of less than about 1.5% by weight. In one embodiment, the *cannabis* cultivar produces an assayable combined delta-9-tetrahydrocannabinol and tetrahydrocannabinolic acid concentration of less than about 1.4% by weight. In one embodiment, the *cannabis* cultivar produces an assayable combined delta-9-tetrahydrocannabinol and tetrahydrocannabinolic acid concentration of less than about 1.3% by weight. In one embodiment, the *cannabis* cultivar produces an assayable combined delta-9-tetrahydrocannabinol and tetrahydrocannabinolic acid concentration of less than about 1.2% by weight. In one embodiment, the *cannabis* cultivar produces an assayable combined delta-9-tetrahydrocannabinol and tetrahydrocannabinolic acid concentration of less than about 1% by weight. In one embodiment, the *cannabis* cultivar produces an assayable combined delta-9-tetrahydrocannabinol and tetrahydrocannabinolic acid concentration of less than about 0.5% by weight. In one embodiment, the *cannabis* cultivar produces an assayable combined delta-9-tetrahydrocannabinol and tetrahydrocannabinolic acid concentration of less than about 0.3% by weight. In one embodiment, the *cannabis* cultivar produces an assayable combined delta-9-tetrahydrocannabinol and tetrahydrocannabinolic acid concentration of less than about 0.2% by weight. In one embodiment, the *cannabis* cultivar produces an assayable combined delta-9-tetraydrocanabinol and tetrahydrocannabinolic acid concentration of less than about 0.1% by weight. In one embodiment, the *cannabis* cultivar produces an assayable combined delta-9-tetrahydrocannabinol and tetrahydrocannabinolic acid concentration of less than about 0.09% by weight. In one embodiment, the *cannabis* cultivar produces an assayable combined delta-9-tetrahydrocannabinol and tetrahydrocannabinolic acid concentration of less than about 0.08% by weight. In one embodiment, the *cannabis* cultivar produces an assayable combined delta-9-tetrahydrocannabinol and tetrahydrocannabinolic acid concentration of less than about 0.07% by weight. In one embodiment, the *cannabis* cultivar produces an assayable combined delta-9-tetrahydrocannabinol and tetrahydrocannabinolic acid concentration of less than about 0.06% by weight. In one embodiment, the *cannabis* cultivar produces an assayable combined delta-9-tetrahydrocannabinol and tetrahydrocannabinolic acid concentration of less than about 0.05% by weight. In one embodiment, the *cannabis* cultivar produces an assayable combined delta-9-tetrahydrocannabinol and tetrahydrocannabinolic acid concentration of less than about 0.04% by weight. In one embodiment, the *cannabis* cultivar produces an assayable combined delta-9-tetrahydrocannabinol and tetrahydrocannabinolic acid concentration of less than about 0.03% by weight. In one embodiment, the *cannabis* cultivar produces an assayable combined delta-9-tetrahydrocannabinol and tetrahydrocannabinolic acid concentration of less than about 0.02% by weight. In one embodiment, the *cannabis* cultivar produces an assayable combined delta-9-tetrahydrocannabinol and tetrahydrocannabinolic acid concentration of less than about 0.01% by weight. In one embodiment, the *cannabis* cultivar produces an assayable combined delta-9-tetrahydrocannabinol and tetrahydrocannabinolic acid concentration of about 0.07% by weight.

In one embodiment, the estimated active cannabidiol concentration is between about 18% and about 60% by weight. In one embodiment, the estimated active cannabidiol concentration is between about 20% and about 60% by weight. In one embodiment, the estimated active cannabidiol concentration is between about 20% and about 50% by weight. In one embodiment, the estimated active cannabidiol concentration is between about 20% and about 40% by weight. In one embodiment, the estimated active cannabidiol concentration is between about 20% and about 30% by weight. In one embodiment, the estimated active cannabidiol concentration is between about 20% and about 25% by weight. In one embodiment, the estimated active cannabidiol concentration is between about 25% and about 40% by weight. In one embodiment, the estimated active cannabidiol concentration is between about 25% and about 30% by weight. It should be understood that any subvalue or subrange from within the values described above are contemplated for use with the embodiments described herein.

In one embodiment, the estimated active cannabidiol concentration is at least about 18% by weight. In one embodiment, the estimated active cannabidiol concentration is at least about 19% by weight. In one embodiment, the estimated active cannabidiol concentration is at least about 20% by weight. In one embodiment, the estimated active cannabidiol concentration is at least about 21% by weight. In one embodiment, the estimated active cannabidiol concentration is at least about 22% by weight. In one embodiment, the estimated active cannabidiol concentration is at least about 23% by weight. In one embodiment, the estimated active cannabidiol concentration is at least about 24% by weight. In one embodiment, the estimated active cannabidiol concentration is at least about 25% by weight. In one embodiment, the estimated active cannabidiol concentration is at least about 26% by weight. In one embodiment, the estimated active cannabidiol concentration is at least about 27% by weight. In one embodiment, the estimated active cannabidiol concentration is at least about 28% by weight. In one embodiment, the estimated active cannabidiol concentration is at least about 29% by weight. In one embodiment, the estimated active cannabidiol concentration is at least about 30% by weight.

In one aspect, this invention is directed to a *cannabis* strain or product thereof, wherein the ratio of estimated active cannabidiol to estimated active THC is between about 400:1 and about 15:1. In one embodiment, the ratio of active cannabidiol to active THC is between about 300:1 and about 20:1. In one embodiment, the ratio of active cannabidiol to active THC is between about 300:1 and about 25:1. In one embodiment, the ratio of active cannabidiol to active THC is between about 300:1 and about 30:1. In one embodiment, the ratio of active cannabidiol to active THC is between about 300:1 and about 50:1. In one embodiment, the ratio of active cannabidiol to active THC is between about 300:1 and about 70:1. In one embodiment, the ratio of active cannabidiol to active THC is between about 300:1 and about 80:1. In one embodiment, the ratio of active cannabidiol to active THC is between about 300:1 and about 100:1. In one embodiment, the ratio of active cannabidiol to active THC is between about 300:1 and about 200:1.

The concentration of cannabinoids can be determined based on a sample taken from any portion of the *cannabis* plant. The concentration of cannabinoids can be determined based on a sample taken at any point in the life cycle of the plant. In a preferred embodiment, the sample is taken from a flower (or inflorescence) of a *cannabis* plant. In one embodiment, the sample is taken from one or more flowers, leaves, stems, or a combination thereof. In one embodiment, the sample is taken during a vegetative stage of the *cannabis* life cycle. In one embodiment, the sample is taken during the flowering stage of the *cannabis* life cycle.

In one aspect, the cannabinoid and/or terpene composition of a strain of *cannabis* is consistent between batches. In one embodiment, the cannabinoid and/or terpene composition of a particular strain is consistent between batches grown and harvested at different times. In one embodiment, the cannabinoid and/or terpene composition of a particular strain is consistent between batches grown and/or harvested at different locations (e.g., different cultivation facilities). The term "consistent" means that the concentration of a given cannabinoid and/or terpene present in a particular strain does not vary by more than 20%, preferably 15%, 10%, or 5%. In one embodiment, the cannabinoid is a phytocannabinoid. In one embodiment, the cannabinoid is CBD. In one embodiment, the cannabinoid is THC. In one embodiment, the cannabinoid is CBN. In one embodiment, the cannabinoid is at least one of cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabinolic acid (THCA), or tetrahydrocannabivarinic acid (THCVA).

In one aspect, the cannabinoid and/or terpene composition of the strain is determined by assaying the concentration of at least one cannabinoid in a subset (e.g., sample) of the harvested product. In one embodiment, THC concentration is assayed. In one embodiment, CBD concentration is assayed. In one embodiment, the cannabinoid is CBN. In one embodiment, the cannabinoid is at least one of cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabinolic acid (THCA), or tetrahydrocannabivarinic acid (THCVA). In one embodiment, the concentration of one or more terpenes is assayed.

Assays used heretofore to determine cannabinoid concentrations have shown significant deviation for the same plant. Such deviation is a problem for the *cannabis* industry as a whole, and particularly the medical *cannabis* industry, which requires reproducibility. After careful examination, it is contemplated that the moisture content of the assayed composition is a critical parameter in the variability of the assayed concentrations. Surprisingly, such variability can be minimized by rendering the moisture content consistent from assay to assay. In one aspect, this invention relates to a method of assaying cannabinoid concentration of a *cannabis* sample such that the assay provides reproducible results between different samples, e.g., batches and/or strains.

In one embodiment, the moisture content of a sample to be tested (e.g., for cannabinoid content) is adjusted to a consistent level prior to performing the assay. In one embodiment, a sample to be tested is adjusted to 40% moisture or less. In one embodiment, a sample to be tested is adjusted to about 40% moisture. In one embodiment, a sample to be tested is adjusted to about 30% moisture. In one embodiment, a sample to be tested is adjusted to about 20% moisture. In one embodiment, a sample to be tested is adjusted to about 15% moisture. In one embodiment, a sample to be tested is adjusted to about 14% moisture. In one embodiment, a sample to be tested is adjusted to about 13% moisture. In one embodiment, a sample to be tested is adjusted to about 12% moisture. In one embodiment, a sample to be tested is adjusted to about 11% moisture. In one embodiment, a sample to be tested is adjusted to about 10% moisture. In one embodiment, a sample to be tested is adjusted to about 9% moisture. In one embodiment, a sample to be tested is adjusted to about 8% moisture. In one embodiment, a sample to be tested is adjusted to about 7% moisture. In one embodiment, a sample to be tested is adjusted to about 6% moisture. In one embodiment, a sample to be tested is adjusted to about 5% moisture. In yet another approach, the composition is lyophilized prior to assay. Methods for determining moisture content are well-known in the art.

The moisture content of a sample to be tested can be adjusted using any method for adjusting moisture content. In one embodiment, the moisture content is adjusted by placing the sample in a hydrator or humidity chamber at a desired humidity level for a period of time before it is assayed. In one embodiment, the moisture content is adjusted by dehydrating the sample to a desired moisture content. The sample can be dehydrated using any dehydration method. In one embodiment, the moisture content is adjusted by lyophilizing the sample. In one embodiment, the moisture content of more than one sample is adjusted at the same time. In one embodiment, the moisture content of the sample is determined before the adjusting step. In one embodiment, the moisture content of the sample is not determined before the adjusting step.

In one embodiment, the concentration of cannabinoids is determined irrespective of the moisture content. For example, the dry weight of the sample can be determined, and the cannabinoid content is determined relative to the dry weight.

After the desired moisture content has been achieved, the cannabinoid content can be determined using any method. Methods include, without limitation, radioimmunoassay, gas chromatography/mass spectrometry, gas chromatography, liquid chromatography, liquid chromatography/mass spectrometry, and enzyme immunoassay.

EXAMPLES

In view of the foregoing, those of skill in the art should appreciate that changes can be made in the specific aspects that are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

THCA Synthase Cloning and Sequencing

Figure 1:
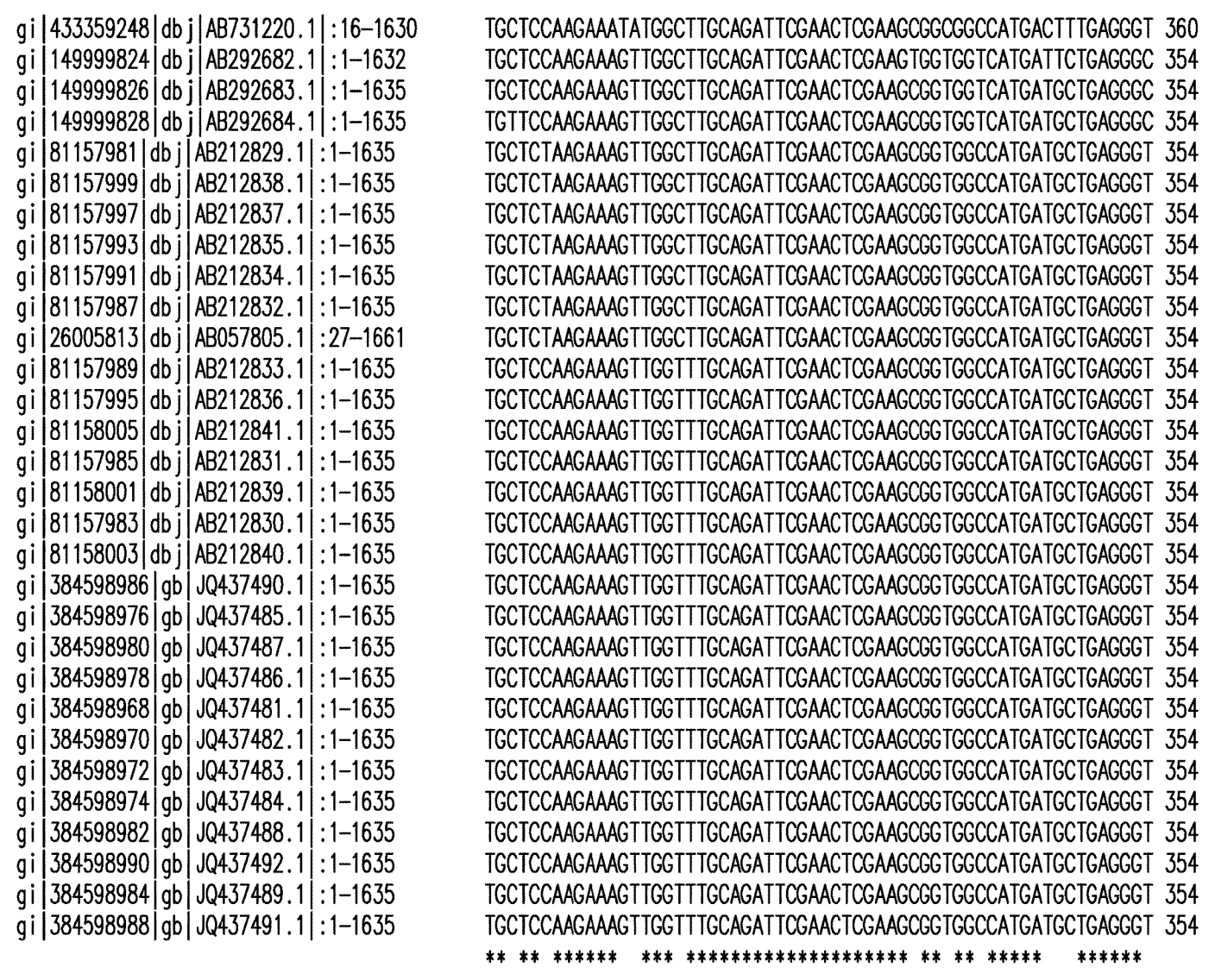
Figure 1:
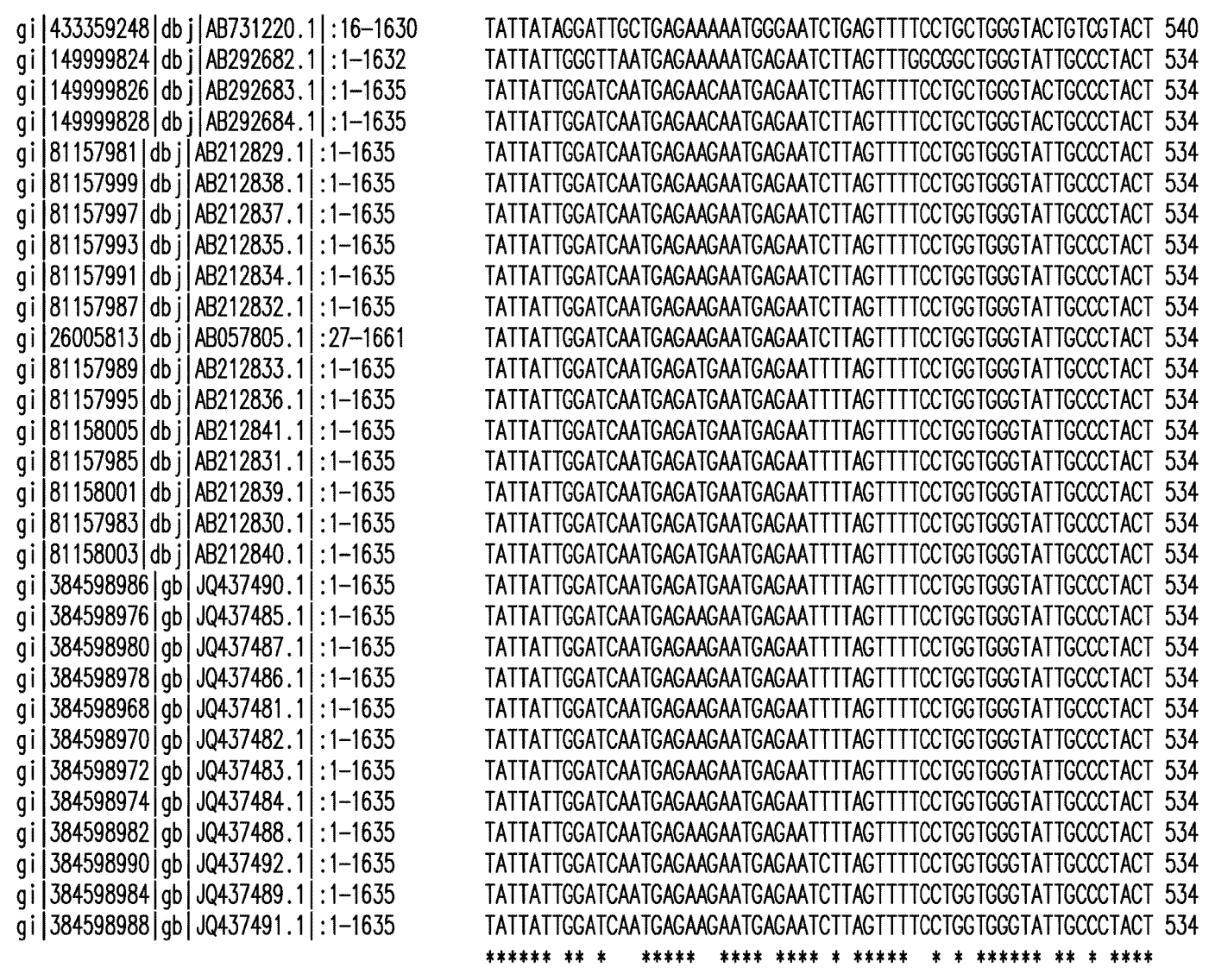
Figure 1:
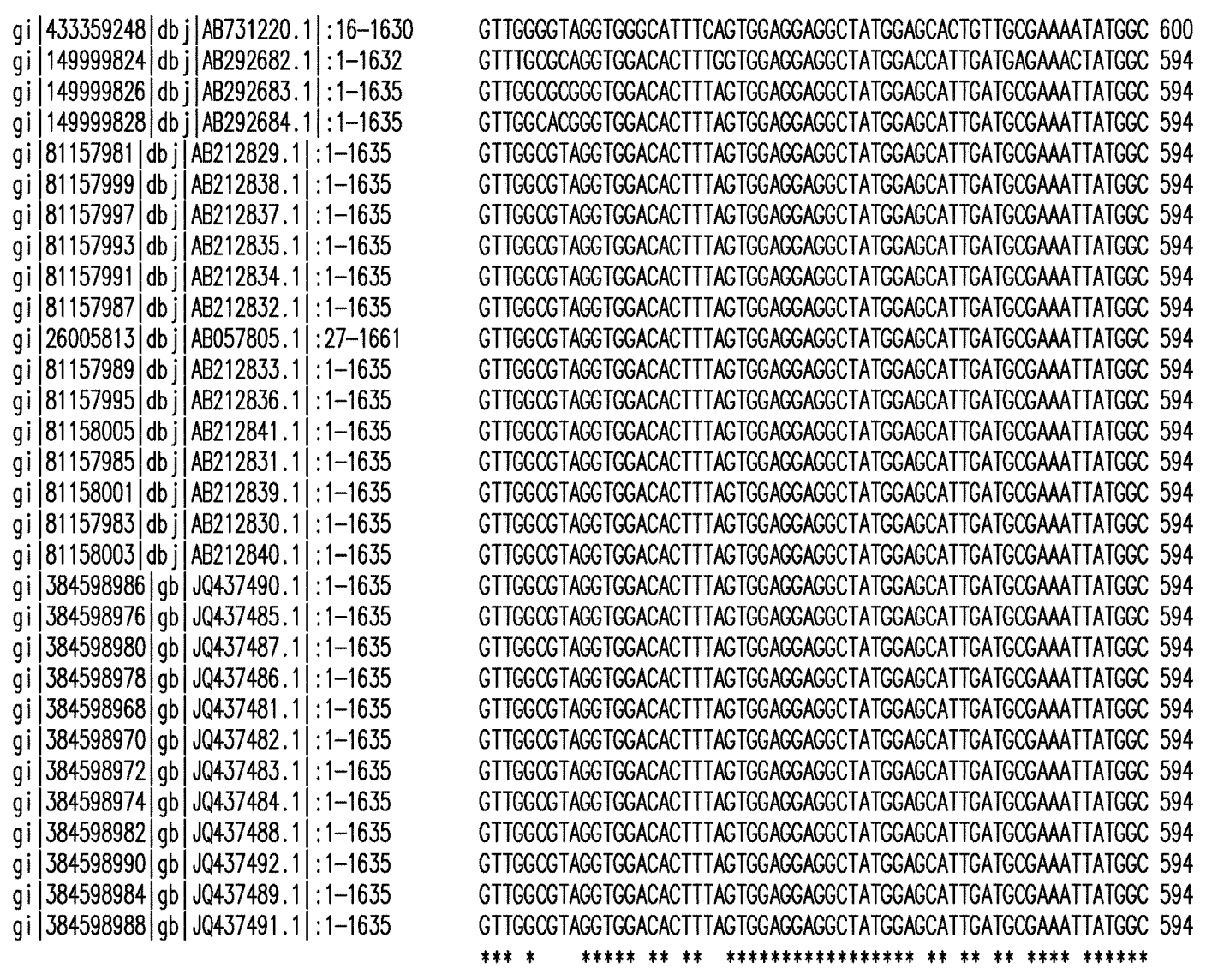
Figure 1:
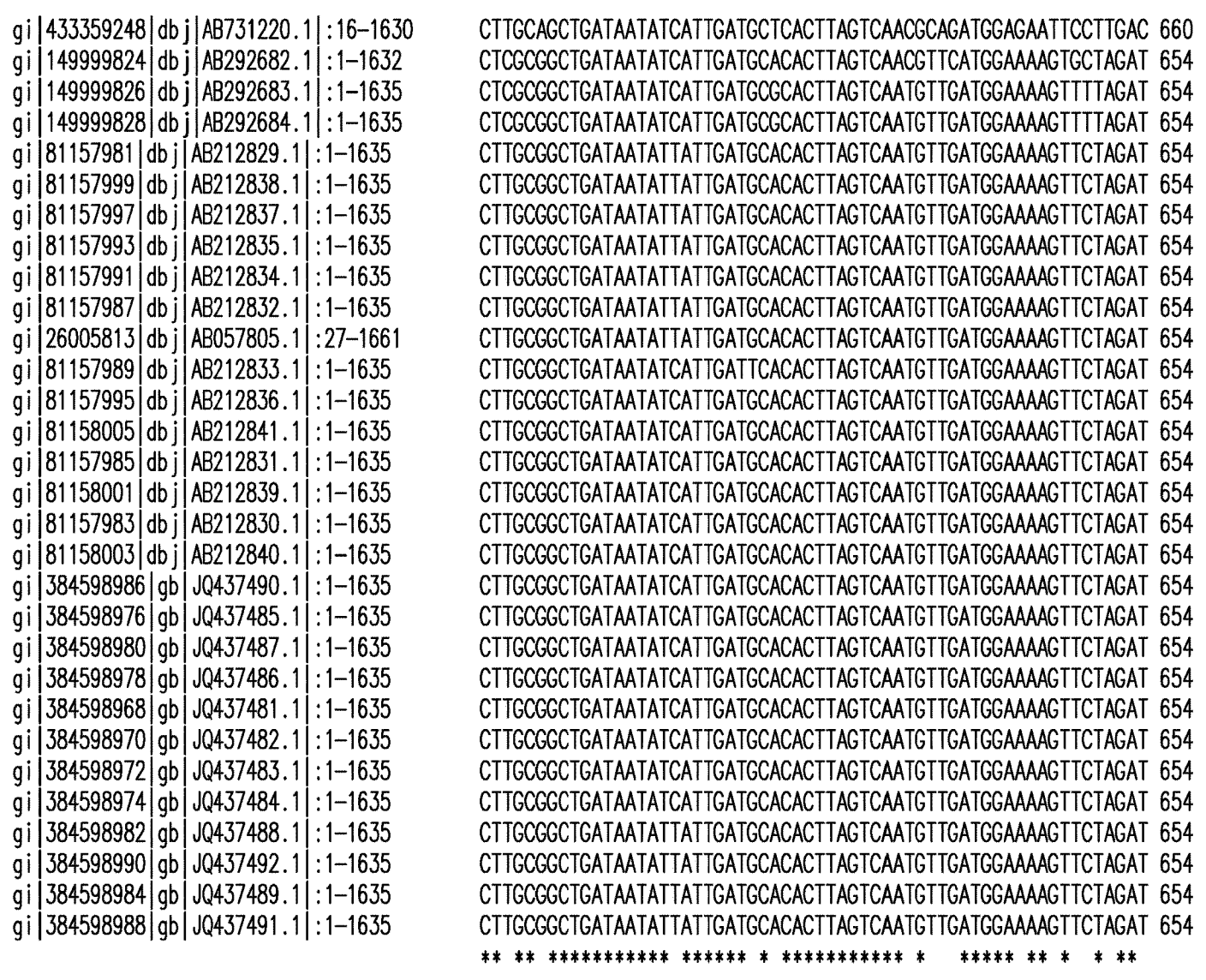
Figure 1:
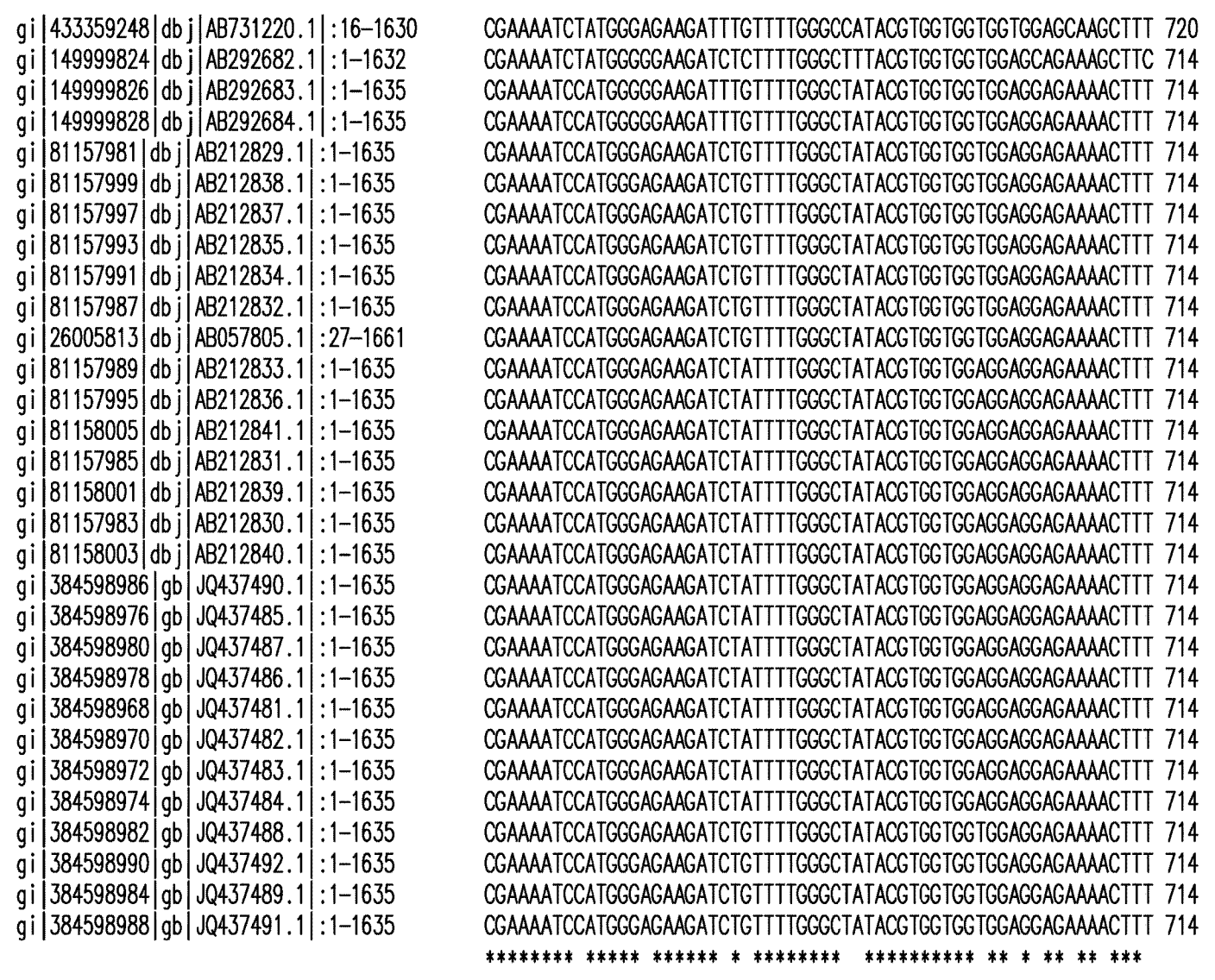
Figure 1:
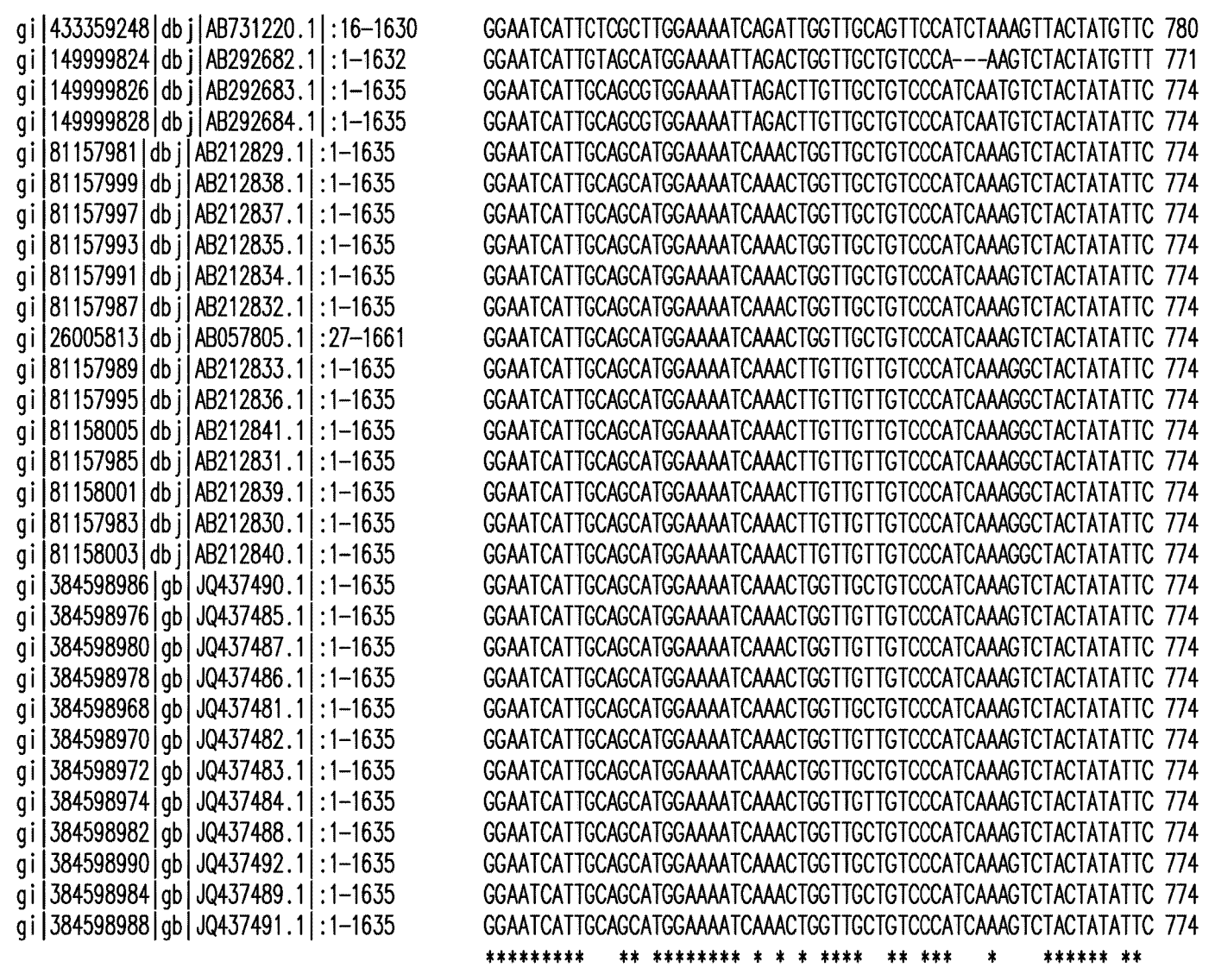
Figure 1:
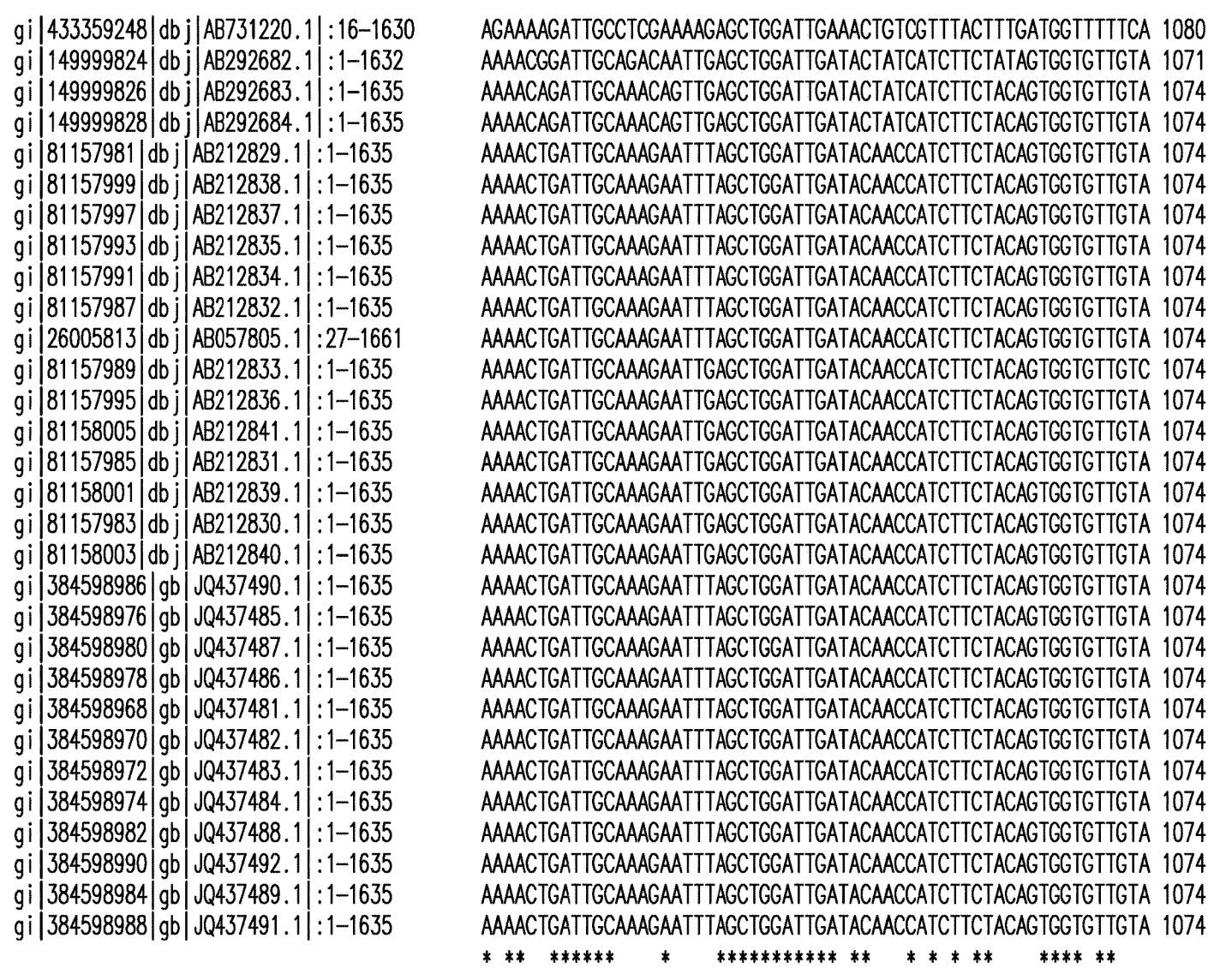
Figure 1:
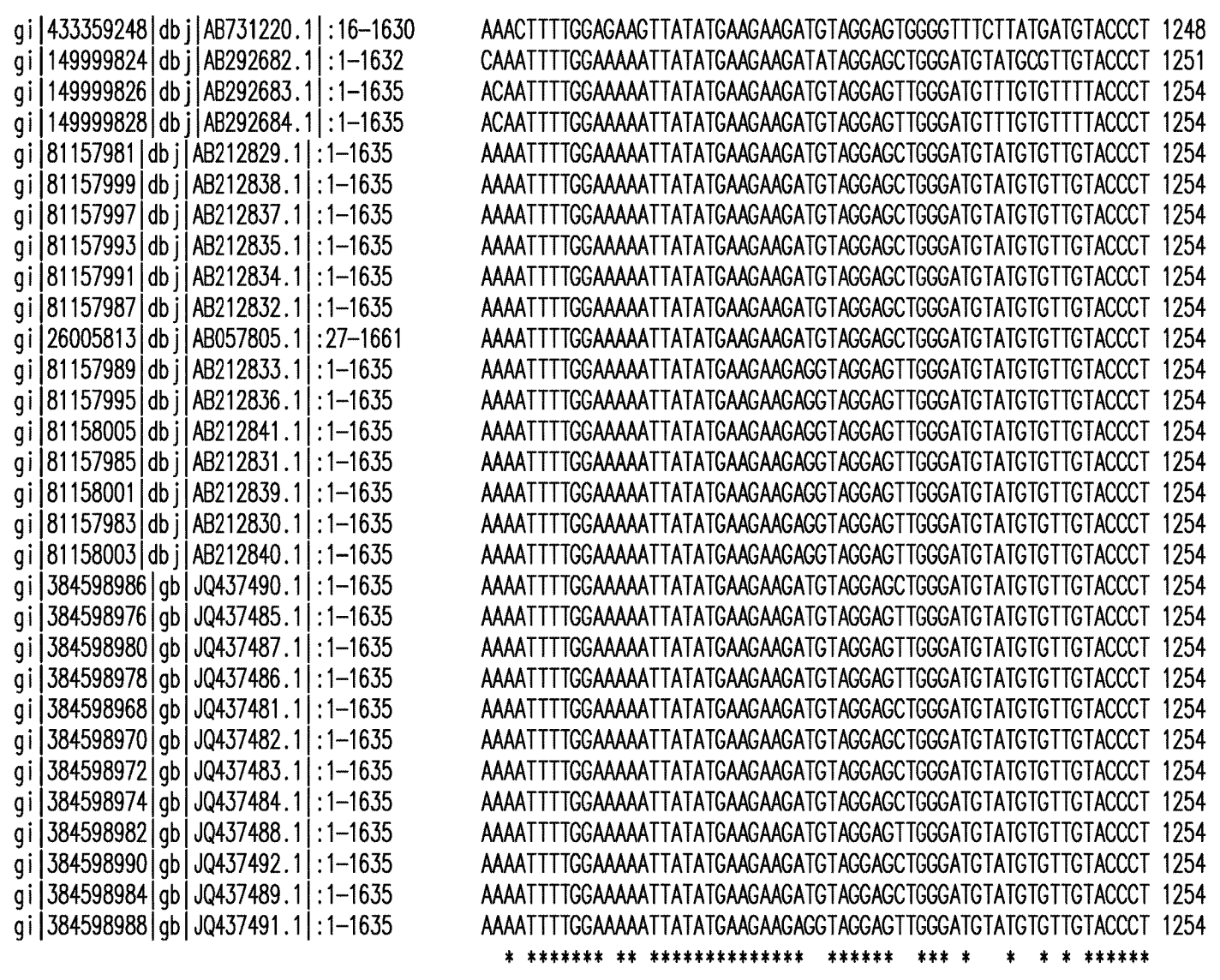
Figure 1:
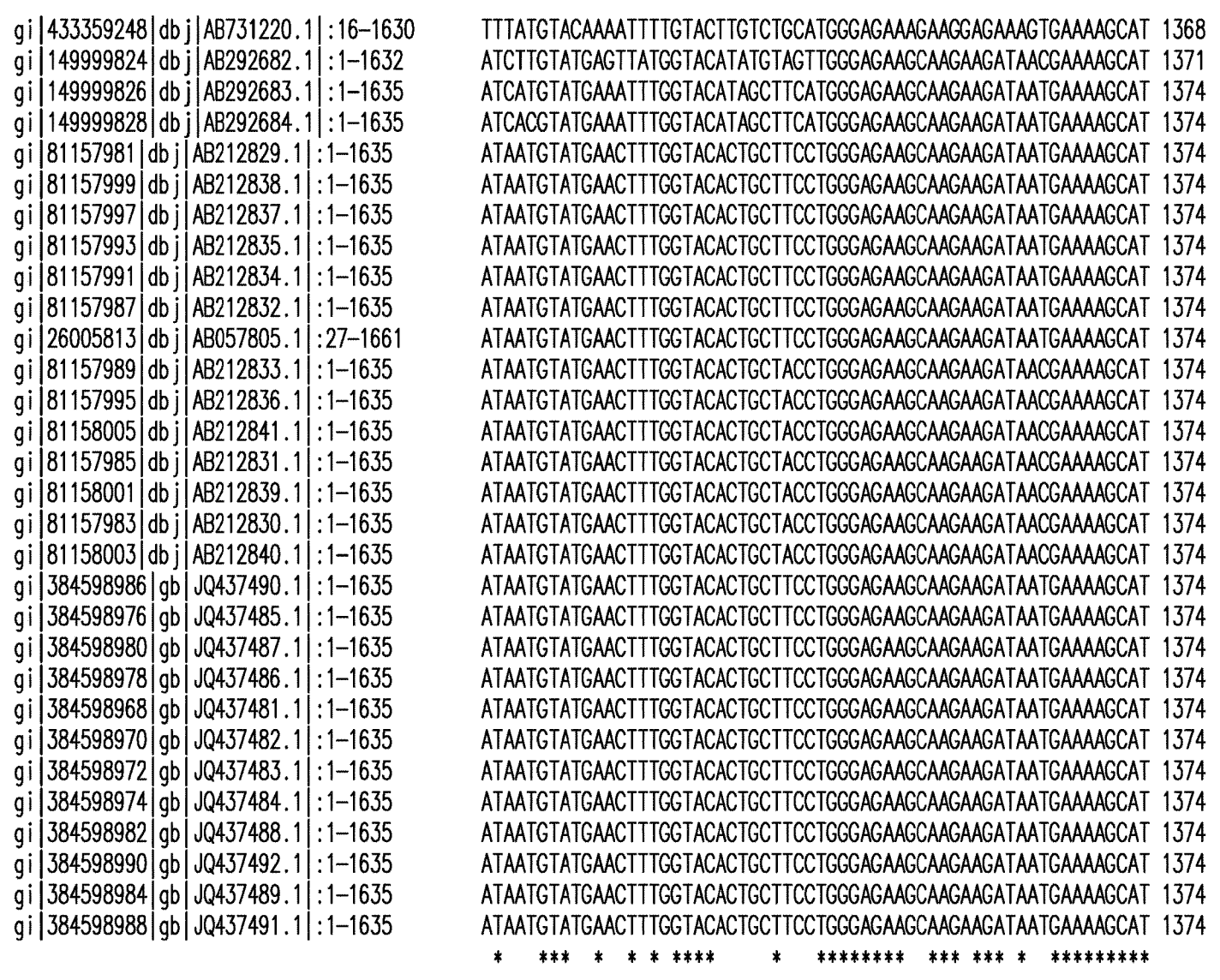
Figure 1:
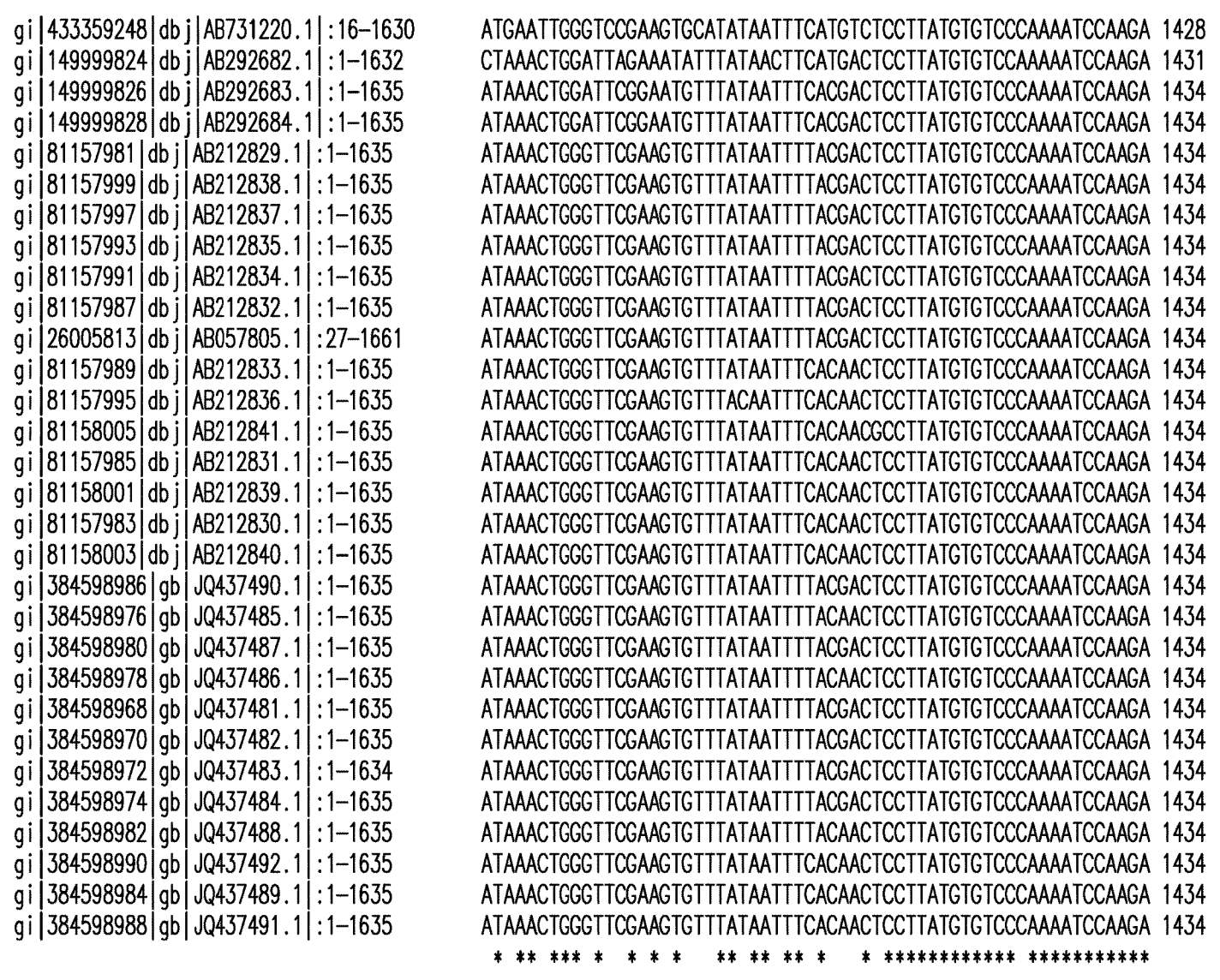

Several *Cannabis sativa* THCA synthase sequences were aligned, and FIG. 1 shows the alignment obtained using the CLUSTAL O (1.2.1) multiple sequence alignment program available at world wide web.ebi.ac.uk/Tools/msa/clustalw2.

Alignments of 30 THCA synthase gene accessions in GenBank have identified highly conserved sequence regions (13 regions of 21 to 42 bp) from which PCR primers can be generated for DNA amplification followed by cloning into intermediate vectors. To reduce errors introduced by PCR, an editing enzyme can be used and multiple independent amplifications can provide DNA for sequencing; thus, allowing the removal of rare mutations that may arise from the process of amplification. In certain embodiments, the THCA synthase gene sequence of *cannabis* strains used by TWEED® can be used to ensure functionality of antisense RNA (asRNA).

The THCA synthase coding genes from 3 *Cannabis sativa* strains (DK-1, ND-1 and SH-4) were amplified by polymerase chain reaction (PCR) using proof-reading polymerase PHUSION® from THERMO FISHER® in order to avoid PCR mistakes and the PCR products were cloned into pGEM vector for sequencing. Two or three independent clones (in pGEM vector) from each PCR reaction were sequenced to verify sequence. DK-1 and SH-4 used for alignment in FIG. 2 are representative sequences of clones, and the DNA sequence was confirmed with at least 2 sequencing reactions that resulted in the identical sequences and enabled the assembly of the full gene sequence.

The cloned THCA synthase sequences obtained for DK-1 and SH-4 were aligned with NCBI sequences AB057805.1 (SEQ ID NO:40); AB212829.1 (SEQ ID NO:28); AB212833.1 (SEQ ID NO:24); AB292683.1 (SEQ ID NO:41); JQ437487.1 (SEQ ID NO:2); and JQ437491.1 (SEQ ID NO:13) as shown in FIG. 2. The sequences of THCA synthase from DK-1_full (SEQ ID NO:46), and SH-4_full (SEQ ID NO:47), and from the ND strain showed identity to AB057805-1 (SEQ ID NO:40). In addition, FIG. 2 also depicts the consensus sequence (SEQ ID NO:86). Sequence alignment was performed using DNAMAN®.

Example 2

Design of RNA Interfering Constructs

In order to avoid off-target effects by silencing unrelated genes/proteins, conserved domains were avoided when designing RNA interference constructs. Conserved protein domains were identified in the THCA synthase by searching for conserved domains in the National Center for Biotechnology Information (NCBI) database. FIG. 5 depicts the protein domains berberine and berberine-like (BBE) domains and FAD-binding domain located in the region of amino acid interval 480-538 and amino acid interval 81-218, respectively of the THCA synthase. FAD-binding domains are present in various enzymes that bind FAD as cofactor. BBE domains are found in multiple enzymes that are involved in the biosynthesis of various isoquinoline alkaloids. A GlcD domain, located in the region of amino acid interval 81-540 and depicted in FIG. 5, was also identified. This domain is a Glycolate oxidase subunit GlcD domain that is characteristic for prokaryotic enzymes and was therefore of little concern. FAD binding and BBE domains, however, were avoided when designing RNA interfering constructs.

Example 3

Design of Antisense Constructs

For creating an expression cassette encoding RNAi constructs to induce RNA silencing via double-stranded RNA formation, full antisense RNA encoding DNA (SEQ ID NO:81) was amplified by PCR. The primers used for PCR were THCA-FullAS-F (SEQ ID NO:59) and THCA-FullAS-R (SEQ ID NO:60). The PCR fragment was cloned into pGEM vector and the sequence was verified.

In order to create a base vector suitable for transgenic expression of antisense RNA or interfering RNA, a promoter and a suitable multiple cloning site was inserted into vector pCAMBIA1391 to create the pCAMBIA1391-35S vector, depicted in FIG. 6. The 35S promoter (CaMV35S) is a Cauliflower mosaic virus promoter and can be used as universal promoter for constitutive antisense expression in *Cannabis sativa* and is also useful in RNA interference constructs. Alternatively, the tCUP promoter (tomato cryptic promoter) can also be used for high constitutive expression in *Cannabis sativa*.

The full antisense RNA encoding DNA was excised from the intermediate pGEM vector and cloned into base plant transformation vector pCAMBIA1391-35S at a site between 35S promoter and NOS terminator (MluI-BstEII sites as shown in FIG. 6, and the presence of the insert was verified by restriction analysis and can be verified by sequencing.

Example 4

Design of Small Hair Pin Constructs

For creating a vector to induce RNA silencing via RNA interference, a small hair pin RNA construct was designed as a sense-loop-antisense RNA encoding DNA corresponding to the 5'-end of the THCA synthase gene coding sequencing. The sense portion of the construct corresponds to about 200 base pairs (SEQ ID NO:61) and avoids all conserved domains and potential silencing of other enzymes encoding genes in *Cannabis sativa*. The sense portion is also located in the RNA region identified as most accessible (see FIGS. 3 and 4). The sense portion was amplified using primers THCA-hpRNA1-SN-F1 (SEQ ID NO:51) and THCA-hpRNA1-SN-R1 (SEQ ID NO:52) and is followed by the loop portion (SEQ ID NO:62). The loop portion is followed by the antisense portion (SEQ ID NO:63), which was amplified using THCA-hpRNA1-AS-F1(SEQ ID NO:53) and THCA-hpRNA1-AN-R1 (SEQ ID NO:54). The sequence of the complete sense-loop-antisense RNA encoding DNA is provided as SEQ ID NO:64. In order to create a base vector suitable for transgenic expression of interfering RNA a promoter and a suitable multiple cloning site were inserted into vector pCAMBIA1391 to create the pCAMBIA1391-35S vector, depicted in FIG. 6.

The DNA encoding the small hair pin RNA was excised from the intermediate pGEM vector and cloned into base plant transformation vector pCAMBIA1391-35S at a site between 35S promoter and NOS terminator (MluI-BstEII sites as shown in FIG. 6, and the presence of the insert was verified by restriction analysis and can be verified by sequencing.

Example 5

Design of Large Hair Pin Constructs

For creating a vector to induce RNA silencing via RNA interference, a large hair pin RNA construct was designed as sense-loop-antisense RNA encoding DNA corresponding to the mid-portion of the THCA synthase gene coding sequencing. The sense portion of the construct corresponds to about 550 base pairs (SEQ ID NO:69) and avoids the most likely common domains (FAD binding and BBE domains), and therefore avoids potential silencing of other enzymes encoding genes in *Cannabis sativa*. The sense portion was amplified using primers THCA-hpRNA2-SN-F2 (SEQ ID NO:55) and THCA-hpRNA2-SN-R2 (SEQ ID NO:56) and is followed by the loop portion (SEQ ID NO:70). The loop portion is followed by the antisense portion (SEQ ID NO:71), which was amplified using THCA-hpRNA2-AS-F2 (SEQ ID NO:57) and THCA-hpRNA2-AS-R2 (SEQ ID NO:58). The sequence of the complete sense-loop-antisense RNA encoding DNA is provided as SEQ ID NO:72.

The DNA encoding the small hair pin RNA was excised from the intermediate pGEM vector and cloned into base plant transformation vector pCAMBIA1391-35S at a site between 35S promoter and NOS terminator (MluI-BstEII sites as shown in FIG. 6, and the presence of the insert was verified by restriction analysis and can be verified by sequencing.

Example 6

Transformation of *Cannabis* with the Polynucleotides

*Cannabis* tissue cultures (callus, shoot and root induction) can be established. Transient transformations and GUS staining of *cannabis* after biolistic transformation will be performed to the extent needed. Then, the polynucleotides of the present invention can be transformed into *cannabis* plants. In particular, *Agrobacterium*-mediated transformation of reproductive *cannabis* cells can be also be performed using floral dip/vacuum infiltration methods followed by seed collection and analysis. In addition, *Agrobacterium*-mediated transformation of somatic cells (leaf disk and callus transformation followed by regeneration in tissue cultures) can be performed. In particular embodiments, petioles or floral organs can also be transformed. Biolistic transformation procedures using methodology selected from transient transformation experiments can be performed, and plants can be regenerated from tissue cultures. In addition, PEG-mediated protoplast transformations can be performed. In certain embodiments, a GUS reporter gene can be inserted into the vector before transformation.

The transformants (generated by, e.g., *Agrobacterium*, biolistic, or PEG-mediated transformation) will be subjected to DNA analysis (PCR) and GUS staining.

Example 7

Generation of Stable Transformants, Analysis of THCA Synthase Silencing, and Selection of Most Suitable Strains for Metabolite Analysis and Industrial Applications After regeneration of multiple transformed *cannabis* plants, polynucleotide analysis can be performed to confirm gene integration and to determine RNA expression levels. In addition, mRNA and protein levels of THCA synthase can be determined. The content of one or more bioactive metabolites, such as terpenes or cannabinoids in plant tissues can also be determined. For example, the content of one or more of THC, CBD, and/or Cannabichromene can be determined with well-established procedures, such as the methods described in US Patent Publication 20160139055, which is hereby incorporated in its entirety. Plants in which THCA synthase activity is reduced and which have reduced THC and/or increased CBD content will be selected.

The invention claimed is:

1. A method for altering a content of one or more cannabinoids in a *cannabis* plant, the method comprising down-regulating activity of tetrahydrocannabinolic acid (THCA) synthase in the *cannabis* plant, wherein the THCA synthase is expressed from a THCA synthase gene comprising a polynucleotide sequence selected from SEQ ID NOs: 1-28, 38, 40, 44-45, and 47;
wherein said down-regulating comprises introducing into the plant a selected DNA encoding an antisense RNA or a siRNA effective to suppress expression of the THCA synthase, the selected DNA operably linked to a heterologous promoter.

2. The method of claim 1, wherein altering the content of cannabinoids comprises decreasing delta-9-tetrahydrocannabinol (THC) content or increasing cannabidiol (CBD) content in the *cannabis* plant.

3. The method of claim 2, further comprising selecting a *cannabis* plant with a desired reduced THC content, increased CBD content, or reduced THC content and increased CBD content relative to a *cannabis* plant of a similar genotype that does not comprise the alteration.

4. The method of claim 1, wherein introducing the selected DNA comprises genetic transformation.

5. The method of claim 1, wherein the siRNA is encoded by a polynucleotide having a sequence selected from the group consisting of SEQ ID NO: 61, 63, 64, 69, 71, 72, 68, and a complement thereof.

6. The method of claim 1, wherein the antisense RNA is encoded by a polynucleotide sequence comprising SEQ ID NO: 81 or a fragment thereof capable of reducing the expression of the THCA synthase.

7. A method for altering a content of one or more cannabinoids in a *cannabis* plant, the method comprising down-regulating activity of tetrahydrocannabinolic acid (THCA) synthase in the *cannabis* plant, wherein the THCA synthase is expressed from a THCA synthase gene comprising a polynucleotide sequence selected from SEQ ID NOs: 1-28, 38, 40, 44-45, and 47; wherein said down-regulating comprises:
(a) introducing into a *cannabis* plant or a cell thereof (i) at least one RNA-guided endonuclease comprising at least one nuclear localization signal or nucleic acid encoding at least one RNA-guided endonuclease comprising at least one nuclear localization signal, (ii) at least one guide RNA or DNA encoding at least one guide RNA, and, optionally, (iii) at least one donor polynucleotide; and
(b) culturing the *cannabis* plant or cell thereof such that each guide RNA directs an RNA-guided endonuclease to a targeted site in the chromosomal sequence where the RNA-guided endonuclease introduces a double-stranded break in the targeted site, and the double-stranded break is repaired by a DNA repair process such that the chromosomal sequence is modified, wherein the targeted site is located in the THCA synthase gene and the chromosomal modification interrupts or interferes with transcription and/or translation of the THCA synthase gene.

8. The method of claim 7, wherein the RNA-guided endonuclease is derived from a clustered regularly interspersed short palindromic repeats (CRISPR)/CRISPR-associated (Cas) system.

9. The method of claim 7, wherein down-regulating the activity of the THCA synthase does not insert exogenous genetic material and produces a non-naturally occurring *cannabis* plant or cell thereof.

10. A method for altering a content of one or more cannabinoids in a *cannabis* plant, the method comprising down-regulating activity of tetrahydrocannabinolic acid (THCA) synthase in the *cannabis* plant, wherein the THCA synthase is expressed from a THCA synthase gene comprising a polynucleotide sequence selected from SEQ ID NOs: 1-28, 38, 40, 44-45, and 47; wherein said down-regulating comprises:
  (a) identifying at least one THCA synthase gene locus within a DNA sequence in a *cannabis* plant or a cell thereof;
  (b) identifying at least one custom endonuclease recognition sequence within the at least one THCA synthase gene locus;
  (c) introducing into the *cannabis* plant or a cell thereof at least a first custom endonuclease, wherein the *cannabis* plant or a cell thereof comprises the recognition sequence for the custom endonuclease in or proximal to the THCA synthase gene locus, and the custom endonuclease is expressed transiently or stably;
  (d) assaying the *cannabis* plant or a cell thereof for a custom endonuclease-mediated modification in the DNA making up or flanking the THCA synthase gene locus; and
  (e) identifying the *cannabis* plant, a cell thereof, or a progeny cell thereof as comprising a modification in the THCA synthase gene locus.

11. A transgenic *cannabis* plant produced by the method of claim 1.

12. A seed of the transgenic plant of claim 11, wherein the seed comprises the selected DNA.

13. A method for producing a medical *cannabis* composition, the method comprising:
  (a) obtaining the transgenic *cannabis* plant of claim 11;
  (b) growing the transgenic *cannabis* plant under plant growth conditions to produce transgenic plant tissue from the transgenic *cannabis* plant; and
  (c) preparing the medical *cannabis* composition from the transgenic plant tissue.

* * * * *

SEQUENCE LISTING

```
<160> NUMBER OF SEQ ID NOS: 86

<210> SEQ ID NO 1
<211> LENGTH: 1635
<212> TYPE: DNA
<213> ORGANISM: Cannabis sativa

<400> SEQUENCE: 1
atgaattgct cagcattttc cttttggttt gtttgcaaaa taatattttt ctttctctca      60
ttcaatatcc aaatttcaat agctaatcct caagaaaact tccttaaatg cttctcggaa     120
tatattccta acaatccagc aaatccaaaa ttcatataca ctcaacacga ccaattgtat     180
atgtctgtcc tgaattcgac aatacaaaat cttagattca cctctgatac aaccccaaaa     240
ccactcgtta ttgtcactcc ttcaaatgtc tcccatatcc aggccagtat tctctgctcc     300
aagaaagttg gtttgcagat tcgaactcga agcggtggcc atgatgctga gggtatgtcc     360
tacatatctc aagtcccatt tgttgtagta gacttgagaa acatgcattc gatcaaaata     420
gatgttcata gccaaactgc gtgggttgaa gccggagcta cccttggaga agtttattat     480
tggatcaatg agaagaatga gaattttagt tttcctggtg ggtattgccc tactgttggc     540
gtaggtggac actttagtgg aggaggctat ggagcattga tgcgaaatta tggccttgcg     600
gctgataata ttattgatgc acacttagtc aatgttgatg gaaaagttct agatcgaaaa     660
tccatgggag aagatctgtt ttgggctata cgtggtggtg gaggagaaaa ctttggaatc     720
```

```
attgcagcat ggaaaatcaa actggttgct gtcccatcaa agtctactat attcagtgtt    780
aaaaagaaca tggagataca tgggcttgtc aagttattta acaaatggca aaatattgct    840
tacaagtatg acaaagattt agtactcatg actcacttca taacaaagaa tattacagat    900
aatcatggga agaataagac tacagtacat ggttacttct cttccattttt tcatggtgga    960 gtggatagtc tagtcgactt gatgaacaag agctttcctg agttgggtat taaaaaaact   1020
gattgcaaag aatttagctg gattgataca accatcttct acagtggtgt tgtaaatttt   1080
aacactgcta attttaaaaa ggaaattttg cttgatagat cagctgggaa gaagacggct   1140
ttctcaatta agttagacta tgttaagaaa ccaattcctg aaactgcaat ggtcaaaatt   1200
ttggaaaaat tatatgaaga agatgtagga gttgggatgt atgtgttgta cccttacggt   1260
ggtataatgg aggagatttc agaatcagca attccattcc ctcatcgagc tggaataatg   1320
tatgaacttt ggtacactgc ttcctgggag aagcaagaag ataatgaaaa gcatataaac   1380
tgggttcgaa gtgtttataa ttttacaact ccttatgtgt cccaaaatcc aagattggcg   1440
tatctcaatt atagggacct tgatttagga aaaactaatc ctgagagtcc taataattac   1500
acacaagcac gtatttgggg tgaaaagtat tttggtaaaa attttaacag gttagttaag   1560
gtgaaaacca aagctgatcc caataatttt tttagaaacg aacaaagtat cccacctctt   1620
ccaccgcatc atcat                                                    1635

<210> SEQ ID NO 2
<211> LENGTH: 1635
<212> TYPE: DNA
<213> ORGANISM: Cannabis sativa

<400> SEQUENCE: 2
atgaattgct cagcattttc cttttggttt gtttgcaaaa taatattttt ctttctctca     60
ttcaatatcc aaatttcaat agctaatcct caagaaaact tccttaaatg cttctcggaa    120
tatattccta acaatccagc aaatccaaaa ttcatataca ctcaacacga ccaattgtat    180
atgtctgtcc tgaattcgac aatacaaaat cttagattca cctctgatac aaccccaaaa    240
ccactcgtta ttgtcactcc ttcaaatgtc tcccatatcc aggccagtat tctctgctcc    300
aagaaagttg gtttgcagat tcgaactcga agcggtggcc atgatgctga gggtatgtcc    360
tacatatctc aagtcccatt tgttgtagta gacttgagaa acatgcattc gatcaaaata    420
gatgttcata gccaaactgc gtgggttgaa gccggagcta cccttggaga agtttattat    480
tggatcaatg agaagaatga gaattttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg aaaagttct agatcgaaaa    660 tccatgggag aagatctatt tgggctata cgtggtggag gaggagaaaa ctttggaatc    720
attgcagcat ggaaaatcaa actggttgtt gtcccatcaa agtctactat attcagtgtt    780
aaaaagaaca tggagataca tgggcttgtc aagttattta acaaatggca aaatattgct    840
tacaagtatg acaaagattt agtactcatg actcacttca taacaaagaa tattacagat    900
aatcatggga agaataagac tacagtacat ggttacttct cttccattttt tcatggtgga    960 gtggatagtc tagtcgactt gatgaacaag agctttcctg agttgggtat taaaaaaact   1020
gattgcaaag aatttagctg gattgataca accatcttct acagtggtgt tgtaaatttt   1080
aacactgcta attttaaaaa ggaaattttg cttgatagat cagctgggaa gaagacggct   1140
```

```
ttctcaatta agttagacta tgttaagaaa ccaattcctg aaactgcaat ggtcaaaatt    1200
ttggaaaaat tatatgaaga agatgtagga gttgggatgt atgtgttgta cccttacggt    1260
ggtataatgg aggagatttc agaatcagca attccattcc ctcatcgagc tggaataatg    1320
tatgaacttt ggtacactgc ttcctgggag aagcaagaag ataatgaaaa gcatataaac    1380
tgggttcgaa gtgttttataa ttttacgact ccttatgtgt cccaaaatcc aagattggcg    1440
tatctcaatt atagggacct tgatttagga aaaactaatc ctgagagtcc taataattac    1500
acacaagcac gtatttgggg tgaaaagtat tttggtaaaa attttaacag gttagttaag    1560
gtgaaaacca aagctgatcc caataatttt tttagaaacg aacaaagtat cccacctctt    1620
ccaccgcatc atcat                                                    1635

<210> SEQ ID NO 3
<211> LENGTH: 1635
<212> TYPE: DNA
<213> ORGANISM: Cannabis sativa

<400> SEQUENCE: 3
atgaattgct cagcattttc cttttggttt gtttgcaaaa taatattttt ctttctctca     60
ttcaatatcc aaatttcaat agctaatcct caagaaaact tccttaaatg cttctcggaa    120
tatattccta caatccagc aaatccaaaa ttcatataca ctcaacacga ccaattgtat    180
atgtctgtcc tgaattcgac aatacaaaat cttagattca cctctgatac aaccccaaaa    240
ccactcgtta ttgtcactcc ttcaaatgtc tcccatatcc aggccagtat tctctgctcc    300
aagaaagttg gtttgcagat tcgaactcga agcggtggcc atgatgctga gggtatgtcc    360
tacatatctc aagtcccatt tgttgtagta gacttgagaa acatgcattc gatcaaaata    420
gatgttcata gccaaactgc gtgggttgaa gccggagcta cccttggaga gtttattat     480 tggatcaatg agaagaatga gaattttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg aaaagttct agatcgaaaa    660 tccatgggag aagatctatt tgggctata cgtggtggag gaggagaaaa cttttggaatc    720 attgcagcat ggaaaatcaa actggttgtt gtcccatcaa agtctactat attcagtgtt    780
aaaaagaaca tggagataca tgggcttgtc aagttattta caaatggca aaatattgct    840 tacaagtatg acaaagattt agtactcatg actcacttca taacaaagaa tattacagat    900
aatcatggga agaataagac tacagtacat ggttacttct cttccatttt tcatggtgga    960
gtggatagtc tagtcgactt gatgaacaag agctttcctg agttgggtat aaaaaaaact    1020
gattgcaaag aatttagctg gattgataca accatcttct acagtggtgt tgtaaatttt    1080
aacactgcta attttaaaaa ggaaattttg cttgatagat cagctgggaa gaagacggct    1140
ttctcaatta agttagacta tgttaagaaa ccaattcctg aaactgcaat ggtcaaaatt    1200
ttggaaaaat tatatgaaga agatgtagga gttgggatgt atgtgttgta cccttacggt    1260
ggtataatgg aggagatttc agaatcagca attccattcc ctcatcgagc tggaataatg    1320
tatgaacttt ggtacactgc ttcctgggag aagcaagaag ataatgaaaa gcatataaac    1380
tgggttcgaa gtgttttataa ttttacaact ccttatgtgt cccaaaatcc aagattggcg    1440
tatctcaatt atagggacct tgatttagga aaaactaatc ctgagagtcc taataattac    1500
acacaagcac gtatttgggg tgaaaagtat tttggtaaaa attttaacag gttagttaag    1560
gtgaaaacca aagctgatcc caataatttt tttagaaacg aacaaagtat cccacctctt    1620
```

<210> SEQ ID NO 4
<211> LENGTH: 1635
<212> TYPE: DNA
<213> ORGANISM: Cannabis sativa

<400> SEQUENCE: 4

```
atgaattgct cagcattttc cttttggttt gtttgcaaaa taatattttt ctttctctca      60
ttcaatatcc aaatttcaat agctaatcct caagaaaact tccttaaatg cttctcggaa     120
tatattccta acaatccagc aaatccaaaa ttcatataca ctcaacacga ccaattgtat     180
atgtctgtcc tgaattcgac aatacaaaat cttagattca cctctgatac aaccccaaaa     240
ccactcgtta ttgtcactcc ttcaaatgtc tcccatatcc aggccagtat tctctgctcc     300
aagaaagttg gtttgcagat tcgaactcga agcggtggcc atgatgctga gggtatgtcc     360
tacatatctc aagtcccatt tgttgtagta gacttgagaa acatgcattc gatcaaaata     420
gatgttcata gccaaactgc gtgggttgaa gccggagcta cccttggaga gtttattat      480
tggatcaatg agaagaatga gaattttagt tttcctggtg ggtattgccc tactgttggc     540
gtaggtggac actttagtgg aggaggctat ggagcattga tgcgaaatta tggccttgcg     600
gctgataata tcattgatgc acacttagtc aatgttgatg aaaagttct agatcgaaaa     660
tccatgggag aagatctatt tgggctata cgtggtggag gaggagaaaa ctttggaatc     720
attgcagcat ggaaaatcaa actggttgtt gtcccatcaa agtctactat attcagtgtt     780
aaaaagaaca tggagataca tgggcttgtc aagttattta caaatggca aaatattgct     840
tacaagtatg acaaagattt agtactcatg actcacttca taacaaagaa tattacagat     900
aatcatggga agaataagac tacagtacat ggttacttct cttcaatttt tcatggtgga     960
gtggatagtc tagtcgactt gatgaacaag agctttcctg agttgggtat taaaaaaact    1020
gattgcaaag aatttagctg gattgataca accatcttct acagtggtgt tgtaaatttt    1080
aacactgcta attttaaaaa ggaaattttg cttgatagat cagctgggaa gaagacggct    1140
ttctcaatta agtttagacta tgttaagaaa ccaattcctg aaactgcaat ggtcaaaatt    1200
ttggaaaaat tatatgaaga gatgtagga gttgggatgt atgtgttgta cccttacggt    1260
ggtataatgg aggagatttc agaatcagca attccattcc ctcatcgagc tggaataatg    1320
tatgaacttt ggtacactgc ttcctgggag aagcaagaag ataatgaaaa gcatataaac    1380
tgggttcgaa gtgtttataa ttttacaact cctatgtgt cccaaaatcc aagattggcg     1440
tatctcaatt atagggacct tgatttagga aaaactaatc ctgagagtcc taataattac    1500
acacaagcac gtatttgggg tgaaaagtat tttggtaaaa attttaacag gttagttaag    1560
gtgaaaacca agctgatcc caataatttt tttagaaacg aacaaagtat cccacctctt    1620
ccaccgcatc atcat                                                    1635
```

<210> SEQ ID NO 5
<211> LENGTH: 1635
<212> TYPE: DNA
<213> ORGANISM: Cannabis sativa

<400> SEQUENCE: 5

```
atgaattgct cagcattttc cttttggttt gtttgcaaaa taatattttt ctttctctca      60
ttcaatatcc aaatttcaat agctaatcct caagaaaact tccttaaatg cttctcggaa     120
```

```
tatattccta acaatccagc aaatccaaaa ttcatataca ctcaacacga ccaattgtat      180
atgtctgtcc tgaattcgac aatacaaaat cttagattca cctctgatac aaccccaaaa      240
ccactcgtta ttgtcactcc ttcaaatgtc tcccatatcc aggccagtat tctctgctcc      300
aagaaagttg gtttgcagat tcgaactcga agcggtggcc atgatgctga gggtatgtcc      360
tacatatctc aagtcccatt tgttgtagta gacttgagaa acatgcattc gatcaaaata      420
gatgttcata gccaaactgc gtgggttgaa gccggagcta cccttggaga agtttattat      480
tggatcaatg agaagaatga gaattttagt tttcctggtg ggtattgccc tactgttggc      540
gtaggtggac actttagtgg aggaggctat ggagcattga tgcgaaatta tggccttgcg      600
gctgataata tcattgatgc acacttagtc aatgttgatg gaaaagttct agatcgaaaa      660
tccatgggag aagatctatt tgggctata cgtggtggag gaggagaaaa ctttggaatc       720
attgcagcat ggaaaatcaa actggttgtt gtcccatcaa agtctactat attcagtgtt      780
aaaaagaaca tggagataca tgggcttgtc aagttattta caaatggca aaatattgct       840 tacaagtatg acaagagattt agtactcatg actcacttca taacaaagaa tattacagat     900
aatcatggga agaataagac tacagtacat ggttacttct cttcaatttt tcatggtgga      960
gtggatagtc tagtcgactt gatgaacaag agctttcctg agttgggtat taaaaaaact     1020
gattgcaaag aatttagctg gattgataca accatcttct acagtggtgt tgtaaatttt     1080
aacactgcta attttaaaaa ggaaattttg cttgatagat cagctgggaa gaagacggct     1140
ttctcaatta agttagacta tgttaagaaa ccaattcctg aaactgcaat ggtcaaaatt     1200
ttggaaaaat tatatgaaga agatgtagga gctgggatgt atgtgttgta cccttacggt      1260
ggtataatgg aggagatttc agaatcagca attccattcc ctcatcgagc tggaataatg     1320
tatgaacttt ggtacactgc ttcctgggag aagcaagaag ataatgaaaa gcatataaac     1380
tgggttcgaa gtgtttataa ttttacgact cctttatgtgt cccaaaatcc aagattggcg    1440
tatctcaatt atagggacct tgatttagga aaaactaatc ctgagagtcc taataattac     1500
acacaagcac gtatttgggg tgaaaagtat tttggtaaaa attttaacag gttagttaag     1560
gtgaaaacca aagctgatcc caataatttt tttagaaacg aacaaagtat cccacctctt    1620
ccaccgcatc atcat                                                      1635
```

<210> SEQ ID NO 6
<211> LENGTH: 1635
<212> TYPE: DNA
<213> ORGANISM: Cannabis sativa

<400> SEQUENCE: 6

```
atgaattgct cagcattttc cttttggttt gtttgcaaaa taatattttt ctttctctca       60
ttcaatatcc aaatttcaat agctaatcct caagaaaact tccttaaatg cttctcggaa      120
tatattccta acaatccagc aaatccaaaa ttcatataca ctcaacacga ccaattgtat      180
atgtctgtcc tgaattcgac aatacaaaat cttagattca cctctgatac aaccccaaaa      240
ccactcgtta ttgtcactcc ttcaaatgtc tcccatatcc aggccagtat tctctgctcc      300
aagaaagttg gtttgcagat tcgaactcga agcggtggcc atgatgctga gggtatgtcc      360
tacatatctc aagtcccatt tgttgtagta gacttgagaa acatgcattc gatcaaaata      420
gatgttcata gccaaactgc gtgggttgaa gccggagcta cccttggaga agtttattat      480
tggatcaatg agaagaatga gaattttagt tttcctggtg ggtattgccc tactgttggc      540
gtaggtggac actttagtgg aggaggctat ggagcattga tgcgaaatta tggccttgcg      600
```

```
gctgataata tcattgatgc acacttagtc aatgttgatg aaaagttct agatcgaaaa      660 tccatgggag aagatctatt ttgggctata cgtggtggag gaggagaaaa ctttggaatc      720
attgcagcat ggaaaatcaa actggttgct gtcccatcaa agtctactat attcagtgtt      780
aaaaagaaca tggagataca tgggcttgtc aagttattta caaatggca aaatattgct      840 tacaagtatg acaaagattt agtactcatg actcacttca taacaaagaa tattacagat      900
aatcatggga agaataagac tacagtacat ggttacttct cttcaatttt tcatggtgga      960
gtggatagtc tagtcgactt gatgaacaag agctttcctg agttgggtat taaaaaaact     1020
gattgcaaag aatttagctg gattgataca accatcttct acagtggtgt tgtaaatttt     1080
aacactgcta atttttaaaaa ggaaattttg cttgatagat cagctgggaa gaagacggct     1140
ttctcaatta gttagacta tgttaagaaa ccaattcctg aaactgcaat ggtcaaaatt      1200
ttggaaaaat tatatgaaga agatgtagga gctgggatgt atgtgttgta cccttacggt     1260
ggtataatgg aggagatttc agaatcagca attccattcc ctcatcgagc tggaataatg     1320
tatgaacttt ggtacactgc ttcctgggag aagcaagaag ataatgaaaa gcatataaac     1380
tgggttcgaa gtgtttataa ttttacgact ccttatgtgt cccaaaatcc aagattggcg     1440
tatctcaatt atagggacct tgatttagga aaaactaatc ctgagagtcc taataattac     1500
acacaagcac gtatttgggg tgaaaagtat tttggtaaaa attttaacag gttagttaag     1560
gtgaaaacca agctgatcc caataatttt tttagaaacg aacaaagtat cccacctctt     1620
ccaccgcatc atcat                                                     1635

<210> SEQ ID NO 7
<211> LENGTH: 1635
<212> TYPE: DNA
<213> ORGANISM: Cannabis sativa

<400> SEQUENCE: 7
atgaattgct cagcattttc cttttggttt gtttgcaaaa taatattttt ctttctctca       60
ttcaatatcc aaatttcaat agctaatcct caagaaaact tccttaaatg cttctcggaa      120
tatattccta acaatccagc aaatccaaaa ttcatataca ctcaacacga ccaattgtat      180
atgtctgtcc tgaattcgac aatacaaaat cttagattca cctctgatac aaccccaaaa      240
ccactcgtta ttgtcactcc ttcaaatgtc tcccatatcc aggccagtat tctctgctcc      300
aagaaagttg gtttgcagat tcgaactcga agcggtggcc atgatgctga gggtatgtcc      360
tacatatctc aagtcccatt tgttgtagta gacttgagaa catgcattc gatcaaaata      420 gatgttcata gccaaactgc gtgggttgaa gccggagcta cccttggaga agtttattat      480
tggatcaatg agaagaatga gaattttagt tttcctggtg ggtattgccc tactgttggc      540
gtaggtggac actttagtgg aggaggctat ggagcattga tgcgaaatta tggccttgcg      600
gctgataata tcattgatgc acacttagtc aatgttgatg aaaagttct agatcgaaaa      660 tccatgggag aagatctatt ttgggctata cgtggtggag gaggagaaaa ctttggaatc      720
attgcagcat ggaaaatcaa actggttgtt gtcccatcaa agtctactat attcagtgtt      780
aaaaagaaca tggagataca tgggcttgtc aagttattta caaatggca aaatattgct      840 tacaagtatg acaaagattt agtactcatg actcacttca taacaaagaa tattacagat      900
aatcatggga agaataagac tacagtacat ggttacttct cttcaatttt tcatggtgga      960
gtggatagtc tagtcgactt gatgaacaag agctttcctg agttgggtat taaaaaaact     1020
```

```
gattgcaaag aatttagctg gattgataca accatcttct acagtggtgt tgtaaatttt    1080
aacactgcta attttaaaaa ggaaattttg cttgatagat cagctgggaa gaagacggct    1140
ttctcaatta agttagacta tgttaagaaa ccaattccag aaactgcaat ggtcaaaatt    1200
ttggaaaaat tatatgaaga agatgtagga gctgggatgt atgtgttgta cccttacggt    1260
ggtataatgg aggagatttc agaatcagca attccattcc ctcatcgagc tggaataatg    1320
tatgaacttt ggtacactgc ttcctgggag aagcaagaag ataatgaaaa gcatataaac    1380
tgggttcgaa gtgtttataa ttttacgact ccttatgtgt cccaaaatcc aagattggcg    1440
tatctcaatt atagggacct tgatttagga aaaactaatc ctgagagtcc taataattac    1500
acacaagcac gtatttgggg tgaaaagtat tttggtaaaa attttaacag gttagttaag    1560
gtgaaaacca aagctgatcc caataatttt tttagaaacg aacaaagtat cccacctctt    1620
ccaccgcatc atcat                                                     1635

<210> SEQ ID NO 8
<211> LENGTH: 1635
<212> TYPE: DNA
<213> ORGANISM: Cannabis sativa

<400> SEQUENCE: 8
atgaattgct cagcattttc cttttggttt gtttgcaaaa taatattttt ctttctctca      60
ttcaatatcc aaatttcaat agctaatcct caagaaaact tccttaaatg cttctcggaa     120
tatattccta caatccagc aaatccaaaa ttcatataca ctcaacacga ccaattgtat      180
atgtctgtcc tgaattcgac aatacaaaat cttagattca cctctgatac aaccccaaaa    240
ccactcgtta ttgtcactcc ttcaaatgtc tcccatatcc aggccagtat tctctgctcc    300
aagaaagttg gttgcagat tcgaactcga agcggtggcc atgatgctga gggtatgtcc      360
tacatttctc aagtcccatt tgttgtagta gacttgagaa acatgcattc gatcaaaata    420
gatgttcata gccaaactgc gtgggttgaa gccggagcta cccttggaga gtttattat     480 tggatcaatg agaagaatga gaattttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg gaaaagttct agatcgaaaa    660
tccatgggag aagatctatt tgggctatac gtggtggag gaggagaaaa ctttggaatc    720
attgcagcat ggaaaatcaa actggttgct gtcccatcaa agtctactat attcagtgtt    780
aaaaagaaca tggagataca tgggcttgtc aagttattta caaatggca aaatattgct    840 tacaagtatg acaaagattt agtactcatg actcacttca taacaaagaa tattacagat    900
aatcatggga agaataagac tacagtacat ggttacttct cttccatttt tcatggtgga    960
gtggatagtc tagtcgactt gatgaacaag agctttcctg agttgggtat taaaaaaact   1020
gattgcaaag aatttagctg gattgataca accatcttct acagtggtgt tgtaaatttt    1080
aacactgcta attttaaaaa ggaaattttg cttgatagat cagctgggaa gaagacggct    1140
ttctcaatta agttagacta tgttaagaaa ccaattcctg aaactgcaat ggtcaaaatt    1200
ttggaaaaat tatatgaaga agatgtagga gctgggatgt atgtgttgta cccttacggt    1260
ggtataatgg aggagatttc agaatcagca attccattcc ctcatcgagc tggaataatg    1320
tatgaacttt ggtacactgc ttcctgggag aagcaagaag ataatgaaaa gcatataaac    1380
tgggttcgaa gtgtttataa ttttacgact ccttatgtgt cccaaaatcc aagattggcg    1440
tatctcaatt atagggacct tgatttagga aaaactaatc ctgagagtcc taataattac    1500
```

| | | |
|---|---|---|
| acacaagcac gtatttgggg tgaaaagtat tttggtaaaa attttaacag gttagttaag | 1560 |
| gtgaaaacca aagctgatcc caataatttt tttagaaacg aacaaagtat cccacctctt | 1620 |
| ccaccgcatc atcat | 1635 |

<210> SEQ ID NO 9
<211> LENGTH: 1635
<212> TYPE: DNA
<213> ORGANISM: Cannabis sativa

<400> SEQUENCE: 9

| | | |
|---|---|---|
| atgaattgct cagcattttc cttttggttt gtttgcaaaa taatattttt ctttctctca | 60 |
| ttcaatatcc aaatttcaat agctaatcct caagaaaact tccttaaatg cttctcggaa | 120 |
| tatattccta acaatccagc aaatccaaaa ttcatataca ctcaacacga ccaattgtat | 180 |
| atgtctgtcc tgaattcgac aatacaaaat cttagattca cctctgatac aaccccaaaa | 240 |
| ccactcgtta ttgtcactcc ttcaaatgtc tcccatatcc aggccagtat tctctgctcc | 300 |
| aagaaagttg gtttgcagat tcgaactcga agcggtggcc atgatgctga gggtttgtcc | 360 |
| tacatatctc aagtcccatt tgctatagta gacttgagaa acatgcatac ggtcaaagta | 420 |
| gatattcata gccaaactgc gtgggttgaa gccggagcta cccttggaga gtttattat | 480 |
| tggatcaatg agatgaatga gaattttagt tttcctggtg ggtattgccc tactgttggc | 540 |
| gtaggtggac actttagtgg aggaggctat ggagcattga tgcgaaatta tggccttgcg | 600 |
| gctgataata tcattgatgc acacttagtc aatgttgatg aaaagttct agatcgaaaa | 660 |
| tccatgggag aagatctatt tgggctatac gtggtggag gaggagaaaa ctttggaatc | 720 |
| attgcagcat ggaaaatcaa acttgttgtt gtcccatcaa aggctactat attcagtgtt | 780 |
| aaaaagaaca tggagataca tgggcttgtc aagttattta caaatggca aaatattgct | 840 |
| tacaagtatg acaaagattt aatgctcacg actcacttca gaactaggaa attacagat | 900 |
| aatcatggga agaataagac tacagtacat ggttacttct cttccatttt tcttggtgga | 960 |
| gtggatagtc tagttgactt gatgaacaag agctttcctg agttgggtat taaaaaaact | 1020 |
| gattgcaaag aattgagctg gattgataca accatcttct acagtggtgt tgtaaattac | 1080 |
| aacactgcta attttaaaaa ggaaattttg cttgatagat cagctgggaa gaagacggct | 1140 |
| ttctcaatta gttagacta tgttaagaaa ctaaatacctg aaactgcaat ggtcaaaatt | 1200 |
| ttggaaaaat tatatgaaga gaggtagga gttgggatgt atgtgttgta cccttacggt | 1260 |
| ggtataatgg atgagatttc agaatcagca attccattcc ctcatcgagc tggataatg | 1320 |
| tatgaacttt ggtacactgc tacctgggag aagcaagaag ataacgaaaa gcatataaac | 1380 |
| tgggttcgaa gtgtttataa tttcacaact ccttatgtgt cccaaaatcc aagattggcg | 1440 |
| tatctcaatt atagggacct tgatttagga aaaactaatc ctgagagtcc taataattac | 1500 |
| acacaagcac gtatttgggg tgaaaagtat tttggtaaaa attttaacag gttagttaag | 1560 |
| gtgaaaacca aagctgatcc caataatttt tttagaaacg aacaaagtat cccacctctt | 1620 |
| ccaccgcatc atcat | 1635 |

<210> SEQ ID NO 10
<211> LENGTH: 1635
<212> TYPE: DNA
<213> ORGANISM: Cannabis sativa

<400> SEQUENCE: 10

```
atgaattgct cagcatttc ctttggttt gttgcaaaa taatattttt ctttctctca    60
ttcaatatcc aaatttcaat agctaatcct caagaaaact tccttaaatg cttctcggaa   120
tatattccta acaatccagc aaatccaaaa ttcatataca ctcaacacga ccaattgtat   180
atgtctgtcc tgaattcgac aatacaaaat cttagattca cctctgatac aaccccaaaa   240
ccactcgtta ttgtcactcc ttcaaatgtc tcccatatcc aggccagtat tctctgctcc   300
aagaaagttg gtttgcagat tcgaactcga agcggtggcc atgatgctga gggtttgtcc   360
tacatatctc aagtcccatt tgctatagta gacttgagaa acatgcatac ggtcaaagta   420
gatattcata gccaaactgc gtgggttgaa gccggagcta cccttggaga agtttattat   480
tggatcaatg agatgaatga aatttagt tttcctggtg ggtattgccc tactgttggc   540
gtaggtggac actttagtgg aggaggctat ggagcattga tgcgaaatta tggccttgcg   600
gctgataata tcattgatgc acacttagtc aatgttgatg gaaaagttct agatcgaaaa   660
tccatgggag aagatctatt ttgggctata cgtggtggag gaggagaaaa ctttggaatc   720
attgcagcat ggaaaatcaa acttgttgtt gtcccatcaa aggctactat attcagtgtt   780
aaaaagaaca tggagataca tgggcttgtc aagttattta acaaatggca aaatattgct   840
tacaagtatg acaaagattt aatgctcacg actcacttca gaactaggaa tattacagat   900
aatcatggga agaataagac tacagtacat ggttacttct cttccatttt tcttggtgga   960
gtggatagtc tagttgactt gatgaacaag agctttcctg agttgggtat taaaaaaact  1020
gattgcaaag aattgagctg gattgataca accatcttct acagtggtgt tgtaaattac  1080
aacactgcta atttaaaaa ggaaattttg cttgatagat cagctgggaa gaagacggct  1140
ttctcaatta gttagacta tgttaagaaa ctaatacctg aaactgcaat ggtcaaaatt  1200
ttggaaaaat tatatgaaga gaggtagga gttgggatgt atgtgttgta ccttacggt   1260
ggtataatgg atgagattc agaatcagca attccattcc ctcatcgagc tggaataatg  1320
tatgaacttt ggtacactgc tacctgggag aagcaagaag ataacgaaaa gcatataaac  1380
tgggttcgaa gtgtttataa tttcacaact cctttatgtgt cccaaaatcc aagattggcg  1440
tatctcaatt atagggacct tgatttagga aaaactaatc ctgagagtcc taataattac  1500
acacaagcac gtatttgggg tgaaaagtat tttggtaaaa atttaacag gttagttaag  1560
gtgaaaacca agctgatcc caataatttt tttagaaacg aacaaagtat cccacctctt  1620
ccaccgcatc atcat                                                  1635

<210> SEQ ID NO 11
<211> LENGTH: 1635
<212> TYPE: DNA
<213> ORGANISM: Cannabis sativa

<400> SEQUENCE: 11
atgaattgct cagcatttc ctttggttt gttgcaaaa taatattttt ctttctctca    60
ttcaatatcc aaatttcaat agctaatcct caagaaaact tccttaaatg cttctcggaa   120
tatattccta acaatccagc aaatccaaaa ttcatataca ctcaacacga ccaattgtat   180
atgtctgtcc tgaattcgac aatacaaaat cttagattca cctctgatac aaccccaaaa   240
ccactcgtta ttgtcactcc ttcaaatgtc tcccatatcc aggccagtat tctctgctcc   300
aagaaagttg gtttgcagat tcgaactcga agcggtggcc atgatgctga gggtttgtcc   360
tacatatctc aagtcccatt tgctatagta gacttgagaa acatgcatac ggtcaaagta   420
gatattcata gccaaactgc gtgggttgaa gccggagcta cccttggaga agtttattat   480
```

```
tggatcaatg agatgaatga gaattttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg gaaagttct agatcgaaaa     660 tccatgggag aagatctatt ttgggctata cgtggtggag gaggagaaaa ctttggaatc    720
attgcagcat ggaaaatcaa acttgttgtt gtcccatcaa aggctactat attcagtgtt    780
aaaaagaaca tggagataca tgggcttgtc aagttattta acaaatggca aaatattgct    840
tacaagtatg acaaagattt aatgctcacg actcacttca gaactaggaa tattacagat    900
aatcatggga agaataagac tacagtacat ggttacttct cttccatttt tcttggtgga    960
gtggatagtc tagttgactt gatgaacaag agctttcctg agttgggtat taaaaaaact   1020
gattgcaaag aattgagctg gattgataca accatcttct acagtggtgt tgtaaattac   1080
aacactgcta attttaaaaa ggaaattttg cttgatagat cagctgggaa gaagacggct   1140
ttctcaatta gttagacta tgttaagaaa ctaatacctg aaactgcaat ggtcaaaatt    1200
ttggaaaaat tatatgaaga gaggtagga gttgggatgt atgtgttgta cccttacggt     1260
ggtataatgg atgagatttc agaatcagca attccattcc ctcatcgagc tggaataatg   1320
tatgaacttt ggtacactgc tacctgggag aagcaagaag ataacgaaaa gcatataaac   1380
tgggttcgaa gtgtttataa tttcacaact ccttatgtgt cccaaaatcc aagattggcg   1440
tatctcaatt atagggacct tgatttagga aaaactaatc ctgagagtcc taataattac   1500
acacaagcac gtatttgggg tgaaaagtat tttggtaaaa attttaacag gttagttaag   1560
gtgaaaacca aagctgatcc caataatttt tttagaaacg aacaaagtat cccacctctt   1620
ccaccgcatc atcat                                                   1635

<210> SEQ ID NO 12
<211> LENGTH: 1635
<212> TYPE: DNA
<213> ORGANISM: Cannabis sativa

<400> SEQUENCE: 12
atgaattgct cagcattttc cttttggttt gtttgcaaaa taatattttt ctttctctca     60
ttcaatatcc aaatttcaat agctaatcct caagaaaact tccttaaatg cttctcggaa    120
tatattccta caaatccagc aaatccaaaa ttcatataca ctcaacacga ccaattgtat    180
atgtctgtcc tgaattcgac aatacaaaat cttagattca cctctgatac aaccccaaaa    240
ccactcgtta ttgtcactcc ttcaaatgtc tcccatatcc aggccagtat tctctgctcc    300
aagaaagttg gtttgcagat tcgaactcga agcggtggcc atgatgctga gggtatgtcc    360
tacatttctc aagtcccatt tgttgtagta gacttgagga acatgcattc gatcaaaata    420
gatgttcata gccaaactgc gtgggttgaa gccggagcta cccttggaga agtttattat    480
tggatcaatg agaagaatga gaatcttagt tttcctggtg ggtattgccc tactgttggc    540
gtaggtggac actttagtgg aggaggctat ggagcattga tgcgaaatta tggccttgcg    600
gctgataata ttattgatgc acacttagtc aatgttgatg gaaagttct agatcgaaaa     660 tccatgggag aagatctgtt ttgggctata cgtggtggtg gaggagaaaa ctttggaatc    720
attgcagcat ggaaaatcaa actggttgct gtcccatcaa agtctactat attcagtgtt    780
aaaaagaaca tggagataca tgggcttgtc aagttattta acaaatggca aaatattgct    840
tacaagtatg acaaagattt agtactcatg actcacttca taacaaagaa tattacagat    900
```

-continued

```
aatcatggga agaataagac tacagtacat ggttacttct cttcaatttt tcatggtgga    960
gtggatagtc tagtcgactt gatgaacaag agctttcctg agttgggtat taaaaaaact   1020
gattgcaaag aatttagctg gattgataca accatcttct acagtggtgt tgtaaatttt   1080
aacactgcta attttaaaaa ggaaattttg cttgatagat cagctgggaa gaagacggct   1140
ttctcaatta agttagacta tgttaagaaa ccaattcctg aaactgcaat ggtcaaaatt   1200
ttggaaaaat tatatgaaga agatgtagga gctgggatgt atgtgttgta cccttacggt   1260
ggtataatgg aggagatttc agaatcagca attccattcc ctcatcgagc tggaataatg   1320
tatgaacttt ggtacactgc ttcctgggag aagcaagaag ataatgaaaa gcatataaac   1380
tgggttcgaa gtgtttataa tttcacaact ccttatgtgt cccaaaatcc aagattggcg   1440
tatctcaatt atagggacct tgatttagga aaaactaatc ctgagagtcc taataattac   1500
acacaagcac gtatttgggg tgaaaagtat tttggtaaaa attttaacag gttagttaag   1560
gtgaaaacca agctgatcc caataatttt tttagaaacg aacaaagtat cccacctctt   1620
ccaccgcatc atcat                                                   1635

<210> SEQ ID NO 13
<211> LENGTH: 1635
<212> TYPE: DNA
<213> ORGANISM: Cannabis sativa

<400> SEQUENCE: 13
atgaattgct cagcattttc cttttggttt gtttgcaaaa taatatttttt ctttctctca     60 ttcaatatcc aaatttcaat agctaatcct caagaaaact tccttaaatg cttctcggaa    120
tatattccta acaatccagc aaatccaaaa ttcatataca ctcaacacga ccaattgtat    180
atgtctgtcc tgaattcgac aatacaaaat cttagattca cctctgatac aaccccaaaa    240
ccactcgtta ttgtcactcc ttcaaatgtc tcccatatcc aggccagtat tctctgctcc    300
aagaaagttg gtttgcagat tcgaactcga agcggtggcc atgatgctga gggtatgtcc    360
tacatttctc aagtcccatt tgttgtagta gacttgagga acatgcattc gatcaaaata    420
gatgttcata gccaaactgc gtgggttgaa gccggagcta cccttggaga agtttattat    480
tggatcaatg agaagaatga gaatcttagt tttcctggtg ggtattgccc tactgttggc    540
gtaggtggac actttagtgg aggaggctat ggagcattga tgcgaaatta tggccttgcg    600
gctgataata ttattgatgc acacttagtc aatgttgatg aaaagttct agatcgaaaa    660 tccatgggag aagatctgtt tgggctatac gtggtggtg gaggagaaaa ctttggaatc    720
attgcagcat ggaaaatcaa actggttgct gtcccatcaa agtctactat attcagtgtt    780
aaaaagaaca tggagataca tgggcttgtc aagttattta caaatggcaa aaatattgct    840
tacaagtatg acaaagattt agtactcatg actcacttca taacaaagaa tattacagat    900
aatcatggga agaataagac tacagtacat ggttacttct cttcaattttt tcatggtgga    960 gtggatagtc tagtcgactt gatgaacaag agctttcctg agttgggtat taaaaaaact   1020
gattgcaaag aatttagctg gattgataca accatcttct acagtggtgt tgtaaatttt   1080
aacactgcta attttaaaaa ggaaattttg cttgatagat cagctgggaa gaagacggct   1140
ttctcaatta agttagacta tgttaagaaa ccaattcctg aaactgcaat ggtcaaaatt   1200
ttggaaaaat tatatgaaga agaggtagga gttgggatgt atgtgttgta cccttacggt   1260
ggtataatgg aggagatttc agaatcagca attccattcc ctcatcgagc tggaataatg   1320
tatgaacttt ggtacactgc ttcctgggag aagcaagaag ataatgaaaa gcatataaac   1380
```

```
tgggttcgaa gtgtttataa tttcacaact ccttatgtgt cccaaaatcc aagattggcg    1440
tatctcaatt atagggacct tgatttagga aaaactaatc ctgagagtcc taataattac    1500
acacaagcac gtatttgggg tgaaaagtat tttggtaaaa attttaacag gttagttaag    1560
gtgaaaacca agctgatcc caataatttt tttagaaacg aacaaagtat cccacctctt     1620
ccaccgcatc atcat                                                     1635
```

<210> SEQ ID NO 14
<211> LENGTH: 1635
<212> TYPE: DNA
<213> ORGANISM: Cannabis sativa

<400> SEQUENCE: 14

```
atgaattgct cagcattttc cttttggttt gtttgcaaaa taatattttt ctttctctca     60
ttcaatatcc aaatttcaat agctaatcct caagaaaact tccttaaatg cttctcggaa    120
tatattccta acaatccagc aaatccaaaa ttcatataca ctcaacacga ccaattgtat    180
atgtctgtcc tgaattcgac aatacaaaat cttagattca cctctgatac aaccccaaaa    240
ccactcgtta ttgtcactcc ttcaaatgtc tcccatatcc aggccagtat tctctgctcc    300
aagaaagttg gtttgcagat tcgaactcga agcggtggcc atgatgctga gggtttgtcc    360
tacatatctc aagtcccatt tgctatagta gacttgagaa acatgcatac ggtcaaagta    420
gatattcata gccaaactgc gtgggttgaa gccggagcta cccttggaga gtttattat     480 tggatcaatg agatgaatga aattttagt tttcctggtg ggtattgccc tactgttggc     540
gtaggtggac actttagtgg aggaggctat ggagcattga tgcgaaatta tggccttgcg    600
gctgataata tcattgatgc acacttagtc aatgttgatg aaaagttct agatcgaaaa    660 tccatgggag aagatctatt tgggctata cgtggtggag gaggagaaaa ctttggaatc    720
attgcagcat ggaaaatcaa actggttgct gtcccatcaa agtctactat attcagtgtt    780
aaaaagaaca tggagataca tgggcttgtc aagttattta caaatggca aaatattgct    840 tacaagtatg acaaagattt agtactcatg actcacttca taacaaagaa tattacagat    900
aatcatggga agaataagac tacagtacat ggttacttct cttcaattt tcatggtgga    960 gtggatagtc tagtcgactt gatgaacaag agctttcctg agttgggtat taaaaaact    1020 gattgcaaag aatttagctg gattgataca accatcttct acagtggtgt tgtaaatttt    1080
aacactgcta attttaaaaa ggaaattttg cttgatagat cagctgggaa gaagacggct    1140
ttctcaatta gttagacta tgttaagaaa ccaattcctg aaactgcaat ggtcaaaatt    1200
ttggaaaaat tatatgaaga agatgtagga gctggatgt atgtgttgta cccttacggt    1260
ggtataatgg aggagatttc agaatcagca attccattcc ctcatcgagc tggataatg    1320 tatgaacttt ggtacactgc ttcctgggag aagcaagaag ataatgaaaa gcatataaac    1380
tgggttcgaa gtgtttataa ttttacgact ccttatgtgt cccaaaatcc aagattggcg    1440
tatctcaatt atagggacct tgatttagga aaaactaatc ctgagagtcc taataattac    1500
acacaagcac gtatttgggg tgaaaagtat tttggtaaaa attttaacag gttagttaag    1560
gtgaaaacca agctgatcc caataatttt tttagaaacg aacaaagtat cccacctctt     1620
ccaccgcatc atcat                                                     1635
```

<210> SEQ ID NO 15
<211> LENGTH: 1635
<212> TYPE: DNA

<213> ORGANISM: Cannabis sativa

<400> SEQUENCE: 15

| | |
|---|---|
| atgaattgct cagcattttc cttttggttt gtttgcaaaa taatattttt ctttctctca | 60 |
| ttcaatatcc aaatttcaat agctaatcct caagaaaact tccttaaatg cttctcggaa | 120 |
| tatattccta acaatccagc aaatccaaaa ttcatataca ctcaacacga ccaattgtat | 180 |
| atgtctgtcc tgaattcgac aatacaaaat cttagattca cctctgatac aaccccaaaa | 240 |
| ccactcgtta ttgtcactcc ttcaaatgtc tcccatatcc aggccagtat tctctgctcc | 300 |
| aagaaagttg gtttgcagat tcgaactcga agcggtggcc atgatgctga gggtatgtcc | 360 |
| tacatttctc aagtcccatt tgttgtagta gacttgagga acatgcattc gatcaaaata | 420 |
| gatgttcata gccaaactgc gtgggttgaa gccggagcta cccttggaga agtttattat | 480 |
| tggatcaatg agaagaatga gaatcttagt tttcctggtg ggtattgccc tactgttggc | 540 |
| gtaggtggac actttagtgg aggaggctat ggagcattga tgcgaaatta tggccttgcg | 600 |
| gctgataata ttattgatgc acacttagtc aatgttgatg gaaaagttct agatcgaaaa | 660 |
| tccatgggag aagatctgtt tgggctatac gtggtggtg gaggagaaaa ctttggaatc | 720 |
| attgcagcat ggaaaatcaa actggttgct gtcccatcaa agtctactat attcagtgtt | 780 |
| aaaaagaaca tggagataca tgggcttgtc aagttattta caaatggca aaatattgct | 840 |
| tacaagtatg acaaagattt agtactcatg actcacttca taacaaagaa tattacagat | 900 |
| aatcatggga agaataagac tacagtacat ggttacttct cttcaatttt tcatggtgga | 960 |
| gtggatagtc tagtcgactt gatgaacaag agctttcctg agttgggtat taaaaaaact | 1020 |
| gattgcaaag aatttagctg gattgataca accatcttct acagtggtgt tgtaaatttt | 1080 |
| aacactgcta attttaaaaa ggaaattttg cttgatagat cagctgggaa gagacggct | 1140 |
| ttctcaatta gttagacta tgttaagaaa ccaattcctg aaactgcaat ggtcaaaatt | 1200 |
| ttggaaaaat tatatgaaga gatgtagga gttgggatgt atgtgttgta cccttacggt | 1260 |
| ggtataatgg aggagatttc agaatcagca attccattcc ctcatcgagc tggaataatg | 1320 |
| tatgaacttt ggtacactgc ttcctgggag aagcaagaag ataatgaaaa gcatataaac | 1380 |
| tgggttcgaa gtgtttataa ttttacaact ccttatgtgt cccaaaatcc aagattggcg | 1440 |
| tatctcaatt atagggacct tgatttagga aaaactaatc ctgagagtcc taataattac | 1500 |
| acacaagcac gtatttgggg tgaaaagtat tttggtaaaa attttaacag gttagttaag | 1560 |
| gtgaaaacca aagctgatcc caataatttt tttagaaacg aacaaagtat cccacctctt | 1620 |
| ccaccgcatc atcat | 1635 |

<210> SEQ ID NO 16
<211> LENGTH: 1635
<212> TYPE: DNA
<213> ORGANISM: Cannabis sativa

<400> SEQUENCE: 16

| | |
|---|---|
| atgaattgct cagcattttc cttttggttt gtttgcaaaa taatattttt ctttctctca | 60 |
| ttcaatatcc aaatttcatt agctaatcct caagaaaact tccttaaatg cttctcggaa | 120 |
| tatattccta acaatccagc aaatccaaaa ttcatataca ctcaacacga ccaattgtat | 180 |
| atgtctgtcc tgaattcgac aatacaaaat cttagattca cctctgatac aaccccaaaa | 240 |
| ccactcgtta ttgtcactcc ttcaaatgtc tcccatatcc aggccagtat tctctgctcc | 300 |
| aagaaagttg gtttgcagat tcgaactcga agcggtggcc atgatgctga gggtttgtcc | 360 |

```
tacatatctc aagtcccatt tgctatagta gacttgagaa acatgcatac ggtcaaagta      420
gatattcata gccaaactgc gtgggttgaa gccggagcta cccttggaga agtttattat      480
tggatcaatg agatgaatga gaattttagt tttcctggtg ggtattgccc tactgttggc      540
gtaggtggac actttagtgg aggaggctat ggagcattga tgcgaaatta tggccttgcg      600
gctgataata tcattgatgc acacttagtc aatgttgatg gaaaagttct agatcgaaaa      660
tccatgggag aagatctatt tgggctata cgtggtggag gaggagaaaa ctttggaatc       720
attgcagcat ggaaaatcaa acttgttgtt gtcccatcaa aggctactat attcagtgtt      780
aaaaagaaca tggagataca tgggcttgtc aagttattta acaaatggca aaatattgct      840
tacaagtatg acaaagattt aatgctcacg actcacttca gaactaggaa tattacagat      900
aatcatggga agaataagac tacagtacat ggttacttct cttccatttt tcttggtgga      960
gtggatagtc tagttgactt gatgaacaag agctttcctg agttgggtat taaaaaaact     1020
gattgcaaag aattgagctg gattgataca accatcttct acagtggtgt tgtaaattac     1080
aacactgcta attttaaaaa ggaaattttg cttgatagat cagctgggaa gaagacggct     1140
ttctcaatta agttagacta tgttaagaaa ctaatacctg aaactgcaat ggtcaaaatt     1200
ttggaaaaat tatatgaaga agaggtagga gttgggatgt atgtgttgta cccttacggt     1260
ggtataatgg atgagatttc agaatcagca attccattcc ctcatcgagc tggaataatg     1320
tatgaacttt ggtacactgc tacctgggag aagcaagaag ataacgaaaa gcatataaac     1380
tgggttcgaa gtgttataa tttcacaacg ccttatgtgt cccaaaatcc aagattggcg      1440
tatctcaatt ataggggacct tgatttagga aaaactaatc ctgagagtcc taataattac     1500
acacaagcac gtatttgggg tgaaaagtat tttggtaaaa attttaacag gttagttaag     1560
gtgaaaacca agctgatcc caataatttt tttagaaacg aacaaagtat cccacctctt      1620
ccaccgcatc atcat                                                      1635

<210> SEQ ID NO 17
<211> LENGTH: 1635
<212> TYPE: DNA
<213> ORGANISM: Cannabis sativa

<400> SEQUENCE: 17
atgaattgct cagcattttc cttttggttt gtttgcaaaa taatattttt ctttctctca       60
ttcaatatcc aaatttcaat agctaatcct caagaaaact tccttaaatg cttctcggaa      120
tatattccta caaatccagc aaatccaaaa ttcatataca ctcaacacga ccaattgtat      180
atgtctgtcc tgaattcgac aatacaaaat cttagattca cctctgatgc aaccccaaaa      240
ccactcgtta ttgtcactcc ttcaaatgtc tcccatatcc aggccagtat tctctgctcc      300
aagaaagttg gtttgcagat tcgaactcga agcggtggcc atgatgctga gggtttgtcc      360
tacatatctc aagtcccatt tgctatagta gacttgagaa acatgcatac ggtcaaagta      420
gatattcata gccaaactgc gtgggttgaa gccggagcta cccttggaga agtttattat      480
tggatcaatg agatgaatga gaattttagt tttcctggtg ggtattgccc tactgttggc      540
gtaggtggac actttagtgg aggaggctat ggagcattga tgcgaaatta tggccttgcg      600
gctgataata tcattgatgc acacttagtc aatgttgatg gaaaagttct agatcgaaaa      660
tccatgggag aagatctatt tgggctata cgtggtggag gaggagaaaa ctttggaatc       720
attgcagcat ggaaaatcaa acttgttgtt gtcccatcaa aggctactat attcagtgtt      780
```

```
aaaaagaaca tggagataca tgggcttgtc aagttattta acaaatggca aaatattgct      840
tacaagtatg acaaagattt aatgctcacg actcacttca gaactaggaa tattacagat      900
aatcatggga agaataagac tacagtacat ggttacttct cttccatttt tcttggtgga      960
gtggatagtc tagttgactt gatgaacaag agctttcctg agtgggtat taaaaaaact     1020 gattgcaaag aattgagctg gattgataca accatcttct acagtggtgt tgtaaattac     1080
aacactgcta attttaaaaa ggaaattttg cttgatagat cagctgggaa gaagacggct     1140
ttctcaatta agttagacta tgttaagaaa ctaatacctg aaactgcaat ggtcaaaatt     1200
ttggaaaaat tatatgaaga agaggtagga gttgggatgt atgtgttgta cccttacggt     1260
ggtataatgg atgagatttc agaatcagca attccattcc ctcatcgagc tggaataatg     1320
tatgaacttt ggtacactgc tacctgggag aagcaagaag ataacgaaaa gcatataaac     1380
tgggttcgaa gtgtttataa tttcacaact ccttatgtgt cccaaaatcc aagattggcg     1440
tatctcaatt atagggacct tgatttagga aaaactaatc ctgagagtcc taataattac     1500
acacaagcac gtatttgggg tgaaaagtat tttggtaaaa attttaacag gttagttaag     1560
gtgaaaacca agctgatcc caataatttt tttagaaacg aacaaagtat cccacctctt     1620
ccaccgcatc atcat                                                      1635

<210> SEQ ID NO 18
<211> LENGTH: 1635
<212> TYPE: DNA
<213> ORGANISM: Cannabis sativa

<400> SEQUENCE: 18
atgaattgct cagcattttc cttttggttt gtttgcaaaa taataatttt ctttctctca       60
ttcaatatcc aaatttcaat agctaatcct caagaaaact tccttaaatg cttctcggaa      120
tatattccta caatccagc aaatccaaaa ttcatataca ctcaacacga ccaattgtat      180
atgtctgtcc tgaattcgac aatacaaaat cttagattca cctctgatac aaccccaaaa      240
ccactcgtta ttgtcactcc ttcaaatgtc tcccatatcc aggccagtat tctctgctcc      300
aagaaagttg gtttgcagat tcgaactcga agcggtggcc atgatgctga gggtttgtcc      360
tacatatctc aagtcccatt tgctatagta gacttgagaa acatgcatac ggtcaaagta      420
gatattcata gccaaactgc gtgggttgaa gccggagcta cccttggaga gtttattat      480 tggatcaatg agatgaatga gaattttagt tttcctggtg ggtattgccc tactgttggc      540
gtaggtggac actttagtgg aggaggctat ggagcattga tgcgaaatta tggccttgcg      600
gctgataata tcattgatgc acacttagtc aatgttgatg aaaagttct agatcgaaaa      660 tccatgggag aagatctatt tgggctata cgtggtggag gaggagaaaa ctttggaatc      720
attgcagcat ggaaaatcaa acttgttgtt gtcccatcaa aggctactat attcagtgtt      780
aaaaagaaca tggagataca tgggcttgtc aagttattta acaaatggca aaatattgct      840
tacaagtatg acaaagattt aatgctcacg actcacttca gaactaggaa tattacagat      900
aatcatggga agaataagac tacagtacat ggttacttct cttccatttt tcttggtgga      960
gtggatagtc tagttgactt gatgaacaag agctttcctg agtgggtat taaaaaaact     1020 gattgcaaag aattgagctg gattgataca accatcttct acagtggtgt tgtaaattac     1080
aacactgcta attttaaaaa ggaaattttg cttgatagat cagctgggaa gaagacggct     1140
ttctcaatta agttagacta tgttaagaaa ctaatacctg aaactgcaat ggtcaaaatt     1200
ttggaaaaat tatatgaaga agaggtagga gttgggatgt atgtgttgta cccttacggt     1260
```

```
ggtataatgg atgagatttc agaatcagca attccattcc ctcatcgagc tggaataatg     1320
tatgaacttt ggtacactgc tacctgggag aagcaagaag ataacgaaaa gcatataaac     1380
tgggttcgaa gtgtttataa tttcacaact ccttatgtgt cccaaaatcc aagattggcg     1440
tatctcaatt atagggacct tgatttagga aaaactaatc ctgagagtcc taataattac     1500
acacaagcac gtatttgggg tgaaaagtat tttggtaaaa attttaacag gttagttaag     1560
gtgaaaacca aagctgatcc caataatttt tttagaaacg aacaaagtat cccacctctt     1620
ccaccgcatc atcat                                                     1635
```

<210> SEQ ID NO 19
<211> LENGTH: 1635
<212> TYPE: DNA
<213> ORGANISM: Cannabis sativa

<400> SEQUENCE: 19

```
atgaattgct cagcattttc cttttggttt gtttgcaaaa taatattttt ctttctctca       60
ttccatatcc aaatttcaat agctaatcct cgagaaaact tccttaaatg cttctcaaaa      120
catattccca acaatgtagc aaatccaaaa ctcgtataca ctcaacacga ccaattgtat      180
atgtctatcc tgaattcgac aatacaaaat cttagattca tctctgatac aaccccaaaa      240
ccactcgtta ttgtcactcc ttcaaataac tcccatatcc aagcaactat tttatgctct      300
aagaaagttg gcttgcagat tcgaactcga agcggtggcc atgatgctga gggtatgtcc      360
tacatatctc aagtcccatt tgttgtagta gacttgagaa acatgcattc gatcaaaata      420
gatgttcata gccaaactgc gtgggttgaa gccggagcta cccttggaga agtttattat      480
tggatcaatg agaagaatga gaatcttagt tttcctggtg ggtattgccc tactgttggc      540
gtaggtggac actttagtgg aggaggctat ggagcattga tgcgaaatta tggccttgcg      600
gctgataata ttattgatgc acacttagtc aatgttgatg aaaagttcct agatcgaaaa      660
tccatgggag aagatctgtt tgggctata cgtggtggtg gaggagaaaa cttttggaatc      720 attgcagcat ggaaaatcaa actggttgct gtcccatcaa agtctactat attcagtgtt      780
aaaaagaaca tggagataca tgggcttgtc aagttattta caaatggca aaatattgct      840 tacaagtatg acaaagattt agtactcatg actcacttca taacaaagaa tattacagat      900
aatcatggga agaataagac tacagtacat ggttacttct cttcaatttt tcatggtgga      960
gtggatagtc tagtcgactt gatgaacaag agctttcctg agttgggtat taaaaaaact     1020
gattgcaaag aatttagctg gattgataca accatcttct acagtggtgt tgtaaatttt     1080
aacactgcta attttaaaaa ggaaattttg cttgatagat cagctgggaa gaagacggct     1140
ttctcaatta agttagacta tgttaagaaa ccaattccag aaactgcaat ggtcaaaatt     1200
ttggaaaaat tatatgaaga gatgtagga gctgggatgt atgtgttgta cccttacggt     1260
ggtataatgg aggagatttc agaatcagca attccattcc ctcatcgagc tggaataatg     1320
tatgaacttt ggtacactgc ttcctgggag aagcaagaag ataatgaaaa gcatataaac     1380
tgggttcgaa gtgtttataa ttttacgact ccttatgtgt cccaaaatcc aagattggcg     1440
tatctcaatt atagggacct tgatttagga aaaactaatc atgcgagtcc taataattac     1500
acacaagcac gtatttgggg tgaaaagtat tttggtaaaa attttaacag gttagttaag     1560
gtgaaaacta agttgatcc caataatttt tttagaaacg aacaaagtat cccacctctt      1620
ccaccgcatc atcat                                                     1635
```

<210> SEQ ID NO 20
<211> LENGTH: 1635
<212> TYPE: DNA
<213> ORGANISM: Cannabis sativa

<400> SEQUENCE: 20

| | | | | | |
|---|---|---|---|---|---|
| atgaattgct | cagcattttc | cttttggttt | gtttgcaaaa | taatattttt | ctttctctca | 60 |
| ttccatatcc | aaatttcaat | agctaatcct | cgagaaaact | tccttaaatg | cttctcaaaa | 120 |
| catattccca | acaatgtagc | aaatccaaaa | ctcgtataca | ctcaacacga | ccaattgtat | 180 |
| atgtctatcc | tgaattcgac | aatacaaaat | cttagattca | tctctgatac | aaccccaaaa | 240 |
| ccactcgtta | ttgtcactcc | ttcaaataac | tcccatatcc | aagcaactat | tttatgctct | 300 |
| aagaaagttg | gcttgcagat | tcgaactcga | agcggtggcc | atgatgctga | gggtatgtcc | 360 |
| tacatatctc | aagtcccatt | tgttgtagta | gacttgagaa | acatgcattc | gatcaaaata | 420 |
| gatgttcata | gccaaactgc | gtgggttgaa | gccggagcta | cccttggaga | agtttattat | 480 |
| tggatcaatg | agaagaatga | aatcttagt | tttcctggtg | ggtattgccc | tactgttggc | 540 |
| gtaggtggac | actttagtgg | aggaggctat | ggagcattga | tgcgaaatta | tggccttgcg | 600 |
| gctgataata | ttattgatgc | acacttagtc | aatgttgatg | aaaagttct | agatcgaaaa | 660 |
| tccatgggag | aagatctgtt | tgggctata | cgtggtggtg | gaggagaaaa | ctttggaatc | 720 |
| attgcagcat | ggaaaatcaa | actggttgct | gtcccatcaa | agtctactat | attcagtgtt | 780 |
| aaaaagaaca | tggagataca | tgggcttgtc | aagttattta | acaaatggca | aaatattgct | 840 |
| tacaagtatg | acaagatttt | agtactcatg | actcacttca | taacaaagaa | tattacagat | 900 |
| aatcatggga | agaataagac | tacagtacat | ggttacttct | cttcaatttt | tcatggtgga | 960 |
| gtggatagtc | tagtcgactt | gatgaacaag | agctttcctg | agttgggtat | taaaaaaact | 1020 |
| gattgcaaag | aatttagctg | gattgataca | accatcttct | acagtggtgt | tgtaaatttt | 1080 |
| aacactgcta | atttaaaaa | ggaaattttg | cttgatagat | cagctgggaa | gaagacggct | 1140 |
| ttctcaatta | agttagacta | tgttaagaaa | ccaattccag | aaactgcaat | ggtcaaaatt | 1200 |
| ttggaaaaat | tatatgaaga | gatgtagga | gctgggatgt | atgtgttgta | cccttacggt | 1260 |
| ggtataatgg | aggagatttc | agaatcagca | attccattcc | ctcatcgagc | tggaataatg | 1320 |
| tatgaacttt | ggtacactgc | ttcctgggag | aagcaagaag | ataatgaaaa | gcatataaac | 1380 |
| tgggttcgaa | gtgtttataa | ttttacgact | ccttatgtgt | cccaaaatcc | aagattggcg | 1440 |
| tatctcaatt | atagggacct | tgatttagga | aaaactaatc | atgcgagtcc | taataattac | 1500 |
| acacaagcac | gtatttgggg | tgaaaagtat | tttggtaaaa | attttaacag | gttagttaag | 1560 |
| gtgaaaacta | agttgatcc | caataatttt | tttagaaacg | aacaaagtat | cccacctctt | 1620 |
| ccaccgcatc | atcat | | | | | 1635 |

<210> SEQ ID NO 21
<211> LENGTH: 1635
<212> TYPE: DNA
<213> ORGANISM: Cannabis sativa

<400> SEQUENCE: 21

| | | | | | |
|---|---|---|---|---|---|
| atgaattgct | cagcattttc | cttttggttt | gtttgcaaaa | taatattttt | ctttctctca | 60 |
| ttcaatatcc | aaatttcatt | agctaatcct | caagaaaact | tccttaaatg | cttctcggaa | 120 |
| tatattccta | caatccagc | aaatccaaaa | ttcatataca | ctcaacacga | ccaattgtat | 180 |
| atgtctgtcc | tgaattcgac | aatacaaaat | cttagattca | cctctgatac | aaccccaaaa | 240 |

```
ccactcgtta ttgtcactcc ttcaaatgtc tcccatatcc aggccagtat tctctgctcc    300
aagaaagttg gtttgcagat tcgaactcga agcggtggcc atgatgctga gggtttgtcc    360
tacatatctc aagtcccatt tgctatagta gacttgagaa acatgcatac ggtcaaagta    420
gatattcata gccaaactgc gtgggttgaa gccggagcta cccttggaga agtttattat    480
tggatcaatg agatgaatga gaattttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg gaaaagttct agatcgaaaa    660
tccatgggag aagatctatt tgggctata cgtggtggag gaggagaaaa ctttggaatc    720
attgcagcat ggaaaatcaa acttgttgtt gtcccatcaa aggctactat attcagtgtt    780
aaaaagaaca tggagatacg tgggcttgtc aagttattta caaatggca aaatattgct    840 tacaagtatg acaaagattt aatgctcacg actcacttca gaactaggaa tattacagat    900
aatcatggga gaataagac tacagtacat ggttacttct cttccatttt tcttggtgga    960
gtggatagtc tagttgactt gatgaacaag agctttcctg agttgggtat taaaaaaact   1020
gattgcaaag aattgagctg gattgataca accatcttct acagtggtgt tgtaaattac   1080
aacactgcta attttaaaaa ggaaattttg cttgatagat cagctgggaa gaagacggct   1140
ttctcaatta gttagacta tgttaagaaa ctaatacctg aaactgcaat ggtcaaaatt   1200
ttggaaaaat tatatgaaga gaggtagga gttgggatgt atgtgttgta cccttacggt   1260
ggtataatgg atgagatttc agaatcagca attccattcc ctcatcgagc tggaataatg   1320
tatgaacttt ggtacactgc tacctgggag aagcaagaag ataacgaaaa gcatataaac   1380
tgggttcgaa gtgtttacaa tttcacaact ccttatgtgt cccaaaatcc aagattggcg   1440
tatctcaatt atagggacct tgatttagga aaaactaatc ctgagagtcc taataattac   1500
acacaagcac gtatttgggg tgaaaagtat tttggtaaaa attttaacag gttagttaag   1560
gtgaaaacca aagctgatcc caataatttt tttagaaacg aacaaagtat cccacctctt   1620
ccaccgcatc atcat                                                    1635
```

<210> SEQ ID NO 22
<211> LENGTH: 1635
<212> TYPE: DNA
<213> ORGANISM: Cannabis sativa

<400> SEQUENCE: 22

```
atgaattgct cagcattttc cttttggttt gtttgcaaaa taatatttt ctttctctca     60 ttccatatcc aaatttcaat agctaatcct cgagaaaact tccttaaatg cttctcaaaa   120
catattccca acaatgtagc aaatccaaaa ctcgtataca ctcaacacga ccaattgtat   180
atgtctatcc tgaattcgac aatacaaaat cttagattca tctctgatac aaccccaaaa   240
ccactcgtta ttgtcactcc ttcaaataac tcccatatcc aagcaactat tttatgctct   300
aagaaagttg gcttgcagat tcgaactcga agcggtggcc atgatgctga gggtatgtcc   360
tacatatctc aagtcccatt tgttgtagta gacttgagaa acatgcattc gatcaaaata   420
gatgttcata gccaaactgc gtgggttgaa gccggagcta cccttggaga agtttattat   480
tggatcaatg agaagaatga gaatcttagt tttcctggtg gtattgccc tactgttggc    540 gtaggtggac actttagtgg aggaggctat ggagcattga tgcgaaatta tggccttgcg   600
gctgataata ttattgatgc acacttagtc aatgttgatg gaaaagttct agatcgaaaa   660
```

```
tccatgggag aagatctgtt ttgggctata cgtggtggtg gaggagaaaa ctttggaatc      720
attgcagcat ggaaaatcaa actggttgct gtcccatcaa agtctactat attcagtgtt      780
aaaaagaaca tggagataca tgggcttgtc aagttattta acaaatggca aaatattgct      840
tacaagtatg acaaagattt agtactcatg actcacttca taacaaagaa tattacagat      900
aatcatggga agaataagac tacagtacat ggttacttct cttcaatttt tcatggtgga      960
gtggatagtc tagtcgactt gatgaacaag agctttcctg agttgggtat taaaaaaact     1020
gattgcaaag aatttagctg gattgataca accatcttct acagtggtgt tgtaaatttt     1080
aacactgcta attttaaaaa ggaaattttg cttgatagat cagctgggaa gaagacggct     1140
ttctcaatta agttagacta tgttaagaaa ccaattccag aaactgcaat ggtcaaaatt     1200
ttggaaaaat tatatgaaga gatgtgtagga gctgggatgt atgtgttgta ccctacggt      1260 ggtataatgg aggagatttc agaatcagca attccattcc ctcatcgagc tggaataatg     1320
tatgaacttt ggtacactgc ttcctgggag aagcaagaag ataatgaaaa gcatataaac     1380
tgggttcgaa gtgtttataa ttttacgact ccttatgtgt cccaaaatcc aagattggcg     1440
tatctcaatt atagggacct tgatttagga aaaactaatc atgcgagtcc taataattac     1500
acacaagcac gtatttgggg tgaaaagtat tttggtaaaa attttaacag gttagttaag     1560
gtgaaaacta agttgatccc caataatttt tttagaaacg aacaaagtat cccacctctt     1620
ccaccgcatc atcat                                                      1635

<210> SEQ ID NO 23
<211> LENGTH: 1635
<212> TYPE: DNA
<213> ORGANISM: Cannabis sativa

<400> SEQUENCE: 23
atgaattgct cagcattttc cttttggttt gtttgcaaaa taatattttt ctttctctca       60
ttccatatcc aaatttcaat agctaatcct cgagaaaact tccttaaatg cttctcaaaa      120
catattccca acaatgtagc aaatccaaaa ctcgtataca ctcaacacga ccaattgtat      180
atgtctatcc tgaattcgac aatacaaaat cttagattca tctctgatac aaccccaaaa      240
ccactcgtta ttgtcactcc ttcaaataac tcccatatcc aagcaactat tttatgctct      300
aagaaagttg gcttgcagat tcgaactcga agcggtggcc atgatgctga gggtatgtcc      360
tacatatctc aagtcccatt tgttgtagta gacttgagaa acatgcattc gatcaaaata      420
gatgttcata gccaaactgc gtgggttgaa gccggagcta cccttggaga agtttattat      480
tggatcaatg agaagaatga gaatcttagt tttcctggtg ggtattgccc tactgttggc      540
gtaggtggac actttagtgg aggaggctat ggagcattga tgcgaaatta tggccttgcg      600
gctgataata ttattgatgc acacttagtc aatgttgatg gaaaagttct agatcgaaaa      660
tccatgggag aagatctgtt ttgggctata cgtggtggtg gaggagaaaa ctttggaatc      720
attgcagcat ggaaaatcaa actggttgct gtcccatcaa agtctactat attcagtgtt      780
aaaaagaaca tggagataca tgggcttgtc aagttattta acaaatggca aaatattgct      840
tacaagtatg acaaagattt agtactcatg actcacttca taacaaagaa tattacagat      900
aatcatggga agaataagac tacagtacat ggttacttct cttcaatttt tcatggtgga      960
gtggatagtc tagtcgactt gatgaacaag agctttcctg agttgggtat taaaaaaact     1020
gattgcaaag aatttagctg gattgataca accatcttct acagtggtgt tgtaaatttt     1080
aacactgcta attttaaaaa ggaaattttg cttgatagat cagctgggaa gaagacggct     1140
```

-continued

| | |
|---|---|
| ttctcaatta agttagacta tgttaagaaa ccaattccag aaactgcaat ggtcaaaatt | 1200 |
| ttggaaaaat tatatgaaga agatgtagga gctgggatgt atgtgttgta cccttacggt | 1260 |
| ggtataatgg aggagatttc agaatcagca attccattcc ctcatcgagc tggaataatg | 1320 |
| tatgaacttt ggtacactgc ttcctgggag aagcaagaag ataatgaaaa gcatataaac | 1380 |
| tgggttcgaa gtgtttataa ttttacgact ccttatgtgt cccaaaatcc aagattggcg | 1440 |
| tatctcaatt atagggacct tgatttagga aaaactaatc atgcgagtcc taataattac | 1500 |
| acacaagcac gtatttgggg tgaaaagtat tttggtaaaa attttaacag gttagttaag | 1560 |
| gtgaaaacta aagttgatcc caataatttt tttagaaacg aacaaagtat cccacctctt | 1620 |
| ccaccgcatc atcat | 1635 |

<210> SEQ ID NO 24
<211> LENGTH: 1635
<212> TYPE: DNA
<213> ORGANISM: Cannabis sativa

<400> SEQUENCE: 24

| | |
|---|---|
| atgaattgct cagcattttc cttttggttt gtttgcaaaa taatattttt ctttctctca | 60 |
| ttcaatatcc aaatttcaat agctaatcct caagaaaact tccttaaatg cttctcggaa | 120 |
| tatattccta caatccagc aaatccaaaa ttcatataca ctcaacacga ccaattgtat | 180 |
| atgtctgtcc tgaattcgac aatacaaaat cttagattca cctctgatac aaccccaaaa | 240 |
| ccactcgtta ttgtcactcc ttcaaatgtc tcccatatcc aggccagtat tctctgctcc | 300 |
| aagaaagttg gtttgcagat tcgaactcga agcggtggcc atgatgctga gggtttgtcc | 360 |
| tacatatctc aagtcccatt tgctatagta gacttgagaa acatgcatac ggtcaaagta | 420 |
| gatattcata gccaaactgc gtgggttgaa gccggagcta cccttggaga agtttattat | 480 |
| tggatcaatg agatgaatga gaattttagt tttcctggtg ggtattgccc tactgttggc | 540 |
| gtaggtggac actttagtgg aggaggctat ggagcattga tgcgaaatta tggccttgcg | 600 |
| gctgataata tcattgattc acacttagtc aatgttgatg aaaagttct agatcgaaaa | 660 |
| tccatgggag aagatctatt tgggctata cgtggtggag gaggagaaaa ctttggaatc | 720 |
| attgcagcat ggaaaatcaa acttgttgtt gtcccatcaa aggctactat attcagtgtt | 780 |
| aaaaagaaca tggagataca tgggcttgtc aagttattta acaaatggca aaatattgct | 840 |
| tacaagtatg acaaagattt aatgctcacg actcacttca gaactaggaa tattacagat | 900 |
| aatcatggga agaataagac tacagtacat ggttacttct cttccatttt tcttggtgga | 960 |
| gtggatagtc tagttgactt gatgaacaag agctttcctg agttgggtat taaaaaaact | 1020 |
| gattgcaaag aattgagctg gattgataca accatcttct acagtggtgt tgtcaattac | 1080 |
| aacactgcta attttaaaaa ggaaattttg cttgatagat cagctgggaa gaagacggct | 1140 |
| ttctcaatta agttagacta tgttaagaaa ctaatacctg aaactgcaat ggtcaaaatt | 1200 |
| ttggaaaaat tatatgaaga agaggtagga gttgggatgt atgtgttgta cccttacggt | 1260 |
| ggtataatgg atgagatttc agaatcagca attccattcc ctcatcgagc tggaataatg | 1320 |
| tatgaacttt ggtacactgc tacctgggag aagcaagaag ataacgaaaa gcatataaac | 1380 |
| tgggttcgaa gtgtttataa tttcacaact ccttatgtgt cccaaaatcc aagattggcg | 1440 |
| tatctcaatt atagggacct tgatttagga aaaactaatc ctgagagtcc taataattac | 1500 |
| acacaagcac gtatttgggg tgaaaagtat tttggtaaaa attttaacag gttagttaaa | 1560 |

```
gtgaaaacca aagctgatcc caataatttt tttagaaacg aacaaagtat cccacctctt    1620
ccaccgcatc atcat                                                    1635

<210> SEQ ID NO 25
<211> LENGTH: 1635
<212> TYPE: DNA
<213> ORGANISM: Cannabis sativa

<400> SEQUENCE: 25
atgaattgct cagcattttc cttttggttt gtttgcaaaa taatattttt ctttctctca     60
ttccatatcc aaatttcaat agctaatcct cgagaaaact tccttaaatg cttctcaaaa    120
catattccca acaatgtagc aaatccaaaa ctcgtataca ctcaacacga ccaattgtat    180
atgtctatcc tgaattcgac aatacaaaat cttagattca tctctgatac aaccccaaaa    240
ccactcgtta ttgtcactcc ttcaaataac tcccatatcc aagcaactat tttatgctct    300
aagaaagttg gcttgcagat tcgaactcga agcggtggcc atgatgctga gggtatgtcc    360
tacatatctc aagtcccatt tgttgtagta gacttgagaa acatgcattc gatcaaaata    420
gatgttcata gccaaactgc gtgggttgaa gccggagcta cccttggaga agtttattat    480
tggatcaatg agaagaatga gaatcttagt tttcctggtg ggtattgccc tactgttggc    540
gtaggtggac actttagtgg aggaggctat ggagcattga tgcgaaatta tggccttgcg    600
gctgataata ttattgatgc acacttagtc aatgttgatg aaaagttct agatcgaaaa     660 tccatgggag aagatctgtt tgggctata cgtggtggtg gaggagaaaa ctttggaatc    720
attgcagcat ggaaaatcaa actggttgct gtcccatcaa agtctactat attcagtgtt    780
aaaaagaaca tggagataca tgggcttgtc aagttattta caaatggca aaatattgct    840 tacaagtatg acaagatt agtactcatg actcacttca taacaaagaa tattacagat    900
aatcatggga agaataagac tacagtacat ggttacttct cttcaatttt tcatggtgga    960
gtggatagtc tagtcgactt gatgaacaag agctttcctg agttgggtat taaaaaaact   1020
gattgcaaag aatttagctg gattgataca accatcttct acagtggtgt tgtaaatttt   1080
aacactgcta attttaaaaa ggaaattttg cttgatagat cagctgggaa gaagacggct   1140
ttctcaatta agttagacta tgttaagaaa ccaattccag aaactgcaat ggtcaaaatt   1200
ttggaaaaat tatatgaaga agatgtagga gctgggatgt atgtgttgta cccttacggt   1260
ggtataatgg aggagatttc agaatcagca attccattcc ctcatcgagc tggaataatg   1320
tatgaacttt ggtacactgc ttcctgggag aagcaagaag ataatgaaaa gcatataaac   1380
tgggttcgaa gtgttttataa ttttacgact cctattgtgt cccaaaatcc aagattggcg   1440
tatctcaatt atagggacct tgatttagga aaaactaatc atgcgagtcc taataattac   1500
acacaagcac gtatttgggg tgaaaagtat tttggtaaaa attttaacag gttagttaag   1560
gtgaaaacta aagttgatcc caataatttt tttagaaacg aacaaagtat cccacctctt   1620
ccaccgcatc atcat                                                   1635

<210> SEQ ID NO 26
<211> LENGTH: 1635
<212> TYPE: DNA
<213> ORGANISM: Cannabis sativa

<400> SEQUENCE: 26
atgaattgct cagcattttc cttttggttt gtttgcaaaa taatattttt ctttctctca     60
ttcaatatcc aaatttcaat agctaatcct caagaaaact tccttaaatg cttctcggaa    120
```

```
tatattccta acaatccagc aaatccaaaa ttcatataca ctcaacacga ccaattgtat    180
atgtctgtcc tgaattcaac aatacaaaat cttagattca cctctgatac aaccccaaaa    240
ccactcgtta ttgtcactcc ttcaaatgtc tcccatatcc aggccagtat tctctgctcc    300
aagaaagttg gtttgcagat tcgaactcga agcggtggcc atgatgctga gggtttgtcc    360
tacatatctc aagtcccatt tgctatagta gacttgagaa acatgcatac ggtcaaagta    420
gatattcata gccaaactgc gtgggttgaa gccggagcta cccttggaga agtttattat    480
tggatcaatg agatgaatga gaattttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg aaaagttct agatcgaaaa     660
tccatgggag aagatctatt tgggctata cgtggtggag gaggagaaaa ctttggaatc     720
attgcagcat ggaaaatcaa acttgttgtt gtcccatcaa aggctactat attcagtgtt    780
aaaaagaaca tggagataca tgggcttgtc aagttattta acaatggca aaatattgct      840
tacaagtatg acaaagattt aatgctcacg actcacttca gaactaggaa tattacagat    900
aatcatggga agaataagac tacagtacat ggttacttct cttccatttt tcttggtgga    960
gtggatagtc tagttgactt gatgaacaag agctttcctg agttgggtat taaaaaaact   1020
gattgcaaag aattgagctg gattgataca accatcttct acagtggtgt tgtaaattac   1080
aacactgcta attttaaaaa ggaaattttg cttgatagat cagctgggaa gaagacggct   1140
ttctcaatta agttagacta tgttaagaaa ctaatacctg aaactgcaat ggtcaaaatt   1200
ttggaaaaat tatatgaaga agaggtagga gttgggatgt atgtgttgta cccttacggt   1260
ggtataatgg atgagatttc agaatcagca attccattcc ctcatcgagc tggaataatg   1320
tatgaacttt ggtacactgc tacctgggag aagcaagaag ataacgaaaa gcatataaac   1380
tgggttcgaa gtgtttataa tttcacaact ccttatgtgt cccaaaatcc aagattggcg   1440
tatctcaatt atagggacct tgatttagga aaaactaatc ctgagagtcc taataattac   1500
acacaagcac gtatttgggg tgaaaagtat tttggtaaaa attttaacag gttagttaag   1560
gtgaaaacca aagctgatcc caataatttt tttagaaacg aacaaagtat cccacctctt   1620
ccaccgcatc atcat                                                    1635
```

<210> SEQ ID NO 27
<211> LENGTH: 1635
<212> TYPE: DNA
<213> ORGANISM: Cannabis sativa

<400> SEQUENCE: 27

```
atgaattgct cagcattttc cttttggttt gtttgcaaaa taatattttt ctttctctca      60
ttcaatatcc aaatttcaat agctaatcct caagaaaact tccttaaatg cttctcggaa    120
tatattccta acaatccagc aaatccaaaa ttcatataca ctcaacacga ccaattgtat    180
atgtctgtcc tgaattcgac aatacaaaat cttagattca cctctgatac aaccccaaaa    240
ccactcgtta ttgtcactcc ttcaaatgtc tcccatatcc aggccagtat tctctgctcc    300
aagaaagttg gtttgcagat tcgaactcga agcggtggcc atgatgctga gggtttgtcc    360
tacatatctc aagtcccatt tgctatagta gacttgagaa acatgcatac ggtcaaagta    420
gatattcata gccaaactgc gtgggttgaa gccggagcta cccttggaga agtttattat    480
tggatcaatg agatgaatga gaattttagt tttcctggtg ggtattgccc tactgttggc    540
```

```
gtaggtggac actttagtgg aggaggctat ggagcattga tgcgaaatta tggccttgcg    600
gctgataata tcattgatgc acacttagtc aatgttgatg gaaaagttct agatcgaaaa    660
tccatgggag aagatctatt ttgggctata cgtggtggag gaggagaaaa ctttggaatc    720
attgcagcat ggaaaatcaa acttgttgtt gtcccatcaa aggctactat attcagtgtt    780
aaaaagaaca tggagataca tgggcttgtc aagttattta acaaatggca aaatattgct    840
tacaagtatg acaaagattt aatgctcacg actcacttca gaactaggaa tattacagat    900
aatcatggga agaataagac tacagtacat ggttacttct cttccatttt tcttggtgga    960
gtggatagtc tagttgactt gatgaacaag agctttcctg agttgggtat taaaaaaact   1020
gattgcaaag aattgagctg gattgataca accatcttct acagtggtgt tgtaaattac   1080
aacactgcta attttaaaaa ggaaattttg cttgatagat cagctgggaa gaagacggct   1140
ttctcaatta agttagacta tgttaagaaa ctaaatacctg aaactgcaat ggtcaaaatt   1200
ttggaaaaat tatatgaaga gaggtagga gttgggatgt atgtgttgta cccttacggt    1260
ggtataatgg atgagatttc agaatcagca attccattcc ctcatcgagc tggaataatg   1320
tatgaacttt ggtacactgc tacctgggag aagcaagaag ataacgaaaa gcatataaac   1380
tgggttcgaa gtgtttataa tttcacaact ccttatgtgt cccaaaatcc aagattggcg   1440
tatctcaatt atagggacct tgatttagga aaaactaatc ctgagagtcc taataattac   1500
acacaagcac gtatttgggg tgaaaagtat tttggtaaaa attttaacag gttagttaag   1560
gtgaaaacca agctgatcc caataatttt tttagaaacg aacaaagtat cccacctctt   1620
ccaccgcatc atcat                                                     1635

<210> SEQ ID NO 28
<211> LENGTH: 1635
<212> TYPE: DNA
<213> ORGANISM: Cannabis sativa

<400> SEQUENCE: 28
atgaattgct cagcattttc cttttggttt gtttgcaaaa taatattttt ctttctctca     60
ttccatatcc aaatttcaat agctaatcct cgagaaaact tccttaaatg cttctcaaaa    120
catattccca acaatgtagc aaatccaaaa ctcgtataca ctcaacacga ccaattgtat    180
atgtctctcc tgaattcgac aatacaaaat cttagattca tctctgatac aaccccaaaa    240
ccactcgtta ttgtcactcc ttcaaataac tcccatatcc aagcaactat tttatgctct    300
aagaaagttg gcttgcagat tcgaactcga agcggtggcc atgatgctga gggtatgtcc    360
tacatttctc aagtcccatt tgttgtagta gacttgagga catgcattc gatcaaaata    420
gatgttcata gccaaactgc gtgggttgaa gccggagcta cccttggaga gtttattat    480
tggatcaatg agaagaatga gaatcttagt tttcctggtg ggtattgccc tactgttggc    540
gtaggtggac actttagtgg aggaggctat ggagcattga tgcgaaatta tggccttgcg    600
gctgataata ttattgatgc acacttagtc aatgttgatg gaaaagttct agatcgaaaa    660
tccatgggag aagatctgtt ttgggctata cgtggtggtg gaggagaaaa ctttggaatc    720
attgcagcat ggaaaatcaa actggttgct gtcccatcaa agtctactat attcagtgtt    780
aaaaagaaca tggagataca tgggcttgtc aagttattta acaaatggca aaatattgct    840
tacaagtatg acaaagattt agtactcatg actcacttca taacaaagaa tattacagat    900
aatcatggga agaataagac tacagtacat ggttacttct cttccatttt tcatggtgga    960
gtggatagtc tagtcgactt gatgaacaag agctttcctg agttgggtat taaaaaaact   1020
```

```
gattgcaaag aatttagctg gattgataca accatcttct acagtggtgt tgtaaatttt   1080
aacactgcta attttaaaaa ggaaattttg cttgatagat cagctgggaa gaagacggct   1140
ttctcaatta agttagacta tgttaagaaa ccaattcctg aaactgcaat ggtcaaaatt   1200
ttggaaaaat tatatgaaga agatgtagga gctgggatgt atgtgttgta cccttacggt   1260
ggtataatgg aggagatttc agaatcagca attccattcc ctcatcgagc tggaataatg   1320
tatgaacttt ggtacactgc ttcctgggag aagcaagaag ataatgaaaa gcatataaac   1380
tgggttcgaa gtgtttataa ttttacgact ccttatgtgt cccaaaatcc aagattggcg   1440
tatctcaatt atagggacct tgatttagga aaaactaatc atgcgagtcc taataattac   1500
acacaagcac gtatttgggg tgaaaagtat tttggtaaaa attttaacag gttagttaag   1560
gtgaaaacta agttgatcc caataatttt tttagaaacg aacaaagtat cccacctctt   1620
ccaccgcatc atcat                                                    1635

<210> SEQ ID NO 29
<211> LENGTH: 1227
<212> TYPE: DNA
<213> ORGANISM: Cannabis sativa

<400> SEQUENCE: 29
ataaactccc atatccaagc aactatttta tgctctaaga agttggcctt gcagattcga     60
actcgaagcg gtggccatga tgctgagggt atgtcctaca tatctcaagt cccatttgtt    120
gtagtagact tgagaaacat gcattcgatc aaaatagatg ttcatagcca aactgcgtgg    180
gttgaagccg gagctaccct tggagaagtt tattattgga tcaatgagaa gaatgagaat    240
cttagttttc ctggtgggta ttgccctact gttggcgtag gtggacactt tagtggagga    300
ggctatggag cattgatgcg aaattatggc cttgcggctg ataatattat tgatgcacac    360
ttagtcaatg ttgatggaaa agttctagat cgaaaatcca tgggagaaga tctgttttgg    420
gctatacgtg gtggtggagg agaaaaacttt ggaatcattg cagcatggaa aatcaaactg    480
gttgctgtcc catcaaagtc tactatattc agtgttaaaa agaacatgga gatacatggg    540
cttgtcaagt tatttaacaa atggcaaaat attgcttaca agtatgacaa agatttagta    600
ctcatgactc acttcataac aaagaatatt acagataatc atgggaagaa taagactaca    660
gtacatggtt acttctcttc aatttttcat ggtggagtgg atagtctagt cgacttgatg    720
aacaagagct ttcctgagtt gggtattaaa aaaactgatt gcaaagaatt tagctggatt    780
gatacaacca tcttctacag tggtgttgta aattttaaca ctgctaattt taaaaggaa    840 attttgcttg atagatcagc tgggaagaag acggctttct caattaagtt agactatgtt    900
aagaaaccaa ttccagaaac tgcaatggtc aaaattttgg aaaaattata tgaagaagat    960
gtaggagctg ggatgtatgt gttgtacct tacggtggta atggagga gatttcagaa   1020 tcagcaattc cattccctca tcgagctgga ataatgtatg aactttggta cactgcttcc   1080
tgggagaagc aagaagataa tgaaaagcat ataaactggg ttcgaagtgt ttataatttt   1140
acgactcctt atgtgtccca aaatccaaga ttggcgtatc tcaattatag ggaccttgat   1200
ttaggaaaaa ctaatcatgc gagtcct                                       1227

<210> SEQ ID NO 30
<211> LENGTH: 1227
<212> TYPE: DNA
<213> ORGANISM: Cannabis sativa
```

<400> SEQUENCE: 30

```
aataactccc atatccaagc aactatttta tgctctaaga aagttggctt gcagattcga      60
actcgaagcg gtggccatga tgctgagggt atgtcctaca tatctcaagt cccatttgtt     120
gtagtagact tgagaaacat gcattcgatc aaaatagatg ttcatagcca aactgcgtgg     180
gttgaagccg gagctaccct tggagaagtt tattattgga tcaatgagaa gaatgagaat     240
cttagttttc ctggtgggta ttgccctact gttggcgtag gtggacactt tagtggagga     300
ggctatggag cattgatgcg aaattatggc cttgcggctg ataatattat tgatgcacac     360
ttagtcaatg ttgatggaaa agttctagat cgaaaatcca tgggagaaga tctgttttgg     420
gctatacgtg gtggtggagg agaaaacttt ggaatcattg cagcatggaa aatcaaactg     480
gttgctgtcc catcaaagtc tactatattc agtgttaaaa agaacatgga gatacatggg     540
cttgtcaagt tatttaacaa atggcaaaat attgcttaca gtatgacaa agatttagta     600
ctcatgactc acttcataac aaagaatatt acagataatc atgggaagaa taagactaca     660
gtacatggtt acttctcttc aattttcat ggtggagtgg atagtctagt cgacttgatg      720
aacaagagct ttcctgagtt gggtattaaa aaaactgatt gcaagaatt tagctggatt      780
gatacaacca tcttctacag tggtgttgta aattttaaca ctgctaattt taaaaaggaa     840
attttgcttg atagatcagc tgggaagaag acggctttct caattaagtt agactatgtt     900
aagaaaccaa ttccagaaac tgcaatggtc aaaattttgg aaaaattata tgaagaagat     960
gtaggagctg ggatgtatgt gttgtacccct tacggtggta taatggagga gatttcagaa   1020
tcagcaattc cattccctca tcgagctgga ataatgtatg aactttggta cactgcttcc   1080
tgggagaagc aagaagataa tgaaaagcat ataaactggg ttcgaagtgt ttataatttt   1140
acgactcctt atgtgtccca aaatccaaga ttggcgtatc tcaattatag ggaccttgat   1200
ttaggaaaaa ctaatcatgc gagtcct                                        1227
```

<210> SEQ ID NO 31
<211> LENGTH: 1227
<212> TYPE: DNA
<213> ORGANISM: Cannabis sativa

<400> SEQUENCE: 31

```
aataactccc atatccaagc aactatttta tgctctaaga aagttggctt gcagattcga      60
actcgaagcg gtggccatga tgctgagggt atgtcctaca tatctcaagt cccatttgtt     120
gtagtagact tgagaaacat gcattcgatc aaaatagatg ttcatagcca aactgcgtgg     180
gttgaagccg gagctaccct tggagaagtt tattattgga tcaatgagaa gaatgagaat     240
cttagttttc ctggtgggta ttgccctact gttggcgtag gtggacactt tagtggagga     300
ggctatggag cattgatgcg aaattatggc cttgcggctg ataatattat tgatgcacac     360
ttagtcaatg ttgatggaaa agttctagat cgaaaatcca tgggagaaga tctgttttgg     420
gctatacgtg gtggtggagg agaaaacttt ggaatcattg cagcatggaa aatcaaactg     480
gttgctgtcc catcaaagtc tactatattc agtgttaaaa agaacatgga gatacatggg     540
cttgtcaagt tatttaacaa atggcaaaat attgcttaca gtatgacaa agatttagta     600
ctcatgactc acttcataac aaagaatatt acagataatc atgggaagaa taagactaca     660
gtacatggtt acttctcttc aattttcat ggtggagtgg atagtctagt cgacttgatg      720
aacaagagct ttcctgagtt gggtattaaa aaaactgatt gcaagaatt tagctggatt      780
gatacaacca tcttctacag tggtgttgta aattttaaca ctgctaattt taaaaaggaa     840
```

```
attttgcttg atagatcagc tgggaagaag acggctttct caattaagtt agactatgtt      900
aagaaaccaa ttccagaaac tgcaatggtc aaaattttgg aaaaattata tgaagaagat      960
gtaggagctg ggatgtatgt gttgtaccct tacggtggta taatggagga gatttcagaa     1020
tcagcaattc cattccctca tcgagctgga ataatgtatg aactttggta cactgcttcc     1080
tgggagaagc aagaagataa tgaaaagcat ataaactggg ttcgaagtgt ttataatttt     1140
acgactcctt atgtgtccca aaatccaaga ttggcgtatc tcaattatag ggaccttgat     1200
ttaggaaaaa ctaatcatgc gagtcct                                         1227
```

<210> SEQ ID NO 32
<211> LENGTH: 1227
<212> TYPE: DNA
<213> ORGANISM: Cannabis sativa

<400> SEQUENCE: 32

```
aataactccc atatccaagc aactatttta tgctctaaga agttggctt gcagattcga       60 actcgaagcg gtggccatga tgctgagggt atgtcctaca tttctcaagt cccatttgtt     120
gtagtagact tgagaaacat gcattcgatc aaaatagatg ttcatagcca aactgcgtgg     180
gttgaagccg gagctaccct tggagaagtt tattattgga tcaatgagaa gaatgagaat     240
cttagttttc ctggtgggta ttgccctact gttggcgtag gtggacactt tagtggagga     300
ggctatggag cattgatgcg aaattatggc cttgcggctg ataatattat tgatgcacac     360
ttagtcaatg ttgatggaaa agttctagat cgaaaatcca tgggagaaga tctgttttgg     420
gctatacgtg gtggtggagg agaaaacttt ggaatcattg cagcatggaa aatcaaactg     480
gttgctgtcc catcaaagtc tactatattc agtgttaaaa agaacatgga gatacatggg     540
cttgtcaagt tatttaacaa atggcaaaat attgcttaca agtatgacaa agatttagta     600
ctcatgactc acttcataac aaagaatatt acagataatc atgggaagaa taagactaca     660
gtacatggtt acttctcttc aattttttcat ggtggagtgg atagtctagt cgacttgatg     720
aacaagagct ttcctgagtt gggtattaaa aaaactgatt gcaaagaatt tagctggatt     780
gatacaacca tcttctacag tggtgttgta aattttaaca ctgctaattt taaaaaggaa     840
attttgcttg atagatcagc tgggaagaag acggctttct caattaagtt agactatgtt     900
aagaaaccaa ttcctgaaac tgcaatggtc aaaattttgg aaaaattata tgaagaagat     960
gtaggagctg ggatgtatgt gttgtaccct tacggtggta taatggagga gatttcagaa    1020
tcagcaattc cattccctca tcgagctgga ataatgtatg aactttggta cactgcttcc    1080
tgggagaagc aagaagataa tgaaaagcat ataaactggg ttcgaagtgt ttataatttt    1140
acgactcctt atgtgtccca aaatccaaga ttggcgtatc tcaattatag ggaccttgat    1200
ttaggaaaaa ctaatcatgc gagtcct                                        1227
```

<210> SEQ ID NO 33
<211> LENGTH: 1227
<212> TYPE: DNA
<213> ORGANISM: Cannabis sativa

<400> SEQUENCE: 33

```
aataactccc atatccaagc aactatttta tgctctaaga agttggctt gcagattcga       60 actcgaagcg gtggccatga tgctgagggt atgtcctaca tatctcaagt cccatttgtt     120
gtagtagact tgagaaacat gcattcgatc aaaatagatg ttcatagcca aactgcgtgg     180
```

```
gttgaagccg gagctaccct tggagaagtt tattattgga tcaatgagaa gaatgagaat     240
cttagttttc ctggtgggta ttgccctact gttggcgtag gtggacactt tagtggagga     300
ggctatggag cattgatgcg aaattatggc cttgcggctg ataatattat tgatgcacac     360
ttagtcaatg ttgatggaaa agttctagat cgaaaatcca tgggagaaga tctgttttgg     420
gctatacgtg gtggtggagg agaaaacttt ggaatcattg cagcatggaa aatcaaactg     480
gttgctgtcc catcaaagtc tactatattc agtgttaaaa agaacatgga gatacatggg     540
cttgtcaagt tatttaacaa atggcaaaat attgcttaca agtatgacaa agatttagta     600
ctcatgactc acttcataac aaagaatatt acagataatc atgggaagaa taagactaca     660
gtacatggtt acttctcttc aattttttcat ggtggagtgg atagtctagt cgacttgatg     720
aacaagagct ttcctgagtt gggtattaaa aaaactgatt gcaaagaatt tagctggatt     780
gatacaacca tcttctacag tggtgttgta aattttaaca ctgctaattt taaaaaggaa     840
attttgcttg atagatcagc tgggaagaag acggctttct caattaagtt agactatgtt     900
aagaaaccaa ttccagaaac tgcaatggtc aaaattttgg aaaaattata tgaagaagat     960
gtaggagctg ggatgtatgt gttgtaccct tacggtggta taatggagga gatttcagaa    1020
tcagcaattc cattccctca tcgagctgga ataatgtatg aactttggta cactgcttcc    1080
tgggagaagc aagaagataa tgaaaagcat ataaactggg ttcgaagtgt ttataatttt    1140
acgactcctt atgtgtccca aaatccaaga ttggcgtatc tcaattatag ggaccttgat    1200
ttaggaaaaa ctaatcatgc gagtcct                                        1227

<210> SEQ ID NO 34
<211> LENGTH: 1227
<212> TYPE: DNA
<213> ORGANISM: Cannabis sativa

<400> SEQUENCE: 34
aataactccc atatccaagc aactatttta tgctctaaga aagttggctt gcagattcga      60
actcgaagcg gtggccatga tgctgagggt atgtcctaca tatctcaagt cccatttgtt     120
gtagtagact tgagaaacat gcattcgatc aaaatagatg ttcatagcca aactgcgtgg     180
gttgaagccg gagctaccct tggagaagtt tattattgga tcaatgagaa gaatgagaat     240
cttagttttc ctggtgggta ttgccctact gttggcgtag gtggacactt tagtggagga     300
ggctatggag cattgatgcg aaattatggc cttgcggctg ataatattat tgatgcacac     360
ttagtcaatg ttgatggaaa agttctagat cgaaaatcca tgggagaaga tctgttttgg     420
gctatacgtg gtggtggagg agaaaacttt ggaatcattg cagcatggaa aatcaaactg     480
gttgctgtcc catcaaagtc tactatattc agtgttaaaa agaacatgga gatacatggg     540
cttgtcaagt tatttaacaa atggcaaaat attgcttaca agtatgacaa agatttagta     600
ctcatgactc acttcataac aaagaatatt acagataatc atgggaagaa taagactaca     660
gtacatggtt acttctcttc aattttttcat ggtggagtgg atagtctagt cgacttgatg     720
aacaagagct ttcctgagtt gggtattaaa aaaactgatt gcaaagaatt tagctggatt     780
gatacaacca tcttctacag tggtgttgta aattttaaca ctgctaattt taaaaaggaa     840
attttgcttg atagatcagc tgggaagaag acggctttct caattaagtt agactatgtt     900
aagaaaccaa ttccagaaac tgcaatggtc aaaattttgg aaaaattata tgaagaagat     960
gtaggagctg ggatgtatgt gttgtaccct tacggtggta taatggagga gatttcagaa    1020
tcagcaattc cattccctca tcgagctgga ataatgtatg aactttggta cactgcttcc    1080
```

```
tgggagaagc aagaagataa tgaaaagcat ataaactggg ttcgaagtgt ttataatttt    1140
acgactcctt atgtgtccca aaatccaaga ttggcgtatc tcaattatag ggaccttgat    1200
ttaggaaaaa ctaatcatgc gagtcct                                        1227
```

<210> SEQ ID NO 35
<211> LENGTH: 1227
<212> TYPE: DNA
<213> ORGANISM: Cannabis sativa

<400> SEQUENCE: 35

```
aataactccc atatccaagc aactatttta tgctctaaga agttggcttg cagattcga      60 actcgaagcg gtggccatga tgctgagggt atgtcctaca tatctcaagt cccatttgtt    120
gtagtagact tgagaaacat gcattcgatc aaaatagatg ttcatagcca aactgcgtgg    180
gttgaagccg gagctaccct tggagaagtt tattattgga tcaatgagaa gaatgagaat    240
cttagttttc ctggtgggta ttgccctact gttggcgtag gtggacactt tagtggagga    300
ggctatggag cattgatgcg aaattatggc cttgcggctg ataatattat tgatgcacac    360
ttagtcaatg ttgatggaaa agttctagat cgaaaatcca tgggagaaga tctgttttgg    420
gctatacgtg gtggtggagg agaaaacttt ggaatcattg cagcatggaa aatcaaactg    480
gttgctgtcc catcaaagtc tactatattc agtgttaaaa agaacatgga gatacatggg    540
cttgtcaagt tatttaacaa atggcaaaat attgcttaca gtatgacaa  agatttagta    600 ctcatgactc acttcataac aaagaatatt acagataatc atgggaagaa taagactaca    660
gtacatggtt acttctcttc aatttttcat ggtggagtgg atagtctagt cgacttgatg    720
aacaagagct ttcctgagtt gggtattaaa aaaactgatt gcaaagaatt tagctggatt    780
gatacaacca tcttctacag tggtgttgta aattttaaca ctgctaattt taaaaaggaa    840
attttgcttg atagatcagc tgggaagaag acggctttct caattaagtt agactatgtt    900
aagaaaccaa ttccagaaac tgcaatggtc aaaattttgg aaaaattata tgaagaagat    960
gtaggagctg ggatgtatgt gttgtaccct tacggtggta taatggagga gatttcagaa   1020
tcagcaattc cattccctca tcgagctgga ataatgtatg aactttggta cactgcttcc   1080
tgggagaagc aagaagataa tgaaaagcat ataaactggg ttcgaagtgt ttataatttt   1140
acgactcctt atgtgtccca aaatccaaga ttggcgtatc tcaattatag ggaccttgat   1200
ttaggaaaaa ctaatcatgc gagtcct                                       1227
```

<210> SEQ ID NO 36
<211> LENGTH: 1227
<212> TYPE: DNA
<213> ORGANISM: Cannabis sativa

<400> SEQUENCE: 36

```
aataactccc atatccaagc aactatttta tgctctaaga agttggcttg cagattcga      60 actcgaagcg gtggccatga tgctgagggt atgtcctaca tttctcaagt cccatttgtt    120
gtagtagact tgaggaacat gcattcgatc aaaatagatg ttcatagcca aactgcgtgg    180
gttgaagccg gagctaccct tggagaagtt tattattgga tcaatgagaa gaatgagaat    240
cttagttttc ctggtgggta ttgccctact gttggcgtag gtggacactt tagtggagga    300
ggctatggag cattgatgcg aaattatggc cttgcggctg ataatattat tgatgcacac    360
ttagtcaatg ttgatggaaa agttctagat cgaaaatcca tgggagaaga tctgttttgg    420
```

```
gctatacgtg gtggtggagg agaaaacttt ggaatcattg cagcatggaa aatcaaactg    480
gttgctgtcc catcaaagtc tactatattc agtgttaaaa agaacatgga gatacatggg    540
cttgtcaagt tatttaacaa atggcaaaat attgcttaca agtatgacaa agatttagta    600
ctcatgactc acttcataac aaagaatatt acagataatc atgggaagaa taagactaca    660
gtacatggtt acttctcttc aattttcat ggtggagtgg atagtctagt cgacttgatg    720
aacaagagct ttcctgagtt gggtattaaa aaaactgatt gcaaagaatt tagctggatt    780
gatacaacca tcttctacag tggtgttgta aattttaaca ctgctaattt taaaaaggaa    840
attttgcttg atagatcagc tgggaagaag acggctttct caattaagtt agactatgtt    900
aagaaaccaa ttcctgaaac tgcaatggtc aaaattttgg aaaaattata tgaagaagat    960
gtaggagctg ggatgtatgt gttgtaccct tacggtggta taatggagga gatttcagaa   1020
tcagcaattc cattccctca tcgagctgga ataatgtatg aactttggta cactgcttcc   1080
tgggagaagc aagaagataa tgaaaagcat ataaactggg ttcgaagtgt ttataatttt   1140
acgactcctt atgtgtccca aaatccaaga ttggcgtatc tcaattatag ggaccttgat   1200
ttaggaaaaa ctaatcatgc gagtcct                                       1227

<210> SEQ ID NO 37
<211> LENGTH: 134
<212> TYPE: DNA
<213> ORGANISM: Cannabis sativa

<400> SEQUENCE: 37
ttgtatatgt ctgtcctgaa ttcgacaata caaaatctta gattcacctc tgatacaacc     60
ccaaaaccac tcgttattgt cactccttca aatgtctccc atatccaggc cactattcta    120
tgctccaaga aagt                                                     134

<210> SEQ ID NO 38
<211> LENGTH: 1635
<212> TYPE: DNA
<213> ORGANISM: Cannabis sativa

<400> SEQUENCE: 38
atgaattgct cagcattttc cttttggttt gtttgcaaaa taatattttt ctttctctca     60
ttcaatatcc aaatttcaat agctaatcct caagaaaact tccttaaatg cttctcggaa    120
tatattccta caatccagc aaatccaaaa ttcatataca ctcaacacga ccaattgtat    180
atgtctgtcc tgaattcgac aatacaaaat cttagattca cctctgatac aaccccaaaa    240
ccactcgtta ttgtcactcc ttcaaatgtc tcccatatcc aggccagtat tctctgctcc    300
aagaaagttg gtttgcagat tcgaactcga agcggtggcc atgatgctga gggtttgtcc    360
tacatatctc aagtcccatt tgctatagta gacttgagaa acatgcatac ggtcaaagta    420
gatattcata gccaaactgc gtgggttgaa gccggagcta cccttggaga agtttattat    480
tggatcaatg agatgaatga aattttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg aaaagttct agatcgaaaa    660 tccatgggag aagatctatt tgggctata cgtggtggag gaggagaaaa ctttggaatc    720
attgcagcat ggaaaatcaa acttgttgtt gtcccatcaa aggctactat attcagtgtt    780
aaaaagaaca tggagataca tgggcttgtc aagttattta acaaatggca aaatattgct    840
tacaagtatg acaaagattt aatgctcacg actcacttca gaactaggaa tattacagat    900
```

| | |
|---|---|
| aatcatggga agaataagac tacagtacat ggttacttct cttccatttt tcttggtgga | 960 |
| gtggatagtc tagttgactt gatgaacaag agctttcctg agttgggtat taaaaaaact | 1020 |
| gattgcaaag aattgagctg gattgataca accatcttct acagtggtgt tgtaaattac | 1080 |
| aacactgcta atttaaaaa ggaaattttg cttgatagat cagctgggaa gaagacggct | 1140 |
| ttctcaatta agttagacta tgttaagaaa ctaatacctg aaactgcaat ggtcaaaatt | 1200 |
| ttggaaaaat tatatgaaga gaggtagga gttgggatgt atgtgttgta cccttacggt | 1260 |
| ggtataatgg atgagatttc agaatcagca attccattcc ctcatcgagc tggaataatg | 1320 |
| tatgaacttt ggtacactgc tacctgggag aagcaagaag ataacgaaaa gcatataaac | 1380 |
| tgggttcgaa gtgtttataa tttcacaact ccttatgtgt cccaaaatcc aagattggcg | 1440 |
| tatctcaatt atagggacct tgatttagga aaaactaatc ctgagagtcc taataattac | 1500 |
| acacaagcac gtatttgggg tgaaaagtat tttggtaaaa atttaacag gttagttaag | 1560 |
| gtgaaaacca agctgatcc caataatttt tttagaaacg aacaaagtat cccacctctt | 1620 |
| ccaccgcatc atcat | 1635 |

<210> SEQ ID NO 39
<211> LENGTH: 1634
<212> TYPE: DNA
<213> ORGANISM: Cannabis sativa

<400> SEQUENCE: 39

| | |
|---|---|
| atgaagtact caacattctc tttttggttt ctttgcaaaa tattagtttc acttctctca | 60 |
| ttctctatcc aaacttctca agctaatcca catgacaact ttcttcaatg cttctccaaa | 120 |
| catatcaaca acaataacaa taatcaattg taaaactca tacacactcc aaatgatcca | 180 |
| tcatatatct ctgtcctaaa ttcaactata caaaacctta gattcgcttc tccttcaaca | 240 |
| ccaaaaccac tagttatcat cacacccttca aatacatccc atgtccaagc ctgtgtttta | 300 |
| tgctccaaga aatatggctt gcagattcga actcgaagcg gcggccatga ctttgagggt | 360 |
| gcctcctatg tgtctaaagt cccatttgtg atattagata tgagaaatct acgttcaatc | 420 |
| actgtagacg tagataccaa aactgcatgg gttgaagctg gagctaccat tggtgaactt | 480 |
| tattatagga ttgctgagaa aaatgggaat ctgagttttc ctgctgggta ctgtcgtact | 540 |
| gttgggttag gtgggcattt cagtggagga ggctatggag cactgttgcg aaaatatggc | 600 |
| cttgcagctg ataatatcat tgatgctcac ttagtcaacg cagatggaga attccttgac | 660 |
| cgaaaatcta tgggagaaga tttgttttgg gccatacgtg gtggtggtgg agcaagcttt | 720 |
| ggaatcattc tcgcttggaa aatcagattg gttgcagttc catctaaagt tactatgttc | 780 |
| tctgttagta aaaacttgga gatgaatgag actgtgaaga tatataacaa atggcaaaat | 840 |
| actgcttaca gtttgacaa agatttgtta ctctttgtta gcttcatgac tattaattct | 900 |
| accgattcac aagggaaata caagacaact atacaagctt cattctcttc tatatttctt | 960 |
| ggtagggttg agagtctcct catattgatg caaagaaat tcctgagtt gggaattgaa | 1020 |
| agaaaagatt gcctcgaaaa gagctggatt gaaactgtcg tttactttga tggttttca | 1080 |
| agtgggata caccagaatc tttacttaat acaacatttc aacaaatgt attttcaag | 1140 |
| gtgaaattag actatgtgaa gaagccagtt ccagaagttg tgatggtaaa acttttggag | 1200 |
| aagttatatg aagaagatgt aggagtgggg tttcttatga tgtaccctta tggtggtaaa | 1260 |
| atggatgaga tttcagaatc agcaattcca ttccctcatc gagctggatt tatgtacaaa | 1320 |

| | |
|---|---|
| attttgtact tgtctgcatg ggagaaagaa ggagaaagtg aaaagcatat gaattgggtc | 1380 |
| cgaagtgcat ataatttcat gtctccttat gtgtcccaaa atccaagagc tacatatctc | 1440 |
| aattataggg accttgattt gggaacaaat aacgagaagg gtcctattag ttactcacaa | 1500 |
| gcaagtgttt ggggtaaaaa gtattttggt atgaactta agaggttagt taatgtgaaa | 1560 |
| accaaggtcg atccaagtaa tttctttaga aacgaacaaa gcatcccacc acttctgtcg | 1620 |
| cgacgcctct aaat | 1634 |

<210> SEQ ID NO 40
<211> LENGTH: 1885
<212> TYPE: DNA
<213> ORGANISM: Cannabis sativa

<400> SEQUENCE: 40

| | |
|---|---|
| aaaaaaatca ttaggactga agaaaaatga attgctcagc attttccttt tggtttgttt | 60 |
| gcaaataat atttttcttt ctctcattcc atatccaaat ttcaatagct aatcctcgag | 120 |
| aaaacttcct taaatgcttc tcaaaacata ttcccaacaa tgtagcaaat ccaaaactcg | 180 |
| tatacactca acacgaccaa ttgtatatgt ctatcctgaa ttcgacaata caaaatctta | 240 |
| gattcatctc tgatacaacc ccaaaaccac tcgttattgt cactccttca aataactccc | 300 |
| atatccaagc aactattta tgctctaaga aagttggctt gcagattcga actcgaagcg | 360 |
| gtggccatga tgctgagggt atgtcctaca tatctcaagt cccatttgtt gtagtagact | 420 |
| tgagaaacat gcattcgatc aaaatagatg ttcatagcca aactgcgtgg gttgaagccg | 480 |
| gagctaccct tggagaagtt tattattgga tcaatgagaa gaatgagaat cttagttttc | 540 |
| ctggtgggta ttgccctact gttggcgtag gtggacactt tagtggagga ggctatggag | 600 |
| cattgatgcg aaattatggc cttgcggctg ataaatattat tgatgcacac ttagtcaatg | 660 |
| ttgatggaaa agttctagat cgaaaatcca tgggagaaga tctgttttgg gctatacgtg | 720 |
| gtggtggagg agaaaacttt ggaatcattg cagcatggaa aatcaaactg ttgctgtcc | 780 |
| catcaaagtc tactatattc agtgttaaaa agaacatgga gatacatggg cttgtcaagt | 840 |
| tatttaacaa atggcaaaat attgcttaca agtatgacaa agatttagta ctcatgactc | 900 |
| acttcataac aaagaatatt acagataatc atgggaagaa taagactaca gtacatggtt | 960 |
| acttctcttc aattttcat ggtggagtgg atagtctagt cgacttgatg aacaagagct | 1020 |
| ttcctgagtt gggtattaaa aaaactgatt gcaaagaatt tagctggatt gatacaacca | 1080 |
| tcttctacag tggtgttgta aattttaaca ctgctaattt taaaaaggaa attttgcttg | 1140 |
| atagatcagc tgggaagaag acggctttct caattaagtt agactatgtt aagaaaccaa | 1200 |
| ttccagaaac tgcaatggtc aaattttgg aaaaattata tgaagaagat gtaggagctg | 1260 |
| ggatgtatgt gttgtacct tacggtggta taatggagga gatttcagaa tcagcaattc | 1320 |
| cattccctca tcgagctgga ataatgtatg aactttggta cactgcttcc tgggagaagc | 1380 |
| aagaagataa tgaaaagcat ataaactggg ttcgaagtgt ttataatttt acgactcctt | 1440 |
| atgtgtccca aaatccaaga ttggcgtatc tcaattatag ggaccttgat ttaggaaaaa | 1500 |
| ctaatcatgc gagtcctaat aattacacac aagcacgtat ttgggtgaa aagtattttg | 1560 |
| gtaaaatttt taacaggtta gttaaggtga aaactaaagt tgatcccaat aatttttta | 1620 |
| gaaacgaaca aagtatccca cctcttccac cgcatcatca ttaattatct ttaaatagat | 1680 |
| atatttccct tatcaattag ttaatcatta ccatacat acatttattg tatatagttt | 1740 |
| atctactcat attatgtatg ctcccaagta tgaaaatcta cattagaact gtgtagacaa | 1800 |

<210> SEQ ID NO 41
<211> LENGTH: 1638
<212> TYPE: DNA
<213> ORGANISM: Cannabis sativa

<400> SEQUENCE: 41

```
atgaagtgct caacattctg tttttggtat gtttgcaaga taatattttt ctttctctca      60
ttcaatatcc aaatttcaat agctaatcct caagaaaact tccttaaatg cttctcacaa     120
tatattccca ccaatgtaac aaatgcaaaa ctcgtataca ctcaacacga ccaattttat     180
atgtctatcc tgaattcgac catacaaaat cttagattta cctctgacac aaccccaaaa     240
ccacttgtta tcatcactcc tttaaatgtc tcccatatcc aaggcactat tctatgctcc     300
aagaaagttg gcttgcagat tcgaactcga agcggtggtc atgatgctga gggcatgtcc     360
tacatatctc aagtcccatt tgttatagta gacttgagaa acatgcattc ggtcaaaata     420
gatgttcata gccaaactgc atgggttgaa gccggagcta cccttggaga gtttattat     480
tggatcaatg agaacaatga gaatcttagt tttcctgctg gtactgccc tactgttggc     540
gcgggtggac actttagtgg aggaggctat ggagcattga tgcgaaatta tggcctcgcg     600
gctgataata tcattgatgc gcacttagtc aatgttgatg gaaaagtttt agatcgaaaa     660
tccatggggg aagatttgtt ttgggctata cgtggtggtg gaggagaaaa ctttggaatc     720
attgcagcgt ggaaaattag acttgttgct gtcccatcaa tgtctactat attcagtgtt     780
aaaaagaaca tggagataca tgagcttgtc aagttagtta acaaatggca aaatattgct     840
tacatgtatg aaaaagaatt attactcttt actcacttta taaccaggaa tattacagat     900
aatcaaggga gaataagac aacaatacac agttacttct cctccatttt ccatggtgga     960
gtggatagtc tagtcgactt gatgaacaag agctttcctg aattgggtat taaaaaaaca    1020
gattgcaaac agttgagctg gattgatact atcatcttct acagtggtgt tgtaaattac    1080
aacacaactt attttaaaaa agaaattttg cttgatagat caggtgggcg gaaggcggct    1140
ttctcgatta gttagacta tgttaagaaa ccgattccag aaaccgcaat ggtcacaatt    1200
ttggaaaaat tatatgaaga agatgtagga gttgggatgt ttgtgttta cccttatggt    1260
ggtataatgg atgagatttc agaatcagca attccattcc ctcatcgagc tggaatcatg    1320
tatgaaattt ggtacatagc ttcatgggag aagcaagaag ataatgaaaa gcatataaac    1380
tggattcgga atgtttataa tttcacgact ccttatgtgt cccaaaatcc aagaatggcg    1440
tatctcaatt atagggacct tgatttagga aaaactaatt tcgagagtcc taataattac    1500
acacaagcac gtatttgggg tgaaaagtat tttggtaaaa attttaatag gttagtaaaa    1560
gtaaaaacca aggttgatcc cgataatttc tttagaaacg aacaaagcat cccacctctt    1620
cccctgcgtc atcattaa                                                  1638
```

<210> SEQ ID NO 42
<211> LENGTH: 1635
<212> TYPE: DNA
<213> ORGANISM: Cannabis sativa

<400> SEQUENCE: 42

```
atgaagtgct caacattctc cttttggttt gtttgcaaga taatattttt ctttttctca      60
```

```
ttcaatatcc aaacttccat tgctaatcct cgagaaaact tccttaaatg cttctcgcaa      120
tatattccca ataatgcaac aaatctaaaa ctcgtataca ctcaaaacaa cccattgtat      180
atgtctgtcc taaattcgac aatacacaat cttagattca cctctgacac aaccccaaaa      240
ccacttgtta tcgtcactcc ttcacatgtc tctcatatcc aaggcactat tctatgctcc      300
aagaaagttg gcttgcagat tcgaactcga agtggtggtc atgattctga gggcatgtcc      360
tacatatctc aagtcccatt tgttatagta gacttgagaa acatgcgttc aatcaaaata      420
gatgttcata gccaaactgc atgggttgaa gccggagcta cccttggaga agtttattat      480
tgggttaatg agaaaaatga gaatcttagt ttggcggctg ggtattgccc tactgtttgc      540
gcaggtggac actttggtgg aggaggctat ggaccattga tgagaaacta tggcctcgcg      600
gctgataata tcattgatgc acacttagtc aacgttcatg gaaagtgct agatcgaaaa       660
tctatggggg aagatctctt ttgggcttta cgtggtggtg gagcagaaag cttcggaatc      720
attgtagcat ggaaaattag actggttgct gtcccaaagt ctactatgtt tagtgttaaa      780
aagatcatgg agatacatga gcttgtcaag ttagttaaca aatggcaaaa tattgcttac      840
aagtatgaca aagatttatt actcatgact cacttcataa ctaggaacat tacagataat      900
caagggaaga ataagacagc aatacacact tacttctctt cagttttcct tggtggagtg      960
gatagtctag tcgacttgat gaacaagagt tttcctgagt tgggtattaa aaaacggat     1020
tgcagacaat tgagctggat tgatactatc atcttctata tggtgttgt aaattacgac     1080
actgataatt ttaacaagga aattttgctt gatagatccg ctgggcagaa cggtgctttc     1140
aagattaagt tagactacgt taagaaacca attccagaat ctgtatttgt ccaaattttg     1200
gaaaaattat atgaagaaga tataggagct gggatgtatg cgttgtaccc ttacggtggt     1260
ataatggatg agatttcaga atcagcaatt ccattccctc atcgagctgg aatcttgtat     1320
gagttatggt acatatgtag ttgggagaag caagaagata acgaaaagca tctaaactgg     1380
attagaaata tttataactt catgactcct tatgtgtcca aaaatccaag attggcatat     1440
ctcaattata gagaccttga tataggaata aatgatccca agaatccaaa taattacaca     1500
caagcacgta tttggggtga aagtattttt ggtaaaaatt ttgacaggct agtaaaagtg     1560
aaaacccctgg ttgatcccaa taactttttt agaaacgaac aaagcatccc acctcttcca     1620
cggcatcgtc attaa                                                       1635
```

<210> SEQ ID NO 43
<211> LENGTH: 1638
<212> TYPE: DNA
<213> ORGANISM: Cannabis sativa

<400> SEQUENCE: 43

```
atgaagtgct caacattctg tttttggtat gtttgcaaga taatattttt ctttctctca       60
ttcaatatcc aaatttcaat agctaatcct caagaaaact tccttaaatg cctctcacaa      120
tatattccca ccaatgtaac aaatgcaaaa ctcgtataca ctcaacacga ccaattttat      180
atgtctatct taaattcgac cgtacaaaat cttagattta cctctgacac aaccccaaaa      240
ccacttgtta tcaccactcc tttaaatgtc tcccatatcc aaggcactat tctatgttcc      300
aagaaagttg gcttgcagat tcgaactcga agcggtggtc atgatgctga gggcatgtcc      360
tacatatctc aagtcccatt tgttatagta gacttgagaa acatgcattc ggtcaaaata      420
gatgttcata gccaaactgc atgggttgaa tccggagcta cccttggaga agtttattat      480
tggatcaatg agaacaatga gaatcttagt tttcctgctg ggtactgccc tactgttggc      540
```

```
acgggtggac actttagtgg aggaggctat ggagcattga tgcgaaatta tggcctcgcg      600
gctgataata tcattgatgc gcacttagtc aatgttgatg gaaaagtttt agatcgaaaa      660
tccatggggg aagatttgtt ttgggctata cgtggtggtg gaggagaaaa ctttggaatc      720
attgcagcgt ggaaaattag acttgttgct gtcccatcaa tgtctactat attcagtgtt      780
aaaaagaaca tggagataca tgagcttgtc aagttagtta acaaatggca aaatattgct      840
tacatgtatg aaaaagaatt attactcttt actcacttta taaccaggaa attacagat       900
aatcaaggga agaataagac aacaatacac agttacttct cctccatttt ccatggtgga      960
gtggatagtc tagtcgactt gatgaacaag agctttcctg aattgggtat aaaaaaaaca     1020
gattgcaaac agttgagctg gattgatact atcatcttct acagtggtgt tgtaaattac     1080
aacacaacta attttaaaaa agaaattttg cttgatagat caggtgggcg gaaggcggct     1140
ttctcgatta agttagacta tgttaagaaa ccgattccag aaaccgcaat ggtcacaatt     1200
tggaaaaat tatatgaaga agatgtagga gttgggatgt tgtgtttta cccttatggt      1260
ggtataatgg atgagatttc agaatcagca attccattcc ctcatcgagc tggaatcacg     1320
tatgaaattt ggtacatagc ttcatgggag aagcaagaag ataatgaaaa gcatataaac     1380
tggattcgga atgtttataa tttcacgact ccttatgtgt cccaaaatcc aagaatggcg     1440
tatctcaatt atagggacct tgatttagga aaaactaatt tcgagagtcc taataattac     1500
acacaagcac gtatttgggg tgaaaagtat tttggtaaaa attttaatag gttagtaaaa     1560
gtaaaaacca aggttgatcc cgataaatttc tttagaaacg aacaaagcat cccacctctt     1620
cccctgcgtc atcattaa                                                    1638
```

<210> SEQ ID NO 44
<211> LENGTH: 1635
<212> TYPE: DNA
<213> ORGANISM: Cannabis sativa

<400> SEQUENCE: 44

```
atgaattgct cagcattttc cttttggttt gtttgcaaaa taatattttt ctttctctca       60
ttccatatcc aaatttcaat agctaatcct cgagaaaact tccttaaatg cttctcaaaa      120
catattccca acaatgtagc aaatccaaaa ctcgtataca ctcaacacga ccaattgtat      180
atgtctatcc tgaattcgac aatacaaaat cttagattca tctctgatac aaccccaaaa      240
ccactcgtta ttgtcactcc ttcaaataac tcccatatcc aagcaactat tttatgctct      300
aagaaagttg gcttgcagat tcgaactcga agcggtggcc atgatgctga gggtatgtcc      360
tacatatctc aagtcccatt tgttgtagta gacttgagaa acatgcattc gatcaaaata      420
gatgttcata gccaaactgc gtgggttgaa gccggagcta cccttggaga agtttattat      480
tggatcaatg agaagaatga gaatcttagt tttcctggtg ggtattgccc tactgttggc      540
gtaggtggac actttagtgg aggaggctat ggagcattga tgcgaaatta tggccttgcg      600
gctgataata ttattgatgc acacttagtc aatgttgatg gaaaagttct agatcgaaaa      660
tccatgggag aagatctgtt ttgggctata cgtggtggtg gaggagaaaa ctttggaatc      720
attgcagcat ggaaaatcaa acttgttgct gtcccatcaa agtctactat attcagtgtt      780
aaaaagaaca tggagataca tgggcttgtc aagttattta caaatggca aaatattgct       840
tacaagtatg acaagatttt agtactcatg actcacttca taacaaagaa attacagat       900
aatcatggga agaataagac tacagtacat ggttacttct cttcaatttt tcatggtgga      960
```

| | |
|---|---|
| gtggatagtc tagtcgactt gatgaacaag agctttcctg agttgggtat taaaaaaact | 1020 |
| gattgcaaag aatttagctg gattgataca accatcttct acagtggtgt tgtaaatttt | 1080 |
| aacactgcta attttaaaaa ggaaattttg cttgatagat cagctgggaa gaagacggct | 1140 |
| ttctcaatta agttagacta tgttaagaaa ccaattccag aaactgcaat ggtcaaaatt | 1200 |
| ttggaaaaat tatatgaaga agatgtagga gctgggatgt atgtgttgta cccttacggt | 1260 |
| ggtataatgg aggagatttc agaatcagca attccattcc ctcatcgagc tggaataatg | 1320 |
| tatgaacttt ggtacactgc ttcctgggag aagcaagaag ataatgaaaa gcatataaac | 1380 |
| tgggttcgaa gtgtttataa ttttacgact ccttatgtgt cccaaaatcc aagattggcg | 1440 |
| tatctcaatt atagggacct tgatttagga aaaactaatc atgcgagtcc taataattac | 1500 |
| acacaagcac gtatttgggg tgaaaagtat tttggtaaaa attttaacag gttagttaag | 1560 |
| gtgaaaacta agttgatcc caataatttt tttagaaacg aacaaagtat cccacctctt | 1620 |
| ccaccgcatc atcat | 1635 |

<210> SEQ ID NO 45
<211> LENGTH: 1824
<212> TYPE: DNA
<213> ORGANISM: Cannabis sativa

<400> SEQUENCE: 45

| | |
|---|---|
| tgaagaaaaa aaatgaattg ctcagcattt tccttttggt ttgtttgcaa aataatattt | 60 |
| ttctttctct cattccatat ccaaatttca atagctaatc ctcgagaaaa cttccttaaa | 120 |
| tgcttctcaa aacatattcc caacaatgta gcaaatccaa aactcgtata cactcaacac | 180 |
| gaccaattgt atatgtctat cctgaattcg acaatacaaa atcttagatt catctctgat | 240 |
| acaaccccaa aaccactcgt tattgtcact ccttcaaata actcccatat ccaagcaact | 300 |
| attttatgct ctaagaaagt tggcttgcag attcgaactc gaagcggtgg ccatgatgct | 360 |
| gagggtatgt cctacatatc tcaagtccca tttgttgtag tagacttgag aaacatgcat | 420 |
| tcgatcaaaa tagatgttca tagccaaact gcgtgggttg aagccggagc tacccttgga | 480 |
| gaagtttatt attggatcaa tgagaagaat gagaatctta gttttcctgg tgggtattgc | 540 |
| cctactgttg gcgtaggtgg acactttagt ggaggaggct atggagcatt gatgcgaaat | 600 |
| tatgccttg cggctgataa tattattgat gcacacttag tcaatgttga tggaaaagtt | 660 |
| ctagatcgaa aatccatggg agaagatctg ttttgggcta tacgtggtgg tggaggagaa | 720 |
| aactttggaa tcattgcagc atggaaaatc aaactggttg ctgtcccatc aaagtctact | 780 |
| atattcagtg ttaaaagaa catggagata catgggcttg tcaagttatt taacaaatgg | 840 |
| caaaatattg cttacaagta tgacaaagat ttagtactca tgactcactt cataacaaag | 900 |
| aatattacag ataatcatgg gaagaataag actacagtac atggttactt ctcttcaatt | 960 |
| tttcatggtg gagtggatag tctagtcgac ttgatgaaca agagctttcc tgagttgggt | 1020 |
| attaaaaaaa ctgattgcaa agaatttagc tggattgata caaccatctt ctacagtggt | 1080 |
| gttgtaaatt ttaacactgc taattttaaa aaggaaattt tgcttgatag atcagctggg | 1140 |
| aagaagacgg ctttctcaat taagttagac tatgttaaga aaccaattcc agaaactgca | 1200 |
| atggtcaaaa ttttggaaaa attatatgaa gaagatgtag gagctgggat gtatgtgttg | 1260 |
| tacccttacg gtggtataat ggaggagatt cagaatcag caattccatt ccctcatcga | 1320 |
| gctggaataa tgtatgaact tggtacact gcttcctggg agaagcaaga agataatgaa | 1380 |
| aagcatataa actgggttcg aagtgtttat aattttacga ctccttatgt gtcccaaaat | 1440 |

```
ccaagattgg cgtatctcaa ttatagggac cttgatttag gaaaaactaa tcatgcgagt   1500
cctaataatt acacacaagc acgtatttgg ggtgaaaagt attttggtaa aaattttaac   1560
aggttagtta aggtgaaaac taaagttgat cccaataatt ttttagaaa cgaacaaagt    1620 atcccacctc ttccaccgca tcatcattaa ttatctttaa atagatatat ttcccttatc   1680
aattagttaa tcattatacc atacatacat ttattgtata tagtttatct actcatatta   1740
tgtatgctcc caagtatgaa atctacatt agaactgtgt agacaatcat aagatatatt    1800
taataaaata aattgtctttt ctta                                          1824
```

<210> SEQ ID NO 46
<211> LENGTH: 1657
<212> TYPE: DNA
<213> ORGANISM: Cannabis sativa

<400> SEQUENCE: 46

```
atgaattgct cagcattttc cttttggttt gtttgcaaaa taatattttt ctttctctca     60
ttccatatcc aaatttcaat agctaatcct cgagaaaact tccttaaatg cttctcaaaa    120
catattccca acaatgtagc aaatccaaaa ctcgtataca ctcaacacga ccaattgtat    180
atgtctatcc tgaattcgac aatacaaaat cttagattca tctctgatac aaccccaaaa    240
ccactcgtta ttgtcactcc ttcaaataac tcccatatcc aagcaactat tttatgctct    300
aagaaagttg gcttgcagat tcgaactcga agcggtggcc atgatgctga gggtatgtcc    360
tacatatctc aagtcccatt tgttgtagta gacttgagaa acatgcattc gatcaaaata    420
gatgttcata gccaaactgc gtgggttgaa gccggagcta cccttggaga gtttattat     480 tggatcaatg agaagaatga gaatcttagt tttcctggtg ggtattgccc tactgttggc    540
gtaggtggac actttagtgg aggaggctat ggagcattga tgcgaaatta tggccttgcg    600
gctgataata ttattgatgc acacttagtc aatgttgatg gaaagttct agatcgaaaa     660 tccatgggag aagatctgtt ttgggctata cgtggtggtg gaggagaaaa ctttggaatc    720
attgcagcat ggaaaatcaa actggttgct gtcccatcaa agtctactat attcagtgtt    780 aaaagaaca tggagataca tgggcttgtc aagttattta acaaatggca aaatattgct     840
tacaagtatg acaaagattt agtactcatg actcacttca taacaaagaa tattacagat    900
aatcatggga agaataagac tacagtacat ggttacttct cttcaatttt tcatggtgga    960
gtggatagtc tagtcgactt gatgaacaag agctttcctg agttgggtat taaaaaaact   1020
gattgcaaag aatttagctg gattgataca accatcttct acagtggtgt tgtaaatttt    1080
aacactgcta attttaaaaa ggaaattttg cttgatagat cagctgggaa gaagacggct    1140
ttctcaatta agttagacta tgttaagaaa ccaattccag aaactgcaat ggtcaaaatt    1200
ttggaaaaat tatatgaaga agatgtagga gctgggatgt atgtgttgta cccttacggt    1260
ggtataatgg aggagatttc agaatcagca attccattcc ctcatcgagc tggaataatg    1320
tatgaacttt ggtacactgc ttcctgggag aagcaagaag ataatgaaaa gcatataaac    1380
tgggttcgaa gtgtttataa ttttacgact ccttatgtgt cccaaaatcc aagattggcg    1440
tatctcaatt atagggacct tgatttagga aaaactaatc atgcgagtcc taataattac    1500
acacaagcac gtatttgggg tgaaaagtat tttggtaaaa attttaacag gttagttaag    1560
gtgaaaacta aagttgatcc caataatttt tttagaaacg aacaaagtat cccacctctt    1620
ccaccgcatc atcatatctt gctgaaaaac tcgagcc                             1657
```

<210> SEQ ID NO 47
<211> LENGTH: 1657
<212> TYPE: DNA
<213> ORGANISM: Cannabis sativa

<400> SEQUENCE: 47

| | | | | |
|---|---|---|---|---|
| atgaattgct cagcattttc cttttggttt gtttgcaaaa taatattttt ctttctctca | 60 |
| ttccatatcc aaatttcaat agctaatcct cgagaaaact tccttaaatg cttctcaaaa | 120 |
| catattccca acaatgtagc aaatccaaaa ctcgtataca ctcaacacga ccaattgtat | 180 |
| atgtctatcc tgaattcgac aatacaaaat cttagattca tctctgatac aaccccaaaa | 240 |
| ccactcgtta ttgtcactcc ttcaaataac tcccatatcc aagcaactat tttatgctct | 300 |
| aagaaagttg gcttgcagat tcgaactcga agcggtggcc atgatgctga gggtatgtcc | 360 |
| tacatatctc aagtcccatt tgttgtagta gacttgagaa acatgcattc gatcaaaata | 420 |
| gatgttcata gccaaactgc gtgggttgaa gccggagcta cccttggaga agtttattat | 480 |
| tggatcaatg agaagaatga gaatcttagt tttcctggtg ggtattgccc tactgttggc | 540 |
| gtaggtggac actttagtgg aggaggctat ggagcattga tgcgaaatta tggccttgcg | 600 |
| gctgataata ttattgatgc acacttagtc aatgttgatg aaaagttct agatcgaaaa | 660 |
| tccatgggag aagatctgtt tgggctata cgtggtggtg gaggagaaaa ctttggaatc | 720 |
| attgcagcat ggaaaatcaa actggttgct gtcccatcaa agtctactat attcagtgtt | 780 |
| aaaaagaaca tggagataca tgggcttgtc aagttattta caaatggca aaatattgct | 840 |
| tacaagtatg acaagatt agtactcatg actcacttca taacaaagaa tattacagat | 900 |
| aatcatggga agaataagac tacagtacat ggttacttct cttcaatttt tcatggtgga | 960 |
| gtggatagtc tagtcgactt gatgaacaag agctttcctg agttgggtat taaaaaaact | 1020 |
| gattgcaaag aatttagctg gattgataca accatcttct acagtggtgt tgtaaatttt | 1080 |
| aacactgcta attttaaaaa ggaaattttg cttgatagat cagctgggaa gaagacggct | 1140 |
| ttctcaatta agttagacta tgttaagaaa ccaattccag aaactgcaat ggtcaaaatt | 1200 |
| ttggaaaaat tatatgaaga agatgtagga gctgggatgt atgtgttgta cccttacggt | 1260 |
| ggtataatgg aggagatttc agaatcagca attccattcc ctcatcgagc tggaataatg | 1320 |
| tatgaacttt ggtacactgc ttcctgggag aagcaagaag ataatgaaaa gcatataaac | 1380 |
| tggggttcgaa gtgtttataa ttttacgact ccttatgtgt cccaaaatcc aagattggcg | 1440 |
| tatctcaatt atagggacct tgatttagga aaaactaatc atgcgagtcc taataattac | 1500 |
| acacaagcac gtatttgggg tgaaaagtat tttggtaaaa attttaacag gttagttaag | 1560 |
| gtgaaaacta agttgatcc caataatttt tttagaaacg aacaaagtat cccacctctt | 1620 |
| ccaccgcatc atcatatctt gctgaaaaac tcgagcc | 1657 |

<210> SEQ ID NO 48
<211> LENGTH: 33
<212> TYPE: DNA
<213> ORGANISM: Artificial sequence
<220> FEATURE:
<223> OTHER INFORMATION: Oligonucleotide

<400> SEQUENCE: 48
tgaagaaaaa aaatgaattg ctcagcattt tcc           33

<210> SEQ ID NO 49
<211> LENGTH: 33

```
<212> TYPE: DNA
<213> ORGANISM: Artificial sequence
<220> FEATURE:
<223> OTHER INFORMATION: Oligonucleotide

<400> SEQUENCE: 49
ccaccgcatc atcattaatt atctttaaat aga                               33

<210> SEQ ID NO 50
<211> LENGTH: 33
<212> TYPE: DNA
<213> ORGANISM: Artificial sequence
<220> FEATURE:
<223> OTHER INFORMATION: Oligonucleotide

<400> SEQUENCE: 50
tctatttaaa gataattaat gatgatgcgg tgg                               33

<210> SEQ ID NO 51
<211> LENGTH: 39
<212> TYPE: DNA
<213> ORGANISM: Artificial sequence
<220> FEATURE:
<223> OTHER INFORMATION: Oligonucleotide

<400> SEQUENCE: 51
cgtgagctca cgcgtccaaa tttcaatagc taatcctcg                         39

<210> SEQ ID NO 52
<211> LENGTH: 32
<212> TYPE: DNA
<213> ORGANISM: Artificial sequence
<220> FEATURE:
<223> OTHER INFORMATION: Oligonucleotide

<400> SEQUENCE: 52
gtcggatccc aaatgggact tgagatatgt ag                                32

<210> SEQ ID NO 53
<211> LENGTH: 32
<212> TYPE: DNA
<213> ORGANISM: Artificial sequence
<220> FEATURE:
<223> OTHER INFORMATION: Oligonucleotide

<400> SEQUENCE: 53
gtcggatccg ttttggggtt gtatcagaga tg                                32

<210> SEQ ID NO 54
<211> LENGTH: 43
<212> TYPE: DNA
<213> ORGANISM: Artificial sequence
<220> FEATURE:
<223> OTHER INFORMATION: Oligonucleotide

<400> SEQUENCE: 54
cagctgcagg tcacccgggc tttctctcat tccatatcca aat                    43

<210> SEQ ID NO 55
<211> LENGTH: 36
<212> TYPE: DNA
<213> ORGANISM: Artificial sequence
<220> FEATURE:
<223> OTHER INFORMATION: Oligonucleotide

<400> SEQUENCE: 55
```
cgtgagctca cgcgtggcta tacgtggtgg tggagg                                    36

<210> SEQ ID NO 56
<211> LENGTH: 32
<212> TYPE: DNA
<213> ORGANISM: Artificial sequence
<220> FEATURE:
<223> OTHER INFORMATION: Oligonucleotide

<400> SEQUENCE: 56
gtcggatccc acttcgaacc cagtttatat gc                                        32

<210> SEQ ID NO 57
<211> LENGTH: 31
<212> TYPE: DNA
<213> ORGANISM: Artificial sequence
<220> FEATURE:
<223> OTHER INFORMATION: Oligonucleotide

<400> SEQUENCE: 57
gtcggatccg gtacaacaca tacatcccag c                                         31

<210> SEQ ID NO 58
<211> LENGTH: 40
<212> TYPE: DNA
<213> ORGANISM: Artificial sequence
<220> FEATURE:
<223> OTHER INFORMATION: Oligonucleotide

<400> SEQUENCE: 58
cagctgcagg tcacccgggc atgggagaag atctgttttg                                40

<210> SEQ ID NO 59
<211> LENGTH: 37
<212> TYPE: DNA
<213> ORGANISM: Artificial sequence
<220> FEATURE:
<223> OTHER INFORMATION: Oligonucleotide

<400> SEQUENCE: 59
cgtgagctca cgcgtggctc gagtttttca gcaagat                                   37

<210> SEQ ID NO 60
<211> LENGTH: 38
<212> TYPE: DNA
<213> ORGANISM: Artificial sequence
<220> FEATURE:
<223> OTHER INFORMATION: Oligonucleotide

<400> SEQUENCE: 60
cagggtcacc cggggaattg ctcagcattt tccttttg                                  38

<210> SEQ ID NO 61
<211> LENGTH: 173
<212> TYPE: DNA
<213> ORGANISM: Artificial sequence
<220> FEATURE:
<223> OTHER INFORMATION: Oligonucleotide

<400> SEQUENCE: 61
ccaaatttca atagctaatc ctcgagaaaa cttccttaaa tgcttctcaa acatattcc           60 caacaatgta gcaaatccaa aactcgtata cactcaacac gaccaattgt atatgtctat         120
cctgaattcg acaatacaaa atcttagatt catctctgat acaaccccaa aac                173

```
<210> SEQ ID NO 62
<211> LENGTH: 142
<212> TYPE: DNA
<213> ORGANISM: Artificial sequence
<220> FEATURE:
<223> OTHER INFORMATION: Oligonucleotide

<400> SEQUENCE: 62
ccactcgtta ttgtcactcc ttcaaataac tcccatatcc aagcaactat tttatgctct      60
aagaaagttg gcttgcagat tcgaactcga agcggtggcc atgatgctga gggtatgtcc     120
tacatatctc aagtcccatt tg                                              142

<210> SEQ ID NO 63
<211> LENGTH: 191
<212> TYPE: DNA
<213> ORGANISM: Artificial sequence
<220> FEATURE:
<223> OTHER INFORMATION: Oligonucleotide

<400> SEQUENCE: 63
gttttggggt tgtatcagag atgaatctaa gattttgtat tgtcgaattc aggatagaca      60
tatacaattg gtcgtgttga gtgtatacga gttttggatt tgctacattg ttgggaatat     120
gttttgagaa gcatttaagg aagttttctc gaggattagc tattgaaatt tggatatgga     180
atgagagaaa g                                                          191

<210> SEQ ID NO 64
<211> LENGTH: 511
<212> TYPE: DNA
<213> ORGANISM: Artificial sequence
<220> FEATURE:
<223> OTHER INFORMATION: Oligonucleotide

<400> SEQUENCE: 64
ccaaatttca atagctaatc ctcgagaaaa cttccttaaa tgcttctcaa aacatattcc      60
caacaatgta gcaaatccaa aactcgtata cactcaacac gaccaattgt atatgtctat     120
cctgaattcg acaatacaaa atcttagatt catctctgat acaacccccaa aacccactcg    180 ttattgtcac tccttcaaat aactcccata tccaagcaac tatttatgc tctaagaaag      240 ttggcttgca gattcgaact cgaagcggtg gccatgatgc tgagggtatg tcctacatat     300
ctcaagtccc atttggatcc gttttggggt tgtatcagag atgaatctaa gattttgtat    360
tgtcgaattc aggatagaca tatacaattg gtcgtgttga gtgtatacga gttttggatt    420
tgctacattg ttgggaatat gttttgagaa gcatttaagg aagttttctc gaggattagc    480
tattgaaatt tggatatgga atgagagaaa g                                    511

<210> SEQ ID NO 65
<211> LENGTH: 24
<212> TYPE: DNA
<213> ORGANISM: Artificial sequence
<220> FEATURE:
<223> OTHER INFORMATION: Oligonucleotide

<400> SEQUENCE: 65
ccaaatttca atagctaatc ctcg                                             24

<210> SEQ ID NO 66
<211> LENGTH: 23
<212> TYPE: DNA
<213> ORGANISM: Artificial sequence
<220> FEATURE:
```

<223> OTHER INFORMATION: Oligonucleotide

<400> SEQUENCE: 66
caaatgggac ttgagatatg tag                                              23

<210> SEQ ID NO 67
<211> LENGTH: 23
<212> TYPE: DNA
<213> ORGANISM: Artificial sequence
<220> FEATURE:
<223> OTHER INFORMATION: Oligonucleotide

<400> SEQUENCE: 67
gttttggggt tgtatcagag atg                                              23

<210> SEQ ID NO 68
<211> LENGTH: 24
<212> TYPE: DNA
<213> ORGANISM: Artificial sequence
<220> FEATURE:
<223> OTHER INFORMATION: Oligonucleotide

<400> SEQUENCE: 68
ctttctctca ttccatatcc aaat                                             24

<210> SEQ ID NO 69
<211> LENGTH: 569
<212> TYPE: DNA
<213> ORGANISM: Artificial sequence
<220> FEATURE:
<223> OTHER INFORMATION: Oligonucleotide

<400> SEQUENCE: 69
ggctatacgt ggtggtggag gagaaaactt tggaatcatt gcagcatgga aaatcaaact      60
ggttgctgtc ccatcaaagt ctactatatt cagtgttaaa agaacatgg agatacatgg      120 gcttgtcaag ttatttaaca aatggcaaaa tattgcttac aagtatgaca agatttagt      180 actcatgact cacttcataa caaagaatat tacagataat catgggaaga ataagactac     240
agtacatggt tacttctctt caattttttca tggtggagtg gatagtctag tcgacttgat   300
gaacaagagc tttcctgagt tgggtattaa aaaaactgat tgcaaagaat ttagctggat    360
tgatacaacc atcttctaca gtggtgttgt aaattttaac actgctaatt ttaaaaagga    420
aattttgctt gatagatcag ctgggaagaa gacggctttc tcaattaagt tagactatgt    480
taagaaacca attccagaaa ctgcaatggt caaaattttg aaaaattat atgaagaaga    540 tgtaggagct gggatgtatg tgttgtacc                                      569

<210> SEQ ID NO 70
<211> LENGTH: 141
<212> TYPE: DNA
<213> ORGANISM: Artificial sequence
<220> FEATURE:
<223> OTHER INFORMATION: Oligonucleotide

<400> SEQUENCE: 70
cttacggtgg tataatggag gagatttcag aatcagcaat tccattccct catcgagctg     60
gaataatgta tgaactttgg tacactgctt cctgggagaa gcaagaagat aatgaaaagc   120
atataaactg ggttcgaagt g                                              141

<210> SEQ ID NO 71
<211> LENGTH: 590

```
<212> TYPE: DNA
<213> ORGANISM: Artificial sequence
<220> FEATURE:
<223> OTHER INFORMATION: Oligonucleotide

<400> SEQUENCE: 71
ggtacaacac atacatccca gctcctacat cttcttcata taatttttcc aaaatttgga       60
ccattgcagt ttctggaatt ggtttcttaa catagtctaa cttaattgag aaagccgtct      120
tcttcccagc tgatctatca agcaaaattt cctttttaaa attagcagtg ttaaaattta      180
caacaccact gtagaagatg gttgtatcaa tccagctaaa ttctttgcaa tcagttttt       240
taatacccaa ctcaggaaag ctcttgttca tcaagtcgac tagactatcc actccaccat      300
gaaaaattga agagaagtaa ccatgtactg tagtcttatt cttcccatga ttatctgtaa      360
tattctttgt tatgaagtga gtcatgagta ctaaatcttt gtcatacttg taagcaatat      420
tttgccattt gttaaataac ttgacaagcc catgtatctc catgttcttt taacactga       480
atatagtaga ctttgatggg acagcaacca gtttgatttt ccatgctgca atgattccaa      540
agttttctcc tccaccacca cgtatagccc aaaacagatc ttctcccatg                 590

<210> SEQ ID NO 72
<211> LENGTH: 1305
<212> TYPE: DNA
<213> ORGANISM: Artificial sequence
<220> FEATURE:
<223> OTHER INFORMATION: Oligonucleotide

<400> SEQUENCE: 72
ggctatacgt ggtggtggag gagaaaactt tggaatcatt gcagcatgga aaatcaaact       60
ggttgctgtc ccatcaaagt ctactatatt cagtgttaaa aagaacatgg agatacatgg      120
gcttgtcaag ttatttaaca aatggcaaaa tattgcttac aagtatgaca agatttagt       180
actcatgact cacttcataa caaagaatat tacagataat catgggaaga ataagactac      240
agtacatggt tacttctctt caattttca tggtggagtg gatagtctag tcgacttgat       300
gaacaagagc tttcctgagt tgggtattaa aaaaactgat tgcaaagaat ttagctggat      360
tgatacaacc atcttctaca gtggtgttgt aaattttaac actgctaatt ttaaaaagga      420
aattttgctt gatagatcag ctgggaagaa gacggctttc tcaattaagt tagactatgt      480
taagaaacca attccagaaa ctgcaatggt caaaattttg gaaaaattat atgaagaaga      540
tgtaggagct gggatgtatg tgttgtaccc ttacggtggt ataatggagg agatttcaga      600
atcagcaatt ccattccctc atcgagctgg aataatgtat gaactttggt acactgcttc      660
ctgggagaag caagaagata tgaaaagca tataaactgg gttcgaagtg atccggtac       720
aacatataca tcccagctcc tacatcttct tcatataatt tttccaaaat tttgaccatt      780
gcagttctg gaattggttt cttaacatag tctaacttaa ttgagaaagc cgtcttcttc      840
ccagctgatc tatcaagcaa aatttccttt taaaattag cagtgttaaa atttacaaca      900
ccactgtaga agatggttgt atcaatccag ctaaattctt tgcaatcagt ttttaata       960
cccaactcag gaaagctctt gttcatcaag tcgactagac tatccactcc accatgaaaa     1020
attgaagaga agtaaccatg tactgtagtc ttattcttcc catgattatc tgtaatattc     1080
tttgttatga agtgagtcat gagtactaaa tctttgtcat acttgtaagc aatattttgc     1140
catttgttaa ataacttgac aagcccatgt atctccatgt tctttttaac actgaatata     1200
gtagactttg atgggacagc aaccagtttg attttccatg ctgcaatgat tccaaagttt     1260
```
tctcctccac caccacgtat agcccaaaac agatcttctc ccatg                    1305

<210> SEQ ID NO 73
<211> LENGTH: 36
<212> TYPE: DNA
<213> ORGANISM: Artificial sequence
<220> FEATURE:
<223> OTHER INFORMATION: Oligonucleotide

<400> SEQUENCE: 73
cgtgagctca cgcgtggcta tacgtggtgg tggagg                              36

<210> SEQ ID NO 74
<211> LENGTH: 21
<212> TYPE: DNA
<213> ORGANISM: Artificial sequence
<220> FEATURE:
<223> OTHER INFORMATION: Oligonucleotide

<400> SEQUENCE: 74
ggctatacgt ggtggtggag g                                              21

<210> SEQ ID NO 75
<211> LENGTH: 32
<212> TYPE: DNA
<213> ORGANISM: Artificial sequence
<220> FEATURE:
<223> OTHER INFORMATION: Oligonucleotide

<400> SEQUENCE: 75
gtcggatccc acttcgaacc cagtttatat gc                                  32

<210> SEQ ID NO 76
<211> LENGTH: 23
<212> TYPE: DNA
<213> ORGANISM: Artificial sequence
<220> FEATURE:
<223> OTHER INFORMATION: Oligonucleotide

<400> SEQUENCE: 76
cacttcgaac ccagtttata tgc                                            23

<210> SEQ ID NO 77
<211> LENGTH: 31
<212> TYPE: DNA
<213> ORGANISM: Artificial sequence
<220> FEATURE:
<223> OTHER INFORMATION: Oligonucleotide

<400> SEQUENCE: 77
gtcggatccg gtacaacaca tacatcccag c                                   31

<210> SEQ ID NO 78
<211> LENGTH: 22
<212> TYPE: DNA
<213> ORGANISM: Artificial sequence
<220> FEATURE:
<223> OTHER INFORMATION: Oligonucleotide

<400> SEQUENCE: 78
ggtacaacac atacatccca gc                                             22

<210> SEQ ID NO 79
<211> LENGTH: 40
<212> TYPE: DNA
<213> ORGANISM: Artificial sequence

```
<220> FEATURE:
<223> OTHER INFORMATION: Oligonucleotide

<400> SEQUENCE: 79
cagctgcagg tcacccgggc atgggagaag atctgttttg                40

<210> SEQ ID NO 80
<211> LENGTH: 21
<212> TYPE: DNA
<213> ORGANISM: Artificial sequence
<220> FEATURE:
<223> OTHER INFORMATION: Oligonucleotide

<400> SEQUENCE: 80
catgggagaa gatctgtttt g                                    21

<210> SEQ ID NO 81
<211> LENGTH: 1657
<212> TYPE: DNA
<213> ORGANISM: Artificial sequence
<220> FEATURE:
<223> OTHER INFORMATION: Oligonucleotide

<400> SEQUENCE: 81
ggctcgagtt tttcagcaag atatgatgat gcggtggaag aggtgggata ctttgttcgt    60
ttctaaaaaa attattggga tcaactttag ttttcacctt aactaacctg ttaaaatttt   120
taccaaaata cttttcaccc caaatacgtg cttgtgtgta attattagga ctcgcatgat   180
tagtttttcc taaatcaagg tccctataat tgagatacgc caatcttgga ttttgggaca   240
cataaggagt cgtaaaatta taaacacttc gaacccagtt tatatgcttt tcattatctt   300
cttgcttctc ccaggaagca gtgtaccaaa gttcatacat tattccagct cgatgaggga   360
atggaattgc tgattctgaa atctcctcca ttataccacc gtaagggtac aacacataca   420
tcccagctcc tacatcttct tcatataatt tttccaaaat tttgaccatt gcagtttctg   480
gaattggttt cttaacatag tctaacttaa ttgagaaagc cgtcttcttc ccagctgatc   540
tatcaagcaa aatttccttt ttaaaattag cagtgttaaa atttacaaca ccactgtaga   600
agatggttgt atcaatccag ctaaattctt tgcaatcagt tttttttaata cccaactcag   660 gaaagctctt gttcatcaag tcgactagac tatccactcc accatgaaaa attgaagaga   720
agtaaccatg tactgtagtc ttattcttcc catgattatc tgtaatattc tttgttatga   780
agtgagtcat gagtactaaa tctttgtcat acttgtaagc aatattttgc catttgttaa   840
ataacttgac aagcccatgt atctccatgt tctttttaac actgaatata gtagactttg   900
atgggacagc aaccagtttg attttccatg ctgcaatgat tccaaagttt tctcctccac   960
caccacgtat agcccaaaac agatcttctc ccatggattt tcgatctaga acttttccat  1020
caacattgac taagtgtgca tcaataatat tatcagccgc aaggccataa tttcgcatca  1080
atgctccata gcctcctcca ctaaagtgtc cacctacgcc aacagtaggg caatacccac  1140
caggaaaact aagattctca ttcttctcat tgatccaata ataaacttct ccaagggtag  1200
ctccggcttc aacccacgca gtttggctat gaacatctat tttgatcgaa tgcatgtttc  1260
tcaagtctac tacaacaaat gggacttgag atatgtagga cataccctca gcatcatggc  1320
caccgcttcg agttcgaatc tgcaagccaa cttttcttaga gcataaaata gttgcttgga  1380
tatgggagtt atttgaagga gtgacaataa cgagtggttt tggggttgta tcagagatga  1440
atctaagatt ttgtattgtc gaattcagga tagacatata caattggtcg tgttgagtgt  1500
```

```
atacgagttt tggatttgct acattgttgg gaatatgttt tgagaagcat ttaaggaagt    1560
tttctcgagg attagctatt gaaatttgga tatggaatga gagaaagaaa aatattattt    1620
tgcaaacaaa ccaaaaggaa aatgctgagc aattcat                             1657

<210> SEQ ID NO 82
<211> LENGTH: 37
<212> TYPE: DNA
<213> ORGANISM: Artificial sequence
<220> FEATURE:
<223> OTHER INFORMATION: Oligonucleotide

<400> SEQUENCE: 82
cgtgagctca cgcgtggctc gagttttca gcaagat                              37

<210> SEQ ID NO 83
<211> LENGTH: 22
<212> TYPE: DNA
<213> ORGANISM: Artificial sequence
<220> FEATURE:
<223> OTHER INFORMATION: Oligonucleotide

<400> SEQUENCE: 83
ggctcgagtt tttcagcaag at                                             22

<210> SEQ ID NO 84
<211> LENGTH: 38
<212> TYPE: DNA
<213> ORGANISM: Artificial sequence
<220> FEATURE:
<223> OTHER INFORMATION: Oligonucleotide

<400> SEQUENCE: 84
cagggtcacc cggggaattg ctcagcattt tccttttg                            38

<210> SEQ ID NO 85
<211> LENGTH: 24
<212> TYPE: DNA
<213> ORGANISM: Artificial sequence
<220> FEATURE:
<223> OTHER INFORMATION: Oligonucleotide

<400> SEQUENCE: 85
gaattgctca gcattttcct tttg                                           24

<210> SEQ ID NO 86
<211> LENGTH: 1635
<212> TYPE: DNA
<213> ORGANISM: Artificial sequence
<220> FEATURE:
<223> OTHER INFORMATION: Consensus sequence

<400> SEQUENCE: 86
atgaaktgct carcattyts yttttggtwt gtttgcaara taatattttt ctttctctca     60
ttcmatatcc aaatttcaat agctaatcct cragaaaact tccttaaatg cttctcrvaa    120
yatattccya mcaatsyarc aaatscaaaa ytcrtataca ctcaacacga ccaattktat    180
atgtctvtcc tgaattcgac matacaaaat cttagattya yctctgayac aaccccaaaa    240
ccactygtta tyrtcactcc ttyaaatrwc tcccatatcc argsmastat tytmtgctcy    300
aagaaagttg gyttgcagat tcgaactcga agcggtggyc atgatgctga gggywtgtcc    360
tacatwtctc aagtcccatt tgytrtagta gacttgagra acatgcatwc grtcaaarta    420
gatrttcata gccaaactgc rtgggttgaa gccggagcta cccttggaga agtttattat    480
```

```
tggatcaatg agawsaatga gaatyttagt tttcctgstg ggtaytgccc tactgttggc    540
gyrggtggac actttagtgg aggaggctat ggagcattga tgcgaaatta tggcctygcg    600
gctgataata tyattgatkc rcacttagtc aatgttgatg gaaaagttyt agatcgaaaa    660
tccatgggrg aagatytrtt ttgggctata cgtggtggwg gaggagaaaa ctttggaatc    720
attgcagcrt ggaaaatyar actkgttgyt gtcccatcaa wgkctactat attcagtgtt    780
aaaaagaaca tggagataca tgrgcttgtc aagttaktta acaaatggca aaatattgct    840
tacawgtatg amaaagawtt adtrctcwyk actcacttya kaachargaa tattacagat    900
aatcawggga agaataagac wacartacay rgttacttct cytcmatttt ycwtggtgga    960
gtggatagtc tagtygactt gatgaacaag agctttcctg arttgggtat taaaaaaacw   1020
gattgcaaas arttkagctg gattgatacw aycatcttct acagtggtgt tgtmaattwy   1080
aacacwrctw attttaaaaa rgaaatttg cttgatagat cagstgggmr gaagrcggct   1140
ttctcratta agttagacta tgttaagaaa cyratwccwg aaacygcaat ggtcamaatt   1200
ttggaaaaat tatatgaaga agakgtagga gytgggatgt wtgtgttkta cccttayggt   1260
ggtataatgg akgagatttc agaatcagca attccattcc ctcatcgagc tggaatmatg   1320
tatgaamttt ggtacaywgc twcmtgggag aagcaagaag ataaygaaaa gcatataaac   1380
tggrttcgra rtgtttataa tttyacract ccttatgtgt cccaaaatcc aagawtggcg   1440
tatctcaatt atagggacct tgatttagga aaaactaaty hygmgagtcc taataattac   1500
acacaagcac gtatttgggg tgaaaagtat tttggtaaaa attttaayag gttagtwaar   1560
gtraaaacya argytgatcc crataattty tttagaaacg aacaaagyat cccacctctt   1620
ccmcygcrtc atcat                                                    1635
```